US011518789B2

(12) United States Patent
Ittig et al.

(10) Patent No.: US 11,518,789 B2
(45) Date of Patent: Dec. 6, 2022

(54) VIRULENCE ATTENUATED BACTERIA BASED PROTEIN DELIVERY

(71) Applicant: UNIVERSITÄT BASEL, Basel (CH)

(72) Inventors: Simon Ittig, Bottmingen (CH); Marlise Amstutz, Basel (CH); Christoph Kasper, Olten (CH)

(73) Assignee: Universitaet Basel, Basel (CH)

( * ) Notice: Subject to any disclaimer, the term of this patent is extended or adjusted under 35 U.S.C. 154(b) by 301 days.

(21) Appl. No.: 16/471,264

(22) PCT Filed: Dec. 20, 2017

(86) PCT No.: PCT/EP2017/083853
§ 371 (c)(1),
(2) Date: Jun. 19, 2019

(87) PCT Pub. No.: WO2018/115140
PCT Pub. Date: Jun. 28, 2018

(65) Prior Publication Data

US 2020/0123207 A1 Apr. 23, 2020

(30) Foreign Application Priority Data

Dec. 20, 2016 (EP) .................................... 16205439

(51) Int. Cl.

| | |
|---|---|
| ***A61K 39/02*** | (2006.01) |
| ***A61K 45/00*** | (2006.01) |
| ***A61K 47/00*** | (2006.01) |
| ***A01N 63/00*** | (2020.01) |
| ***A61K 48/00*** | (2006.01) |
| ***C07K 14/24*** | (2006.01) |
| ***A61P 35/00*** | (2006.01) |
| ***C12N 1/20*** | (2006.01) |
| ***C12N 1/36*** | (2006.01) |
| ***C12N 15/74*** | (2006.01) |
| *A61K 38/00* | (2006.01) |

(52) U.S. Cl.
CPC .............. *C07K 14/24* (2013.01); *A61P 35/00* (2018.01); *C12N 1/20* (2013.01); *C12N 1/36* (2013.01); *C12N 15/74* (2013.01); *A61K 38/00* (2013.01); *C07K 2319/02* (2013.01); *C07K 2319/036* (2013.01); *C07K 2319/21* (2013.01); *C07K 2319/41* (2013.01); *C07K 2319/50* (2013.01)

(58) Field of Classification Search
CPC .... C07K 15/25; C07K 2319/02; C07K 14/24; A61K 38/164; A61K 39/00; A61K 2039/522
USPC ........................ 424/93.1, 93.2, 234.1, 235.1
See application file for complete search history.

(56) References Cited

U.S. PATENT DOCUMENTS

| | | | |
|---|---|---|---|
| 7,763,420 | B2 | 7/2010 | Stritzker et al. |
| 10,889,823 | B2 | 1/2021 | Arrieumerlou |
| 2004/0147719 | A1 | 7/2004 | Cornelis |
| 2008/0187520 | A1 | 8/2008 | Polack et al. |
| 2011/0183908 | A1 | 7/2011 | Ruter |
| 2015/0140037 | A1 | 5/2015 | Galan et al. |
| 2017/0198297 | A1 | 7/2017 | Ittig et al. |
| 2019/0015497 | A1 | 1/2019 | Ittig et al. |
| 2019/0194670 | A1 | 6/2019 | Ittig et al. |

FOREIGN PATENT DOCUMENTS

| | | | |
|---|---|---|---|
| WO | 1999045098 | 9/1999 | |
| WO | WO99/45098 | * 9/1999 | |
| WO | WO 200002996 | 1/2000 | |
| WO | 2002026819 | 4/2002 | |
| WO | WO 2002077249 | 10/2002 | |
| WO | 2007044406 | 4/2007 | |
| WO | WO 2008019183 | 2/2008 | |
| WO | WO 2009115531 | 9/2009 | |
| WO | WO 2015042705 | 4/2015 | |
| WO | 2015177197 | 11/2015 | |
| WO | WO-2015177197 A1 | * 11/2015 | ........... C07K 14/195 |
| WO | WO 2018115140 | 6/2018 | |

OTHER PUBLICATIONS

Hoppner, Horm Re. 2002, 58 Suppl. 3:7-15 (Year: 2002).*
Bowie et al., Science, 1990, 247:1306-1310 (Year: 1990).*
Burgess et al., J. Cell Biol., 1990; 111:2129-2138 (Year: 1990).*
Lazar et al., Mol. Cell. Biol., 1988; 8:1247-1252 (Year: 1988).*
Letzelter, 2006; The discovery of SycO reveals a new function for Type Three Secretion Effector Chaperones (dissertation) (Year: 2006).*
Burdette et al., (2018) "Developing Gram-negative bacteria for the secretion of heterologous proteins", Microb Cell Fact, 17(196):1-16.
Bohme et al., (2012) "Concerted Actions of a Thermo-labile Regulator and a Unique Intergenic RNA Thermosensor Control Yersinia Virulence", Plos Pathogens, 8(2):1-24.
Chamekh et al., (2008) "Delivery of 1 Biologically Active Anti-Inflammatory Cytokines IL-10 and IL-1ra In Vivo by the Shigella Type III Secretion Apparatus", The Journal of Immunology, 180(6):4292-4298.
Corrales et al., (2014) "Direct activation of STING in the tumor microenvironment with synthetic cyclic dinucleotide derivatives leads to potent and systemic tumor-specific immunity", Journal for Immunotherapy of Cancer, 2(3):010.
De et al., (2009) "Determinants for the Activation and Autoinhibition of the Diguanylate Cyclase Response Regulator WspR", Journal of Molecular Biology, 393(3):619-633.
Li et al., (2014) "Tumor suppressor activity of RIG-I", Molecular & Celluar Oncology, 1(4): e968016-e968016-6.

(Continued)

*Primary Examiner* — Gary B Nickol
*Assistant Examiner* — Lakia J Jackson-Tongue
(74) *Attorney, Agent, or Firm* — Bozicevic, Field & Francis LLP; Shweta Chandra

(57) ABSTRACT

The present invention relates to recombinant virulence attenuated Gram-negative bacterial strains and its use in a method of treating cancer in a subject.

17 Claims, 68 Drawing Sheets

Specification includes a Sequence Listing.

(56) References Cited

OTHER PUBLICATIONS

Russmann et al., (2001) "Protection Against Murine Listeriosis by Oral Vaccination with Recombinant *Salmonella* Expressing Hybrid Yersinia Type III Proteins", The Journal of Immunology, 167(1):357-365.
Wu et al., (2014) "Innate Immune Sensing and Signaling of Cytosolic Nucleic Acids", Annual Review of Immunology, 32(1):461-488.
Ziemann et al., (2016) "Gene name errors are widespread in the scientific literature.", Genome Biology, 17(177):1-3.
Briones et al., (2006) "Cre Reporter System To Monitor the Translocation of Type III Secreted Proteins into Host Cells", Infection and Immnunity, 1084-1090.
Ahmed Kamal et al., (2014) "Apoptosi s-inducing agents: a patent review (2010-2013)", Expert Opinion on Therapeutic Patents, 1(3):339-354.
Akeda, Y &, Galan J.E. (2005) "Chaperone release and unfolding of substrates in type III secretion"; Nature 437; pp. 911-915.
Boyd AP, et al (2000) "Yersinia enterocolitica can deliver Yop proteins into a wide range of cell types: development of a delivery system for heterologous proteins"; Eur J Cell Biol.79(10); pp. 659-671.
Cardenal-Munoz,and Ramos-Morales (2011) "Analysis of the Expression, Secretion and Translocation of the *Salmonella enterica* Type III Secretion System Effector SteA"; PLOS One 6(10); pp. 1-13.
Chen, Li-Mei, et al., (2006) "Optimization of the Delivery of Heterologous Proteins by the *Salmonella enterica* Serovar Typhimurium Type III Secretion System for Vaccine Development", Infection and Immunity, 74(10):5826-5833.
Culliton, Barbara J. (1986) "NIH considers major change in definition of recombinant DNA"; Science 2344773); pp. 146.
Feldman M. et al. (2002) "SycE allows secretion of YopE-DHFR hybrids by the Yersinia enterocolitica type III Ysc system"; Molecular Microbiology 46(4); pp. 1183-1197.
Fensterle J et al, (2008) "Cancer immunotherapy based on recombinant *Salmonella enterica* serovar Typhimurium aroA strains secreting prostate-specific antigen and cholera toxin subunit B", Cancer Gene Therapy, Appleton & Lange, GB, 15(2):85-93.
Garcia, Julie Torruellas, et al., (2006) "Measurement of Effector Protein Injection by Type III and Type IV Secretion Systems by Using a 13-Residue Phosphorylatable Glycogen Synthase Kinase Tag", Infection and Immunity, 74(10):5645-5657.
Gentschev Ivaylo et al, (2005) "Use of a recombinant *Salmonella enterica* serovar Typhimurium strain expressing C-Raf for protection against C-Raf induced lung adenoma in mice", BMC Cancer, Biomed Central, London, GB, 5(1):1-9.
Gosh P. (2004) "Process of Protein Transport by the Type III Secretion System"; Microbiology and Molecular Biology Reviews 68(4); pp. 771-795.
Iriarte, Maite, et al., (1998) "TyeA, a protein involved in control of Yop release and in translocation of Yersinia Yop effectors", The EMBO Journal, 17(7):1907-1918.
Jacobi, C. A. et al. (1998) "In vitro and in vivo expression studies of yopE from Yeresinia enterocolitica using the gfp reporter gene"; Molecular microbiology 30(4); pp. 865-882.
Karavolos et al. (2015) "Type III Secretion of the *Salmonella* Effector Protein SopE Is Mediated via an N-Terminal Amino Acid Signal and Not an mRNA Sequence"; Journal Of Bacteriology 187(5); pp. 1559-1567.
Lee, V. T. & Schneewind, O. (2002) "Yop Fusions to Tightly Folded Protein Domains and Their Effects on Yersinia enterocolitica Type III Secretion"; Journal Of Bacteriology, vol. 184, No. 13; pp. 3740-3745.
Lloyd et al (2001) "Yersinian YopE is targeted for Type III secretion by N-terminal, not mRNA, signals"; Molecular Microbiology 39(2); pp. 520-531.
Mota and Cornelis (2005) "The bacterial injection kit: type III secretion systems"; Ann Med.37(4); pp. 234-249.
Simon J. Ittig et al., (2015) "A bacterial type III secretion-based protein delivery tool for broad applications in cell biology", The Journal of Cell Biology : JCB, 211(4):913-931.
Stadler et al., (2014) "The use of a neutral peptide aptamer scaffold to anchor BH3 peptides constitutes a viable approach to studying their function", Cell Death and Disease, 5(1):1-9.
Viboud et al., "Yersinia Outer Proteins: Role in Modulation of Host Cell Signaling Responses and Pathogensis", Annu. Rev. Microbial. 2005, 59:69-89.
Wiedig, et al. (2005) "Induction of CD8+ T cell responses by Yersinia vaccine carrier strains"; Vaccine.23(42); pp. 4984-4998.
Y. Zhang et al., (2011) "Type III Secretion System-Dependent Translocation of Ectopically Expressed Yop Effectors into Macrophages by Intracellular Yersinia pseudotuberculosis", Infection and Immunity, 79(11):4322-4331.
Dittmann, Svea, et al., (2007) "The Yersinia enterocolitica type three secretion chaperone SycO is integrated into the Yop regulatory network and binds to the Yop secretion protein YscM1", BMC Microbiology, 7(67):1-10.
Xu, Hui, et al., (2014) "Structural basis for the prion-like MAVS filaments in antiviral innate immunity", eLife, pp. 1-25.

* cited by examiner

A

A

B

YopE1-138 XhoI XbaI BstBI

GTTCGCCACG CTCGAGTCTA GATTCGAA

HindIII *myc* epitope

AAGCTTGGGC CCGAACAAAA ACTCATCTCA

GAAGAGGATCTGAATAGCGC CGTCGACCAT

6x His - tag ★★★

CATCATCATC ATCATTGAGT TTAAACGGTC

TCCAGCTTGG CTGTTTTGG C

Figure 3A

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT | Y. enterocolitica | MRS40 pIML421 [yopHΔ1–352, yopOΔ65–558, yopP23, yopE21, yopM23, yopT135] | | | | | Nal | Iriarte and Cornelis, 1998 |
| ΔHOPEMT asd yopB | Y. enterocolitica ΔyopH,O,P,E,M,T | MRS40 pIML421 [yopBΔ89-217, yopHΔ1–352, yopOΔ65–558, yopP23, yopE21, yopM23, yopT135] | | | | | Nal Kan | |
| ΔHOPEMT asd | Y. enterocolitica ΔyopH,O,P,E,M,T | MRS40 asdΔ292-610 pIML421 [yopHΔ1–352, yopOΔ65–558, yopP23, yopE21, yopM23, yopT135] | | | | | Nal | Kudryashev et al., 2013 |
| ΔHOPEMT asd inv | Y. enterocolitica ΔyopH,O,P,E,M,T | MRS40 asdΔ292-610 invAΔ352-2225::aphA-3 pIML421 [yopHΔ1–352, yopOΔ65–558, yopP23, yopE21, yopM23, yopT135] | | | | 445/446, 447/448, 449/450 | Nal Kan | |
| ΔHOPEMT asd inv yadA | Y. enterocolitica ΔyopH,O,P,E,M,T ΔinvA ΔyadA | MRS40 asdΔ292-610 invAΔ587-836 (vector cointegration) yadAΔ89-354::aphA3 pIML421 [yopHΔ1–352, yopOΔ65–558, yopP23, yopE21, yopM23, yopT135] | | | | 352/353, 354/355, 356/357 | Nal Kan Tet | |

Figure 3B

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pBad_Si1 | Y. enterocolitica ΔyopH,O,P,E,M,T Δasd | EGFP (Arabinose inducible), SycE-YopE1-138-MycHis fragment | | pBad-MycHisA (Invitrogen) | pBad_Si_1 | 285/286 (EGFP), 287/288 (sycE-YopE1-138) | Nal Amp | |
| ΔHOPEMT asd pBad_Si2 | Y. enterocolitica ΔyopH,O,P,E,M,T Δasd | SycE-$YopE_{1-138}$-MycHis fragment | YopE1-138-MycHis | pBad-MycHisA (Invitrogen) | pBad_Si_2 | 287/288 (sycE-YopE1-138) | Nal Amp | |
| ΔHOPEMT asd pSi_85 | Y. enterocolitica ΔyopH,O,P,E,M,T Δasd | | YopE1-138-Bid | pBad_Si_2 | pSi_85 | 387/391 | Nal Amp | |
| ΔHOPEMT asd pSi_87 | Y. enterocolitica ΔyopH,O,P,E,M,T Δasd | | YopE1-138-t-Bid | pBad_Si_2 | pSi_87 | 389/391 | Nal Amp | |

Figure 3C

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_120 | Y. enterocolitica ΔyopH,O,P,E,M,T Δasd | | YopE1-138-ET1 | pBad_Si_2 | pSi_120 | 436/437 | Nal Amp | |
| ΔHOPEMT asd pSi_121 | Y. enterocolitica ΔyopH,O,P,E,M,T Δasd | | YopE1-138-z-BIM | pbad_Si_1 | pSi_121 | 438/439 | Nal Amp | |
| ΔHOPEMT asd pSi_132 | Y. enterocolitica ΔyopH,O,P,E,M,T Δasd | | YopE1-138-TEV protease S219V | pBad_Si_2 | pSi_132 | 463/464 | Nal Amp | |
| ΔHOPEMT asd pSi_158 | Y. enterocolitica ΔyopH,O,P,E,M,T Δasd | | YopE1-138 - 2xTEVsite - EGFP | pBad_Si_2 | pSi_158 | 511/476 | Nal Amp | |
| ΔHOPEMT asd pSi_151 | Y. enterocolitica ΔyopH,O,P,E,M,T Δasd | | YopE1-138-Ink4C | pBad_Si_2 | pSi_151 | 494/495 | Nal Amp | |

Figure 3D

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_156 | Y. enterocolitica ΔyopH,O,P,E,M,T Δasd | | YopE1-138-2x TEVsite - ET1 | pBad_Si_2 | pSi_156 | 504/505 | Nal Amp | |
| ΔHOPEMT asd pSi_159 | Y. enterocolitica ΔyopH,O,P,E,M,T Δasd | | YopE1-138-2xTEVsite - EGFP - NLS | pBad_Si_2 | pSi_159 | 511/513 | Nal Amp | |
| ΔHOPEMT asd pSi_160 | Y. enterocolitica ΔyopH,O,P,E,M,T Δasd | | YopE1-138-2xTEVsite - NLS - EGFP | pBad_Si_2 | pSi_160 | 512/476 | Nal Amp | |
| ΔHOPEMT asd pSi_161 | Y. enterocolitica ΔyopH,O,P,E,M,T Δasd | | YopE1-138-2x TEVsite - INK4C | pBad_Si_2 | pSi_161 | 508/509 | Nal Amp | |
| ΔHOPEMT asd pSi_164 | Y. enterocolitica ΔyopH,O,P,E,M,T Δasd | | YopE1-138-2x TEVsite - Flag - INK4C | pBad_Si_2 | pSi_164 | 515/509 | Nal Amp | |

Figure 3E

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_318 | Y. enterocolitica ΔyopH,O,P,E,M,T Δasd | | YopE1-138-Y. enterocolitica codon optimized murine tBid BH3 part | pBad_Si_2 | pSi_318 | 677/678 | Nal Amp | |
| ΔHOPEMT asd pSi_322 | Y. enterocolitica ΔyopH,O,P,E,M,T Δasd | | YopE1-138-Y. enterocolitica codon optimized murine Bax BH3 part | pBad_Si_2 | pSi_322 | 682/683 | Nal Amp | |
| S. enterica SL1344 ΔaroA | S. enterica subsp. enterica serovar Typhimurium SL1344 ΔaroA | | | | | | | Hoiseth and Stocker, 1981 |
| ΔHOPEMT asd pSi_315 | Y. enterocolitica ΔyopH,O,P,E,M,T Δasd | | YopE1-138-Y. enterocolitica codon optimized murine tBid | pBad_Si_2 | pSi_315 | synthetic construct | Nal Amp | |
| ΔHOPEMT asd pSi_236 | Y. enterocolitica ΔyopH,O,P,E,M,T Δasd | | YopE1-138-Ubiquitin | pBad_Si_2 | pSi_236 | 585/586 | Nal Amp | |
| ΔHOPEMT asd pSi_237_II | Y. enterocolitica ΔyopH,O,P,E,M,T Δasd | | YopE1-138-Ubiquitin-Flag-INK4C-MycHis | pSi_236 | pSI_237_II | 588/509 | Nal Amp | |

Figure 3F

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_357 | Y. enterocolitica ΔyopH,O,P,E, M,T (Δasd) | | YopE1-138-Y. enterocolitica codon optimized murine tBid BH3 | pBad_Si_2 | pSi_357 | 733/735 | Nal Amp | |
| ΔHOPEMT Or: ΔHOPEMT asd pSi_358 | Y. enterocolitica ΔyopH,O,P,E, M,T (Δasd) | | YopE1-138-Y. enterocolitica codon optimized murine Bax BH3 | pBad_Si_2 | pSi_358 | 736/738 | Nal Amp | |
| ΔHOPEMT Or: ΔHOPEMT asd pSi_371 | Y. enterocolitica ΔyopH,O,P,E, M,T (Δasd) | | YopE1-138-(Y. enterocolitica codon optimized murine tBid BH3)$_2$ | pSi_357 | pSi_371 | 733/734 | Nal Amp | |
| ΔHOPEMT Or: ΔHOPEMT asd pSi_373 | Y. enterocolitica ΔyopH,O,P,E, M,T (Δasd) | | YopE1-138-Y. enterocolitica codon optimized murine tBid BH3-. enterocolitica codon optimized murine Bax BH3 | pSi_358 | pSi_373 | 733/734 | Nal Amp | |

Figure 3G

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_353 | Y. enterocolitica ΔyopH,O,P,E,M,T (Δasd) | | YopE1-138-Y. enterocolitica codon optimized murine tBid BH3 extended (by 4 Aa) | pBad_Si_2 | pSi_353 | 725/726 | Nal Amp | |
| ΔHOPEMT Or: ΔHOPEMT asd pSi_354 | Y. enterocolitica ΔyopH,O,P,E,M,T (Δasd) | | YopE1-138-10 Aa linker-Y. enterocolitica codon optimized murine tBid BH3 | pBad_Si_2 | pSi_354 | 727/728 | Nal Amp | |
| ΔHOPEMT Or: ΔHOPEMT asd pSi_374 | Y. enterocolitica ΔyopH,O,P,E,M,T (Δasd) | | YopE1-138-Y. enterocolitica codon optimized murine Bax BH3-. enterocolitica codon optimized murine tBid BH3 | pSi_357 | pSi_374 | 736/737 | Nal Amp | |

Figure 3H

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_453 | Y. enterocolitica ΔyopH,O,P,E,M,T (Δasd) | | $YopE_{1-138}$- Y. enterocolitica codon optimized human RIG-1 two CARD domains (Aa. 1-245) | pBad_Si_2 | pSi_453 | synthetic construct | Nal Amp | |
| ΔHOPEMT Or: ΔHOPEMT asd pSi_454 | Y. enterocolitica ΔyopH,O,P,E,M,T (Δasd) | | $YopE_{1-138}$- Y. enterocolitica codon optimized murine RIG-1 two CARD domains (Aa. 1-246) | pBad_Si_2 | pSi_454 | synthetic construct | Nal Amp | |
| ΔHOPEMT Or: ΔHOPEMT asd pSi_452 | Y. enterocolitica ΔyopH,O,P,E,M,T (Δasd) | | $YopE_{1-138}$- Y. enterocolitica codon optimized S. cerevisiae GCN4 (Aa. 249-278) - Y. enterocolitica codon optimized P. aeruginosa WspR (Aa. 172-347) | pBad_Si_2 | pSi_452 | synthetic construct | Nal Amp | |

Figure 3I

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_428 | Y. enterocolitica ΔyopH,O,P,E,M,T (Δasd) | | $YopE_{1-138}$- Y. enterocolitica codon optimized murine IRF3 S397D | pBad_Si_2 | pSi_428 | synthetic construct | Nal Amp | |
| ΔHOPEMT Or: ΔHOPEMT asd pSi_482 | Y. enterocolitica ΔyopH,O,P,E,M,T (Δasd) | | $YopE_{1-138}$- Y. enterocolitica codon optimized V. Cholerae DncV (M3toL413) | pBad_Si_2 | pSi_482 | synthetic construct | Nal Amp | |
| ΔHOPEMT Or: ΔHOPEMT asd pSi_483 | Y. enterocolitica ΔyopH,O,P,E,M,T (Δasd) | | $YopE_{1-138}$- Y. enterocolitica codon optimized B. cereus_DisA-like (PDB: 2FB5; Aa. 76-205) | pBad_Si_2 | pSi_483 | synthetic construct | Nal Amp | |
| ΔHOPEMT Or: ΔHOPEMT asd pSi_484 | Y. enterocolitica ΔyopH,O,P,E,M,T (Δasd) | | $YopE_{1-138}$- Y. enterocolitica codon optimized Anemonae (N. vectensis) cGAS (Ensembl: A7SFB5.1) | pBad_Si_2 | pSi_484 | synthetic construct | Nal Amp | |

Figure 3J

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pYV-asd | Y. enterocolitica ΔyopH,O,P,E,M,T Δ*asd* | MRS40 pIML421 [yopHΔ1–352, yopOΔ65–558, yopP23, yopE21, yopM23, yopT135, pYV-asd] | / | pKNG101 | pSi_417 (Mutator | PCR1: 869/870; PCR2: 871/872; PCR3: 873/874; overlapping PCR 869/874 | Nal | |
| ΔHOPEMT asd pBad-asd | Y. enterocolitica ΔyopH,O,P,E,M,T Δ*asd* | MRS40 pIML421 [yopHΔ1–352, yopOΔ65–558, yopP23, yopE21, yopM23, yopT135] | YopE1-138-MycHis | pBad_Si_2 | pSi_397 | 600/601 | Nal | |
| ΔHOPEMT *virF-hairpinI* | Y. enterocolitica ΔyopH,O,P,E,M,T | MRS40 [yopHΔ1–352, yopOΔ65–558, yopP23, yopE21, yopM23, yopT135 virFΔ-111 – -57] | / | pKNG101 | pSI_441 (Mutator) | synthetic construct | Nal | |
| ΔHOPEMT *virF-hairpinI* pSi_371 | Y. enterocolitica ΔyopH,O,P,E,M,T Δ*virF-hairpinI* | MRS40 [yopHΔ1–352, yopOΔ65–558, yopP23, yopE21, yopM23, yopT135 virFΔ-111 – -57] | YopE1-138-(Y. enterocolitica codon optimized murine tBid BH3)$_2$ | pBad_Si_2 | pSi_371 | 733/734 | Nal Amp | |

Figure 3K

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT pYV-$YopE_{1-138}$- murine tBID BH3 | Y. enterocolitica ΔyopH,O,P,E,M,T | MRS40 [yopHΔ1–352, yopOΔ65–558, yopP23, yopE21, yopM23, yopT135 yopE::tBID BH3] | $YopE_{1-138}$-tBID BH3 | pKNG101 | pSI_408 (Mutator) | synthetic construct | Nal | |
| ΔHOPEMT pYV-$YopE_{1-138}$- murine $(tBID BH3)_2$ | Y. enterocolitica ΔyopH,O,P,E,M,T | MRS40 [yopHΔ1–352, yopOΔ65–558, yopP23, yopE21, yopM23, yopT135 yopE::$(tBID BH3)_2$] | $YopE_{1-138}$-$(tBID BH3)_2$ | pKNG101 | pSI_437 (Mutator) | synthetic construct | \| | |
| ΔHOPEMT pYV-*virF-hairpinI* - $YopE_{1-138}$- murine $(tBID BH3)_2$ | Y. enterocolitica ΔyopH,O,P,E,M,T, yopE::$(tBID BH3)_2$ | MRS40 [yopHΔ1–352, yopOΔ65–558, yopP23, yopE21, yopM23, yopT135 yopE::$(tBID BH3)_2$ virFΔ-111 – -57] | $YopE_{1-138}$-$(tBID BH3)_2$ | pKNG101 | pSI_441 (Mutator) | synthetic construct | Nal | |
| ΔHOPEMT asd pYV-asd-$YopE_{1-138}$- murine $(tBID BH3)_2$ | Y. enterocolitica ΔyopH,O,P,E,M,T Δ*asd* pYV-asd | MRS40 pIML421 [yopHΔ1–352, yopOΔ65–558, yopP23, yopE21, yopM23, yopT135, yopE::$(tBID BH3)_2$ pYV-asd] | $YopE_{1-138}$-$(tBID BH3)_2$ | pKNG101 | pSI_437 (Mutator) | synthetic construct | Nal | |

Figure 3L

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT pYV-$YopE_{1-138}$- murine RIG-1 CARD domains | Y. enterocolitica ΔyopH,O,P,E,M,T | MRS40 [yopHΔ1–352, yopOΔ65–558, yopP23, yopE21, yopM23, yopT135 yopE::RIG-1 CARD domains | $YopE_{1-138}$- RIG-1 CARD domains | pKNG101 | pSI_456 (Mutator) | synthetic construct | Nal | |
| ΔHOPEMT pYV-pAra-*virF* | Y. enterocolitica ΔyopH,O,P,E,M,T | MRS40 [yopHΔ1–352, yopOΔ65–558, yopP23, yopE21, yopM23, yopT135 pAra::virF] | / | pKNG101 | pSI_439 (Mutator) | synthetic construct | | |
| ΔHOPEMT pYV-pAra-*virF* pSi_371 | Y. enterocolitica ΔyopH,O,P,E,M,T, pYV-pAra-*virF* | MRS40 [yopHΔ1–352, yopOΔ65–558, yopP23, yopE21, yopM23, yopT135 pAra::virF] | $YopE_{1-138}$-(Y. enterocolitica codon optimized murine tBid $BH3)_2$ | pBad_Si_2 | pSi_371 | 733/734 | Nal Amp | |

Figure 3M

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT pYV-*virF-hairpinI* -$YopE_{1-138}$- murine RIG-1 CARD domains | Y. enterocolitica ΔyopH,O,P,E,M,T yopE::murine RIG-1 CARD domains | MRS40 [yopHΔ1–352, yopOΔ65–558, yopP23, yopE21, yopM23, yopT135 virFΔ-111 – -57 yopE::RIG-1 CARD domains | $YopE_{1-138}$- RIG-1 CARD domains | pKNG101 | pSI_441 (Mutator) | synthetic construct | Nal | |
| ΔHOPEMT Or: ΔHOPEMT asd pSi_521 | Y. enterocolitica ΔyopH,O,P,E,M,T (Δasd) | | $YopE_{1-138}$- Y. enterocolitica codon optimized murine RIG-1 two CARD domains (Aa. 1-229) | pBad_Si_2 | pSi_521 | 1021/1022 | Nal Amp | |

Figure 3N

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_522 | Y. enterocolitica ΔyopH,O,P,E,M,T (Δasd) | | $YopE_{1-138}$- Y. enterocolitica codon optimized murine RIG-1 two CARD domains (Aa. 1-218) | pBad_Si_2 | pSi_522 | 1021/1023 | Nal Amp | |
| ΔHOPEMT Or: ΔHOPEMT asd pSi_517 | Y. enterocolitica ΔyopH,O,P,E,M,T (Δasd) | | $YopE_{1-138}$- Y. enterocolitica codon optimized murine MDA5 two CARD domains (Aa. 1-294) | pBad_Si_2 | pSi_517 | synthetic construct | Nal Amp | |

Figure 3O

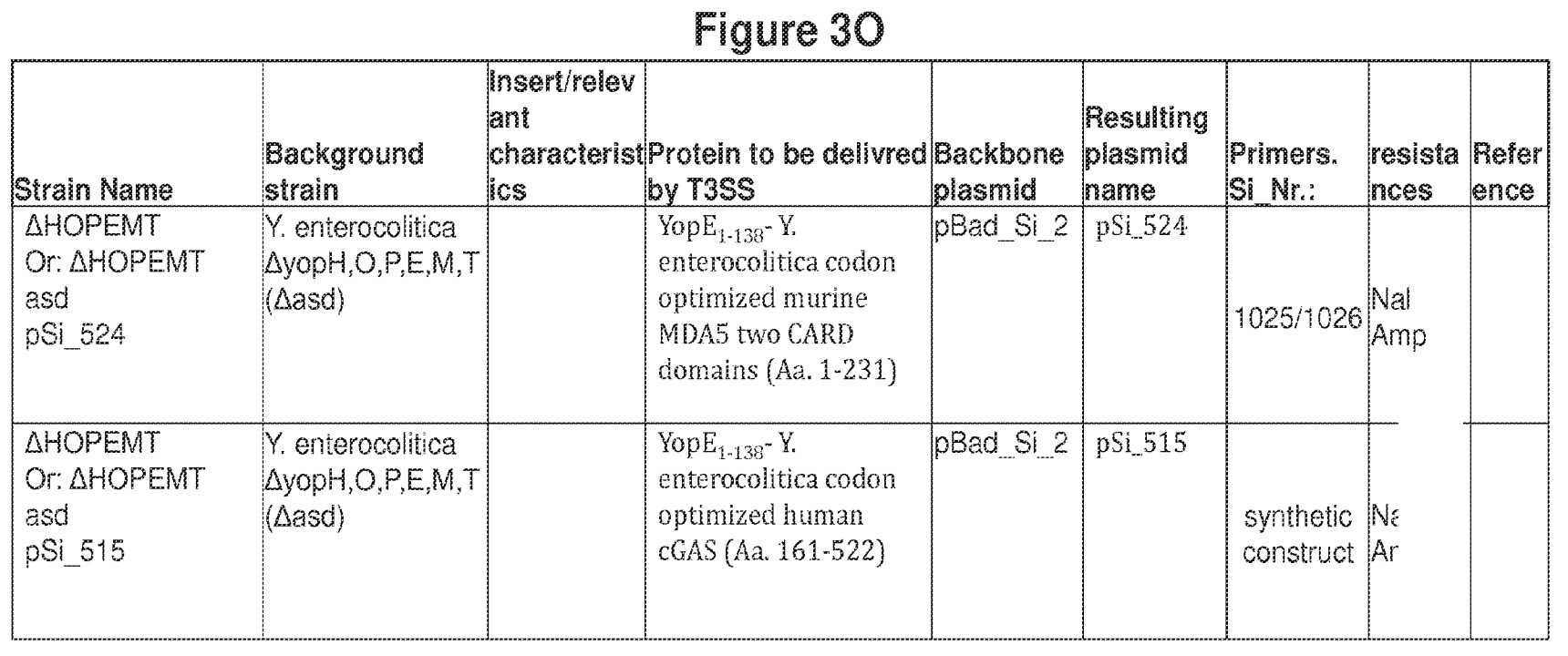

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT<br>Or: ΔHOPEMT asd<br>pSi_524 | Y. enterocolitica ΔyopH,O,P,E,M,T (Δasd) | | $YopE_{1-138}$- Y. enterocolitica codon optimized murine MDA5 two CARD domains (Aa. 1-231) | pBad_Si_2 | pSi_524 | 1025/1026 | Nal Amp | |
| ΔHOPEMT<br>Or: ΔHOPEMT asd<br>pSi_515 | Y. enterocolitica ΔyopH,O,P,E,M,T (Δasd) | | $YopE_{1-138}$- Y. enterocolitica codon optimized human cGAS (Aa. 161-522) | pBad_Si_2 | pSi_515 | synthetic construct | Na Ar | |

Figure 3P

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT Or: ΔHOPEMT asd pSi_539 | Y. enterocolitica ΔyopH,O,P,E,M,T (Δasd) | | $YopE_{1-138}$- Y. enterocolitica codon optimized human MAVS CARD (Aa. 1-100) | pBad_Si_2 | pSi_539 | synthetic construct | Nal Amp | |
| ΔHOPEMT Or: ΔHOPEMT asd pSi_503 | Y. enterocolitica ΔyopH,O,P,E,M,T (Δasd) | | $YopE_{1-138}$- Y. enterocolitica codon optimized Anemonae (N. vectensis) cGAS (Aa. 60-422) (Ensembl: A7SFB5.1) | pBad_Si_2 | pSi_484 | 1010/1012 | | |
| ΔHOPEMT Or: ΔHOPEMT asd pSi_518 | Y. enterocolitica ΔyopH,O,P,E,M,T (Δasd) | | $YopE_{1-138}$- Y. enterocolitica codon optimized Listeria monocytogenes CdaA (Aa. 101-273) | pBad_Si_2 | pSi_518 | synthetic construct | Nal Amp | |

Figure 3Q

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT-yopB pSi_539 | Y. enterocolitica ΔyopH,O,P,E,M,T,B | Deletion of *yopB* | $YopE_{1-138}$- Y. enterocolitica codon optimized human MAVS CARD (Aa. 1-100) | pBad_Si_2 | pSi_539 | synthetic construct | Nal Amp | |
| ΔHOPEMT-yopB pSi_454 | Y. enterocolitica ΔyopH,O,P,E,M,T,B | Deletion of *yopB* | $YopE_{1-138}$- Y. enterocolitica codon optimized murine RIG-1 two CARD domains (Aa. 1-246) | pBad_Si_2 | pSi_454 | synthetic construct | Nal Amp | |

Figure 11
A
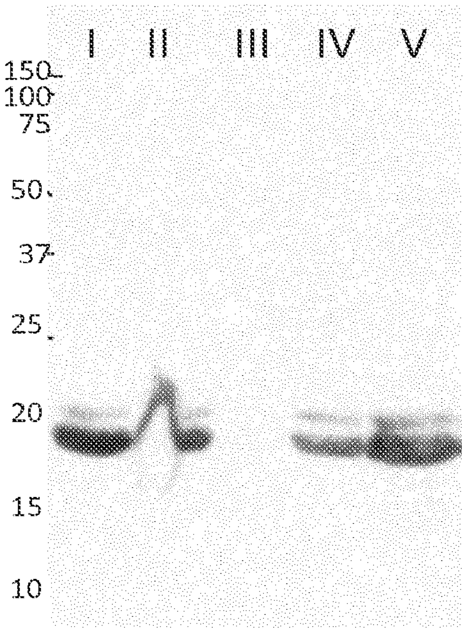
B
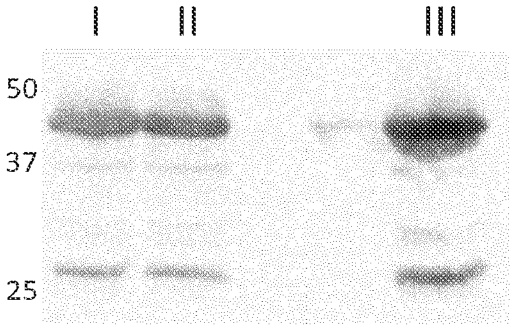

SEQUENCE LISTING

```
<160> NUMBER OF SEQ ID NOS: 131

<210> SEQ ID NO 1
<211> LENGTH: 219
<212> TYPE: PRT
<213> ORGANISM: Yersinia enterocolitica

<400> SEQUENCE: 1

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Gly Ser Gly Pro Leu Arg
    130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                165                 170                 175

Pro Phe Ser Gln Trp Gly Thr Val Gly Gly Ala Ala Ser Ala Tyr Val
            180                 185                 190

Ala Ser Gly Val Asp Leu Thr Gln Ala Ala Asn Glu Ile Lys Gly Leu
        195                 200                 205

Gly Gln Gln Met Gln Gln Leu Leu Ser Leu Met
    210                 215


<210> SEQ ID NO 2
<211> LENGTH: 138
```

<212> TYPE: PRT
<213> ORGANISM: Yersinia enterocolitica

<400> SEQUENCE: 2

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr
130 135

<210> SEQ ID NO 3
<211> LENGTH: 169
<212> TYPE: PRT
<213> ORGANISM: Artificial Sequence
<220> FEATURE:
<223> OTHER INFORMATION: YopE1-138-MycHis

<400> SEQUENCE: 3

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Phe Glu
130 135 140

Lys Leu Gly Pro Glu Gln Lys Leu Ile Ser Glu Glu Asp Leu Asn Ser
145 150 155 160

Ala Val Asp His His His His His His
165

<210> SEQ ID NO 4
<211> LENGTH: 20
<212> TYPE: PRT

<213> ORGANISM: Salmonella enterica

<400> SEQUENCE: 4

```
Met Pro Tyr Thr Ser Val Ser Thr Tyr Ala Arg Ala Leu Ser Gly Asn
1               5                   10                  15

Lys Leu Pro His
            20
```

<210> SEQ ID NO 5
<211> LENGTH: 210
<212> TYPE: PRT
<213> ORGANISM: Salmonella enterica

<400> SEQUENCE: 5

```
Met Pro Tyr Thr Ser Val Ser Thr Tyr Ala Arg Ala Leu Ser Gly Asn
1               5                   10                  15

Lys Leu Pro His Val Ala Ala Gly Asp Tyr Glu Asn Lys Leu Ser Thr
            20                  25                  30

Lys Ile Met Lys Gly Ile Leu Tyr Val Leu Thr Ala Gly Leu Ala Tyr
        35                  40                  45

Gly Phe Thr Arg Val Ile Glu His Tyr Cys Asn Val Thr Pro Lys Val
    50                  55                  60

Ala Glu Phe Cys Ala Asn Ala Gly Asn Ile His Asn His Leu Ala Asp
65                  70                  75                  80

Ala Val Arg Asp Gly Leu Phe Thr Ile Asp Val Glu Leu Ser Asp Gly
                85                  90                  95

Arg Met Leu Thr Phe Glu Gln Leu Ser Leu Ile Ala Glu Gly Lys Pro
            100                 105                 110

Ile Val Arg Ile Ser Asp Gly Glu His Thr Val Glu Val Glu Gly Thr
        115                 120                 125

Phe Glu Glu Ile Cys Met Arg Leu Glu Glu Gly Phe Phe Glu Ala Pro
    130                 135                 140

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
                165                 170                 175

Cys Leu Glu Tyr Tyr Ile Ala Arg Ala Ser Asn Met Gln Glu Ala Lys
            180                 185                 190

Ala Gln Trp Ala Ala Asp Ile Lys Ala Arg Tyr His Asn Tyr Leu Asp
        195                 200                 205

Asn Tyr
    210
```

<210> SEQ ID NO 6
<211> LENGTH: 81
<212> TYPE: PRT
<213> ORGANISM: Salmonella enterica

<400> SEQUENCE: 6

```
Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60
```

His Phe His Arg Gly Ser Ala Ser Glu Gly Arg Ala Val Leu Thr Asn
65 70 75 80

Lys

<210> SEQ ID NO 7
<211> LENGTH: 105
<212> TYPE: PRT
<213> ORGANISM: Salmonella enterica

<400> SEQUENCE: 7

Val Thr Lys Ile Thr Leu Ser Pro Gln Asn Phe Arg Ile Gln Lys Gln
1 5 10 15

Glu Thr Thr Leu Leu Lys Glu Lys Ser Thr Glu Lys Asn Ser Leu Ala
20 25 30

Lys Ser Ile Leu Ala Val Lys Asn His Phe Ile Glu Leu Arg Ser Lys
35 40 45

Leu Ser Glu Arg Phe Ile Ser His Lys Asn Thr Glu Ser Ser Ala Thr
50 55 60

His Phe His Arg Gly Ser Ala Ser Glu Gly Arg Ala Val Leu Thr Asn
65 70 75 80

Lys Val Val Lys Asp Phe Met Leu Gln Thr Leu Asn Asp Ile Asp Ile
85 90 95

Arg Gly Ser Ala Ser Lys Asp Pro Ala
100 105

<210> SEQ ID NO 8
<211> LENGTH: 310
<212> TYPE: PRT
<213> ORGANISM: Artificial Sequence
<220> FEATURE:
<223> OTHER INFORMATION: YopE1-138 - Ink4C

<400> SEQUENCE: 8

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Met Ala
130 135 140

Glu Pro Trp Gly Asn Glu Leu Ala Ser Ala Ala Ala Arg Gly Asp Leu
145 150 155 160

Glu Gln Leu Thr Ser Leu Leu Gln Asn Asn Val Asn Val Asn Ala Gln
165 170 175

Asn Gly Phe Gly Arg Thr Ala Leu Gln Val Met Lys Leu Gly Asn Pro

```
            180                 185                 190

Glu Ile Ala Arg Arg Leu Leu Leu Arg Gly Ala Asn Pro Asp Leu Lys
        195                 200                 205

Asp Arg Thr Gly Phe Ala Val Ile His Asp Ala Ala Arg Ala Gly Phe
    210                 215                 220

Leu Asp Thr Leu Gln Ala Leu Pro Glu Phe Gln Ala Asp Val Asn Ile
225                 230                 235                 240

Glu Asp Asn Glu Gly Asn Leu Pro Leu His Leu Ala Ala Lys Glu Gly
                245                 250                 255

His Leu Arg Val Val Glu Phe Leu Val Lys His Thr Ala Ser Asn Val
            260                 265                 270

Gly His Arg Asn His Lys Gly Asp Thr Ala Cys Asp Leu Ala Arg Leu
        275                 280                 285

Tyr Gly Arg Asn Glu Val Val Ser Leu Met Gln Ala Asn Gly Ala Gly
    290                 295                 300

Gly Ala Thr Asn Leu Gln
305                 310


<210> SEQ ID NO 9
<211> LENGTH: 465
<212> TYPE: PRT
<213> ORGANISM: Artificial Sequence
<220> FEATURE:
<223> OTHER INFORMATION: YopE1-138 - ET1

<400> SEQUENCE: 9

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Pro
    130                 135                 140

Arg Pro Lys Leu Lys Ser Asp Asp Glu Val Leu Glu Ala Ala Thr Val
145                 150                 155                 160

Val Leu Lys Arg Cys Gly Pro Ile Glu Phe Thr Leu Ser Gly Val Ala
                165                 170                 175

Lys Glu Val Gly Leu Ser Arg Ala Ala Leu Ile Gln Arg Phe Thr Asn
            180                 185                 190

Arg Asp Thr Leu Leu Val Arg Met Met Glu Arg Gly Val Glu Gln Val
        195                 200                 205

Arg His Tyr Leu Asn Ala Ile Pro Ile Gly Ala Gly Pro Gln Gly Leu
    210                 215                 220

Trp Glu Phe Leu Gln Val Leu Val Arg Ser Met Asn Thr Arg Asn Asp
```

```
225                 230                 235                 240

Phe Ser Val Asn Tyr Leu Ile Ser Trp Tyr Glu Leu Gln Val Pro Glu
                245                 250                 255

Leu Arg Thr Leu Ala Ile Gln Arg Asn Arg Ala Val Val Glu Gly Ile
            260                 265                 270

Arg Lys Arg Leu Pro Pro Gly Ala Pro Ala Ala Ala Glu Leu Leu Leu
        275                 280                 285

His Ser Val Ile Ala Gly Ala Thr Met Gln Trp Ala Val Asp Pro Asp
    290                 295                 300

Gly Glu Leu Ala Asp His Val Leu Ala Gln Ile Ala Ala Ile Leu Cys
305                 310                 315                 320

Leu Met Phe Pro Glu His Asp Asp Phe Gln Leu Leu Gln Ala His Ala
                325                 330                 335

Ser Ala Tyr Ser Arg Ala Arg Thr Lys Asn Asn Tyr Gly Ser Thr Ile
            340                 345                 350

Glu Gly Leu Leu Asp Leu Pro Asp Asp Asp Ala Pro Glu Glu Ala Gly
        355                 360                 365

Leu Ala Ala Pro Arg Leu Ser Phe Leu Pro Ala Gly His Thr Arg Arg
    370                 375                 380

Leu Ser Thr Ala Pro Pro Thr Asp Val Ser Leu Gly Asp Glu Leu His
385                 390                 395                 400

Leu Asp Gly Glu Asp Val Ala Met Ala His Ala Asp Ala Leu Asp Asp
                405                 410                 415

Phe Asp Leu Asp Met Leu Gly Asp Gly Asp Ser Pro Gly Pro Gly Phe
            420                 425                 430

Thr Pro His Asp Ser Ala Pro Tyr Gly Ala Leu Asp Met Ala Asp Phe
        435                 440                 445

Glu Phe Glu Gln Met Phe Thr Asp Ala Leu Gly Ile Asp Glu Tyr Gly
    450                 455                 460

Gly
465


<210> SEQ ID NO 10
<211> LENGTH: 324
<212> TYPE: PRT
<213> ORGANISM: Artificial Sequence
<220> FEATURE:
<223> OTHER INFORMATION: YopE1-138 - 2x TEVsite - INK4C

<400> SEQUENCE: 10

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
```

```
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Met Ala Glu Pro
145                 150                 155                 160

Trp Gly Asn Glu Leu Ala Ser Ala Ala Ala Arg Gly Asp Leu Glu Gln
                165                 170                 175

Leu Thr Ser Leu Leu Gln Asn Asn Val Asn Val Asn Ala Gln Asn Gly
            180                 185                 190

Phe Gly Arg Thr Ala Leu Gln Val Met Lys Leu Gly Asn Pro Glu Ile
        195                 200                 205

Ala Arg Arg Leu Leu Leu Arg Gly Ala Asn Pro Asp Leu Lys Asp Arg
    210                 215                 220

Thr Gly Phe Ala Val Ile His Asp Ala Ala Arg Ala Gly Phe Leu Asp
225                 230                 235                 240

Thr Leu Gln Ala Leu Pro Glu Phe Gln Ala Asp Val Asn Ile Glu Asp
                245                 250                 255

Asn Glu Gly Asn Leu Pro Leu His Leu Ala Ala Lys Glu Gly His Leu
            260                 265                 270

Arg Val Val Glu Phe Leu Val Lys His Thr Ala Ser Asn Val Gly His
        275                 280                 285

Arg Asn His Lys Gly Asp Thr Ala Cys Asp Leu Ala Arg Leu Tyr Gly
    290                 295                 300

Arg Asn Glu Val Val Ser Leu Met Gln Ala Asn Gly Ala Gly Gly Ala
305                 310                 315                 320

Thr Asn Leu Gln


<210> SEQ ID NO 11
<211> LENGTH: 479
<212> TYPE: PRT
<213> ORGANISM: Artificial Sequence
<220> FEATURE:
<223> OTHER INFORMATION: YopE1-138 - 2x TEVsite - ET1

<400> SEQUENCE: 11

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Met Pro Arg Pro
145                 150                 155                 160
```

Lys Leu Lys Ser Asp Asp Glu Val Leu Glu Ala Ala Thr Val Val Leu
165 170 175

Lys Arg Cys Gly Pro Ile Glu Phe Thr Leu Ser Gly Val Ala Lys Glu
180 185 190

Val Gly Leu Ser Arg Ala Ala Leu Ile Gln Arg Phe Thr Asn Arg Asp
195 200 205

Thr Leu Leu Val Arg Met Met Glu Arg Gly Val Glu Gln Val Arg His
210 215 220

Tyr Leu Asn Ala Ile Pro Ile Gly Ala Gly Pro Gln Gly Leu Trp Glu
225 230 235 240

Phe Leu Gln Val Leu Val Arg Ser Met Asn Thr Arg Asn Asp Phe Ser
245 250 255

Val Asn Tyr Leu Ile Ser Trp Tyr Glu Leu Gln Val Pro Glu Leu Arg
260 265 270

Thr Leu Ala Ile Gln Arg Asn Arg Ala Val Val Glu Gly Ile Arg Lys
275 280 285

Arg Leu Pro Pro Gly Ala Pro Ala Ala Ala Glu Leu Leu Leu His Ser
290 295 300

Val Ile Ala Gly Ala Thr Met Gln Trp Ala Val Asp Pro Asp Gly Glu
305 310 315 320

Leu Ala Asp His Val Leu Ala Gln Ile Ala Ala Ile Leu Cys Leu Met
325 330 335

Phe Pro Glu His Asp Asp Phe Gln Leu Leu Gln Ala His Ala Ser Ala
340 345 350

Tyr Ser Arg Ala Arg Thr Lys Asn Asn Tyr Gly Ser Thr Ile Glu Gly
355 360 365

Leu Leu Asp Leu Pro Asp Asp Asp Ala Pro Glu Glu Ala Gly Leu Ala
370 375 380

Ala Pro Arg Leu Ser Phe Leu Pro Ala Gly His Thr Arg Arg Leu Ser
385 390 395 400

Thr Ala Pro Pro Thr Asp Val Ser Leu Gly Asp Glu Leu His Leu Asp
405 410 415

Gly Glu Asp Val Ala Met Ala His Ala Asp Ala Leu Asp Asp Phe Asp
420 425 430

Leu Asp Met Leu Gly Asp Gly Asp Ser Pro Gly Pro Gly Phe Thr Pro
435 440 445

His Asp Ser Ala Pro Tyr Gly Ala Leu Asp Met Ala Asp Phe Glu Phe
450 455 460

Glu Gln Met Phe Thr Asp Ala Leu Gly Ile Asp Glu Tyr Gly Gly
465 470 475

<210> SEQ ID NO 12
<211> LENGTH: 380
<212> TYPE: PRT
<213> ORGANISM: Artificial Sequence
<220> FEATURE:
<223> OTHER INFORMATION: YopE1-138 - TEV protease S219V

<400> SEQUENCE: 12

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Glu Ser Leu Phe
    130                 135                 140

Lys Gly Pro Arg Asp Tyr Asn Pro Ile Ser Ser Thr Ile Cys His Leu
145                 150                 155                 160

Thr Asn Glu Ser Asp Gly His Thr Thr Ser Leu Tyr Gly Ile Gly Phe
                165                 170                 175

Gly Pro Phe Ile Ile Thr Asn Lys His Leu Phe Arg Arg Asn Asn Gly
            180                 185                 190

Thr Leu Leu Val Gln Ser Leu His Gly Val Phe Lys Val Lys Asn Thr
        195                 200                 205

Thr Thr Leu Gln Gln His Leu Ile Asp Gly Arg Asp Met Ile Ile Ile
    210                 215                 220

Arg Met Pro Lys Asp Phe Pro Pro Phe Pro Gln Lys Leu Lys Phe Arg
225                 230                 235                 240

Glu Pro Gln Arg Glu Glu Arg Ile Cys Leu Val Thr Thr Asn Phe Gln
                245                 250                 255

Thr Lys Ser Met Ser Ser Met Val Ser Asp Thr Ser Cys Thr Phe Pro
            260                 265                 270

Ser Ser Asp Gly Ile Phe Trp Lys His Trp Ile Gln Thr Lys Asp Gly
        275                 280                 285

Gln Cys Gly Ser Pro Leu Val Ser Thr Arg Asp Gly Phe Ile Val Gly
    290                 295                 300

Ile His Ser Ala Ser Asn Phe Thr Asn Thr Asn Asn Tyr Phe Thr Ser
305                 310                 315                 320

Val Pro Lys Asn Phe Met Glu Leu Leu Thr Asn Gln Glu Ala Gln Gln
                325                 330                 335

Trp Val Ser Gly Trp Arg Leu Asn Ala Asp Ser Val Leu Trp Gly Gly
            340                 345                 350

His Lys Val Phe Met Val Lys Pro Glu Glu Pro Phe Gln Pro Val Lys
        355                 360                 365

Glu Ala Thr Gln Leu Met Asn Arg Arg Arg Arg Arg
    370                 375                 380

<210> SEQ ID NO 13
<211> LENGTH: 332
<212> TYPE: PRT
<213> ORGANISM: Artificial Sequence
<220> FEATURE:
<223> OTHER INFORMATION: YopE1-138 - 2x TEVsite - Flag - INK4C

<400> SEQUENCE: 13

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

```
Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Asp Tyr Lys Asp
145                 150                 155                 160

Asp Asp Asp Lys Met Ala Glu Pro Trp Gly Asn Glu Leu Ala Ser Ala
                165                 170                 175

Ala Ala Arg Gly Asp Leu Glu Gln Leu Thr Ser Leu Leu Gln Asn Asn
            180                 185                 190

Val Asn Val Asn Ala Gln Asn Gly Phe Gly Arg Thr Ala Leu Gln Val
        195                 200                 205

Met Lys Leu Gly Asn Pro Glu Ile Ala Arg Arg Leu Leu Leu Arg Gly
    210                 215                 220

Ala Asn Pro Asp Leu Lys Asp Arg Thr Gly Phe Ala Val Ile His Asp
225                 230                 235                 240

Ala Ala Arg Ala Gly Phe Leu Asp Thr Leu Gln Ala Leu Pro Glu Phe
                245                 250                 255

Gln Ala Asp Val Asn Ile Glu Asp Asn Glu Gly Asn Leu Pro Leu His
            260                 265                 270

Leu Ala Ala Lys Glu Gly His Leu Arg Val Val Glu Phe Leu Val Lys
        275                 280                 285

His Thr Ala Ser Asn Val Gly His Arg Asn His Lys Gly Asp Thr Ala
    290                 295                 300

Cys Asp Leu Ala Arg Leu Tyr Gly Arg Asn Glu Val Val Ser Leu Met
305                 310                 315                 320

Gln Ala Asn Gly Ala Gly Gly Ala Thr Asn Leu Gln
                325                 330
```

<210> SEQ ID NO 14
<211> LENGTH: 245
<212> TYPE: PRT
<213> ORGANISM: Artificial Sequence
<220> FEATURE:
<223> OTHER INFORMATION: YopE1-138-Ubiquitin

<400> SEQUENCE: 14

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60
```

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Met Gln Ile Phe
130 135 140

Val Lys Thr Leu Thr Gly Lys Thr Ile Thr Leu Glu Val Glu Pro Ser
145 150 155 160

Asp Thr Ile Glu Asn Val Lys Ala Lys Ile Gln Asp Lys Glu Gly Ile
165 170 175

Pro Pro Asp Gln Gln Arg Leu Ile Phe Ala Gly Lys Gln Leu Glu Asp
180 185 190

Gly Arg Thr Leu Ser Asp Tyr Asn Ile Gln Lys Glu Ser Thr Leu His
195 200 205

Leu Val Leu Arg Leu Arg Gly Gly Phe Glu Ala Ser Lys Leu Gly Pro
210 215 220

Glu Gln Lys Leu Ile Ser Glu Glu Asp Leu Asn Ser Ala Val Asp His
225 230 235 240

His His His His His
245

<210> SEQ ID NO 15
<211> LENGTH: 419
<212> TYPE: PRT
<213> ORGANISM: Artificial Sequence
<220> FEATURE:
<223> OTHER INFORMATION: YopE1-138-Ubiquitin-Flag-INK4C-MycHis

<400> SEQUENCE: 15

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Met Gln Ile Phe
130 135 140

Val Lys Thr Leu Thr Gly Lys Thr Ile Thr Leu Glu Val Glu Pro Ser
145 150 155 160

Asp Thr Ile Glu Asn Val Lys Ala Lys Ile Gln Asp Lys Glu Gly Ile
165 170 175

-continued

```
Pro Pro Asp Gln Gln Arg Leu Ile Phe Ala Gly Lys Gln Leu Glu Asp
            180                 185                 190

Gly Arg Thr Leu Ser Asp Tyr Asn Ile Gln Lys Glu Ser Thr Leu His
        195                 200                 205

Leu Val Leu Arg Leu Arg Gly Gly Phe Glu Asp Tyr Lys Asp Asp Asp
    210                 215                 220

Asp Lys Met Ala Glu Pro Trp Gly Asn Glu Leu Ala Ser Ala Ala Ala
225                 230                 235                 240

Arg Gly Asp Leu Glu Gln Leu Thr Ser Leu Leu Gln Asn Asn Val Asn
                245                 250                 255

Val Asn Ala Gln Asn Gly Phe Gly Arg Thr Ala Leu Gln Val Met Lys
            260                 265                 270

Leu Gly Asn Pro Glu Ile Ala Arg Arg Leu Leu Leu Arg Gly Ala Asn
        275                 280                 285

Pro Asp Leu Lys Asp Arg Thr Gly Phe Ala Val Ile His Asp Ala Ala
    290                 295                 300

Arg Ala Gly Phe Leu Asp Thr Leu Gln Ala Leu Pro Glu Phe Gln Ala
305                 310                 315                 320

Asp Val Asn Ile Glu Asp Asn Glu Gly Asn Leu Pro Leu His Leu Ala
                325                 330                 335

Ala Lys Glu Gly His Leu Arg Val Val Glu Phe Leu Val Lys His Thr
            340                 345                 350

Ala Ser Asn Val Gly His Arg Asn His Lys Gly Asp Thr Ala Cys Asp
        355                 360                 365

Leu Ala Arg Leu Tyr Gly Arg Asn Glu Val Val Ser Leu Met Gln Ala
    370                 375                 380

Asn Gly Ala Gly Gly Ala Thr Asn Leu Gln Lys Leu Gly Pro Glu Gln
385                 390                 395                 400

Lys Leu Ile Ser Glu Glu Asp Leu Asn Ser Ala Val Asp His His His
                405                 410                 415

His His His
```

<210> SEQ ID NO 16
<211> LENGTH: 318
<212> TYPE: PRT
<213> ORGANISM: Artificial Sequence
<220> FEATURE:
<223> OTHER INFORMATION: YopE1-138 - z-BIM

<400> SEQUENCE: 16

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110
```

```
Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ser
    130                 135                 140

Asp Thr Ser Arg Glu Gln Thr Leu Ala Asn Gly Pro Ala Ser Gln Gly
145                 150                 155                 160

Ser Gly Glu Ser Thr Gly Gly Gly Val Val Leu Pro Ala Gly His Phe
                165                 170                 175

Asp Phe Pro Gln Pro Gly Glu Gly Asp Pro Leu Arg Gly Gly Ile Ser
            180                 185                 190

Met Ser Asn Asn Gln Ser Arg Ser Pro Met Asn Arg Thr Phe Ser Arg
        195                 200                 205

Ser Ser Ser Gly Tyr Phe Ser Val Asp Ser Asp Ser Val Pro Gly Ser
    210                 215                 220

Pro Leu Met Pro Asn Ile Ser Glu Ala Gln Asp Gly Gln Asn Asp Glu
225                 230                 235                 240

Val Trp Leu Ser Glu His Ser His Gln His Leu Gln Met Ala Ala Pro
                245                 250                 255

Val Ala Ala Leu Pro Pro Glu Met Val Val Ala Arg Glu Leu Arg Arg
            260                 265                 270

Ile Gly Asp Glu Phe Asn Arg Leu Tyr Cys Glu Ala Gly Ala Gly Val
        275                 280                 285

Asn Gln Leu Arg Ala Pro Asn Glu His Ala Ile Val Leu Trp Met Asn
    290                 295                 300

Val Ile Ile Gly Arg Leu Val His Phe Phe Leu Arg Arg Arg
305                 310                 315


<210> SEQ ID NO 17
<211> LENGTH: 337
<212> TYPE: PRT
<213> ORGANISM: Artificial Sequence
<220> FEATURE:
<223> OTHER INFORMATION: YopE1-138 - human Bid

<400> SEQUENCE: 17

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Asp
    130                 135                 140

Cys Glu Val Asn Asn Gly Ser Ser Leu Arg Asp Glu Cys Ile Thr Asn
145                 150                 155                 160
```

-continued

```
Leu Leu Val Phe Gly Phe Leu Gln Ser Cys Ser Asp Asn Ser Phe Arg
                165                 170                 175

Arg Glu Leu Asp Ala Leu Gly His Glu Leu Pro Val Leu Ala Pro Gln
            180                 185                 190

Trp Glu Gly Tyr Asp Glu Leu Gln Thr Asp Gly Asn Arg Ser Ser His
        195                 200                 205

Ser Arg Leu Gly Arg Ile Glu Ala Asp Ser Glu Ser Gln Glu Asp Ile
    210                 215                 220

Ile Arg Asn Ile Ala Arg His Leu Ala Gln Val Gly Asp Ser Met Asp
225                 230                 235                 240

Arg Ser Ile Pro Pro Gly Leu Val Asn Gly Leu Ala Leu Gln Leu Arg
                245                 250                 255

Asn Thr Ser Arg Ser Glu Glu Asp Arg Asn Arg Asp Leu Ala Thr Ala
            260                 265                 270

Leu Glu Gln Leu Leu Gln Ala Tyr Pro Arg Asp Met Glu Lys Glu Lys
        275                 280                 285

Thr Met Leu Val Leu Ala Leu Leu Leu Ala Lys Lys Val Ala Ser His
    290                 295                 300

Thr Pro Ser Leu Leu Arg Asp Val Phe His Thr Thr Val Asn Phe Ile
305                 310                 315                 320

Asn Gln Asn Leu Arg Thr Tyr Val Arg Ser Leu Ala Arg Asn Gly Met
                325                 330                 335

Asp
```

<210> SEQ ID NO 18
<211> LENGTH: 277
<212> TYPE: PRT
<213> ORGANISM: Artificial Sequence
<220> FEATURE:
<223> OTHER INFORMATION: YopE1-138 - human t-Bid

<400> SEQUENCE: 18

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Gly Asn
    130                 135                 140

Arg Ser Ser His Ser Arg Leu Gly Arg Ile Glu Ala Asp Ser Glu Ser
145                 150                 155                 160

Gln Glu Asp Ile Ile Arg Asn Ile Ala Arg His Leu Ala Gln Val Gly
                165                 170                 175

Asp Ser Met Asp Arg Ser Ile Pro Pro Gly Leu Val Asn Gly Leu Ala
```

-continued

```
            180                 185                 190

Leu Gln Leu Arg Asn Thr Ser Arg Ser Glu Glu Asp Arg Asn Arg Asp
        195                 200                 205

Leu Ala Thr Ala Leu Glu Gln Leu Leu Gln Ala Tyr Pro Arg Asp Met
    210                 215                 220

Glu Lys Glu Lys Thr Met Leu Val Leu Ala Leu Leu Leu Ala Lys Lys
225                 230                 235                 240

Val Ala Ser His Thr Pro Ser Leu Leu Arg Asp Val Phe His Thr Thr
                245                 250                 255

Val Asn Phe Ile Asn Gln Asn Leu Arg Thr Tyr Val Arg Ser Leu Ala
            260                 265                 270

Arg Asn Gly Met Asp
        275


<210> SEQ ID NO 19
<211> LENGTH: 163
<212> TYPE: PRT
<213> ORGANISM: Artificial Sequence
<220> FEATURE:
<223> OTHER INFORMATION: YopE1-138 - Y. enterocolitica codon optimized
      murine BID BH3 part

<400> SEQUENCE: 19

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Phe Glu
    130                 135                 140

Glu Ile Ile His Asn Ile Ala Arg His Leu Ala Gln Ile Gly Asp Glu
145                 150                 155                 160

Met Asp His


<210> SEQ ID NO 20
<211> LENGTH: 156
<212> TYPE: PRT
<213> ORGANISM: Artificial Sequence
<220> FEATURE:
<223> OTHER INFORMATION: YopE1-138 - Y. enterocolitica codon optimized
      murine Bax BH3 part

<400> SEQUENCE: 20

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30
```

```
Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Lys Lys Leu Ser
    130                 135                 140

Glu Cys Leu Arg Arg Ile Gly Asp Glu Leu Asp Ser
145                 150                 155


<210> SEQ ID NO 21
<211> LENGTH: 276
<212> TYPE: PRT
<213> ORGANISM: Artificial Sequence
<220> FEATURE:
<223> OTHER INFORMATION: YopE1-138-Y. enterocolitica codon optimized
      murine tBid

<400> SEQUENCE: 21

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ser Gln Ala
    130                 135                 140

Ser Arg Ser Phe Asn Gln Gly Arg Ile Glu Pro Asp Ser Glu Ser Gln
145                 150                 155                 160

Glu Glu Ile Ile His Asn Ile Ala Arg His Leu Ala Gln Ile Gly Asp
                165                 170                 175

Glu Met Asp His Asn Ile Gln Pro Thr Leu Val Arg Gln Leu Ala Ala
            180                 185                 190

Gln Phe Met Asn Gly Ser Leu Ser Glu Glu Asp Lys Arg Asn Cys Leu
        195                 200                 205

Ala Lys Ala Leu Asp Glu Val Lys Thr Ala Phe Pro Arg Asp Met Glu
    210                 215                 220

Asn Asp Lys Ala Met Leu Ile Met Thr Met Leu Leu Ala Lys Lys Val
```

```
225                 230                 235                 240

Ala Ser His Ala Pro Ser Leu Leu Arg Asp Val Phe His Thr Thr Val
                245                 250                 255

Asn Phe Ile Asn Gln Asn Leu Phe Ser Tyr Val Arg Asn Leu Val Arg
            260                 265                 270

Asn Glu Met Asp
        275


<210> SEQ ID NO 22
<211> LENGTH: 167
<212> TYPE: PRT
<213> ORGANISM: Artificial Sequence
<220> FEATURE:
<223> OTHER INFORMATION: YopE1-138- codon optimized murine tBid BH3
      extended part

<400> SEQUENCE: 22

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Phe Glu
    130                 135                 140

Glu Ile Ile His Asn Ile Ala Arg His Leu Ala Gln Ile Gly Asp Glu
145                 150                 155                 160

Met Asp His Asn Ile Gln Pro
                165


<210> SEQ ID NO 23
<211> LENGTH: 168
<212> TYPE: PRT
<213> ORGANISM: Artificial Sequence
<220> FEATURE:
<223> OTHER INFORMATION: YopE1-138-10 Aa linker - Y. enterocolitica
      codon optimized murine tBid BH3 part

<400> SEQUENCE: 23

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
```

```
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Phe Glu
    130                 135                 140

Ala Gly Gly Ala Glu Glu Ile Ile His Asn Ile Ala Arg His Leu Ala
145                 150                 155                 160

Gln Ile Gly Asp Glu Met Asp His
                165


<210> SEQ ID NO 24
<211> LENGTH: 186
<212> TYPE: PRT
<213> ORGANISM: Artificial Sequence
<220> FEATURE:
<223> OTHER INFORMATION: YopE1-138-Y. enterocolitica codon optimized
      murine Bax BH3 part- Y. enterocolitica codon optimized murine tBid
      BH3 part

<400> SEQUENCE: 24

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ala Ile Asp
    130                 135                 140

Ala Lys Lys Leu Ser Glu Cys Leu Arg Arg Ile Gly Asp Glu Leu Asp
145                 150                 155                 160

Ser Gly Ala Phe Asp Ala Glu Glu Ile Ile His Asn Ile Ala Arg His
                165                 170                 175

Leu Ala Gln Ile Gly Asp Glu Met Asp His
            180                 185


<210> SEQ ID NO 25
<211> LENGTH: 165
<212> TYPE: PRT
<213> ORGANISM: Artificial Sequence
<220> FEATURE:
<223> OTHER INFORMATION: YopE1-138 - Y. enterocolitica codon optimized
      murine BID BH3 part (ready for insertion of further domains)

<400> SEQUENCE: 25
```

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Gly Ala Ile Asp
130 135 140

Ala Glu Glu Ile Ile His Asn Ile Ala Arg His Leu Ala Gln Ile Gly
145 150 155 160

Asp Glu Met Asp His
165

<210> SEQ ID NO 26
<211> LENGTH: 161
<212> TYPE: PRT
<213> ORGANISM: Artificial Sequence
<220> FEATURE:
<223> OTHER INFORMATION: YopE1-138 - Y. enterocolitica codon optimized murine Bax BH3 part (ready for insertion of further domains)

<400> SEQUENCE: 26

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Gly Ala Ile Asp
130 135 140

Ala Lys Lys Leu Ser Glu Cys Leu Arg Arg Ile Gly Asp Glu Leu Asp
145 150 155 160

Ser

<210> SEQ ID NO 27
<211> LENGTH: 190

<212> TYPE: PRT
<213> ORGANISM: Artificial Sequence
<220> FEATURE:
<223> OTHER INFORMATION: YopE1-138 - (Y. enterocolitica codon optimized murine BID BH3 part)2

<400> SEQUENCE: 27

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ala Ile Asp
    130                 135                 140

Ala Glu Glu Ile Ile His Asn Ile Ala Arg His Leu Ala Gln Ile Gly
145                 150                 155                 160

Asp Glu Met Asp His Gly Ala Phe Asp Ala Glu Glu Ile Ile His Asn
                165                 170                 175

Ile Ala Arg His Leu Ala Gln Ile Gly Asp Glu Met Asp His
            180                 185                 190
```

<210> SEQ ID NO 28
<211> LENGTH: 186
<212> TYPE: PRT
<213> ORGANISM: Artificial Sequence
<220> FEATURE:
<223> OTHER INFORMATION: YopE1-138 - (Y. enterocolitica codon optimized murine BID BH3 part)(Y. enterocolitica codon optimized murine Bax BH3 part)

<400> SEQUENCE: 28

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125
```

```
Leu Gln Lys Asn His Asp Gln Phe Ala Thr Leu Glu Gly Ala Ile Asp
    130                 135                 140

Ala Glu Glu Ile Ile His Asn Ile Ala Arg His Leu Ala Gln Ile Gly
145                 150                 155                 160

Asp Glu Met Asp His Gly Ala Phe Asp Ala Lys Lys Leu Ser Glu Cys
                165                 170                 175

Leu Arg Arg Ile Gly Asp Glu Leu Asp Ser
            180                 185


<210> SEQ ID NO 29
<211> LENGTH: 20
<212> TYPE: PRT
<213> ORGANISM: Mus musculus

<400> SEQUENCE: 29

Glu Glu Ile Ile His Asn Ile Ala Arg His Leu Ala Gln Ile Gly Asp
1               5                   10                  15

Glu Met Asp His
            20


<210> SEQ ID NO 30
<211> LENGTH: 14
<212> TYPE: PRT
<213> ORGANISM: Mus musculus

<400> SEQUENCE: 30

Ile Ala Arg His Leu Ala Gln Ile Gly Asp Glu Met Asp His
1               5                   10


<210> SEQ ID NO 31
<211> LENGTH: 20
<212> TYPE: PRT
<213> ORGANISM: Homo sapiens

<400> SEQUENCE: 31

Glu Asp Ile Ile Arg Asn Ile Ala Arg His Leu Ala Gln Val Gly Asp
1               5                   10                  15

Ser Met Asp Arg
            20


<210> SEQ ID NO 32
<211> LENGTH: 15
<212> TYPE: PRT
<213> ORGANISM: Homo sapiens

<400> SEQUENCE: 32

Ile Ala Arg His Leu Ala Gln Val Gly Asp Ser Met Asp Arg Ser
1               5                   10                  15


<210> SEQ ID NO 33
<211> LENGTH: 17
<212> TYPE: PRT
<213> ORGANISM: Mus musculus

<400> SEQUENCE: 33

Lys Lys Leu Ser Glu Cys Leu Arg Arg Ile Gly Asp Glu Leu Asp Ser
1               5                   10                  15

Asn


<210> SEQ ID NO 34
<211> LENGTH: 14
```

-continued

```
<212> TYPE: PRT
<213> ORGANISM: Mus musculus

<400> SEQUENCE: 34

Leu Ser Glu Cys Leu Arg Arg Ile Gly Asp Glu Leu Asp Ser
1               5                   10


<210> SEQ ID NO 35
<211> LENGTH: 17
<212> TYPE: PRT
<213> ORGANISM: Homo sapiens

<400> SEQUENCE: 35

Lys Lys Leu Ser Glu Cys Leu Lys Arg Ile Gly Asp Glu Leu Asp Ser
1               5                   10                  15

Asn


<210> SEQ ID NO 36
<211> LENGTH: 14
<212> TYPE: PRT
<213> ORGANISM: Homo sapiens

<400> SEQUENCE: 36

Leu Ser Glu Cys Leu Lys Arg Ile Gly Asp Glu Leu Asp Ser
1               5                   10


<210> SEQ ID NO 37
<211> LENGTH: 387
<212> TYPE: PRT
<213> ORGANISM: Artificial Sequence
<220> FEATURE:
<223> OTHER INFORMATION: YopE1-138 - Y. enterocolitica codon optimized
      human RIG-1 two CARD domains (Aa. 1-245)

<400> SEQUENCE: 37

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Thr Glu Gln Arg Arg Ser Leu Gln Ala Phe Gln Asp Tyr Ile Arg Lys
145                 150                 155                 160

Thr Leu Asp Pro Thr Tyr Ile Leu Ser Tyr Met Ala Pro Trp Phe Arg
                165                 170                 175

Glu Glu Glu Val Gln Tyr Ile Gln Ala Glu Lys Asn Asn Lys Gly Pro
            180                 185                 190
```

```
Met Glu Ala Ala Thr Leu Phe Leu Lys Phe Leu Leu Glu Leu Gln Glu
        195                 200                 205

Glu Gly Trp Phe Arg Gly Phe Leu Asp Ala Leu Asp His Ala Gly Tyr
    210                 215                 220

Ser Gly Leu Tyr Glu Ala Ile Glu Ser Trp Asp Phe Lys Lys Ile Glu
225                 230                 235                 240

Lys Leu Glu Glu Tyr Arg Leu Leu Leu Lys Arg Leu Gln Pro Glu Phe
                245                 250                 255

Lys Thr Arg Ile Ile Pro Thr Asp Ile Ile Ser Asp Leu Ser Glu Cys
            260                 265                 270

Leu Ile Asn Gln Glu Cys Glu Glu Ile Leu Gln Ile Cys Ser Thr Lys
        275                 280                 285

Gly Met Met Ala Gly Ala Glu Lys Leu Val Glu Cys Leu Leu Arg Ser
    290                 295                 300

Asp Lys Glu Asn Trp Pro Lys Thr Leu Lys Leu Ala Leu Glu Lys Glu
305                 310                 315                 320

Arg Asn Lys Phe Ser Glu Leu Trp Ile Val Glu Lys Gly Ile Lys Asp
                325                 330                 335

Val Glu Thr Glu Asp Leu Glu Asp Lys Met Glu Thr Ser Asp Ile Gln
            340                 345                 350

Ile Phe Tyr Gln Glu Asp Pro Glu Cys Gln Asn Leu Ser Glu Asn Ser
        355                 360                 365

Cys Pro Pro Ser Glu Val Ser Asp Thr Asn Leu Tyr Ser Pro Phe Lys
    370                 375                 380

Pro Arg Asn
385


<210> SEQ ID NO 38
<211> LENGTH: 388
<212> TYPE: PRT
<213> ORGANISM: Artificial Sequence
<220> FEATURE:
<223> OTHER INFORMATION: YopE1-138 - Y. enterocolitica codon optimized
      murine RIG-1 two CARD domains (Aa. 1-246)

<400> SEQUENCE: 38

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Ala Glu Gln Arg Gln Asn Leu Gln Ala Phe Arg Asp Tyr Ile Lys Lys
145                 150                 155                 160
```

Ile Leu Asp Pro Thr Tyr Ile Leu Ser Tyr Met Ser Ser Trp Leu Glu
165 170 175

Asp Glu Glu Val Gln Tyr Ile Gln Ala Glu Lys Asn Asn Lys Gly Pro
180 185 190

Met Glu Ala Ala Ser Leu Phe Leu Gln Tyr Leu Leu Lys Leu Gln Ser
195 200 205

Glu Gly Trp Phe Gln Ala Phe Leu Asp Ala Leu Tyr His Ala Gly Tyr
210 215 220

Cys Gly Leu Cys Glu Ala Ile Glu Ser Trp Asp Phe Gln Lys Ile Glu
225 230 235 240

Lys Leu Glu Glu His Arg Leu Leu Leu Arg Arg Leu Glu Pro Glu Phe
245 250 255

Lys Ala Thr Val Asp Pro Asn Asp Ile Leu Ser Glu Leu Ser Glu Cys
260 265 270

Leu Ile Asn Gln Glu Cys Glu Glu Ile Arg Gln Ile Arg Asp Thr Lys
275 280 285

Gly Arg Met Ala Gly Ala Glu Lys Met Ala Glu Cys Leu Ile Arg Ser
290 295 300

Asp Lys Glu Asn Trp Pro Lys Val Leu Gln Leu Ala Leu Glu Lys Asp
305 310 315 320

Asn Ser Lys Phe Ser Glu Leu Trp Ile Val Asp Lys Gly Phe Lys Arg
325 330 335

Ala Glu Ser Lys Ala Asp Glu Asp Asp Gly Ala Glu Ala Ser Ser Ile
340 345 350

Gln Ile Phe Ile Gln Glu Glu Pro Glu Cys Gln Asn Leu Ser Gln Asn
355 360 365

Pro Gly Pro Pro Ser Glu Ala Ser Ser Asn Asn Leu His Ser Pro Leu
370 375 380

Lys Pro Arg Asn
385

<210> SEQ ID NO 39
<211> LENGTH: 348
<212> TYPE: PRT
<213> ORGANISM: Artificial Sequence
<220> FEATURE:
<223> OTHER INFORMATION: YopE1-138 - Y. enterocolitica codon optimized S. cerevisiae GCN4 (Aa. 249-278) - Y. enterocolitica codon optimized P. aeruginosa WspR (Aa. 172-347)

<400> SEQUENCE: 39

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Arg Met
130 135 140

Lys Gln Leu Glu Asp Lys Val Glu Glu Leu Leu Ser Lys Asn Tyr His
145 150 155 160

Leu Glu Asn Glu Val Ala Arg Leu Lys Lys Leu Val Asn Ser Asp Gly
165 170 175

Leu Thr Gly Leu Ser Asn Arg Arg His Phe Asp Glu Tyr Leu Glu Met
180 185 190

Glu Trp Arg Arg Ser Leu Arg Glu Gln Ser Gln Leu Ser Leu Leu Met
195 200 205

Ile Asp Val Asp Tyr Phe Lys Ser Tyr Asn Asp Thr Phe Gly His Val
210 215 220

Ala Gly Asp Glu Ala Leu Arg Gln Val Ala Gly Ala Ile Arg Glu Gly
225 230 235 240

Cys Ser Arg Ser Ser Asp Leu Ala Ala Arg Tyr Gly Gly Glu Glu Phe
245 250 255

Ala Met Val Leu Pro Gly Thr Ser Pro Gly Gly Ala Arg Leu Leu Ala
260 265 270

Glu Lys Val Arg Arg Thr Val Glu Ser Leu Gln Ile Ser His Asp Gln
275 280 285

Pro Arg Pro Gly Ser His Leu Thr Val Ser Ile Gly Val Ser Thr Leu
290 295 300

Val Pro Gly Gly Gly Gly Gln Thr Phe Arg Val Leu Ile Glu Met Ala
305 310 315 320

Asp Gln Ala Leu Tyr Gln Ala Lys Asn Asn Gly Arg Asn Gln Val Gly
325 330 335

Leu Met Glu Gln Pro Val Pro Pro Ala Pro Ala Gly
340 345

<210> SEQ ID NO 40
<211> LENGTH: 561
<212> TYPE: PRT
<213> ORGANISM: Artificial Sequence
<220> FEATURE:
<223> OTHER INFORMATION: YopE1-138 - Y. enterocolitica codon optimized murine IRF3 S397D

<400> SEQUENCE: 40

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

-continued

```
Leu Gln Lys Asn His Asp Gln Phe Ala Thr Leu Glu Ser Arg Met Glu
    130                 135                 140

Thr Pro Lys Pro Arg Ile Leu Pro Trp Leu Val Ser Gln Leu Asp Leu
145                 150                 155                 160

Gly Gln Leu Glu Gly Val Ala Trp Leu Asp Glu Ser Arg Thr Arg Phe
                165                 170                 175

Arg Ile Pro Trp Lys His Gly Leu Arg Gln Asp Ala Gln Met Ala Asp
            180                 185                 190

Phe Gly Ile Phe Gln Ala Trp Ala Glu Ala Ser Gly Ala Tyr Thr Pro
        195                 200                 205

Gly Lys Asp Lys Pro Asp Val Ser Thr Trp Lys Arg Asn Phe Arg Ser
    210                 215                 220

Ala Leu Asn Arg Lys Glu Val Leu Arg Leu Ala Ala Asp Asn Ser Lys
225                 230                 235                 240

Asp Pro Tyr Asp Pro His Lys Val Tyr Glu Phe Val Thr Pro Gly Ala
                245                 250                 255

Arg Asp Phe Val His Leu Gly Ala Ser Pro Asp Thr Asn Gly Lys Ser
            260                 265                 270

Ser Leu Pro His Ser Gln Glu Asn Leu Pro Lys Leu Phe Asp Gly Leu
        275                 280                 285

Ile Leu Gly Pro Leu Lys Asp Glu Gly Ser Ser Asp Leu Ala Ile Val
    290                 295                 300

Ser Asp Pro Ser Gln Gln Leu Pro Ser Pro Asn Val Asn Asn Phe Leu
305                 310                 315                 320

Asn Pro Ala Pro Gln Glu Asn Pro Leu Lys Gln Leu Leu Ala Glu Glu
                325                 330                 335

Gln Trp Glu Phe Glu Val Thr Ala Phe Tyr Arg Gly Arg Gln Val Phe
            340                 345                 350

Gln Gln Thr Leu Phe Cys Pro Gly Gly Leu Arg Leu Val Gly Ser Thr
        355                 360                 365

Ala Asp Met Thr Leu Pro Trp Gln Pro Val Thr Leu Pro Asp Pro Glu
    370                 375                 380

Gly Phe Leu Thr Asp Lys Leu Val Lys Glu Tyr Val Gly Gln Val Leu
385                 390                 395                 400

Lys Gly Leu Gly Asn Gly Leu Ala Leu Trp Gln Ala Gly Gln Cys Leu
                405                 410                 415

Trp Ala Gln Arg Leu Gly His Ser His Ala Phe Trp Ala Leu Gly Glu
            420                 425                 430

Glu Leu Leu Pro Asp Ser Gly Arg Gly Pro Asp Gly Glu Val His Lys
        435                 440                 445

Asp Lys Asp Gly Ala Val Phe Asp Leu Arg Pro Phe Val Ala Asp Leu
    450                 455                 460

Ile Ala Phe Met Glu Gly Ser Gly His Ser Pro Arg Tyr Thr Leu Trp
465                 470                 475                 480

Phe Cys Met Gly Glu Met Trp Pro Gln Asp Gln Pro Trp Val Lys Arg
                485                 490                 495

Leu Val Met Val Lys Val Val Pro Thr Cys Leu Lys Glu Leu Leu Glu
            500                 505                 510

Met Ala Arg Glu Gly Gly Ala Ser Ser Leu Lys Thr Val Asp Leu His
        515                 520                 525

Ile Asp Asn Ser Gln Pro Ile Ser Leu Thr Ser Asp Gln Tyr Lys Ala
    530                 535                 540
```

-continued

```
Tyr Leu Gln Asp Leu Val Glu Asp Met Asp Phe Gln Ala Thr Gly Asn
545                 550                 555                 560

Ile


<210> SEQ ID NO 41
<211> LENGTH: 553
<212> TYPE: PRT
<213> ORGANISM: Artificial Sequence
<220> FEATURE:
<223> OTHER INFORMATION: YopE1-138 - Y. enterocolitica codon optimized
      V. Cholerae DncV (M3toL413)

<400> SEQUENCE: 41

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Trp Asn Phe His Gln Tyr Tyr Thr Asn Arg Asn Asp Gly Leu Met Gly
145                 150                 155                 160

Lys Leu Val Leu Thr Asp Glu Glu Lys Asn Asn Leu Lys Ala Leu Arg
                165                 170                 175

Lys Ile Ile Arg Leu Arg Thr Arg Asp Val Phe Glu Glu Ala Lys Gly
            180                 185                 190

Ile Ala Lys Ala Val Lys Lys Ser Ala Leu Thr Phe Glu Ile Ile Gln
        195                 200                 205

Glu Lys Val Ser Thr Thr Gln Ile Lys His Leu Ser Asp Ser Glu Gln
    210                 215                 220

Arg Glu Val Ala Lys Leu Ile Tyr Glu Met Asp Asp Asp Ala Arg Asp
225                 230                 235                 240

Glu Phe Leu Gly Leu Thr Pro Arg Phe Trp Thr Gln Gly Ser Phe Gln
                245                 250                 255

Tyr Asp Thr Leu Asn Arg Pro Phe Gln Pro Gly Gln Glu Met Asp Ile
            260                 265                 270

Asp Asp Gly Thr Tyr Met Pro Met Pro Ile Phe Glu Ser Glu Pro Lys
        275                 280                 285

Ile Gly His Ser Leu Leu Ile Leu Leu Val Asp Ala Ser Leu Lys Ser
    290                 295                 300

Leu Val Ala Glu Asn His Gly Trp Lys Phe Glu Ala Lys Gln Thr Cys
305                 310                 315                 320

Gly Arg Ile Lys Ile Glu Ala Glu Lys Thr His Ile Asp Val Pro Met
                325                 330                 335
```

```
Tyr Ala Ile Pro Lys Asp Glu Phe Gln Lys Lys Gln Ile Ala Leu Glu
            340                 345                 350

Ala Asn Arg Ser Phe Val Lys Gly Ala Ile Phe Glu Ser Tyr Val Ala
        355                 360                 365

Asp Ser Ile Thr Asp Asp Ser Glu Thr Tyr Glu Leu Asp Ser Glu Asn
    370                 375                 380

Val Asn Leu Ala Leu Arg Glu Gly Asp Arg Lys Trp Ile Asn Ser Asp
385                 390                 395                 400

Pro Lys Ile Val Glu Asp Trp Phe Asn Asp Ser Cys Ile Arg Ile Gly
                405                 410                 415

Lys His Leu Arg Lys Val Cys Arg Phe Met Lys Ala Trp Arg Asp Ala
            420                 425                 430

Gln Trp Asp Val Gly Gly Pro Ser Ser Ile Ser Leu Met Ala Ala Thr
        435                 440                 445

Val Asn Ile Leu Asp Ser Val Ala His Asp Ala Ser Asp Leu Gly Glu
    450                 455                 460

Thr Met Lys Ile Ile Ala Lys His Leu Pro Ser Glu Phe Ala Arg Gly
465                 470                 475                 480

Val Glu Ser Pro Asp Ser Thr Asp Glu Lys Pro Leu Phe Pro Pro Ser
                485                 490                 495

Tyr Lys His Gly Pro Arg Glu Met Asp Ile Met Ser Lys Leu Glu Arg
            500                 505                 510

Leu Pro Glu Ile Leu Ser Ser Ala Glu Ser Ala Asp Ser Lys Ser Glu
        515                 520                 525

Ala Leu Lys Lys Ile Asn Met Ala Phe Gly Asn Arg Val Thr Asn Ser
    530                 535                 540

Glu Leu Ile Val Leu Ala Lys Ala Leu
545                 550
```

<210> SEQ ID NO 42
<211> LENGTH: 272
<212> TYPE: PRT
<213> ORGANISM: Artificial Sequence
<220> FEATURE:
<223> OTHER INFORMATION: YopE1-138 - Y. enterocolitica codon optimized B. cereus_DisA-like (PDB: 2FB5; Aa. 76-205)

<400> SEQUENCE: 42

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Ser Ser
    130                 135                 140
```

```
Ser Phe Ile Thr Thr Ala Ile Gln His Leu Ser Ala Arg Lys His Gly
145                 150                 155                 160

Ala Leu Ile Val Val Glu Arg Asn Glu Thr Leu Glu Ala Leu Ile Gln
                165                 170                 175

Thr Gly Thr Thr Leu Asn Ala His Leu Thr Ala Pro Leu Leu Glu Ser
            180                 185                 190

Ile Phe Tyr Pro Gly Asn Pro Leu His Asp Gly Ala Val Leu Val Lys
        195                 200                 205

Asn Asn His Ile Val Ser Ala Ala Asn Ile Leu Pro Leu Thr Lys Ser
    210                 215                 220

Thr Glu Val Asp Pro Glu Leu Gly Thr Arg His Arg Ala Ala Ile Gly
225                 230                 235                 240

Leu Ser Glu Lys Ser Asp Ala Leu Ile Leu Val Val Ser Glu Glu Thr
                245                 250                 255

Gly Arg Thr Ser Phe Ala Leu Asn Gly Ile Leu Tyr Thr Ile Ser Leu
            260                 265                 270


<210> SEQ ID NO 43
<211> LENGTH: 564
<212> TYPE: PRT
<213> ORGANISM: Artificial Sequence
<220> FEATURE:
<223> OTHER INFORMATION: YopE1-138 - Y. enterocolitica codon optimized
      Anemonae (N. vectensis) cGAS (Ensembl: A7SFB5.1)

<400> SEQUENCE: 43

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ala
    130                 135                 140

Thr Leu Glu Arg Leu Leu Asp Leu Leu Arg Glu Tyr His Leu Asp Asp
145                 150                 155                 160

Val Leu Phe His Asn Ser Thr Pro Glu Leu Gly Ile Gln His Arg Ser
                165                 170                 175

Arg Pro Lys Gln Lys Arg Ile Ile Arg Gly Lys Lys Gln Gln Lys Ser
            180                 185                 190

Lys Lys Leu Lys Arg Asn Glu Gln Gln Gln Pro Phe Pro Lys Gly Asp
        195                 200                 205

Leu Glu Thr Leu Arg Arg Phe Ser Val Thr Asp Val Lys Ile Ser Lys
    210                 215                 220

Gln Ser Thr Lys Trp Ala Lys Lys Met Ala Asp Lys His Leu Glu Ile
```

```
225                 230                 235                 240

Ile Arg Lys His Cys Lys Thr Asn Ser Ile Lys Leu Phe Asn His Phe
                245                 250                 255

Glu Tyr Thr Gly Ser Phe Tyr Glu His Leu Lys Thr Ile Asp Ala Asp
            260                 265                 270

Glu Leu Asp Ile Met Val Ala Leu Ser Ile Lys Met Asp Glu Leu Glu
        275                 280                 285

Val Glu Gln Val Thr Pro Gly Tyr Ala Gly Leu Lys Leu Arg Asp Thr
    290                 295                 300

Pro Ser Asn Arg Asn Lys Tyr Asn Asp Leu Thr Ile Ala Asp Asn Tyr
305                 310                 315                 320

Gly Arg Tyr Leu Ser Pro Glu Lys Val Ser Arg Trp Phe Phe Ser Leu
                325                 330                 335

Val Gln Lys Ala Val Asn Thr Tyr Lys Asp Glu Ile Pro Gln Thr Glu
            340                 345                 350

Val Lys Leu Thr Asp Asn Gly Pro Ala Thr Thr Leu Val Ile Thr Tyr
        355                 360                 365

Arg Glu Gly Asp Lys Pro Gln Glu Lys Asn Arg Arg Leu Ser Ile Asp
    370                 375                 380

Leu Val Pro Ala Leu Leu Phe Lys Asp Lys Thr Lys Pro Ala Gly Asp
385                 390                 395                 400

Asp Leu Arg Ala Trp His Tyr Val Ala Lys Thr Ile Pro Lys Gly Ala
                405                 410                 415

Arg Leu Lys Glu Pro Leu Pro Phe Arg Ser Glu Leu Leu Trp Arg Gln
            420                 425                 430

Ser Phe Ser Leu Lys Glu Lys His Leu Met Asp Lys Leu Asp Lys Asp
        435                 440                 445

Asp Asn Gly Cys Arg Arg Glu Met Val Arg Ile Val Lys Thr Ile Val
    450                 455                 460

Lys Lys Asp Pro Thr Leu Ala Gln Leu Ser Ser Tyr His Ile Lys Thr
465                 470                 475                 480

Ala Phe Leu Gln Tyr Asn Phe Ser Asp Val Lys Leu Asp Trp Glu Gly
                485                 490                 495

Lys Lys Leu Ala Glu Arg Phe Leu His Phe Leu Glu Phe Leu Arg Asp
            500                 505                 510

Arg Val Lys Asp Lys Thr Leu Asn Asn Tyr Phe Ile Thr Asp Leu Asn
        515                 520                 525

Leu Leu Asp Asp Leu Asn Asp Ser Asn Ile Asp Asn Ile Ala Asn Arg
    530                 535                 540

Leu Asp Lys Ile Ile Gln Asn Glu Thr Glu Arg Ala Lys Ile Phe Thr
545                 550                 555                 560

Thr Gln Arg Gln


<210> SEQ ID NO 44
<211> LENGTH: 332
<212> TYPE: PRT
<213> ORGANISM: Artificial Sequence
<220> FEATURE:
<223> OTHER INFORMATION: YopE1-138 - Y. enterocolitica codon optimized
      murine MDA5 two CARD domains (minimal: Aa 1-190)

<400> SEQUENCE: 44

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
```

-continued

```
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ser
    130                 135                 140

Ile Val Cys Ser Ala Glu Asp Ser Phe Arg Asn Leu Ile Leu Phe Phe
145                 150                 155                 160

Arg Pro Arg Leu Lys Met Tyr Ile Gln Val Glu Pro Val Leu Asp His
                165                 170                 175

Leu Ile Phe Leu Ser Ala Glu Thr Lys Glu Gln Ile Leu Lys Lys Ile
            180                 185                 190

Asn Thr Cys Gly Asn Thr Ser Ala Ala Glu Leu Leu Leu Ser Thr Leu
        195                 200                 205

Glu Gln Gly Gln Trp Pro Leu Gly Trp Thr Gln Met Phe Val Glu Ala
    210                 215                 220

Leu Glu His Ser Gly Asn Pro Leu Ala Ala Arg Tyr Val Lys Pro Thr
225                 230                 235                 240

Leu Thr Asp Leu Pro Ser Pro Ser Ser Glu Thr Ala His Asp Glu Cys
                245                 250                 255

Leu His Leu Leu Thr Leu Leu Gln Pro Thr Leu Val Asp Lys Leu Leu
            260                 265                 270

Ile Asn Asp Val Leu Asp Thr Cys Phe Glu Lys Gly Leu Leu Thr Val
        275                 280                 285

Glu Asp Arg Asn Arg Ile Ser Ala Ala Gly Asn Ser Gly Asn Glu Ser
    290                 295                 300

Gly Val Arg Glu Leu Leu Arg Arg Ile Val Gln Lys Glu Asn Trp Phe
305                 310                 315                 320

Ser Thr Phe Leu Asp Val Leu Arg Gln Thr Gly Asn
                325                 330
```

<210> SEQ ID NO 45
<211> LENGTH: 457
<212> TYPE: PRT
<213> ORGANISM: Artificial Sequence
<220> FEATURE:
<223> OTHER INFORMATION: YopE1-138 - Y. enterocolitica codon optimized murine MDA5 two CARD domains (extended: Aa 1-315)

<400> SEQUENCE: 45

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45
```

-continued

```
Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ser
    130                 135                 140

Ile Val Cys Ser Ala Glu Asp Ser Phe Arg Asn Leu Ile Leu Phe Phe
145                 150                 155                 160

Arg Pro Arg Leu Lys Met Tyr Ile Gln Val Glu Pro Val Leu Asp His
                165                 170                 175

Leu Ile Phe Leu Ser Ala Glu Thr Lys Glu Gln Ile Leu Lys Lys Ile
            180                 185                 190

Asn Thr Cys Gly Asn Thr Ser Ala Ala Glu Leu Leu Leu Ser Thr Leu
        195                 200                 205

Glu Gln Gly Gln Trp Pro Leu Gly Trp Thr Gln Met Phe Val Glu Ala
    210                 215                 220

Leu Glu His Ser Gly Asn Pro Leu Ala Ala Arg Tyr Val Lys Pro Thr
225                 230                 235                 240

Leu Thr Asp Leu Pro Ser Pro Ser Ser Glu Thr Ala His Asp Glu Cys
                245                 250                 255

Leu His Leu Leu Thr Leu Leu Gln Pro Thr Leu Val Asp Lys Leu Leu
            260                 265                 270

Ile Asn Asp Val Leu Asp Thr Cys Phe Glu Lys Gly Leu Leu Thr Val
        275                 280                 285

Glu Asp Arg Asn Arg Ile Ser Ala Ala Gly Asn Ser Gly Asn Glu Ser
    290                 295                 300

Gly Val Arg Glu Leu Leu Arg Arg Ile Val Gln Lys Glu Asn Trp Phe
305                 310                 315                 320

Ser Thr Phe Leu Asp Val Leu Arg Gln Thr Gly Asn Asp Ala Leu Phe
                325                 330                 335

Gln Glu Leu Thr Gly Gly Gly Cys Pro Glu Asp Asn Thr Asp Leu Ala
            340                 345                 350

Asn Ser Ser His Arg Asp Gly Pro Ala Ala Asn Glu Cys Leu Leu Pro
        355                 360                 365

Ala Val Asp Glu Ser Ser Leu Glu Thr Glu Ala Trp Asn Val Asp Asp
    370                 375                 380

Ile Leu Pro Glu Ala Ser Cys Thr Asp Ser Ser Val Thr Thr Glu Ser
385                 390                 395                 400

Asp Thr Ser Leu Ala Glu Gly Ser Val Ser Cys Phe Asp Glu Ser Leu
                405                 410                 415

Gly His Asn Ser Asn Met Gly Arg Asp Ser Gly Thr Met Gly Ser Asp
            420                 425                 430

Ser Asp Glu Ser Val Ile Gln Thr Lys Arg Val Ser Pro Glu Pro Glu
        435                 440                 445

Leu Gln Leu Arg Pro Tyr Gln Met Glu
    450                 455
```

```
<210> SEQ ID NO 46
<211> LENGTH: 332
<212> TYPE: PRT
<213> ORGANISM: Artificial Sequence
<220> FEATURE:
<223> OTHER INFORMATION: YopE1-138 - Y. enterocolitica codon optimized
      human MDA5 two CARD domains (minimal: Aa 1-190)

<400> SEQUENCE: 46

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ser
    130                 135                 140

Asn Gly Tyr Ser Thr Asp Glu Asn Phe Arg Tyr Leu Ile Ser Cys Phe
145                 150                 155                 160

Arg Ala Arg Val Lys Met Tyr Ile Gln Val Glu Pro Val Leu Asp Tyr
                165                 170                 175

Leu Thr Phe Leu Pro Ala Glu Val Lys Glu Gln Ile Gln Arg Thr Val
            180                 185                 190

Ala Thr Ser Gly Asn Met Gln Ala Val Glu Leu Leu Leu Ser Thr Leu
        195                 200                 205

Glu Lys Gly Val Trp His Leu Gly Trp Thr Arg Glu Phe Val Glu Ala
    210                 215                 220

Leu Arg Arg Thr Gly Ser Pro Leu Ala Ala Arg Tyr Met Asn Pro Glu
225                 230                 235                 240

Leu Thr Asp Leu Pro Ser Pro Ser Phe Glu Asn Ala His Asp Glu Tyr
                245                 250                 255

Leu Gln Leu Leu Asn Leu Leu Gln Pro Thr Leu Val Asp Lys Leu Leu
            260                 265                 270

Val Arg Asp Val Leu Asp Lys Cys Met Glu Glu Glu Leu Leu Thr Ile
        275                 280                 285

Glu Asp Arg Asn Arg Ile Ala Ala Ala Glu Asn Asn Gly Asn Glu Ser
    290                 295                 300

Gly Val Arg Glu Leu Leu Lys Arg Ile Val Gln Lys Glu Asn Trp Phe
305                 310                 315                 320

Ser Ala Phe Leu Asn Val Leu Arg Gln Thr Gly Asn
                325                 330


<210> SEQ ID NO 47
<211> LENGTH: 456
<212> TYPE: PRT
<213> ORGANISM: Artificial Sequence
<220> FEATURE:
```

<223> OTHER INFORMATION: YopE1-138 - Y. enterocolitica codon optimized
human MDA5 two CARD domains (extended: Aa 1-314)

<400> SEQUENCE: 47

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ser
    130                 135                 140

Asn Gly Tyr Ser Thr Asp Glu Asn Phe Arg Tyr Leu Ile Ser Cys Phe
145                 150                 155                 160

Arg Ala Arg Val Lys Met Tyr Ile Gln Val Glu Pro Val Leu Asp Tyr
                165                 170                 175

Leu Thr Phe Leu Pro Ala Glu Val Lys Glu Gln Ile Gln Arg Thr Val
            180                 185                 190

Ala Thr Ser Gly Asn Met Gln Ala Val Glu Leu Leu Leu Ser Thr Leu
        195                 200                 205

Glu Lys Gly Val Trp His Leu Gly Trp Thr Arg Glu Phe Val Glu Ala
    210                 215                 220

Leu Arg Arg Thr Gly Ser Pro Leu Ala Ala Arg Tyr Met Asn Pro Glu
225                 230                 235                 240

Leu Thr Asp Leu Pro Ser Pro Ser Phe Glu Asn Ala His Asp Glu Tyr
                245                 250                 255

Leu Gln Leu Leu Asn Leu Leu Gln Pro Thr Leu Val Asp Lys Leu Leu
            260                 265                 270

Val Arg Asp Val Leu Asp Lys Cys Met Glu Glu Glu Leu Leu Thr Ile
        275                 280                 285

Glu Asp Arg Asn Arg Ile Ala Ala Ala Glu Asn Asn Gly Asn Glu Ser
    290                 295                 300

Gly Val Arg Glu Leu Leu Lys Arg Ile Val Gln Lys Glu Asn Trp Phe
305                 310                 315                 320

Ser Ala Phe Leu Asn Val Leu Arg Gln Thr Gly Asn Asn Glu Leu Val
                325                 330                 335

Gln Glu Leu Thr Gly Ser Asp Cys Ser Glu Ser Asn Ala Glu Ile Glu
            340                 345                 350

Asn Leu Ser Gln Val Asp Gly Pro Gln Val Glu Glu Gln Leu Leu Ser
        355                 360                 365

Thr Thr Val Gln Pro Asn Leu Glu Lys Glu Val Trp Gly Met Glu Asn
    370                 375                 380

Asn Ser Ser Glu Ser Ser Phe Ala Asp Ser Ser Val Val Ser Glu Ser
385                 390                 395                 400
```

```
Asp Thr Ser Leu Ala Glu Gly Ser Val Ser Cys Leu Asp Glu Ser Leu
                405                 410                 415

Gly His Asn Ser Asn Met Gly Ser Asp Ser Gly Thr Met Gly Ser Asp
            420                 425                 430

Ser Asp Glu Glu Asn Val Ala Ala Arg Ala Ser Pro Glu Pro Glu Leu
        435                 440                 445

Gln Leu Arg Pro Tyr Gln Met Glu
    450                 455


<210> SEQ ID NO 48
<211> LENGTH: 219
<212> TYPE: PRT
<213> ORGANISM: Artificial Sequence
<220> FEATURE:
<223> OTHER INFORMATION: YopE1-138 - Y. enterocolitica codon optimized
      human MAVS CARD domain (minimal: Aa 1-77)

<400> SEQUENCE: 48

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Pro
    130                 135                 140

Phe Ala Glu Asp Lys Thr Tyr Lys Tyr Ile Cys Arg Asn Phe Ser Asn
145                 150                 155                 160

Phe Cys Asn Val Asp Val Val Glu Ile Leu Pro Tyr Leu Pro Cys Leu
                165                 170                 175

Thr Ala Arg Asp Gln Asp Arg Leu Arg Ala Thr Cys Thr Leu Ser Gly
            180                 185                 190

Asn Arg Asp Thr Leu Trp His Leu Phe Asn Thr Leu Gln Arg Arg Pro
        195                 200                 205

Gly Trp Val Glu Tyr Phe Ile Ala Ala Leu Arg
    210                 215


<210> SEQ ID NO 49
<211> LENGTH: 142
<212> TYPE: PRT
<213> ORGANISM: Artificial Sequence
<220> FEATURE:
<223> OTHER INFORMATION: YopE1-138 - Y. enterocolitica codon optimized
      murine MAVS CARD domain (minimal: Aa 1-77)

<400> SEQUENCE: 49

Met Lys Ile Ser Ser Phe Ile Ser Thr Ser Leu Pro Leu Pro Ala Ser
1               5                   10                  15
```

```
Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg
    130                 135                 140


<210> SEQ ID NO 50
<211> LENGTH: 1675
<212> TYPE: DNA
<213> ORGANISM: Artificial Sequence
<220> FEATURE:
<223> OTHER INFORMATION: Mutator sequence for generation of YopE1-138 -
      Y. enterocolitica codon optimized murine RIG-1 two CARD domains
      (Aa. 1-246) integrated on the pYV plasmid

<400> SEQUENCE: 50

gaatagacag cgaaagttgt tgaaataatt gagtgatagc ttgttcaaat gaatacattt     60

gatctcctaa tagttagata aaatatcaac ttaaccaaag cactctcggc agaccatcaa    120

ttttagccta taatttttag tttttatttt gtctaatata acaacaaaaa cagcagcggt    180

tttttatata accaccggct attttcccac taagataacc ttgttttaat agccaaggga    240

ataaatagtc atgaaaatat catcatttat ttctacatca ctgcccctgc cggcatcagt    300

gtcaggatct agcagcgtag gagaaatgtc tgggcgctca gtctcacagc aaaaaagtga    360

tcaatatgca aacaatctgg ccgggcgcac tgaaagccct cagggttcca gcttagccag    420

ccgtatcatt gagaggttat catcaatggc ccactctgtg attggattta tccaacgcat    480

gttctcggag gggagccata aaccggtggt gacaccagca ctcacgcctg cacaaatgcc    540

aagccctacg tctttcagtg atagtatcaa gcaacttgct gctgagacgc tgccaaaata    600

catgcagcag ttgagtagct tggatgcaga gacgctgcag aaaaatcatg accagttcgc    660

cacgctcgag tctagaatga ccgccgaaca acgccaaaat ctgcaagcct ttcgcgatta    720

tattaaaaaa attctggatc cgacctatat tctgagctat atgagcagct ggctggaaga    780

tgaagaagtg caatatattc aagccgaaaa aaataataaa ggtccgatgg aagccgccag    840

cctgtttctg caatatctgc tgaaactgca aagcgaaggt tggtttcaag cctttctgga    900

tgccctgtat catgccggtt attgtggtct gtgtgaagcc attgaaagct gggattttca    960

aaaaattgaa aaactggaag aacatcgcct gctgctgcgc cgcctggaac cggaatttaa   1020

agccaccgtg gatccgaatg atattctgag cgaactgagc gaatgtctga ttaatcaaga   1080

atgtgaagaa attcgccaaa ttcgcgatac caaaggtcgc atggccggtg ccgaaaaaat   1140

ggccgaatgt ctgattcgca gcgataaaga aaattggccg aaagtgctgc aactggccct   1200

ggaaaaagat aatagcaaat ttagcgaact gtggattgtg gataaaggtt ttaaacgcgc   1260
```

```
cgaaagcaaa gccgatgaag atgatggtgc cgaagccagc agcattcaaa tttttattca   1320

agaagaaccg gaatgtcaaa atctgagcca aaatccgggt ccgccgagcg aagccagcag   1380

caataatctg catagcccgc tgaaaccgcg caattaatat ggataaaaac aagggggtag   1440

tgtttccccc tttttctatc aatattgcga atatcttcgt ccctgatctt tcaggggcga   1500

atcgtttttt agcatgctca ttgttagaat ttctgactta tctctcttct gtattactac   1560

tcatactctg gaaaatcctg agcatttata tctatggatt gatgcagcac tcgagaaatc   1620

aaaatatcat tgctaagcgt tatatagtat ataccgtgct ttttatactg aaaac         1675


<210> SEQ ID NO 51
<211> LENGTH: 27
<212> TYPE: DNA
<213> ORGANISM: Artificial Sequence
<220> FEATURE:
<223> OTHER INFORMATION: Primer No. : Si_285

<400> SEQUENCE: 51

cataccatgg gagtgagcaa gggcgag                                          27


<210> SEQ ID NO 52
<211> LENGTH: 30
<212> TYPE: DNA
<213> ORGANISM: Artificial Sequence
<220> FEATURE:
<223> OTHER INFORMATION: Primer No. : Si_286

<400> SEQUENCE: 52

ggaagatctt tacttgtaca gctcgtccat                                       30


<210> SEQ ID NO 53
<211> LENGTH: 29
<212> TYPE: DNA
<213> ORGANISM: Artificial Sequence
<220> FEATURE:
<223> OTHER INFORMATION: Primer No. : Si_287

<400> SEQUENCE: 53

cggggtacct caactaaatg accgtggtg                                        29


<210> SEQ ID NO 54
<211> LENGTH: 43
<212> TYPE: DNA
<213> ORGANISM: Artificial Sequence
<220> FEATURE:
<223> OTHER INFORMATION: Primer No. : Si_288

<400> SEQUENCE: 54

gttaaagctt ttcgaatcta gactcgagcg tggcgaactg gtc                        43


<210> SEQ ID NO 55
<211> LENGTH: 30
<212> TYPE: DNA
<213> ORGANISM: Artificial Sequence
<220> FEATURE:
<223> OTHER INFORMATION: Primer No. : Si_387

<400> SEQUENCE: 55

cgtatctaga atggactgtg aggtcaacaa                                       30


<210> SEQ ID NO 56
<211> LENGTH: 23
<212> TYPE: DNA
<213> ORGANISM: Artificial Sequence
```

<220> FEATURE:
<223> OTHER INFORMATION: Primer No. : Si_391

<400> SEQUENCE: 56
cgtatctaga ggcaaccgca gca 23

<210> SEQ ID NO 57
<211> LENGTH: 29
<212> TYPE: DNA
<213> ORGANISM: Artificial Sequence
<220> FEATURE:
<223> OTHER INFORMATION: Primer No. : Si_389

<400> SEQUENCE: 57
gttaaagctt tcagtccatc ccatttctg 29

<210> SEQ ID NO 58
<211> LENGTH: 22
<212> TYPE: DNA
<213> ORGANISM: Artificial Sequence
<220> FEATURE:
<223> OTHER INFORMATION: Primer No. : Si_436

<400> SEQUENCE: 58
cgtatctaga atgccccgcc cc 22

<210> SEQ ID NO 59
<211> LENGTH: 31
<212> TYPE: DNA
<213> ORGANISM: Artificial Sequence
<220> FEATURE:
<223> OTHER INFORMATION: Primer No. : Si_437

<400> SEQUENCE: 59
gttaaagctt ctacccaccg tactcgtcaa t 31

<210> SEQ ID NO 60
<211> LENGTH: 31
<212> TYPE: DNA
<213> ORGANISM: Artificial Sequence
<220> FEATURE:
<223> OTHER INFORMATION: Primer No. : Si_438

<400> SEQUENCE: 60
cgtatctaga atgtctgaca cgtccagaga g 31

<210> SEQ ID NO 61
<211> LENGTH: 32
<212> TYPE: DNA
<213> ORGANISM: Artificial Sequence
<220> FEATURE:
<223> OTHER INFORMATION: Primer No. : Si_439

<400> SEQUENCE: 61
gttaaagctt tcatcttctt cgcaggaaaa ag 32

<210> SEQ ID NO 62
<211> LENGTH: 29
<212> TYPE: DNA
<213> ORGANISM: Artificial Sequence
<220> FEATURE:
<223> OTHER INFORMATION: Primer No. : Si_463

<400> SEQUENCE: 62
cagtctcgag gaaagcttgt ttaaggggc 29

<210> SEQ ID NO 63
<211> LENGTH: 25
<212> TYPE: DNA
<213> ORGANISM: Artificial Sequence
<220> FEATURE:
<223> OTHER INFORMATION: Primer No. : Si_464

<400> SEQUENCE: 63
cagtttcgaa ttagcgacgg cgacg 25

<210> SEQ ID NO 64
<211> LENGTH: 31
<212> TYPE: DNA
<213> ORGANISM: Artificial Sequence
<220> FEATURE:
<223> OTHER INFORMATION: Primer No. : Si_476

<400> SEQUENCE: 64
gttaaagctt ttacttgtac agctcgtcca t 31

<210> SEQ ID NO 65
<211> LENGTH: 24
<212> TYPE: DNA
<213> ORGANISM: Artificial Sequence
<220> FEATURE:
<223> OTHER INFORMATION: Primer No. : Si_494

<400> SEQUENCE: 65
cgtatctaga atggccgagc cttg 24

<210> SEQ ID NO 66
<211> LENGTH: 31
<212> TYPE: DNA
<213> ORGANISM: Artificial Sequence
<220> FEATURE:
<223> OTHER INFORMATION: Primer No. : Si_495

<400> SEQUENCE: 66
gttaaagctt ttattgaaga tttgtggctc c 31

<210> SEQ ID NO 67
<211> LENGTH: 64
<212> TYPE: DNA
<213> ORGANISM: Artificial Sequence
<220> FEATURE:
<223> OTHER INFORMATION: Primer No. : Si_504

<400> SEQUENCE: 67
cgtatctaga gaaaatctgt attttcaaag tgaaaatctg tattttcaaa gtatgccccg 60
cccc 64

<210> SEQ ID NO 68
<211> LENGTH: 30
<212> TYPE: DNA
<213> ORGANISM: Artificial Sequence
<220> FEATURE:
<223> OTHER INFORMATION: Primer No. : Si_505

<400> SEQUENCE: 68
gttaaagctt cccaccgtac tcgtcaattc 30

<210> SEQ ID NO 69
<211> LENGTH: 66
<212> TYPE: DNA
<213> ORGANISM: Artificial Sequence
<220> FEATURE:
<223> OTHER INFORMATION: Primer No. : Si_508

<400> SEQUENCE: 69
cgtatctaga gaaaatctgt attttcaaag tgaaaatctg tattttcaaa gtatggccga 60
gccttg 66

<210> SEQ ID NO 70
<211> LENGTH: 29
<212> TYPE: DNA
<213> ORGANISM: Artificial Sequence
<220> FEATURE:
<223> OTHER INFORMATION: Primer No. : Si_509

<400> SEQUENCE: 70
gttaaagctt ttgaagattt gtggctccc 29

<210> SEQ ID NO 71
<211> LENGTH: 67
<212> TYPE: DNA
<213> ORGANISM: Artificial Sequence
<220> FEATURE:
<223> OTHER INFORMATION: Primer No. : Si_511

<400> SEQUENCE: 71
cgtatctaga gaaaatctgt attttcaaag tgaaaatctg tattttcaaa gtgtgagcaa 60
gggcgag 67

<210> SEQ ID NO 72
<211> LENGTH: 91
<212> TYPE: DNA
<213> ORGANISM: Artificial Sequence
<220> FEATURE:
<223> OTHER INFORMATION: Primer No. : Si_512

<400> SEQUENCE: 72
cgtatctaga gaaaatctgt attttcaaag tgaaaatctg tattttcaaa gtccgccgaa 60
aaaaaaacgt aaagttgtga gcaagggcga g 91

<210> SEQ ID NO 73
<211> LENGTH: 55
<212> TYPE: DNA
<213> ORGANISM: Artificial Sequence
<220> FEATURE:
<223> OTHER INFORMATION: Primer No. : Si_513

<400> SEQUENCE: 73
gttaaagctt ttaaacttta cgtttttttt tcggcggctt gtacagctcg tccat 55

<210> SEQ ID NO 74
<211> LENGTH: 90
<212> TYPE: DNA
<213> ORGANISM: Artificial Sequence
<220> FEATURE:
<223> OTHER INFORMATION: Primer No. : Si_515

<400> SEQUENCE: 74
cgtatctaga gaaaatctgt attttcaaag tgaaaatctg tattttcaaa gtgattataa 60
agatgatgat gataaaatgg ccgagccttg 90

<210> SEQ ID NO 75
<211> LENGTH: 82
<212> TYPE: DNA

<213> ORGANISM: Artificial Sequence
<220> FEATURE:
<223> OTHER INFORMATION: Primer No. : Si_677

<400> SEQUENCE: 75
ttactattcg aagaaattat tcataatatt gcccgccatc tggcccaaat tggtgatgaa 60
atggatcatt aagcttggag ta 82

<210> SEQ ID NO 76
<211> LENGTH: 82
<212> TYPE: DNA
<213> ORGANISM: Artificial Sequence
<220> FEATURE:
<223> OTHER INFORMATION: Primer No. : Si_678

<400> SEQUENCE: 76
tactccaagc ttaatgatcc atttcatcac caatttgggc cagatggcgg gcaatattat 60
gaataatttc ttcgaatagt aa 82

<210> SEQ ID NO 77
<211> LENGTH: 73
<212> TYPE: DNA
<213> ORGANISM: Artificial Sequence
<220> FEATURE:
<223> OTHER INFORMATION: Primer No. : Si_682

<400> SEQUENCE: 77
ttactactcg agaaaaaact gagcgaatgt ctgcgccgca ttggtgatga actggatagc 60
taagcttgga gta 73

<210> SEQ ID NO 78
<211> LENGTH: 73
<212> TYPE: DNA
<213> ORGANISM: Artificial Sequence
<220> FEATURE:
<223> OTHER INFORMATION: Primer No. : Si_683

<400> SEQUENCE: 78
tactccaagc ttagctatcc agttcatcac caatgcggcg cagacattcg ctcagttttt 60
tctcgagtag taa 73

<210> SEQ ID NO 79
<211> LENGTH: 34
<212> TYPE: DNA
<213> ORGANISM: Artificial Sequence
<220> FEATURE:
<223> OTHER INFORMATION: Primer No. : Si_580

<400> SEQUENCE: 79
catgccatgg atttatggtc atagatatga cctc 34

<210> SEQ ID NO 80
<211> LENGTH: 35
<212> TYPE: DNA
<213> ORGANISM: Artificial Sequence
<220> FEATURE:
<223> OTHER INFORMATION: Primer No. : Si_612

<400> SEQUENCE: 80
cggggtacca tgaggtagct tatttcctga taaag 35

<210> SEQ ID NO 81
<211> LENGTH: 35

<212> TYPE: DNA
<213> ORGANISM: Artificial Sequence
<220> FEATURE:
<223> OTHER INFORMATION: Primer No. : Si_613

<400> SEQUENCE: 81
cggggtacca taattgtcca aatagttatg gtagc 35

<210> SEQ ID NO 82
<211> LENGTH: 24
<212> TYPE: DNA
<213> ORGANISM: Artificial Sequence
<220> FEATURE:
<223> OTHER INFORMATION: Primer No. : Si_614

<400> SEQUENCE: 82
catgccatgg cggcaaggct cctc 24

<210> SEQ ID NO 83
<211> LENGTH: 29
<212> TYPE: DNA
<213> ORGANISM: Artificial Sequence
<220> FEATURE:
<223> OTHER INFORMATION: Primer No. : Si_615

<400> SEQUENCE: 83
cggggtacct ttatttgtca acactgccc 29

<210> SEQ ID NO 84
<211> LENGTH: 26
<212> TYPE: DNA
<213> ORGANISM: Artificial Sequence
<220> FEATURE:
<223> OTHER INFORMATION: Primer No. : Si_616

<400> SEQUENCE: 84
cggggtacct gcggggtctt tactcg 26

<210> SEQ ID NO 85
<211> LENGTH: 30
<212> TYPE: DNA
<213> ORGANISM: Artificial Sequence
<220> FEATURE:
<223> OTHER INFORMATION: Primer No. : Si_585

<400> SEQUENCE: 85
cagtctcgag atgcagatct tcgtcaagac 30

<210> SEQ ID NO 86
<211> LENGTH: 43
<212> TYPE: DNA
<213> ORGANISM: Artificial Sequence
<220> FEATURE:
<223> OTHER INFORMATION: Primer No. : Si_586

<400> SEQUENCE: 86
gttaaagctt gctagcttcg aaaccaccac gtagacgtaa gac 43

<210> SEQ ID NO 87
<211> LENGTH: 48
<212> TYPE: DNA
<213> ORGANISM: Artificial Sequence
<220> FEATURE:
<223> OTHER INFORMATION: Primer No. : Si_588

<400> SEQUENCE: 87
cagtttcgaa gattataaag atgatgatga taaaatggcc gagccttg 48

<210> SEQ ID NO 88
<211> LENGTH: 53
<212> TYPE: DNA
<213> ORGANISM: Artificial Sequence
<220> FEATURE:
<223> OTHER INFORMATION: primer No. 733

<400> SEQUENCE: 88
ttactactcg agggtgccat cgatgccgaa gaaattattc ataatattgc ccg 53

<210> SEQ ID NO 89
<211> LENGTH: 39
<212> TYPE: DNA
<213> ORGANISM: Artificial Sequence
<220> FEATURE:
<223> OTHER INFORMATION: primer No. 735

<400> SEQUENCE: 89
tactccttcg aattaatgat ccatttcatc accaatttg 39

<210> SEQ ID NO 90
<211> LENGTH: 50
<212> TYPE: DNA
<213> ORGANISM: Artificial Sequence
<220> FEATURE:
<223> OTHER INFORMATION: primer No. 736

<400> SEQUENCE: 90
ttactactcg agggtgccat cgatgccaaa aaactgagcg aatgtctgcg 50

<210> SEQ ID NO 91
<211> LENGTH: 37
<212> TYPE: DNA
<213> ORGANISM: Artificial Sequence
<220> FEATURE:
<223> OTHER INFORMATION: primer No. 738

<400> SEQUENCE: 91
tactccttcg aattagctat ccagttcatc accaatg 37

<210> SEQ ID NO 92
<211> LENGTH: 43
<212> TYPE: DNA
<213> ORGANISM: Artificial Sequence
<220> FEATURE:
<223> OTHER INFORMATION: primer No. 734

<400> SEQUENCE: 92
tactccttcg aaggcaccat gatccatttc atcaccaatt tgg 43

<210> SEQ ID NO 93
<211> LENGTH: 33
<212> TYPE: DNA
<213> ORGANISM: Artificial Sequence
<220> FEATURE:
<223> OTHER INFORMATION: primer No. 725

<400> SEQUENCE: 93
ttactattcg aagaaattat tcataatatt gcc 33

<210> SEQ ID NO 94
<211> LENGTH: 50
<212> TYPE: DNA
<213> ORGANISM: Artificial Sequence
<220> FEATURE:
<223> OTHER INFORMATION: primer No. 726

<400> SEQUENCE: 94
tactccaagc ttacggttga atattatgat ccatttcatc accaatttgg 50

<210> SEQ ID NO 95
<211> LENGTH: 49
<212> TYPE: DNA
<213> ORGANISM: Artificial Sequence
<220> FEATURE:
<223> OTHER INFORMATION: primer No. 727

<400> SEQUENCE: 95
ttactattcg aagccggtgg tgccgaagaa attattcata atattgccc 49

<210> SEQ ID NO 96
<211> LENGTH: 29
<212> TYPE: DNA
<213> ORGANISM: Artificial Sequence
<220> FEATURE:
<223> OTHER INFORMATION: primer No. 728

<400> SEQUENCE: 96
tactccaagc ttaatgatcc atttcatca 29

<210> SEQ ID NO 97
<211> LENGTH: 40
<212> TYPE: DNA
<213> ORGANISM: Artificial Sequence
<220> FEATURE:
<223> OTHER INFORMATION: primer No. 737

<400> SEQUENCE: 97
tactccttcg aaggcaccgc tatccagttc atcaccaatg 40

<210> SEQ ID NO 98
<211> LENGTH: 394
<212> TYPE: PRT
<213> ORGANISM: Artificial Sequence
<220> FEATURE:
<223> OTHER INFORMATION: YopE1-138 2xTEVsite - EGFP

<400> SEQUENCE: 98

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140
```

Leu Tyr Phe Gln Ser Glu Asn Leu Tyr Phe Gln Ser Val Ser Lys Gly
145 150 155 160

Glu Glu Leu Phe Thr Gly Val Val Pro Ile Leu Val Glu Leu Asp Gly
165 170 175

Asp Val Asn Gly His Lys Phe Ser Val Ser Gly Glu Gly Glu Gly Asp
180 185 190

Ala Thr Tyr Gly Lys Leu Thr Leu Lys Phe Ile Cys Thr Thr Gly Lys
195 200 205

Leu Pro Val Pro Trp Pro Thr Leu Val Thr Thr Leu Thr Tyr Gly Val
210 215 220

Gln Cys Phe Ser Arg Tyr Pro Asp His Met Lys Gln His Asp Phe Phe
225 230 235 240

Lys Ser Ala Met Pro Glu Gly Tyr Val Gln Glu Arg Thr Ile Phe Phe
245 250 255

Lys Asp Asp Gly Asn Tyr Lys Thr Arg Ala Glu Val Lys Phe Glu Gly
260 265 270

Asp Thr Leu Val Asn Arg Ile Glu Leu Lys Gly Ile Asp Phe Lys Glu
275 280 285

Asp Gly Asn Ile Leu Gly His Lys Leu Glu Tyr Asn Tyr Asn Ser His
290 295 300

Asn Val Tyr Ile Met Ala Asp Lys Gln Lys Asn Gly Ile Lys Val Asn
305 310 315 320

Phe Lys Ile Arg His Asn Ile Glu Asp Gly Ser Val Gln Leu Ala Asp
325 330 335

His Tyr Gln Gln Asn Thr Pro Ile Gly Asp Gly Pro Val Leu Leu Pro
340 345 350

Asp Asn His Tyr Leu Ser Thr Gln Ser Ala Leu Ser Lys Asp Pro Asn
355 360 365

Glu Lys Arg Asp His Met Val Leu Leu Glu Phe Val Thr Ala Ala Gly
370 375 380

Ile Thr Leu Gly Met Asp Glu Leu Tyr Lys
385 390

<210> SEQ ID NO 99
<211> LENGTH: 401
<212> TYPE: PRT
<213> ORGANISM: Artificial Sequence
<220> FEATURE:
<223> OTHER INFORMATION: YopE1-138 - 2xTEVsite - NLS - EGFP

<400> SEQUENCE: 99

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

-continued

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Glu Asn
130 135 140

Leu Tyr Phe Gln Ser Val Ser Lys Gly Gln Ser Pro Pro Lys Lys Lys
145 150 155 160

Arg Lys Val Val Ser Lys Gly Glu Glu Leu Phe Thr Gly Val Val Pro
165 170 175

Ile Leu Val Glu Leu Asp Gly Asp Val Asn Gly His Lys Phe Ser Val
180 185 190

Ser Gly Glu Gly Glu Gly Asp Ala Thr Tyr Gly Lys Leu Thr Leu Lys
195 200 205

Phe Ile Cys Thr Thr Gly Lys Leu Pro Val Pro Trp Pro Thr Leu Val
210 215 220

Thr Thr Leu Thr Tyr Gly Val Gln Cys Phe Ser Arg Tyr Pro Asp His
225 230 235 240

Met Lys Gln His Asp Phe Phe Lys Ser Ala Met Pro Glu Gly Tyr Val
245 250 255

Gln Glu Arg Thr Ile Phe Phe Lys Asp Asp Gly Asn Tyr Lys Thr Arg
260 265 270

Ala Glu Val Lys Phe Glu Gly Asp Thr Leu Val Asn Arg Ile Glu Leu
275 280 285

Lys Gly Ile Asp Phe Lys Glu Asp Gly Asn Ile Leu Gly His Lys Leu
290 295 300

Glu Tyr Asn Tyr Asn Ser His Asn Val Tyr Ile Met Ala Asp Lys Gln
305 310 315 320

Lys Asn Gly Ile Lys Val Asn Phe Lys Ile Arg His Asn Ile Glu Asp
325 330 335

Gly Ser Val Gln Leu Ala Asp His Tyr Gln Gln Asn Thr Pro Ile Gly
340 345 350

Asp Gly Pro Val Leu Leu Pro Asp Asn His Tyr Leu Ser Thr Gln Ser
355 360 365

Ala Leu Ser Lys Asp Pro Asn Glu Lys Arg Asp His Met Val Leu Leu
370 375 380

Glu Phe Val Thr Ala Ala Gly Ile Thr Leu Gly Met Asp Glu Leu Tyr
385 390 395 400

Lys

<210> SEQ ID NO 100
<211> LENGTH: 402
<212> TYPE: PRT
<213> ORGANISM: Artificial Sequence
<220> FEATURE:
<223> OTHER INFORMATION: YopE1-138 - 2xTEVsite - EGFP - NLS

<400> SEQUENCE: 100

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

```
Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Val Ser Lys Gly
145                 150                 155                 160

Glu Glu Leu Phe Thr Gly Val Val Pro Ile Leu Val Glu Leu Asp Gly
                165                 170                 175

Asp Val Asn Gly His Lys Phe Ser Val Ser Gly Glu Gly Glu Gly Asp
            180                 185                 190

Ala Thr Tyr Gly Lys Leu Thr Leu Lys Phe Ile Cys Thr Thr Gly Lys
        195                 200                 205

Leu Pro Val Pro Trp Pro Thr Leu Val Thr Thr Leu Thr Tyr Gly Val
    210                 215                 220

Gln Cys Phe Ser Arg Tyr Pro Asp His Met Lys Gln His Asp Phe Phe
225                 230                 235                 240

Lys Ser Ala Met Pro Glu Gly Tyr Val Gln Glu Arg Thr Ile Phe Phe
                245                 250                 255

Lys Asp Asp Gly Asn Tyr Lys Thr Arg Ala Glu Val Lys Phe Glu Gly
            260                 265                 270

Asp Thr Leu Val Asn Arg Ile Glu Leu Lys Gly Ile Asp Phe Lys Glu
        275                 280                 285

Asp Gly Asn Ile Leu Gly His Lys Leu Glu Tyr Asn Tyr Asn Ser His
    290                 295                 300

Asn Val Tyr Ile Met Ala Asp Lys Gln Lys Asn Gly Ile Lys Val Asn
305                 310                 315                 320

Phe Lys Ile Arg His Asn Ile Glu Asp Gly Ser Val Gln Leu Ala Asp
                325                 330                 335

His Tyr Gln Gln Asn Thr Pro Ile Gly Asp Gly Pro Val Leu Leu Pro
            340                 345                 350

Asp Asn His Tyr Leu Ser Thr Gln Ser Ala Leu Ser Lys Asp Pro Asn
        355                 360                 365

Glu Lys Arg Asp His Met Val Leu Leu Glu Phe Val Thr Ala Ala Gly
    370                 375                 380

Ile Thr Leu Gly Met Asp Glu Leu Tyr Lys Pro Pro Lys Lys Lys Arg
385                 390                 395                 400

Lys Val
```

<210> SEQ ID NO 101
<211> LENGTH: 36
<212> TYPE: DNA
<213> ORGANISM: Artificial Sequence
<220> FEATURE:
<223> OTHER INFORMATION: primer No. 869

<400> SEQUENCE: 101
gatcgtcgac ttaagttcaa tggagcgttt aatatc 36

<210> SEQ ID NO 102

<211> LENGTH: 41
<212> TYPE: DNA
<213> ORGANISM: Artificial Sequence
<220> FEATURE:
<223> OTHER INFORMATION: primer No. 870

<400> SEQUENCE: 102
ctttgactgg cgagaaacgc tcttaacatg aggctgagct c 41

<210> SEQ ID NO 103
<211> LENGTH: 41
<212> TYPE: DNA
<213> ORGANISM: Artificial Sequence
<220> FEATURE:
<223> OTHER INFORMATION: primer No. 871

<400> SEQUENCE: 103
gagctcagcc tcatgttaag agcgtttctc gccagtcaaa g 41

<210> SEQ ID NO 104
<211> LENGTH: 40
<212> TYPE: DNA
<213> ORGANISM: Artificial Sequence
<220> FEATURE:
<223> OTHER INFORMATION: primer No. 872

<400> SEQUENCE: 104
gatagccccc gagcctgtgc actttgtcat taacctcagc 40

<210> SEQ ID NO 105
<211> LENGTH: 40
<212> TYPE: DNA
<213> ORGANISM: Artificial Sequence
<220> FEATURE:
<223> OTHER INFORMATION: primer No. 873

<400> SEQUENCE: 105
gctgaggtta atgacaaagt gcacaggctc gggggctatc 40

<210> SEQ ID NO 106
<211> LENGTH: 31
<212> TYPE: DNA
<213> ORGANISM: Artificial Sequence
<220> FEATURE:
<223> OTHER INFORMATION: primer No. 874

<400> SEQUENCE: 106
catgtctaga ccctcagcat aataacgact c 31

<210> SEQ ID NO 107
<211> LENGTH: 24
<212> TYPE: DNA
<213> ORGANISM: Artificial Sequence
<220> FEATURE:
<223> OTHER INFORMATION: primer No. 600

<400> SEQUENCE: 107
catgacatgt tggcgtttct cgcc 24

<210> SEQ ID NO 108
<211> LENGTH: 34
<212> TYPE: DNA
<213> ORGANISM: Artificial Sequence
<220> FEATURE:
<223> OTHER INFORMATION: primer No. 601

<400> SEQUENCE: 108
catgacatgt attaacctca gccctgacta taag 34

<210> SEQ ID NO 109
<211> LENGTH: 138
<212> TYPE: DNA
<213> ORGANISM: Artificial Sequence
<220> FEATURE:
<223> OTHER INFORMATION: Multiple cloning site of pBad_Si_1 and pBad_Si_2

<400> SEQUENCE: 109
gttcgccacg ctcgagtcta gattcgaaaa gcttgggccc gaacaaaaac tcatctcaga 60
agaggatctg aatagcgccg tcgaccatca tcatcatcat cattgagttt aaacggtctc 120
cagcttggct gttttggc 138

<210> SEQ ID NO 110
<211> LENGTH: 371
<212> TYPE: PRT
<213> ORGANISM: Artificial Sequence
<220> FEATURE:
<223> OTHER INFORMATION: YopE1-138 - Y. enterocolitica codon optimized murine RIG1 CARD domains (Aa. 1-229)

<400> SEQUENCE: 110

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Met Thr
130 135 140

Ala Glu Gln Arg Gln Asn Leu Gln Ala Phe Arg Asp Tyr Ile Lys Lys
145 150 155 160

Ile Leu Asp Pro Thr Tyr Ile Leu Ser Tyr Met Ser Ser Trp Leu Glu
165 170 175

Asp Glu Glu Val Gln Tyr Ile Gln Ala Glu Lys Asn Asn Lys Gly Pro
180 185 190

Met Glu Ala Ala Ser Leu Phe Leu Gln Tyr Leu Leu Lys Leu Gln Ser
195 200 205

Glu Gly Trp Phe Gln Ala Phe Leu Asp Ala Leu Tyr His Ala Gly Tyr
210 215 220

Cys Gly Leu Cys Glu Ala Ile Glu Ser Trp Asp Phe Gln Lys Ile Glu
225 230 235 240

Lys Leu Glu Glu His Arg Leu Leu Leu Arg Arg Leu Glu Pro Glu Phe
245 250 255

```
Lys Ala Thr Val Asp Pro Asn Asp Ile Leu Ser Glu Leu Ser Glu Cys
            260                 265                 270

Leu Ile Asn Gln Glu Cys Glu Glu Ile Arg Gln Ile Arg Asp Thr Lys
        275                 280                 285

Gly Arg Met Ala Gly Ala Glu Lys Met Ala Glu Cys Leu Ile Arg Ser
    290                 295                 300

Asp Lys Glu Asn Trp Pro Lys Val Leu Gln Leu Ala Leu Glu Lys Asp
305                 310                 315                 320

Asn Ser Lys Phe Ser Glu Leu Trp Ile Val Asp Lys Gly Phe Lys Arg
                325                 330                 335

Ala Glu Ser Lys Ala Asp Glu Asp Asp Gly Ala Glu Ala Ser Ser Ile
            340                 345                 350

Gln Ile Phe Ile Gln Glu Glu Pro Glu Cys Gln Asn Leu Ser Gln Asn
        355                 360                 365

Pro Gly Pro
    370


<210> SEQ ID NO 111
<211> LENGTH: 360
<212> TYPE: PRT
<213> ORGANISM: Artificial Sequence
<220> FEATURE:
<223> OTHER INFORMATION: YopE1-138 - Y. enterocolitica codon optimized
      murine RIG1 CARD domains (Aa. 1-218)

<400> SEQUENCE: 111

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Ala Glu Gln Arg Gln Asn Leu Gln Ala Phe Arg Asp Tyr Ile Lys Lys
145                 150                 155                 160

Ile Leu Asp Pro Thr Tyr Ile Leu Ser Tyr Met Ser Ser Trp Leu Glu
                165                 170                 175

Asp Glu Glu Val Gln Tyr Ile Gln Ala Glu Lys Asn Asn Lys Gly Pro
            180                 185                 190

Met Glu Ala Ala Ser Leu Phe Leu Gln Tyr Leu Leu Lys Leu Gln Ser
        195                 200                 205

Glu Gly Trp Phe Gln Ala Phe Leu Asp Ala Leu Tyr His Ala Gly Tyr
    210                 215                 220

Cys Gly Leu Cys Glu Ala Ile Glu Ser Trp Asp Phe Gln Lys Ile Glu
225                 230                 235                 240
```

```
Lys Leu Glu Glu His Arg Leu Leu Leu Arg Arg Leu Glu Pro Glu Phe
                245                 250                 255

Lys Ala Thr Val Asp Pro Asn Asp Ile Leu Ser Glu Leu Ser Glu Cys
            260                 265                 270

Leu Ile Asn Gln Glu Cys Glu Glu Ile Arg Gln Ile Arg Asp Thr Lys
        275                 280                 285

Gly Arg Met Ala Gly Ala Glu Lys Met Ala Glu Cys Leu Ile Arg Ser
    290                 295                 300

Asp Lys Glu Asn Trp Pro Lys Val Leu Gln Leu Ala Leu Glu Lys Asp
305                 310                 315                 320

Asn Ser Lys Phe Ser Glu Leu Trp Ile Val Asp Lys Gly Phe Lys Arg
                325                 330                 335

Ala Glu Ser Lys Ala Asp Glu Asp Asp Gly Ala Glu Ala Ser Ser Ile
            340                 345                 350

Gln Ile Phe Ile Gln Glu Glu Pro
        355                 360


<210> SEQ ID NO 112
<211> LENGTH: 436
<212> TYPE: PRT
<213> ORGANISM: Artificial Sequence
<220> FEATURE:
<223> OTHER INFORMATION: YopE1-138 - Y. enterocolitica codon optimized
      murine MDA5 (Aa. 1-294)

<400> SEQUENCE: 112

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ser
    130                 135                 140

Ile Val Cys Ser Ala Glu Asp Ser Phe Arg Asn Leu Ile Leu Phe Phe
145                 150                 155                 160

Arg Pro Arg Leu Lys Met Tyr Ile Gln Val Glu Pro Val Leu Asp His
                165                 170                 175

Leu Ile Phe Leu Ser Ala Glu Thr Lys Glu Gln Ile Leu Lys Lys Ile
            180                 185                 190

Asn Thr Cys Gly Asn Thr Ser Ala Ala Glu Leu Leu Leu Ser Thr Leu
        195                 200                 205

Glu Gln Gly Gln Trp Pro Leu Gly Trp Thr Gln Met Phe Val Glu Ala
    210                 215                 220

Leu Glu His Ser Gly Asn Pro Leu Ala Ala Arg Tyr Val Lys Pro Thr
```

-continued 225 230 235 240

Leu Thr Asp Leu Pro Ser Pro Ser Ser Glu Thr Ala His Asp Glu Cys
245 250 255

Leu His Leu Leu Thr Leu Leu Gln Pro Thr Leu Val Asp Lys Leu Leu
260 265 270

Ile Asn Asp Val Leu Asp Thr Cys Phe Glu Lys Gly Leu Leu Thr Val
275 280 285

Glu Asp Arg Asn Arg Ile Ser Ala Ala Gly Asn Ser Gly Asn Glu Ser
290 295 300

Gly Val Arg Glu Leu Leu Arg Arg Ile Val Gln Lys Glu Asn Trp Phe
305 310 315 320

Ser Thr Phe Leu Asp Val Leu Arg Gln Thr Gly Asn Asp Ala Leu Phe
325 330 335

Gln Glu Leu Thr Gly Gly Gly Cys Pro Glu Asp Asn Thr Asp Leu Ala
340 345 350

Asn Ser Ser His Arg Asp Gly Pro Ala Ala Asn Glu Cys Leu Leu Pro
355 360 365

Ala Val Asp Glu Ser Ser Leu Glu Thr Glu Ala Trp Asn Val Asp Asp
370 375 380

Ile Leu Pro Glu Ala Ser Cys Thr Asp Ser Ser Val Thr Thr Glu Ser
385 390 395 400

Asp Thr Ser Leu Ala Glu Gly Ser Val Ser Cys Phe Asp Glu Ser Leu
405 410 415

Gly His Asn Ser Asn Met Gly Arg Asp Ser Gly Thr Met Gly Ser Asp
420 425 430

Ser Asp Glu Ser
435

<210> SEQ ID NO 113
<211> LENGTH: 373
<212> TYPE: PRT
<213> ORGANISM: Artificial Sequence
<220> FEATURE:
<223> OTHER INFORMATION: YopE1-138 - Y. enterocolitica codon optimized murine MDA5 (Aa. 1-231)

<400> SEQUENCE: 113

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Met Ser
130 135 140

-continued

```
Ile Val Cys Ser Ala Glu Asp Ser Phe Arg Asn Leu Ile Leu Phe Phe
145                 150                 155                 160

Arg Pro Arg Leu Lys Met Tyr Ile Gln Val Glu Pro Val Leu Asp His
                165                 170                 175

Leu Ile Phe Leu Ser Ala Glu Thr Lys Glu Gln Ile Leu Lys Lys Ile
            180                 185                 190

Asn Thr Cys Gly Asn Thr Ser Ala Ala Glu Leu Leu Leu Ser Thr Leu
        195                 200                 205

Glu Gln Gly Gln Trp Pro Leu Gly Trp Thr Gln Met Phe Val Glu Ala
    210                 215                 220

Leu Glu His Ser Gly Asn Pro Leu Ala Ala Arg Tyr Val Lys Pro Thr
225                 230                 235                 240

Leu Thr Asp Leu Pro Ser Pro Ser Ser Glu Thr Ala His Asp Glu Cys
                245                 250                 255

Leu His Leu Leu Thr Leu Leu Gln Pro Thr Leu Val Asp Lys Leu Leu
            260                 265                 270

Ile Asn Asp Val Leu Asp Thr Cys Phe Glu Lys Gly Leu Leu Thr Val
        275                 280                 285

Glu Asp Arg Asn Arg Ile Ser Ala Ala Gly Asn Ser Gly Asn Glu Ser
    290                 295                 300

Gly Val Arg Glu Leu Leu Arg Arg Ile Val Gln Lys Glu Asn Trp Phe
305                 310                 315                 320

Ser Thr Phe Leu Asp Val Leu Arg Gln Thr Gly Asn Asp Ala Leu Phe
                325                 330                 335

Gln Glu Leu Thr Gly Gly Gly Cys Pro Glu Asp Asn Thr Asp Leu Ala
            340                 345                 350

Asn Ser Ser His Arg Asp Gly Pro Ala Ala Asn Glu Cys Leu Leu Pro
        355                 360                 365

Ala Val Asp Glu Ser
    370


<210> SEQ ID NO 114
<211> LENGTH: 349
<212> TYPE: PRT
<213> ORGANISM: Artificial Sequence
<220> FEATURE:
<223> OTHER INFORMATION: YopE1-138- Y. enterocolitica codon optimized B.
      subtilis CdaS L44F constitutive active version

<400> SEQUENCE: 114

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125
```

Leu Gln Lys Asn His Asp Gln Phe Ala Thr Leu Glu Ser Arg Met Lys
    130                 135                 140

Ala Met Arg Tyr Glu Gln Ile Ser Glu Asn Ala Phe Lys Gly Lys Ile
145                 150                 155                 160

Gln Val Tyr Leu Glu Gln Ile Leu Gly Asp Ala Ser Leu Ile Leu Lys
                165                 170                 175

Thr Leu His Glu Lys Asp Gln Cys Leu Phe Cys Glu Leu Asp Asp Leu
            180                 185                 190

Gly His Val Phe Gln Asp Met Gln Gly Ile Ala Ser Ser Phe Tyr Leu
        195                 200                 205

Gln Ser Tyr Ile Glu Glu Phe Thr Pro Ala Phe Ile Glu Leu Ala Lys
    210                 215                 220

Ala Ile Lys Ala Leu Ser Glu His Lys His Gly Ala Leu Ile Val Ile
225                 230                 235                 240

Glu Arg Ala Asp Pro Val Glu Arg Phe Ile Gln Lys Gly Thr Ser Leu
                245                 250                 255

His Ala Glu Ile Ser Ser Ser Leu Ile Glu Ser Ile Phe Phe Pro Gly
            260                 265                 270

Asn Pro Leu His Asp Gly Ala Leu Leu Val Arg Glu Asn Lys Leu Val
        275                 280                 285

Ser Ala Ala Asn Val Leu Pro Leu Thr Thr Lys Glu Val Asp Ile His
    290                 295                 300

Leu Gly Thr Arg His Arg Ala Ala Leu Gly Met Ser Gly Tyr Thr Asp
305                 310                 315                 320

Ala Leu Val Leu Val Val Ser Glu Glu Thr Gly Lys Met Ser Phe Ala
                325                 330                 335

Lys Asp Gly Val Leu Tyr Pro Leu Ile Ser Pro Arg Thr
            340                 345

<210> SEQ ID NO 115
<211> LENGTH: 504
<212> TYPE: PRT
<213> ORGANISM: Artificial Sequence
<220> FEATURE:
<223> OTHER INFORMATION: YopE1-138- Y. enterocolitica codon optimized
      human cGAS (Aa. 161-522)

<400> SEQUENCE: 115

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Gly Ala

-continued

```
    130                 135                 140

Ser Lys Leu Arg Ala Val Leu Glu Lys Leu Lys Leu Ser Arg Asp Asp
145                 150                 155                 160

Ile Ser Thr Ala Ala Gly Met Val Lys Gly Val Val Asp His Leu Leu
                165                 170                 175

Leu Arg Leu Lys Cys Asp Ser Ala Phe Arg Gly Val Gly Leu Leu Asn
            180                 185                 190

Thr Gly Ser Tyr Tyr Glu His Val Lys Ile Ser Ala Pro Asn Glu Phe
        195                 200                 205

Asp Val Met Phe Lys Leu Glu Val Pro Arg Ile Gln Leu Glu Glu Tyr
    210                 215                 220

Ser Asn Thr Arg Ala Tyr Tyr Phe Val Lys Phe Lys Arg Asn Pro Lys
225                 230                 235                 240

Glu Asn Pro Leu Ser Gln Phe Leu Glu Gly Glu Ile Leu Ser Ala Ser
                245                 250                 255

Lys Met Leu Ser Lys Phe Arg Lys Ile Ile Lys Glu Glu Ile Asn Asp
            260                 265                 270

Ile Lys Asp Thr Asp Val Ile Met Lys Arg Lys Arg Gly Gly Ser Pro
        275                 280                 285

Ala Val Thr Leu Leu Ile Ser Glu Lys Ile Ser Val Asp Ile Thr Leu
    290                 295                 300

Ala Leu Glu Ser Lys Ser Ser Trp Pro Ala Ser Thr Gln Glu Gly Leu
305                 310                 315                 320

Arg Ile Gln Asn Trp Leu Ser Ala Lys Val Arg Lys Gln Leu Arg Leu
                325                 330                 335

Lys Pro Phe Tyr Leu Val Pro Lys His Ala Lys Glu Gly Asn Gly Phe
            340                 345                 350

Gln Glu Glu Thr Trp Arg Leu Ser Phe Ser His Ile Glu Lys Glu Ile
        355                 360                 365

Leu Asn Asn His Gly Lys Ser Lys Thr Cys Cys Glu Asn Lys Glu Glu
    370                 375                 380

Lys Cys Cys Arg Lys Asp Cys Leu Lys Leu Met Lys Tyr Leu Leu Glu
385                 390                 395                 400

Gln Leu Lys Glu Arg Phe Lys Asp Lys Lys His Leu Asp Lys Phe Ser
                405                 410                 415

Ser Tyr His Val Lys Thr Ala Phe Phe His Val Cys Thr Gln Asn Pro
            420                 425                 430

Gln Asp Ser Gln Trp Asp Arg Lys Asp Leu Gly Leu Cys Phe Asp Asn
        435                 440                 445

Cys Val Thr Tyr Phe Leu Gln Cys Leu Arg Thr Glu Lys Leu Glu Asn
    450                 455                 460

Tyr Phe Ile Pro Glu Phe Asn Leu Phe Ser Ser Asn Leu Ile Asp Lys
465                 470                 475                 480

Arg Ser Lys Glu Phe Leu Thr Lys Gln Ile Glu Tyr Glu Arg Asn Asn
                485                 490                 495

Glu Phe Pro Val Phe Asp Glu Phe
            500
```

<210> SEQ ID NO 116
<211> LENGTH: 242
<212> TYPE: PRT
<213> ORGANISM: Artificial Sequence
<220> FEATURE:
<223> OTHER INFORMATION: YopE1-138- Y. enterocolitica codon optimized human MAVS CARD (Aa. 1-100)

<400> SEQUENCE: 116

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Met Pro
130 135 140

Phe Ala Glu Asp Lys Thr Tyr Lys Tyr Ile Cys Arg Asn Phe Ser Asn
145 150 155 160

Phe Cys Asn Val Asp Val Val Glu Ile Leu Pro Tyr Leu Pro Cys Leu
165 170 175

Thr Ala Arg Asp Gln Asp Arg Leu Arg Ala Thr Cys Thr Leu Ser Gly
180 185 190

Asn Arg Asp Thr Leu Trp His Leu Phe Asn Thr Leu Gln Arg Arg Pro
195 200 205

Gly Trp Val Glu Tyr Phe Ile Ala Ala Leu Arg Gly Cys Glu Leu Val
210 215 220

Asp Leu Ala Asp Glu Val Ala Ser Val Tyr Glu Ser Tyr Gln Pro Arg
225 230 235 240

Thr Ser

<210> SEQ ID NO 117
<211> LENGTH: 505
<212> TYPE: PRT
<213> ORGANISM: Artificial Sequence
<220> FEATURE:
<223> OTHER INFORMATION: YopE1-138- Y. enterocolitica codon optimized Anemonae (N. vectensis) cGAS (Aa. 60-422) (Ensembl: A7SFB5.1)

<400> SEQUENCE: 117

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

-continued

```
Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Gln Pro
    130                 135                 140

Phe Pro Lys Gly Asp Leu Glu Thr Leu Arg Arg Phe Ser Val Thr Asp
145                 150                 155                 160

Val Lys Ile Ser Lys Gln Ser Thr Lys Trp Ala Lys Lys Met Ala Asp
                165                 170                 175

Lys His Leu Glu Ile Ile Arg Lys His Cys Lys Thr Asn Ser Ile Lys
            180                 185                 190

Leu Phe Asn His Phe Glu Tyr Thr Gly Ser Phe Tyr Glu His Leu Lys
        195                 200                 205

Thr Ile Asp Ala Asp Glu Leu Asp Ile Met Val Ala Leu Ser Ile Lys
    210                 215                 220

Met Asp Glu Leu Glu Val Glu Gln Val Thr Pro Gly Tyr Ala Gly Leu
225                 230                 235                 240

Lys Leu Arg Asp Thr Pro Ser Asn Arg Asn Lys Tyr Asn Asp Leu Thr
                245                 250                 255

Ile Ala Asp Asn Tyr Gly Arg Tyr Leu Ser Pro Glu Lys Val Ser Arg
            260                 265                 270

Trp Phe Phe Ser Leu Val Gln Lys Ala Val Asn Thr Tyr Lys Asp Glu
        275                 280                 285

Ile Pro Gln Thr Glu Val Lys Leu Thr Asp Asn Gly Pro Ala Thr Thr
    290                 295                 300

Leu Val Ile Thr Tyr Arg Glu Gly Asp Lys Pro Gln Glu Lys Asn Arg
305                 310                 315                 320

Arg Leu Ser Ile Asp Leu Val Pro Ala Leu Leu Phe Lys Asp Lys Thr
                325                 330                 335

Lys Pro Ala Gly Asp Asp Leu Arg Ala Trp His Tyr Val Ala Lys Thr
            340                 345                 350

Ile Pro Lys Gly Ala Arg Leu Lys Glu Pro Leu Pro Phe Arg Ser Glu
        355                 360                 365

Leu Leu Trp Arg Gln Ser Phe Ser Leu Lys Glu Lys His Leu Met Asp
    370                 375                 380

Lys Leu Asp Lys Asp Asp Asn Gly Cys Arg Arg Glu Met Val Arg Ile
385                 390                 395                 400

Val Lys Thr Ile Val Lys Lys Asp Pro Thr Leu Ala Gln Leu Ser Ser
                405                 410                 415

Tyr His Ile Lys Thr Ala Phe Leu Gln Tyr Asn Phe Ser Asp Val Lys
            420                 425                 430

Leu Asp Trp Glu Gly Lys Lys Leu Ala Glu Arg Phe Leu His Phe Leu
        435                 440                 445

Glu Phe Leu Arg Asp Arg Val Lys Asp Lys Thr Leu Asn Asn Tyr Phe
    450                 455                 460

Ile Thr Asp Leu Asn Leu Leu Asp Asp Leu Asn Asp Ser Asn Ile Asp
465                 470                 475                 480

Asn Ile Ala Asn Arg Leu Asp Lys Ile Ile Gln Asn Glu Thr Glu Arg
                485                 490                 495

Ala Lys Ile Phe Thr Thr Gln Arg Gln
            500                 505
```

-continued

<210> SEQ ID NO 118
<211> LENGTH: 315
<212> TYPE: PRT
<213> ORGANISM: Artificial Sequence
<220> FEATURE:
<223> OTHER INFORMATION: YopE1-138- Y. enterocolitica codon optimized
Listeria CdaA (Aa. 101-273)

<400> SEQUENCE: 118

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Tyr Gly
    130                 135                 140

Ser Arg Ile Glu Arg Glu Gln His His Leu Ile Glu Ser Ile Glu Lys
145                 150                 155                 160

Ser Thr Gln Tyr Met Ala Lys Arg Arg Ile Gly Ala Leu Ile Ser Val
                165                 170                 175

Ala Arg Asp Thr Gly Met Asp Asp Tyr Ile Glu Thr Gly Ile Pro Leu
            180                 185                 190

Asn Ala Lys Ile Ser Ser Gln Leu Leu Ile Asn Ile Phe Ile Pro Asn
        195                 200                 205

Thr Pro Leu His Asp Gly Ala Val Ile Ile Lys Gly Asn Glu Ile Ala
    210                 215                 220

Ser Ala Ala Ser Tyr Leu Pro Leu Ser Asp Ser Pro Phe Leu Ser Lys
225                 230                 235                 240

Glu Leu Gly Thr Arg His Arg Ala Ala Leu Gly Ile Ser Glu Val Thr
                245                 250                 255

Asp Ser Ile Thr Ile Val Val Ser Glu Glu Thr Gly Gly Ile Ser Leu
            260                 265                 270

Thr Lys Gly Gly Glu Leu Phe Arg Asp Val Ser Glu Glu Glu Leu His
        275                 280                 285

Lys Ile Leu Leu Lys Glu Leu Val Thr Val Thr Ala Lys Lys Pro Ser
    290                 295                 300

Ile Phe Ser Lys Trp Lys Gly Gly Lys Ser Glu
305                 310                 315
```

<210> SEQ ID NO 119
<211> LENGTH: 36
<212> TYPE: DNA
<213> ORGANISM: Artificial Sequence
<220> FEATURE:
<223> OTHER INFORMATION: primer No. 1010

<400> SEQUENCE: 119
cacatgtcta gacaaccgtt tccgaaaggt gatctg 36

<210> SEQ ID NO 120
<211> LENGTH: 37
<212> TYPE: DNA
<213> ORGANISM: Artificial Sequence
<220> FEATURE:
<223> OTHER INFORMATION: primer No. 1012

<400> SEQUENCE: 120
atcccaagct tattggcgtt gggtggtaaa aattttg 37

<210> SEQ ID NO 121
<211> LENGTH: 30
<212> TYPE: DNA
<213> ORGANISM: Artificial Sequence
<220> FEATURE:
<223> OTHER INFORMATION: primer No. 1021

<400> SEQUENCE: 121
cacatgtcta gaatgaccgc cgaacaacgc 30

<210> SEQ ID NO 122
<211> LENGTH: 30
<212> TYPE: DNA
<213> ORGANISM: Artificial Sequence
<220> FEATURE:
<223> OTHER INFORMATION: primer No. 1022

<400> SEQUENCE: 122
catgaagctt acggacccgg attttggctc 30

<210> SEQ ID NO 123
<211> LENGTH: 39
<212> TYPE: DNA
<213> ORGANISM: Artificial Sequence
<220> FEATURE:
<223> OTHER INFORMATION: primer No. 1023

<400> SEQUENCE: 123
catgaagctt acggttcttc ttgaataaaa atttgaatg 39

<210> SEQ ID NO 124
<211> LENGTH: 33
<212> TYPE: DNA
<213> ORGANISM: Artificial Sequence
<220> FEATURE:
<223> OTHER INFORMATION: primer No. 1024

<400> SEQUENCE: 124
catgaagctt attgcagcac tttcggccaa ttt 33

<210> SEQ ID NO 125
<211> LENGTH: 32
<212> TYPE: DNA
<213> ORGANISM: Artificial Sequence
<220> FEATURE:
<223> OTHER INFORMATION: primer No. 1025

<400> SEQUENCE: 125
cacatgtcta gaatgagcat tgtgtgtagc gc 32

<210> SEQ ID NO 126
<211> LENGTH: 29
<212> TYPE: DNA

<213> ORGANISM: Artificial Sequence
<220> FEATURE:
<223> OTHER INFORMATION: primer No. 1026

<400> SEQUENCE: 126
catgaagctt agctttcatc cacggccgg 29

<210> SEQ ID NO 127
<211> LENGTH: 30
<212> TYPE: DNA
<213> ORGANISM: Artificial Sequence
<220> FEATURE:
<223> OTHER INFORMATION: primer No. 1027

<400> SEQUENCE: 127
catgaagctt aattaccggt ttggcgcagc 30

<210> SEQ ID NO 128
<211> LENGTH: 370
<212> TYPE: PRT
<213> ORGANISM: Artificial Sequence
<220> FEATURE:
<223> OTHER INFORMATION: YopE1-138 - Y. enterocolitica codon optimized human RIG1 CARD domains (Aa. 1-228)

<400> SEQUENCE: 128

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Thr Glu Gln Arg Arg Ser Leu Gln Ala Phe Gln Asp Tyr Ile Arg Lys
145                 150                 155                 160

Thr Leu Asp Pro Thr Tyr Ile Leu Ser Tyr Met Ala Pro Trp Phe Arg
                165                 170                 175

Glu Glu Glu Val Gln Tyr Ile Gln Ala Glu Lys Asn Asn Lys Gly Pro
            180                 185                 190

Met Glu Ala Ala Thr Leu Phe Leu Lys Phe Leu Leu Glu Leu Gln Glu
        195                 200                 205

Glu Gly Trp Phe Arg Gly Phe Leu Asp Ala Leu Asp His Ala Gly Tyr
    210                 215                 220

Ser Gly Leu Tyr Glu Ala Ile Glu Ser Trp Asp Phe Lys Lys Ile Glu
225                 230                 235                 240

Lys Leu Glu Glu Tyr Arg Leu Leu Leu Lys Arg Leu Gln Pro Glu Phe
                245                 250                 255
```

```
Lys Thr Arg Ile Ile Pro Thr Asp Ile Ile Ser Asp Leu Ser Glu Cys
            260                 265                 270

Leu Ile Asn Gln Glu Cys Glu Glu Ile Leu Gln Ile Cys Ser Thr Lys
        275                 280                 285

Gly Met Met Ala Gly Ala Glu Lys Leu Val Glu Cys Leu Leu Arg Ser
    290                 295                 300

Asp Lys Glu Asn Trp Pro Lys Thr Leu Lys Leu Ala Leu Glu Lys Glu
305                 310                 315                 320

Arg Asn Lys Phe Ser Glu Leu Trp Ile Val Glu Lys Gly Ile Lys Asp
                325                 330                 335

Val Glu Thr Glu Asp Leu Glu Asp Lys Met Glu Thr Ser Asp Ile Gln
            340                 345                 350

Ile Phe Tyr Gln Glu Asp Pro Glu Cys Gln Asn Leu Ser Glu Asn Ser
        355                 360                 365

Cys Pro
    370


<210> SEQ ID NO 129
<211> LENGTH: 358
<212> TYPE: PRT
<213> ORGANISM: Artificial Sequence
<220> FEATURE:
<223> OTHER INFORMATION: YopE1-138 - Y. enterocolitica codon optimized
      human RIG1 CARD domains (Aa. 1-217)

<400> SEQUENCE: 129

Lys Ile Ser Ser Phe Ile Ser Thr Ser Leu Pro Leu Pro Ala Ser Val
1               5                   10                  15

Ser Gly Ser Ser Ser Val Gly Glu Met Ser Gly Arg Ser Val Ser Gln
            20                  25                  30

Gln Lys Ser Asp Gln Tyr Ala Asn Asn Leu Ala Gly Arg Thr Glu Ser
        35                  40                  45

Pro Gln Gly Ser Ser Leu Ala Ser Arg Ile Ile Glu Arg Leu Ser Ser
    50                  55                  60

Met Ala His Ser Val Ile Gly Phe Ile Gln Arg Met Phe Ser Glu Gly
65                  70                  75                  80

Ser His Lys Pro Val Val Thr Pro Ala Leu Thr Pro Ala Gln Met Pro
                85                  90                  95

Ser Pro Thr Ser Phe Ser Asp Ser Ile Lys Gln Leu Ala Ala Glu Thr
            100                 105                 110

Leu Pro Lys Tyr Met Gln Gln Leu Ser Ser Leu Asp Ala Glu Thr Leu
        115                 120                 125

Gln Lys Asn His Asp Gln Phe Ala Thr Leu Glu Ser Arg Met Thr Thr
    130                 135                 140

Glu Gln Arg Arg Ser Leu Gln Ala Phe Gln Asp Tyr Ile Arg Lys Thr
145                 150                 155                 160

Leu Asp Pro Thr Tyr Ile Leu Ser Tyr Met Ala Pro Trp Phe Arg Glu
                165                 170                 175

Glu Glu Val Gln Tyr Ile Gln Ala Glu Lys Asn Asn Lys Gly Pro Met
            180                 185                 190

Glu Ala Ala Thr Leu Phe Leu Lys Phe Leu Leu Glu Leu Gln Glu Glu
        195                 200                 205

Gly Trp Phe Arg Gly Phe Leu Asp Ala Leu Asp His Ala Gly Tyr Ser
    210                 215                 220

Gly Leu Tyr Glu Ala Ile Glu Ser Trp Asp Phe Lys Lys Ile Glu Lys
225                 230                 235                 240
```

```
Leu Glu Glu Tyr Arg Leu Leu Leu Lys Arg Leu Gln Pro Glu Phe Lys
                245                 250                 255

Thr Arg Ile Ile Pro Thr Asp Ile Ile Ser Asp Leu Ser Glu Cys Leu
            260                 265                 270

Ile Asn Gln Glu Cys Glu Glu Ile Leu Gln Ile Cys Ser Thr Lys Gly
        275                 280                 285

Met Met Ala Gly Ala Glu Lys Leu Val Glu Cys Leu Leu Arg Ser Asp
    290                 295                 300

Lys Glu Asn Trp Pro Lys Thr Leu Lys Leu Ala Leu Glu Lys Glu Arg
305                 310                 315                 320

Asn Lys Phe Ser Glu Leu Trp Ile Val Glu Lys Gly Ile Lys Asp Val
                325                 330                 335

Glu Thr Glu Asp Leu Glu Asp Lys Met Glu Thr Ser Asp Ile Gln Ile
            340                 345                 350

Phe Tyr Gln Glu Asp Pro
        355


<210> SEQ ID NO 130
<211> LENGTH: 243
<212> TYPE: PRT
<213> ORGANISM: Artificial Sequence
<220> FEATURE:
<223> OTHER INFORMATION: YopE1-138 - Y. enterocolitica codon optimized
      murine MAVS CARD domain (Aa. 1-101)

<400> SEQUENCE: 130

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Phe Ala Glu Asp Lys Thr Tyr Lys Tyr Ile Arg Asp Asn His Ser Lys
145                 150                 155                 160

Phe Cys Cys Val Asp Val Leu Glu Ile Leu Pro Tyr Leu Ser Cys Leu
                165                 170                 175

Thr Ala Ser Asp Gln Asp Arg Leu Arg Ala Ser Tyr Arg Gln Ile Gly
            180                 185                 190

Asn Arg Asp Thr Leu Trp Gly Leu Phe Asn Asn Leu Gln Arg Arg Pro
        195                 200                 205

Gly Trp Val Glu Val Phe Ile Arg Ala Leu Gln Ile Cys Glu Leu Pro
    210                 215                 220

Gly Leu Ala Asp Gln Val Thr Arg Val Tyr Gln Ser Tyr Leu Pro Pro
```

225 230 235 240

Gly Thr Ser

<210> SEQ ID NO 131
<211> LENGTH: 504
<212> TYPE: PRT
<213> ORGANISM: Artificial Sequence
<220> FEATURE:
<223> OTHER INFORMATION: YopE1-138- Y. enterocolitica codon optimized murine cGAS (Aa. 146-507)

<400> SEQUENCE: 131

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Ser Arg Glu Pro
130 135 140

Asp Lys Leu Lys Lys Val Leu Asp Lys Leu Arg Leu Lys Arg Lys Asp
145 150 155 160

Ile Ser Glu Ala Ala Glu Thr Val Asn Lys Val Val Glu Arg Leu Leu
165 170 175

Arg Arg Met Gln Lys Arg Glu Ser Glu Phe Lys Gly Val Glu Gln Leu
180 185 190

Asn Thr Gly Ser Tyr Tyr Glu His Val Lys Ile Ser Ala Pro Asn Glu
195 200 205

Phe Asp Val Met Phe Lys Leu Glu Val Pro Arg Ile Glu Leu Gln Glu
210 215 220

Tyr Tyr Glu Thr Gly Ala Phe Tyr Leu Val Lys Phe Lys Arg Ile Pro
225 230 235 240

Arg Gly Asn Pro Leu Ser His Phe Leu Glu Gly Glu Val Leu Ser Ala
245 250 255

Thr Lys Met Leu Ser Lys Phe Arg Lys Ile Ile Lys Glu Glu Val Lys
260 265 270

Glu Ile Lys Asp Ile Asp Val Ser Val Glu Lys Glu Lys Pro Gly Ser
275 280 285

Pro Ala Val Thr Leu Leu Ile Arg Asn Pro Glu Glu Ile Ser Val Asp
290 295 300

Ile Ile Leu Ala Leu Glu Ser Lys Gly Ser Trp Pro Ile Ser Thr Lys
305 310 315 320

Glu Gly Leu Pro Ile Gln Gly Trp Leu Gly Thr Lys Val Arg Thr Asn
325 330 335

Leu Arg Arg Glu Pro Phe Tyr Leu Val Pro Lys Asn Ala Lys Asp Gly

-continued

```
            340                 345                 350

Asn Ser Phe Gln Gly Glu Thr Trp Arg Leu Ser Phe Ser His Thr Glu
        355                 360                 365

Lys Tyr Ile Leu Asn Asn His Gly Ile Glu Lys Thr Cys Cys Glu Ser
    370                 375                 380

Ser Gly Ala Lys Cys Cys Arg Lys Glu Cys Leu Lys Leu Met Lys Tyr
385                 390                 395                 400

Leu Leu Glu Gln Leu Lys Lys Glu Phe Gln Glu Leu Asp Ala Phe Cys
            405                 410                 415

Ser Tyr His Val Lys Thr Ala Ile Phe His Met Trp Thr Gln Asp Pro
            420                 425                 430

Gln Asp Ser Gln Trp Asp Pro Arg Asn Leu Ser Ser Cys Phe Asp Lys
        435                 440                 445

Leu Leu Ala Phe Phe Leu Glu Cys Leu Arg Thr Glu Lys Leu Asp His
    450                 455                 460

Tyr Phe Ile Pro Lys Phe Asn Leu Phe Ser Gln Glu Leu Ile Asp Arg
465                 470                 475                 480

Lys Ser Lys Glu Phe Leu Ser Lys Lys Ile Glu Tyr Glu Arg Asn Asn
            485                 490                 495

Gly Phe Pro Ile Phe Asp Lys Leu
            500
```

VIRULENCE ATTENUATED BACTERIA BASED PROTEIN DELIVERY

REFERENCE TO AN ELECTRONIC SEQUENCE LISTING

The contents of the electronic sequence listing (0192-0091US1_SL.txt; Size: 174 KB; and Date of Creation Dec. 20, 2017) is herein incorporated by reference in its entirety.

THE FIELD OF THE INVENTION

The present invention relates to recombinant virulence attenuated Gram-negative bacterial strains and its use in a method of treating cancer in a subject.

BACKGROUND OF THE INVENTION

Bacteria have evolved different mechanisms to directly inject proteins into target cells [1]. The type III secretion system (T3SS) used by bacteria like *Yersinia, Shigella* and *Salmonella*' functions like a nano-syringe that injects so-called bacterial effector proteins into host cells.

T3SS has been exploited to deliver hybrid peptides and proteins into target cells. Heterologous bacterial T3SS effectors have been delivered in case the bacterium under study is hardly accessible by genetics (like *Chlamydia trachomatis*). Often reporter proteins were fused to possible T3SS secretion signals as to study requirements for T3SS dependent protein delivery, such as the *Bordetella pertussis* adenylate cyclase, murine DHFR or a phosphorylatable tag. Peptide delivery was mainly conducted with the aim of vaccination. This includes viral epitopes, bacterial epitopes (listeriolysin O) as well as peptides representing epitopes of human cancer cells. In few cases functional eukaryotic proteins have been delivered to modulate the host cell, as done with nanobodies[3], nuclear proteins (Cre-recombinase, MyoD)[4,5] or IL10 and IL1ra[6]. None of the above-mentioned systems allows single-protein delivery as in each case one or multiple endogenous effector proteins are still encoded. Furthermore, the vectors used have not been designed in a way allowing simple cloning of other DNA fragments encoding proteins of choice, hindering broad application of the system.

Approaches allowing targeted drug delivery are of great interest. For example, antibodies recognizing surface structures of tumor cells and, in an optimal case, selectively bind to tumor cells are used. To improve the mechanism of such antibodies they can be conjugated to therapeutic agents or to lipid vesicles packed with drugs. One of the challenges with such vesicles is the proper release of the active reagent. Even more complex is the delivery of therapeutic proteins or peptides, especially when intracellular mechanisms are targeted. Many alternative ways have been tried to solve the problem of delivering therapeutic proteins into eukaryotic cells, among which are "cell penetrating peptides" (CPP) or similar technologies as well as various nanoparticle-based methodologies. All these technologies have the drawback of low efficacy and that the cargo taken up by the cell via endocytosis is likely to end up being degraded in lysosomes. Furthermore, the conflict between need for stability of cargo-carrier in the human body and the requirement for destabilization and liberation within the target cell constitutes an intrinsic problem of such technologies. Various bacteria have been shown to replicate within malignant solid tumors when administered from a distal site, including *Escherichia coli, Vibrio cholerae, Salmonella enterica, Listeria monocytogenes, Pseudomonas aeruginosa* and Bifidobacteria. Currently, only *bacillus* Calmette-Guérin (BCG, derived from *Mycobacterium bovis*) is used in clinical practice. BCG is administrated to treat superficial bladder cancer, while the underlying molecular mechanism remains largely unknown. The development of bacterial strains which are capable e.g. to deliver cargo produced inside bacteria to its site of action inside cells like cancer cells, i.e. outside of bacteria, remains a major challenge.

SUMMARY OF THE INVENTION

The present invention relates to recombinant virulence attenuated Gram-negative bacterial strains and its use in a method of treating cancer in a subject. In some embodiments the present invention provides recombinant virulence attenuated Gram-negative bacterial strains and the use thereof for treating cancer in a subject wherein the recombinant virulence attenuated Gram-negative bacterial strains allow the translocation of various type III effectors, but also of type IV effectors, of viral proteins and most importantly of functional eukaryotic proteins into cancer cells e.g. into cells of a malignant solid tumor.

The present invention provides a recombinant virulence attenuated Gram-negative bacterial strain with increased heterologous protein expression and secretion properties and which is surprisingly capable to stably encode the heterologous protein over several days, or even weeks, in vivo.

In a first aspect the present invention relates to a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

In a further aspect the present invention relates to a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein.

In a further aspect the present invention relates to a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response.

In a further aspect the present invention relates to a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject. Likewise the present invention relates to a method of treating cancer in a subject, comprising administering to the subject a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter, wherein the recombinant virulence attenuated Gram-negative bacterial strain is administered in an amount that is sufficient to treat the subject.

Likewise the present invention relates to the use of a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter for the manufacture of a medicament for treating cancer in a subject In a further aspect the present invention relates to a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject. Likewise the present invention relates to a method of treating cancer in a subject, comprising administering to the subject a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein, wherein the recombinant virulence attenuated Gram-negative bacterial strain is administered in an amount that is sufficient to treat the subject. Likewise the present invention relates to the use of a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein for the manufacture of a medicament for treating cancer in a subject.

In a further aspect the present invention relates to a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject.

Likewise the present invention relates to a method of treating cancer in a subject, comprising administering to the subject a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response, wherein the recombinant virulence attenuated Gram-negative bacterial strain is administered in an amount that is sufficient to treat the subject.

Likewise the present invention relates to the use of a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response for the manufacture of a medicament for treating cancer in a subject.

In a further aspect the present invention relates to a pharmaceutical composition comprising a recombinant virulence attenuated Gram-negative bacterial strain and a pharmaceutically acceptable carrier, wherein the recombinant virulence attenuated Gram-negative bacterial strain comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

In a further aspect the present invention relates to a pharmaceutical composition comprising a recombinant virulence attenuated Gram-negative bacterial strain and a pharmaceutically acceptable carrier, wherein the recombinant virulence attenuated Gram-negative bacterial strain comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA thermosensor region upstream of a gene coding for an endogenous AraC-type DNA binding protein.

In a further aspect the present invention relates to a pharmaceutical composition comprising a recombinant virulence attenuated Gram-negative bacterial strain and a pharmaceutically acceptable carrier, wherein the recombinant virulence attenuated Gram-negative bacterial strain comprises a nucleotide molecule comprising a nucleotide sequence encoding a heterologous protein fused in frame to the 3'end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response.

BRIEF DESCRIPTION OF THE FIGURES

FIGS. 3A to Q: *Y. enterocolitica* strains used in this study. List of *Y. enterocolitica* strains used in this study providing information on background strains, plasmids and proteins for T3SS dependent delivery encoded on corresponding plasmids. Further, information on oligonucleotides used for construction of the corresponding plasmid, the backbone plasmid and antibiotic resistances is provided.

FIG. 11: Regulation of T3SS-based secretion by controlling the expression of the master regulator VirF. A: In vitro secretion assay (performed at 37° C.) with *Y. enterocolitica* ΔHOPEMT strains delivering $YopE_{1-138}$-(tBID BH3$)_2$. Expression of VirF is under control of its natural promoter (I+II), an arabinose-inducible promoter (III+IV) or its natural promoter with a deletion of its hairpin I region controlling temperature-dependent expression (V). The secretion assay was performed either in the absence of arabinose (I, III and V) or in the presence of 0.2% arabinose (II and IV). Secreted $YopE_{1-138}$-(tBID BH3$)_2$ was detected using Western blotting with an antibody recognizing the $YopE_{1-138}$ region. B: In vitro secretion assay (performed at 37° C.) with *Y. enterocolitica* ΔHOPEMT strains delivering $YopE_{1-138}$-murine RIG1 caspase activation and recruitment domain (CARD) domains. Expression of VirF is under control of its natural promoter (I+II), or its natural promoter with a deletion of its hairpin I region controlling temperature-dependent expression (III). The secretion assay was performed either in the absence of arabinose (I, and III) or in the presence of 0.2% arabinose (II). Secreted of $YopE_{1-138}$-murine RIG1 CARD domains was detected using Western blotting with an antibody recognizing the $YopE_{1-138}$ region.

DETAILED DESCRIPTION OF THE INVENTION

Figure 1:
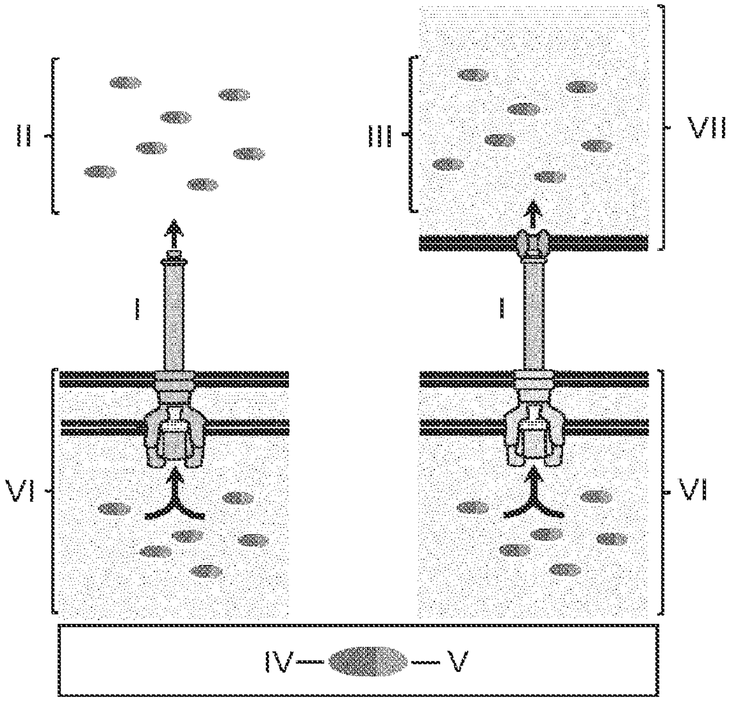
FIG. 1: Characterization of T3SS protein delivery. Schematic representation of T3SS dependent protein secretion into the surrounding medium (in-vitro secretion)(left side) or into eukaryotic cells (right side). I: shows the type 3 secretion system. II indicates proteins secreted into the surrounding medium, III proteins translocated through the membrane into the cytosol of eukaryotic cells (VII). VI shows a stretch of the two bacterial membranes in which the T3SS is inserted and the bacterial cytosol underneath. IV is a fusion protein attached to the $YopE_{1-138}$ N-terminal fragment (V)

The present invention relates to recombinant virulence attenuated Gram-negative bacterial strains and its use in a method of treating cancer e.g. a malignant solid tumor in a subject.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

The term "Gram-negative bacterial strain" as used herein includes the following bacteria: *Aeromonas salmonicida, Aeromonas hydrophila, Aeromonas veronii, Anaeromyxobacter dehalogenans, Bordetella bronchiseptica, Bordetella parapertussis, Bordetella pertussis, Bradyrhizobium japonicum, Burkholderia cenocepacia, Burkholderia cepacia, Burkholderia mallei, Burkholderia pseudomallei, Chlamydia muridarum, Chlamydia trachmoatis, Chlamydophila abortus, Chlamydophila pneumoniae, Chromobacterium violaceum, Citrobacter rodentium, Desulfovibrio vulgaris, Edwardsiella tarda, Endozoicomonas elysicola, Erwinia amylovora, Escherichia albertii, Escherichia coli, Lawsonia intracellularis, Mesorhizobium loti, Myxococcus xanthus, Pantoea agglomerans, Photobacterium damselae, Photorhabdus luminescens, Photorabdus temperate, Pseudoalteromonas spongiae, Pseudomonas aeruginosa, Pseudomonas plecoglossicida, Pseudomonas syringae, Ralstonia solanacearum, Rhizobium* sp, *Salmonella enterica* and other *Salmonella* sp, *Shigella flexneri* and other *Shigella* sp, *Sodalis glossinidius, Vibrio alginolyticus, Vibrio azureus, Vibrio campellii, Vibrio caribbenthicus, Vibrio harvey, Vibrio parahaemolyticus, Vibrio tasmaniensis, Vibrio tubiashii, Xanthomonas axonopodis, Xanthomonas campestris, Xanthomonas oryzae, Yersinia enterocolitica, Yersinia pestis, Yersinia pseudotuberculosis*. Preferred Gram-negative bacterial strains of the invention are Gram-negative bacterial strains comprised by the family of Enterobacteriaceae and Pseudomonadaceae. The Gram-negative bacterial strain of the present invention is normally used for delivery of heterologous proteins by the bacterial T3SS into eukaryotic cells in vitro and/or in vivo, preferably in vivo.

The term "recombinant virulence attenuated Gram-negative bacterial strain" as used herein refers to a recombinant virulence attenuated Gram-negative bacterial strain genetically transformed with a nucleotide molecule like a vector. Virulence of such a recombinant Gram-negative bacterial strain is usually attenuated by deletion of bacterial effector proteins having virulence activity which are transported by one or more bacterial proteins, which are part of a secretion system machinery. Such effector proteins are deliverd by a secretion system machinery into a host cells where they exert their virulence activity toward various host proteins and cellular machineries. Many different effector proteins are known, transported by various secretion system types and displaying a large repertoire of biochemical activities that modulate the functions of host regulatory molecules. Virulence of the recombinant Gram-negative bacterial strain used herein can be attenuated additionally by lack of a siderophore normally or occasionally produced by the Gram-negative bacterial strain so that the strain does not produce the siderophore e.g. is deficient in the production of the siderophore. Thus in a preferred embodiment a recombinant virulence attenuated Gram-negative bacterial strain is used which lacks of a siderophore normally or occasionally produced by the Gram-negative bacterial strain so that the strain does not produce the siderophore e.g. is deficient in the production of a siderophore, more preferably a *Yersinia* strain, in particular *Y. enterocolitica* MRS40 ΔyopH$_2$O,P,E, M,T, *Y. enterocolitica* MRS40 ΔyopH$_2$O,P,E,M,T ΔHairpinI-virF or *Y. enterocolitica MRS*40 ΔyopH$_2$O,P,E, M,T Δasd pYV-asd is used which lack of a siderophore normally or occasionally produced by the Gram-negative bacterial strain so that the strain does not produce the siderophore e.g. is deficient in the production of a siderophore, in particular is deficient in the production of Yersiniabactin. *Y. enterocolitica* MRS40 ΔyopH$_2$O,P,E,M,T which is deficient in the production of Yersiniabactin has been described in WO02077249 and was deposited on 24$^{th}$ of September, 2001, according to the Budapest Treaty on the International Recognition of the Deposit of Microorganisms for the Purposes of Patent Procedure with the Belgian Coordinated Collections of Microorganisms (BCCM) and was given accession number LMG P-21013. The recombinant virulence attenuated Gram-negative bacterial strain preferably does not produce at least one, preferably at least two siderophores e.g. is deficient in the production of at least one, preferably at least two siderophores, more preferably the recombinant virulence attenuated Gram-negative bacterial strain does not produce any siderophore.

The term "siderophore", "iron siderophore" or "iron chelator" which are used interchangeably herein refer to compounds with high affinity for iron e.g. small compounds with high affinity for iron.

Siderophores of Gram-negative bacteria are e.g. Enterobactin and dihydroxybenzoylserine synthetized by *Salmonella, Escherichia, Klebsiella, Shigella, Serratia* (but used by all enterobacteria), Pyoverdins synthetized by *Pseudomonas, Vibriobactin synthetized by Vibrio*, Acinetobactin and Acinetoferrin by *Acinetobacter*, Yersiniabactin and Aerobactin synthetized by *Yersinia*, Ornibactin synthetized by *Burkholderia*, Salmochelin synthetized by *Salmonella*, Aerobactin synthetized by *Escherichia, Shigella, Salmonella*, and *Yersinia*, Alcaligin synthetized by *Bordetella*, Bisucaberin synthetized by *Vibrio*.

Siderophores include hydroxamate, catecholate and mixed ligand siderophores. Several siderophores have to date been approved for use in humans, mainly with the aim of treating iron overload. Preferred siderophores are Deferoxamine (also known as desferrioxamine B, desferoxamine B, DFO-B, DFOA, DFB or desferal), Desferrioxamine E, Deferasirox (Exjade, Desirox, Defrijet, Desifer) and Deferiprone (Ferriprox).

The term "an endogenous protein essential for growth" used herein refers to proteins of the recombinant virulence attenuated Gram-negative bacterial strain without those the Gram-negative bacterial strain cannot grow. Endogenous proteins essential for growth are e.g. an enzyme essential for amino acid production, an enzyme involved in peptidoglycan biosynthesis, an enzyme involved in LPS biosynthesis, an enzyme involved in nucleotide synthesis or a translation initiation factor.

The term "an enzyme essential for amino acid production" used herein refers to enzymes which are related to the amino acid production of the recombinant virulence attenuated Gram-negative bacterial strain and without those the Gram-negative bacterial strain can not grow. Enzymes essential for amino acid production, are e.g. aspartate-beta-semialdehyde dehydrogenase (asd), glutamine synthetase (glnA), tryptophanyl tRNA synthetase (trpS) or serine hydroxymethyl transferase (glyA), or Transketolase 1 (tktA), Transketolase 2 (tktB), Ribulose-phosphate 3-epimerase (rpe), Ribose-5-phosphate isomerase A (rpiA), Transaldolase A (talA), Transaldolase B (talB), phosphoribosylpyrophosphate synthase (prs), ATP phosphoribosyltransferase (hisG), Histidine biosynthesis bifunctional protein HisIE (hisI), 1-(5-phosphoribosyl)-5-[(5-phosphoribosylamino)methylideneamino] imidazole-4-carboxamide isomerase (hisA), Imidazole glycerol phosphate synthase subunit HisH (hisH), Imidazole glycerol phosphate synthase subunit HisF (hisF), Histidine biosynthesis bifunctional protein HisB (hisB), Histidinol-phosphate aminotransferase (hisC), Histidinol dehydrogenase (hisD), 3-dehydroquinate synthase (aroB), 3-dehydroquinate dehydratase (aroD), Shikimate dehydrogenase (NADP (+)) (aroE), Shikimate kinase 2 (aroL), Shikimate kinase 1 (aroK), 3-phosphoshikimate 1-carboxyvinyltransferase (aroA), Chorismate synthase (aroC), P-protein (pheA), T-protein (tyrA), Aromatic-amino-acid aminotransferase (tyrB), Phospho-2-dehydro-3-deoxyheptonate aldolase (aroG), Phospho-2-dehydro-3-deoxyheptonate aldolase (aroH), Phospho-2-dehydro-3-deoxyheptonate aldolase (aroF), Quinate/shikimate dehydrogenase (ydiB), ATP-dependent 6-phosphofructokinase isozyme 1 (pfkA), ATP-dependent 6-phosphofructokinase isozyme 2 (pfkB), Fructose-bisphosphate aldolase class 2 (fbaA), Fructose-bisphosphate aldolase class 1 (fbaB), Triosephosphate isomerase (tpiA), Pyruvate kinase I (pykF), Pyruvate kinase II (pykA), Glyceraldehyde-3-phosphate dehydrogenase A (gapA), Phosphoglycerate kinase (pgk), 2,3-bisphosphoglycerate-dependent phosphoglycerate mutase (gpmA), 2,3-bisphosphoglycerate-independent phosphoglycerate mutase (gpmM/yibO), Probable phosphoglycerate mutase (ytjC/gpmB), enolase (eno), D-3-phosphoglycerate dehydrogenase (serA), Phosphoserine aminotransferase (serC), Phosphoserine phosphatase (serB), L-serine dehydratase 1 (sdaA), L-serine dehydratase 2 (sdaB), L-threonine dehydratase catabolic (tdcB), L-threonine dehydratase biosynthetic (ilvA), L-serine dehydratase (tdcG), Serine acetyltransferase (cysE), Cysteine synthase A (cysK), Cysteine synthase B (cysM), beta-cystathionase (malY), Cystathionine beta-lyase (metC), 5-methyltetrahydropteroyltriglutamate-homocysteine methyltransferase (metE), Methionine synthase (metH), S-adenosylmethionine synthase (metK), Cystathionine gamma-synthase (metB), Homoserine O-succinyltransferase (metA), 5'-methylthioadenosine/S-adenosylhomocysteine nucleosidase (mtnN), S-ribosylhomocysteine lyase (luxS), cystathione beta lyase, cystathione gamma lyase, Serine hydroxymethyltransferase (glyA), Glycine hydroxymethyltransferase (itaE), 3-isopropylmalate dehydratase small subunit (leuD), 3-isopropylmalate dehydratase large subunit (leuC), 3-isopropylmalate dehydrogenase (leuB), L-threonine dehydratase biosynthetic (ilvA), Acetolactate synthase isozyme 3 large subunit (ilvI), Acetolactate synthase isozyme 3 small subunit (ilvH), Acetolactate synthase isozyme 1 small subunit (ilvN), Acetolactate synthase isozyme 2 small subunit (ilvM), Ketol-acid reductoisomerase (NADP(+)) (ilvC), Dihydroxy-acid dehydratase (ilvD), Branched-chain-amino-acid aminotransferase (ilvE), Bifunctional aspartokinase/homoserine dehydrogenase 1 (thrA), Bifunctional aspartokinase/homoserine dehydrogenase 2 (metL), 2-isopropylmalate synthase (leuA), Glutamate-pyruvate aminotransferase (alaA), Aspartate aminotransferase (aspC), Bifunctional aspartokinase/homoserine dehydrogenase 1 (thrA), Bifunctional aspartokinase/homoserine dehydrogenase 2 (metL), Lysine-sensitive aspartokinase 3 (lysC), Aspartate-semialdehyde dehydrogenase (asd), 2-keto-3-deoxy-galactonate aldolase (yagE), 4-hydroxy-tetrahydrodipicolinate synthase (dapA), 4-hydroxy-tetrahydrodipicolinate reductase (dapB), 2,3,4,5-tetrahydropyridine-2,6-dicarboxylate N-succinyltransferase (dapD), Succinyl-diaminopimelate desuccinylase (dapE), Diaminopimelate epimerase (dapF), Putative lyase (yjhH), Acetylornithine/succinyldiaminopimelate aminotransferase (argD), Citrate synthase (gltA), Aconitate hydratase B (acnB), Aconitate hydratase A (acnA), uncharacterized putative aconitate hydratase (ybhJ), isocitrate dehydrogenase (icd), Aspartate aminotransferase (aspC), Glutamate-pyruvate aminotransferase (alaA), Glutamate synthase [NADPH] large chain (gltB), Glutamate synthase [NADPH] small chain (gltD), Glutamine synthetase (glnA), Amino-acid acetyltransferase (argA), Acetylglutamate kinase (argB), N-acetyl-gamma-glutamyl-phosphate reductase (argC), Acetylornithine/succinyldiaminopimelate aminotransferase (argD), Acetylornithine deacetylase (argE), Ornithine carbamoyltransferase chain F (argF), Ornithine carbamoyltransferase chain I (argI), Argininosuccinate synthase (argG), Argininosuccinate lyase (argH), Glutamate 5-kinase (proB), Gamma-glutamyl phosphate reductase (proA), pyrroline-5-carboxylate reductase (proC), ornithine cyclodeaminase, Leucine-tRNA ligase (leuS), Glutamine-tRNA ligase (glnS), Serine-tRNA ligase (serS), Glycine-tRNA ligase beta subunit (glyS), Glycine-tRNA ligase alpha subunit (glyQ), Tyrosine-tRNA ligase (tyrS), Threonine-tRNA ligase (thrS), Phenylalanine-tRNA ligase alpha subunit (pheS), Phenylalanine-tRNA ligase beta subunit (pheT), Arginine-tRNA ligase (argS), Histidine-tRNA ligase (hisS), Valine-tRNA ligase (valS), Alanine-tRNA ligase (alaS), Isoleucine-tRNA ligase (ileS), Proline-tRNA ligase (proS), Cystein-tRNA ligase (cysS), Asparagine-tRNA ligase (asnS), Aspartate-tRNA ligase (aspS), Glutamate-tRNA ligase (gltX), Tryptophan-tRNA ligase (trpS), Glycine-tRNA ligase beta subunit (glyS), Methionine-tRNA ligase (metG), Lysine-tRNA ligase (lysS). Preferred enzymes essential for amino acid production are tktA, rpe, prs, aroK, tyrB, aroH, fbaA, gapA, pgk, eno, tdcG, cysE, metK, glyA, asd, dapA/B/D/E/F, argC, proC, leuS, glnS, serS, glyS/Q, tyrS, thrS, pheS/T, argS, hisS, valS, alaS, ileS, proS, cysS, asnS, aspS, gltX, trpS, glyS, metG, lysS, more preferred are asd, glyA, leuS, glnS, serS, glyS/Q, tyrS, thrS, pheS/T, argS, hisS, valS, alaS, ileS, proS, cysS, asnS, aspS, gltX, trpS, glyS, metG, lysS, most preferred is asd.

The terms "Gram-negative bacterial strain deficient to produce an amino acid essential for growth" and "auxotroph mutant" are used herein interchangeably and refer to Gram-negative bacterial strains which can not grow in the absence of at least one exogenously provided essential amino acid or a precursor thereof. The amino acid the strain is deficient to produce is e.g. aspartate, meso-2,6-diaminopimelic acid, aromatic amino acids or leucine-arginine. Such a strain can be generated by e.g. deletion of the aspartate-beta-semialdehyde dehydrogenase gene (Δasd). Such an auxotroph mutant cannot grow in absence of exogenous meso-2,6-diaminopimelic acid. The mutation, e.g. deletion of the aspartate-beta-semialdehyde dehydrogenase gene is preferred herein for a Gram-negative bacterial strain deficient to produce an amino acid essential for growth of the present invention.

The term "Gram-negative bacterial strain deficient to produce adhesion proteins binding to the eukaryotic cell surface or extracellular matrix" refers to mutant Gram-negative bacterial strains which do not express at least one adhesion protein compared to the adhesion proteins expressed by the corresponding wild type strain. Adhesion proteins may include e.g. extended polymeric adhesion molecules like pili/fimbriae or non-fimbrial adhesins. Fimbrial adhesins include type-1 pili (such as *E. coli* Fim-pili with the FimH adhesin), P-pili (such as Pap-pili with the PapG adhesin from *E. coli*), type 4 pili (as pilin protein from e.g. *P. aeruginosa*) or curli (Csg proteins with the CsgA adhesin from *S. enterica*). Non-fimbrial adhesions include trimeric autotransporter adhesins such as YadA from *Y. enterocolitica*, BpaA (*B. pseudomallei*), Hia (*H. influenzae*), BadA (*B. henselae*), NadA (*N. meningitidis*) or UspA1 (*M. catarrhalis*) as well as other autotransporter adhesins such as AIDA-1 (*E. coli*) as well as other adhesins/invasins such as InvA from *Y. enterocolitica* or Intimin (*E. coli*) or members of the Dr-family or Afa-family (*E. coli*). The terms YadA and InvA as used herein refer to proteins from *Y. enterocolitica*. The autotransporter YadA[7] binds to different forms of collagen as well as fibronectin, while the invasin InvA[8] binds to β-integrins in the eukaryotic cell membrane. If the Gram-negative bacterial strain is a *Y. enterocolitica* strain the strain is preferably deficient in InvA and/or YadA.

As used herein, the term "family of Enterobacteriaceae" comprises a family of gram-negative, rod-shaped, facultatively anaerobic bacteria found in soil, water, plants, and animals, which frequently occur as pathogens in vertebrates. The bacteria of this family share a similar physiology and demonstrate a conservation within functional elements and genes of the respective genomes. As well as being oxidase negative, all members of this family are glucose fermenters and most are nitrate reducers.

Enterobacteriaceae bacteria of the invention may be any bacteria from that family, and specifically includes, but is not limited to, bacteria of the following genera: *Escherichia, Shigella, Edwardsiella, Salmonella, Citrobacter, Klebsiella, Enterobacter, Serratia, Proteus, Erwinia, Morganella, Providencia*, or *Yersinia*. In more specific embodiments, the bacterium is of the *Escherichia coli, Escherichia blattae, Escherichia fergusonii, Escherichia hermanii, Escherichia vuneris, Salmonella enterica, Salmonella bongori, Shigella dysenteriae, Shigella flexneri, Shigella boydii, Shigella sonnei, Enterobacter aerogenes, Enterobacter gergoviae, Enterobacter sakazakii, Enterobacter cloacae, Enterobacter agglomerans, Klebsiella pneumoniae, Klebsiella oxytoca, Serratia marcescens, Yersinia pseudotuberculosis, Yersinia pestis, Yersinia enterocolitica, Erwinia amylovora, Proteus mirabilis, Proteus vulgaris, Proteus penneri, Proteus hauseri, Providencia alcalifaciens*, or *Morganella morganii* species.

Preferably the Gram-negative bacterial strain is selected from the group consisting of the genera *Yersinia, Escherichia, Salmonella, Shigella, Pseudomonas, Chlamydia, Erwinia, Pantoea, Vibrio, Burkholderia, Ralstonia, Xanthomonas, Chromobacterium, Sodalis, Citrobacter, Edwardsiella, Rhizobiae, Aeromonas, Photorhabdus, Bordetella* and *Desulfovibrio*, more preferably from the group consisting of the genera *Yersinia, Escherichia, Salmonella*, and *Pseudomonas*, most preferably from the group consisting of the genera *Yersinia* and *Salmonella*, in particular *Yersinia*.

The term "*Yersinia*" as used herein includes all species of *Yersinia*, including *Yersinia enterocolitica, Yersinia pseudotuberculosis* and *Yersinia pestis*. Preferred is *Yersinia enterocolitica*.

The term "*Salmonella*" as used herein includes all species of *Salmonella*, including *Salmonella enterica* and *S. bongori*. Preferred is *Salmonella enterica*.

"Promoter" as used herein refers to a nucleic acid sequence that regulates expression of a transcriptional unit. A "promoter region" is a regulatory region capable of binding RNA polymerase in a cell and initiating transcription of a downstream (3' direction) coding sequence. Within the promoter region will be found a transcription initiation site (conveniently defined by mapping with nuclease Si), as well as protein binding domains (consensus sequences) responsible for the binding of RNA polymerase such as the putative −35 region and the Pribnow box. The term "operably linked" when describing the relationship between two nucleotide e.g. DNA regions simply means that they are functionally related to each other and they are located on the same nucleic acid fragment. A promoter is operably linked to a structural gene if it controls the transcription of the gene and it is located on the same nucleic acid fragment as the gene. Usually the promoter is functional in said Gram-negative bacterial strain, i.e. the promoter is capable of expressing the fusion protein of the present invention, i.e. the promoter is capable of expressing the fusion protein of the present invention without further genetic engineering or expression of further proteins. Furthermore, a functional promoter must not be naturally counter-regulated to the bacterial T3SS.

The term "extra-chromosomal genetic element" used herein refers to a genetic element other than a chromosome which is endogenously harboured by the Gram-negative bacterial strain of the present invention such as a virulence plasmid or which is an exogenous genetic element with which the Gram-negative bacterial strain is transformed and which is transiently or stably integrated into the chromosome or into a genetic element other than a chromosome which is endogenously harboured such as a virulence plasmid. Such an extra-chromosomal genetic element may be a vector like an expression vector, a vector for homologous recombination or other integration into the chromosome or into a genetic element other than a chromosome which is endogenously harboured such as a virulence plasmid, DNA fragments for homologous recombination or other integration into the chromosome or into a genetic element other than a chromosome which is endogenously harboured such as a virulence plasmid or an RNA element guiding site specific insertion into the chromosome or into a genetic element other than a chromosome which is endogenously harboured such as a virulence plasmid, such as CRISPR/Cas9 and related guide RNA.

The term "RNA thermosensor region" used herein refers to a temperature-sensitive non-coding RNA sequence, which is regulating gene expression of related genes. Usually RNA thermosensor regions function by forming a secondary structure as a RNA hairpin loop, which is stably formed at a repressive temperature and instable at a permissive temperature, and which is masking a RNA sequence essential for translation such as a ribosome binding site, this way regulating expression of a gene related to such a RNA sequence essential for translation.

The term "RNA hairpin structure or parts thereof" used herein refers to a RNA secondary structure formed by intramolecular base-pairing leading to a stem-loop structure. The intramolecular base-paring, generally within the same RNA strand, is formed due to complementary nucleotide sequences or parts thereof.

The term "AraC-type DNA binding protein", also referred as AraC/XylS family, used herein refers to bacterial transcription regulation proteins bind DNA through a helix-turn-helix motif. Most members of the AraC-type DNA binding proteins are positive transcriptional regulators, and can be characterized by a minimal DNA binding domain extending over a 100 residue stretch containing two helix-turn-helix subdomains. AraC-type DNA binding proteins specifically include, but are not limited to: VirF, LcrF, YbtA, Rns, MxiE, AraC, XylS, ExsA, PerA, MmsR, RhaS, TcpN, HrpX, HrpB, GadX, HilC, HilD, MarA, CafR, FapR and InvF. Preferred are AraC-type DNA binding proteins involved in regulation of virulence relevant mechanisms, such as VirF, LcrF, YbtA, Rns, MxiE, ExsA, PerA, HrpX, HrpB, GadX, HilC, HilD, TcpN, CafR, FapR and InvF. More preferred are AraC-type DNA binding proteins involved in regulation of the type three secretion system activity as VirF, LcrF, MxiE, ExsA, PerA, HrpX, HrpB, GadX, HilC, HilD and InvF, most preferred are VirF and/or LcrF.

The term "delivery" used herein refers to the transportation of a protein from a recombinant virulence attenuated Gram-negative bacterial strain to a eukaryotic cell, including the steps of expressing the heterologous protein in the recombinant virulence attenuated Gram-negative bacterial strain, secreting the expressed protein(s) from such recombinant virulence attenuated Gram-negative bacterial strain and translocating the secreted protein(s) by such recombinant virulence attenuated Gram-negative bacterial strain into the cytosol of the eukaryotic cell. Accordingly, the terms "delivery signal" or "secretion signal" which are used interchangeably herein refer to a polypeptide sequence which can be recognized by the secretion and translocation system of the Gram-negative bacterial strain and directs the delivery of a protein from the Gram-negative bacterial strain to eukaryotic cells.

The term "delivery signal from a bacterial effector protein" used herein refers to a delivery signal from a bacterial effector protein functional in the recombinant Gram-negative bacterial strain, i.e. which allows an expressed heterologous protein in the recombinant Gram-negative bacterial strain to be secreted from such recombinant Gram-negative bacterial strain by a secretion system such as the type III, type IV or type VI secretion system or to be translocated by such recombinant Gram-negative bacterial strain into the cytosol of a eukaryotic cell by a secretion system such as the type III, type IV or type VI secretion system. The term "delivery signal from a bacterial effector protein" used herein also comprises a fragment of a delivery signal from a bacterial effector protein i.e. shorter versions of a delivery signal e.g. a delivery signal comprising up to 10, preferably up to 20, more preferably up to 50, even more preferably up to 100, in particular up to 140 amino acids of a delivery signal e.g. of a naturally occurring delivery signal. Thus a nucleotide sequence such as e.g. a DNA sequence encoding a delivery signal from a bacterial effector protein may encode a full length delivery signal or a fragment thereof wherein the fragment usually comprises usually up to 30, preferably up to 60, more preferably up to 150, even more preferably up to 300, in particular up to 420 nucleic acids.

As used herein, the "secretion" of a protein refers to the transportation of a heterologous protein outward across the cell membrane of a recombinant virulence attenuated Gram-negative bacterial strain. The "translocation" of a protein refers to the transportation of a heterologous protein from a recombinant virulence attenuated Gram-negative bacterial strain across the plasma membrane of a eukaryotic cell into the cytosol of such eukaryotic cell.

The term "bacterial protein, which is part of a secretion system machinery" as used herein refers to bacterial proteins constituting essential components of the bacterial type 3 secretion system (T3SS), type 4 secretion system (T4SS) and type 6 secretion system (T6SS), preferably T3SS. Without such proteins, the respective secretion system is nonfunctional in translocating proteins to host cells, even if all other components of the secretion system and the bacterial effector protein to be translocated are still encoded and produced.

The term "bacterial effector protein" as used herein refers to bacterial proteins transported by secretion systems e.g. by bacterial proteins, which are part of a secretion system machinery into host cells. Such effector proteins are deliverd by a secretion system into a host cell where they excert e.g. virulence activity toward various host proteins and cellular machineries. Many different effector proteins are known, transported by various secretion system types and displaying a large repertoire of biochemical activities that modulate the functions of host regulatory molecules. Secretion systems include type 3 secretion system (T3SS), type 4 secretion system (T4SS) and type 6 secretion system (T6SS). Some effector proteins (as *Shigella flexneri* IpaC) as well belong to the class of bacterial protein, which are part of a secretion system machinery and allow protein translocation. The recombinant virulence attenuated Gram-negative bacterial strain used herein usually comprises bacterial proteins constituting essential components of the bacterial type 3 secretion system (T3SS), type 4 secretion system (T4SS) and/or the type 6 secretion system (T6SS), preferably of the type 3 secretion system (T3SS). The term "bacterial proteins constituting essential components of the bacterial T3SS" as used herein refers to proteins, which are naturally forming the injectisome e.g. the injection needle or are otherwise essential for its function in translocating proteins into eukaryotic cells. Proteins forming the injectisome or are otherwise essential for its function in translocating proteins into eukaryotic cells include, but are not limited to: SctC, YscC, MxiD, InvG, SsaC, EscC, HrcC, HrcC (Secretin), SctD, YscD, MxiG, Prg, SsaD, EscD, HrpQ, HrpW, FliG (Outer MS ring protein), SctJ, YscJ, MxiJ, PrgK, SsaJ, EscJ, HrcJ, HrcJ, FliF (Inner MS ring protein), SctR, YscR, Spa24, SpaP, SpaP, SsaR, EscR, HrcR, HrcR, FliP (Minor export apparatus protein), SctS, YscS, Spa9 (SpaQ), SpaQ, SsaS, EscS, HrcS, HrcS, FliQ (Minor export apparatus protein), SctT, YscT, Spa29 (SpaR), SpaR, SsaT, EscT, HrcT, HrcT, FliR (Minor export apparatus protein), SctU, YscU, Spa40, SpaS, SpaS, SsaU, EscU, HrcU, HrcU, FlhB (Export apparatus switch protein), SctV, YscV, MxiA, InvA, SsaV, EscV, HrcV, HrcV, FlhA (Major export apparatus protein), SctK, YscK, MxiK, OrgA, HrpD (Accessory cytosolic protein), SctQ, YscQ, Spa33, SpaO, SpaO, SsaQ, EscQ, HrcQA+B, HrcQ, FliM+FliN (C ring protein), SctL, YscL, MxiN, OrgB, SsaK, EscL, Orf5, HrpE, HrpF, FliH (Stator), SctN, YscN, Spa47, SpaL, InvC, SsaN, EscN, HrcN, HrcN, FliI (ATPase), SctO, YscO, Spa13, SpaM, InvI, SsaO, Orf15, HrpO, HrpD, FliJ (Stalk), SctF, YscF, MxiH, Prgl, SsaG, EscF, HrpA, HrpY (Needle filament protein), SctI, YscI, MxiI, PrgJ, SsaI, EscI, rOrf8, HrpB, HrpJ, (Inner rod protein), SctP, YscP, Spa32, SpaN, InvJ, SsaP, EscP, Orf16, HrpP, HpaP, FliK (Needle length regulator), LcrV, IpaD, SipD (Hydrophilic translocator, needle tip protein), YopB, IpaB, SipB, SseC, EspD, HrpK, PopF1, PopF2 (Hydrophobic translocator, pore protein), YopD, IpaC, SipC, SseD, EspB (Hydrophobic translocator, pore protein), YscW, MxiM, InvH (Pilotin), SctW, YopN, MxiC, InvE, SsaL, SepL, HrpJ, HpaA (Gatekeeper).

The term "T6SS effector protein" or "bacterial T6SS effector protein" as used herein refers to proteins which are naturally injected by T6S systems into the cytosol of eukaryotic cells or bacteria and to proteins which are naturally secreted by T6S systems that might e.g form translocation pores into the eukaryotic membrane. The term "T4SS effector protein" or "bacterial T4SS effector protein" as used herein refers to proteins which are naturally injected by T4S systems into the cytosol of eukaryotic cells and to proteins which are naturally secreted by T4S systems that might e.g form the translocation pore into the eukaryotic membrane.

The term "T3SS effector protein" or "bacterial T3SS effector protein" as used herein refers to proteins which are naturally injected by T3S systems into the cytosol of eukaryotic cells and to proteins which are naturally secreted by T3 S systems that might e.g form the translocation pore into the eukaryotic membrane (including pore-forming tranlocators (as *Yersinia* YopB and YopD) and tip-proteins like *Yersinia* LcrV). Preferably proteins which are naturally injected by T3S systems into the cytosol of eukaryotic cells are used. These virulence factors will paralyze or reprogram the eukaryotic cell to the benefit of the pathogen. T3S effectors display a large repertoire of biochemical activities and modulate the function of crucial host regulatory molecules and include AvrA, AvrB, AvrBs2, AvrBS3, AvrBsT, AvrD, AvrD1, AvrPphB, AvrPphC, AvrPphEPto, AvrPpiBPto, AvrPto, AvrPtoB, AvrRpm1, AvrRpt2, AvrXv3, CigR, EspF, EspG, EspH, EspZ, ExoS, ExoT, GogB, GtgA, GtgE, GALA family of proteins, HopAB2, HopAO1, HopI1, HopM1, HopN1, HopPtoD2, HopPtoE, HopPtoF, HopPtoN, HopU1, HsvB, IcsB, IpaA, IpaB, IpaC, IpaH, IpaH7.8, IpaH9.8, IpgB1, IpgB2, IpgD, LcrV, Map, OspC1, OspE2, OspF, OspG, OspI, PipB, PipB2, PopB, PopP2, PthXo1, PthXo6, PthXo7, SifA, SifB, SipA/SspA, SipB, SipC/SspC, SipD/SspD, SlrP, SopA, SopB/SigD, SopD, SopE, SopE2, SpiC/SsaB, SptP, SpvB, SpvC, SrfH, SrfJ, Sse, SseB, SseC, SseD, SseF, SseG, SseI/SrfH, SseJ, SseK1, SseK2, SseK3, SseL, SspH1, SspH2, SteA, SteB, SteC, SteD, SteE, TccP2, Tir, VirA, VirPphA, VopF, XopD, YopB, YopD YopE, YopH, YopJ, YopM, YopO, YopP, YopT, YpkA.

The term "recombinant virulence attenuated Gram-negative bacterial strain accumulating in a malignant solid tumor" or "the recombinant virulence attenuated Gram-negative bacterial strain accumulates in a malignant solid tumor" as used herein refers to a recombinant virulence attenuated Gram-negative bacterial strain which replicates within a malignant solid tumor thereby increasing the bacterial count of this recombinant virulence attenuated Gram-negative bacterial strain inside the malignant solid tumor. Surprisingly it has been found that the recombinant virulence attenuated Gram-negative bacterial strain after administration to the subject accumulates specifically in the malignant solid tumor i.e. accumulates specifically in the organ where the malignant tumor is present, wherein the bacterial counts of the recombinant virulence attenuated Gram-negative bacterial strain in organs where no malignant solid tumor is present is low or not detectable.

In case of extracellular residing bacteria as *Yersinia*, the bacteria mostly accumulate within the intercellular space formed between tumor cells. Intracellular growing bacteria as *Salmonella* will mostly invade tumor cells and reside inside such cells, while extracellular accumulations might still occur. Bacterial counts of the recombinant virulence attenuated Gram-negative bacterial strain accumulated inside the malignant solid tumor can be e.g. in the range of $10^4$ to $10^9$ bacteria per gram of tumor tissue.

The term "cancer" used herein refers to a disease in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. The term "cancer" used herein comprises solid tumors i.e. malignant solid tumors such as e.g. sarcomas, carcinomas, and lymphomas and non-solid tumors such as e.g. leukemias (cancers of the blood). Malignant solid tumors are preferred.

The term "malignant solid tumor" or "malignant solid tumor indication" used herein refers to an abnormal mass of tissue that usually does not contain cysts or liquid areas. Solid tumors may be benign (not cancer), or malignant (cancer). Malignant solid tumors are treated with the methods of the present invention. Different types of malignant solid tumors are named for the type of cells that form them. Examples of malignant solid tumors are sarcomas, carcinomas, and lymphomas. Leukemias (cancers of the blood) generally do not form malignant solid tumors (definition according to the national cancer institute of the Malignant solid tumors include, but are not limited to, abnormal mass of cells which may stem from different tissue types such as liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung and thus include malignant solid liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung tumors. Preferred malignant solid tumors which can be treated with the methods of the present invention are malignant solid tumors which stem from skin, breast, liver, pancreas, bladder, prostate and colon and thus include malignant solid skin, breast, liver, pancreas, bladder, prostate and colon tumors. Equally preferred malignant solid tumors which can be treated with the methods of the present invention are malignant solid tumors associated with liver cancer, such as hepatocellular carcinoma.

The term "bacterial effector protein which is virulent toward eukaryotic cells" as used herein refers to bacterial effector proteins, which are transported by secretion systems into host cells where they excert their virulence activity toward various host proteins and cellular machineries. Many different effector proteins are known, transported by various secretion system types and displaying a large repertoire of biochemical activities that modulate the functions of host regulatory molecules. Secretion systems include type 3 secretion system (T3SS), type 4 secretion system (T4SS) and type 6 secretion system (T6SS). Importantly, some effector proteins which are virulent toward eukaryotic cells (as *Shigella flexneri* IpaC) as well belong to the class of bacterial proteins, which are part of a secretion system machinery. In case the bacterial effector protein which is virulent toward eukaryotic cells is as well essential for the function of the secretion machinery, such a protein is excluded from this definition. T3SS effector proteins which are virulent towards eukaryotic cells refers to proteins as *Y. enterocolitica* YopE, YopH, YopJ, YopM, YopO, YopP, YopT or *Shigella flexneri* OspF, IpgD, IpgB1 or *Salmonella enterica* SopE, SopB, SptP or *P. aeruginosa* ExoS, ExoT, ExoU, ExoY or *E. coli* Tir, Map, EspF, EspG, EspH, EspZ. T4SS effector proteins which are virulent towards eukaryotic cells refers to proteins as *Legionella pneumophila* LidA, SidC, SidG, SidH, SdhA, SidJ, SdjA, SdeA, SdeA, SdeC, LepA, LepB, WipA, WipB, YlfA, YlfB, VipA, VipF, VipD, VpdA, VpdB, DrrA, LegL3, LegL5, LegL7, LegLC4, LegLC8, LegC5, LegG2, Ceg10, Ceg23, Ceg29 or *Bartonella henselae* BepA, BepB, BepC, BepD, BepE, BepF BepG or *Agrobacterium tumefaciens* VirD2, VirE2, VirE3, VirF or *H. pylori* CagA or *Bordetella pertussis* pertussis toxin. T6SS effector proteins which are virulent towards eukaryotic cells refers to proteins as *Vibrio cholerae* VgrG proteins (as VgrG1).

The term "T3SS effector protein which is virulent toward eukaryotic cells" or "bacterial T3SS effector protein which is virulent toward eukaryotic cells" as used herein refers to proteins which are naturally injected by T3S systems into the cytosol of eukaryotic cells and to proteins which are naturally secreted by T3 S systems that might e.g form the translocation pore into the eukaryotic membrane, which are virulence factors toward eukaryotic cells i.e. to proteins which paralyze or reprogram the eukaryotic cell to the benefit of the pathogen. Effectors display a large repertoire of biochemical activities and modulate the function of crucial host regulatory mechanisms such as e.g. phagocytosis and the actin cytoskeleton, inflammatory signaling, apoptosis, endocytosis or secretory pathways[2,9] and include AvrA, AvrB, AvrBs2, AvrB S3, AvrBsT, AvrD, AvrD1, AvrPphB, AvrPphC, AvrPphEPto, AvrPpiBPto, AvrPto, AvrPtoB, AvrRpm1, AvrRpt2, AvrXv3, CigR, EspF, EspG, EspH, EspZ, ExoS, ExoT, GogB, GtgA, GtgE, GALA family of proteins, HopAB2, HopAO1, HopI1, HopM1, HopN1, HopPtoD2, HopPtoE, HopPtoF, HopPtoN, HopU1, HsvB, IcsB, IpaA, IpaH, IpaH7.8, IpaH9.8, IpgB1, IpgB2, IpgD, LcrV, Map, OspC1, OspE2, OspF, OspG, OspI, PipB, PipB2, PopB, PopP2, PthXo1, PthXo6, PthXo7, SifA, SifB, SipA/SspA, SlrP, SopA, SopB/SigD, SopD, SopE, SopE2, SpiC/SsaB, SptP, SpvB, SpvC, SrfH, SrfJ, Sse, SseB, SseC, SseD, SseF, SseG, SseI/SrfH, SseJ, SseK1, SseK2, SseK3, SseL, SspH1, SspH2, SteA, SteB, SteC, SteD, SteE, TccP2, Tir, VirA, VirPphA, VopF, XopD, YopE, YopH, YopJ, YopM, YopO, YopP, YopT, YpkA.

T3SS effector genes of *Yersinia* which are virulent to a eukaryotic cell and can be deleted/mutated from e.g. *Y. enterocolitica* are YopE, YopH, YopM, YopO, YopP (also named YopJ), and YopT[10]. The respective effector genes which are virulent to a eukaryotic cell can be deleted/mutated from *Shigella flexneri* (e.g. OspF, IpgD, IpgB1), *Salmonella enterica* (e.g. SopE, SopB, SptP), *P. aeruginosa* (e.g ExoS, ExoT, ExoU, ExoY) or *E. coli* (e.g. Tir, Map, EspF, EspG, EspH, EspZ). The nucleic acid sequences of these genes are available to those skilled in the art, e.g., in the Genebank Database (yopH, yopO, yopE, yopP, yopM, yopT from NC 002120 GI:10955536; *S. flexneri* effector proteins from AF386526.1 GI:18462515; *S. enterica* effectors from NC_016810.1 GI:378697983 or FQ312003.1 GI:301156631; *P. aeruginosa* effectors from AE004091.2 GI:110227054 or CP000438.1 GI:115583796 and *E. coli* effector proteins from NC_011601.1 GI:215485161).

For the purpose of the present invention, genes are denoted by letters of lower case and italicised to be distinguished from proteins. In case the genes (denoted by letters of lower case and italicised) are following a bacterial species name (like *E. coli*), they refer to a mutation of the corresponding gene in the corresponding bacterial species. For example, YopE refers to the effector protein encoded by the yopE gene. *Y. enterocolitica* yopE represents a *Y. enterocolitica* having a mutaion in the yopE gene.

As used herein, the terms "polypeptide", "peptide", "protein", "polypeptidic" and "peptidic" are used interchangeably to designate a series of amino acid residues connected to each other by peptide bonds between the alpha-amino and carboxy groups of adjacent residues. Preferred are proteins which have an amino acid sequence comprising at least 10 amino acids, more preferably at least 20 amino acids.

According to the present invention, “a heterologous protein” includes naturally occurring proteins or a part thereof and also includes artificially engineered proteins or a part thereof. As used herein, the term “heterologous protein” refers to a protein or a part thereof other than the T3 SS effector protein or N-terminal fragment thereof to which it can be fused. In particular the heterologous protein as used herein refers to a protein or a part thereof, which do not belong to the proteome, i.e. the entire natural protein complement of the specific recombinant virulence attenuated Gram-negative bacterial strain provided and used by the invention, e.g. which do not belong to the proteome, i.e. the entire natural protein complement of a specific bacterial strain of the genera *Yersinia, Escherichia, Salmonella* or *Pseudomonas*. Usually the heterologous protein is of animal origin including human origin. Preferably the heterologous protein is a human protein or a part thereof. More preferably the heterologous protein is selected from the group consisting of proteins involved in induction or regulation of an interferon (IFN) response, proteins involved in apoptosis or apoptosis regulation, cell cycle regulators, ankyrin repeat proteins, cell signaling proteins, reporter proteins, transcription factors, proteases, small GTPases, GPCR related proteins, nanobody fusion constructs and nanobodies, bacterial T3SS effectors, bacterial T4SS effectors and viral proteins. Particular preferably the heterologous protein is selected from the group consisting of proteins involved in induction or regulation of an interferon (IFN) response, proteins involved in apoptosis or apoptosis regulation, cell cycle regulators, ankyrin repeat proteins, reporter proteins, small GTPases, GPCR related proteins, nanobody fusion constructs, bacterial T3SS effectors, bacterial T4SS effectors and viral proteins. Even more particular preferred are heterologous proteins selected from the group consisting of proteins involved in induction or regulation of an interferon (IFN) response, proteins involved in apoptosis or apoptosis regulation, cell cycle regulators, and ankyrin repeat proteins. Most preferred are proteins involved in apoptosis or apoptosis regulation or proteins involved in induction or regulation of an interferon (IFN) response, in particular proteins involved in induction or regulation of an interferon (IFN) response, like animal, preferably human heterologous proteins involved in apoptosis or apoptosis regulation or human proteins involved in induction or regulation of an interferon (IFN) response. Proteins involved in induction or regulation of an interferon (IFN) response are preferably proteins, involved in induction or regulation of a type I interferon (IFN) response, more preferably human proteins involved in induction or regulation of a type I interferon (IFN) response.

In some embodiments the Gram-negative bacterial strain of the present invention comprises two nucleotide sequences encoding the identical or two different heterologous proteins fused independently from each other in frame to the 3'end of a nucleotide sequence encoding a delivery signal from a bacterial effector protein. In some embodiments the the Gram-negative bacterial strain of the present invention comprises three nucleotide sequences encoding the identical or three different heterologous proteins fused independently from each other in frame to the 3'end of a nucleotide sequence encoding a delivery signal from a bacterial effector protein. The heterologous protein expressed by the recombinant virulence attenuated Gram-negative bacterial strain has usually a molecular weight of between 1 and 150 kD, preferably between 1 and 120 kD, more preferably between land 100 kDa, most preferably between 10 and 80 kDa.

In some embodiments a part of a heterologous protein comprises a domain of a heterologous protein. Thus in some embodiments the Gram-negative bacterial strain of the present invention comprises a nucleotide sequence encoding a domain of a heterologous protein. Preferably the Gram-negative bacterial strain of the present invention comprises a nucleotide sequence encoding one or two domains of a heterologous protein, more preferably two domains of a heterologous protein.

In some embodiments the Gram-negative bacterial strain of the present invention comprises a nucleotide sequence encoding repeated domains of a heterologous protein or two or more domains of different heterologous proteins fused in frame to the 3'end of a nucleotide sequence encoding a delivery signal from a bacterial effector protein.

The term “heterologous proteins which belong to the same functional class of proteins” as used herein refers to heterologous proteins which have the same function e.g. heterologous proteins having enzymatic activity, heterologous proteins which act in the same pathway such as e.g. cell cycle regulation, or share a common specific feature as e.g. belonging to the same class of bacterial effector proteins. Functional classes of proteins are e.g. proteins involved in apoptosis or apoptosis regulation, proteins which act as cell cycle regulators, ankyrin repeat proteins, cell signaling proteins, proteins involved in induction or regulation of an interferon (IFN) response, reporter proteins, transcription factors, proteases, small GTPases, GPCR related proteins, nanobody fusion constructs and nanobodies, bacterial T3SS effectors, bacterial T4SS effectors or viral proteins which act jointly in the biological process of establishing virulence to eukaryotic cells.

According to the present invention, “a domain of a heterologous protein” includes domains of naturally occurring proteins and also includes domains of artificially engineered proteins. As used herein, the term “domain of a heterologous protein” refers to a domain of a heterologous protein other than a domain of a T3SS effector protein or a domain other than a domain comprising the N-terminal fragment thereof to which it can be fused to achieve a fusion protein. In particular the domain of a heterologous protein as used herein refers to a domain of a heterologous protein, which do not belong to the proteome, i.e. the entire natural protein complement of the specific recombinant Gram-negative bacterial strain provided and used by the invention, e.g. which do not belong to the proteome, i.e. the entire natural protein complement of a specific bacterial strain of the genera *Yersinia, Escherichia, Salmonella* or *Pseudomonas*. Usually the domain of the heterologous protein is of animal origin including human origin. Preferably the domain of the heterologous protein is a domain of a human protein. More preferably the domain of the heterologous protein is a domain of a protein selected from the group consisting of proteins involved in apoptosis or apoptosis regulation, proteins involved in induction or regulation of an interferon (IFN) response, cell cycle regulators, ankyrin repeat proteins, cell signaling proteins, reporter proteins, transcription factors, proteases, small GTPases, GPCR related proteins, nanobody fusion constructs and nanobodies, bacterial T3SS effectors, bacterial T4SS effectors and viral proteins. Particular preferably the domain of the heterologous protein is a domain of a protein selected from the group consisting of proteins involved in apoptosis or apoptosis regulation, proteins involved in induction or regulation of an interferon (IFN) response, cell cycle regulators, ankyrin repeat proteins, reporter proteins, small GTPases, GPCR related proteins, nanobody fusion constructs, bacterial T3SS effectors, bacterial T4SS effectors and viral proteins. Even more particular preferred are domains of heterologous proteins selected from the group consisting of proteins involved in apoptosis or apoptosis regulation, proteins involved in induction or regulation of an interferon (IFN) response, cell cycle regulators, and ankyrin repeat proteins. Most preferred are domains of proteins involved in induction or regulation of an interferon (IFN) response, like animal proteins involved in induction or regulation of an interferon (IFN) response, preferably domains of human heterologous proteins involved in induction or regulation of an interferon (IFN) response.

The term "repeated domains of a heterologous protein" as used herein refers to a fusion protein consisting of several repetitions of a domain of a heterologous protein, where these domains might either be directly fused to each other or where a variable linker e.g. a linker between 1 and 30, preferably between 2 and 15, more preferably between 3 and 10 amino acids might be introduced in between the domains. Preferably repeated identical domains or repeated domains which have an amino acid sequence identity of more than 80%, usually more than 85%, preferably more than 90%, even more preferably more than 95%, in particular more than 96%, more particular more than 97%, even more particular more than 98%, most particular more than 99% are used. Also preferred are identical domains which have an amino acid identity of 100%. Preferably two repeated domains, more preferably two repeated identical domains or two repeated domains having an amino acid sequence identity of more than 90%, preferably more than 95%, most preferably 100% are comprised by the fusion protein as referred herein. More than two, e.g. three, four, five or six repeated domains are also contemplated by the present invention.

The term "two or more domains of different heterologous proteins" as used herein refers to a fusion protein consisting of one or several repetitions of at least two domains of different heterologous proteins e.g. at least two domains of heterologous proteins having an amino acid sequence identity of 80% or less, preferably 60% or less, more preferably 40% or less, where these different domains might either be directly fused to each other or where a variable linker e.g. a linker between 1 and 30, preferably between 2 and 15, more preferably between 3 and 10 amino acids might be introduced in between the domains. Preferably two domains of different heterologous proteins are comprised by the fusion protein as referred herein. More than two, e.g. three, four, five or six domains of different heterologous proteins are also contemplated by the present invention.

The domain of a heterologous protein expressed by the recombinant Gram-negative bacterial strain has usually a molecular weight of between 1-50 kDa, preferably between 1-30 kDa, more preferably between 1-20 kDa, most preferably between 1-10 kDa.

According to the present invention "proteins involved in induction or regulation of an IFN response" include, but are not limited to, cGAS, STING, TRIF, TBK1, IKKepsilon, IRF3, TREX1, VPS34, ATG9a, DDX3, LC3, DDX41, IFI16, MRE11, DNA-PK, RIG1, MDA5, LGP2, IPS-1/MAVS/Cardif/VISA, Trim25, Trim32, Trim56, Riplet, TRAF2, TRAF3, TRAF5, TANK, IRF3, IRF7, IRF9, STAT1, STAT2, PKR, TLR3, TLR7, TLR9, DAI, IFI16, IFIX, MRE11, DDX41, LSm14A, LRRFIP1, DHX9, DHX36, DHX29, DHX15, Ku70, IFNAR1, IFNAR2, TYK2, JAK1, ISGF3, IL10R2, IFNLR1, IFNGR1, IFNGR2, JAK2, STAT4, cyclic dinucleotide generating enzymes (cyclic-di-AMP, cyclic-di-GMP and cyclic-di-GAMP cyclases) as WspR, DncV, DisA and DisA-like, CdaA, CdaS and cGAS or a fragment thereof.

According to the present invention "proteins involved in induction or regulation of a type I IFN response" include, but are not limited to, cGAS, STING, TRIF, TBK1, IKKepsilon, IRF3, TREX1, VPS34, ATG9a, DDX3, LC3, DDX41, IFI16, MRE11, DNA-PK, RIG1, MDA5, LGP2, IPS-1/MAVS/Cardif/VISA, Trim25, Trim32, Trim56, Riplet, TRAF2, TRAF3, TRAF5, TANK, IRF3, IRF7, IRF9, STAT1, STAT2, PKR, TLR3, TLR7, TLR9, DAI, IFI16, IFIX, MRE11, DDX41, LSm14A, LRRFIP1, DHX9, DHX36, DHX29, DHX15, Ku70, cyclic dinucleotide generating enzymes (cyclic-di-AMP, cyclic-di-GMP and cyclic-di-GAMP cyclases) as WspR, DncV, DisA and DisA-like, CdaA, CdaS and cGAS or a fragment thereof.

Preferred proteins involved in induction or regulation of a type I IFN response are selected from the group consisting of cGAS, STING, TRIF, TBK1, IKKepsilon, IRF3, TREX1, VPS34, ATG9a, DDX3, LC3, DDX41, IFI16, MRE11, DNA-PK, RIG1, MDA5, LGP2, IPS-1/MAVS/Cardif/VISA, Trim25, Trim32, Trim56, Riplet, TRAF2, TRAF3, TRAF5, TANK, IRF3, IRF7, IRF9, STAT1, STAT2, PKR, LSm14A, LRRFIP1, DHX29, DHX15, and cyclic dinucleotide generating enzymes such as cyclic-di-AMP, cyclic-di-GMP and cyclic-di-GAMP cyclases selected from the group consisting of WspR, DncV, DisA and DisA-like, CdaA, CdaS and cGAS or a fragment thereof.

More preferred proteins involved in induction or regulation of a type I IFN response are selected from the group consisting of cGAS (as Uniprot. Q8N884 for the human protein), RIG1 (as Uniprot. 095786 for the human protein), MDA5 (as Uniprot. Q9BYX4 for the human protein), IPS-1/MAVS (as Uniprot. Q7Z434 for the human protein), IRF3 (as Uniprot. Q14653 for the human protein), IRF7 (as Uniprot. Q92985 for the human protein), IRF9 (as Uniprot. Q00978 for the human protein) and cyclic dinucleotide generating enzymes such as cyclic-di-AMP, cyclic-di-GMP and cyclic-di-GAMP cyclases selected from the group consisting of WspR (as Uniprot. Q9HXT9 for the *P. aeruginosa* protein), DncV (as Uniprot. Q9KVG7 for the *V. cholerae* protein), DisA and DisA-like (as Uniprot. Q812L9 for the *B. cereus* protein), CdaA (as Uniprot. Q8Y5E4 for the *L. monocytogenes* protein), CdaS (as Uniprot. 031854 or constitutive active L44F mutation as in Seq ID No.114 for the *B. subtilis* protein) and cGAS (as Uniprot. Q8N884 for the human protein) or a fragment of these proteins.

IPS-1/MAVS/Cardif/VISA refer to the eukaryotic mitochondrial antiviral-signaling protein containing an N-terminal CARD domain and with the Uniprot (www.uniprot.org) identifier for the human sequence "Q7Z434" and "Q8VCF0" for the murine sequence. The terms "IPS-1/MAVS", "MAVS/IPS-1" and "MAVS" are used herein interchangeably and refer to the eukaryotic mitochondrial antiviral-signaling protein containing an N-terminal CARD domain and with the Uniprot (www.uniprot.org) identifier for the human sequence "Q7Z434" and "Q8VCF0" for the murine sequence.

In some embodiments the heterologous proteins involved in induction or regulation of a type I IFN response are selected from the group consisting of a CARD domain containing proteins or a fragment thereof and cyclic dinucleotide generating enzymes such as cyclic-di-AMP, cyclic-di-GMP and cyclic-di-GAMP cyclases or a fragment thereof.

A fragment of a heterologous proteins involved in induction or regulation of a IFN response or a type I IFN response contains usually between 25 and 1000 amino acids, preferably between 50 and 600 amino acids, more preferably between 100 and 400 amino acids, even more preferably between 100 and 362 amino acids. In some embodiments a fragment of a heterologous proteins involved in induction or regulation of a IFN response or a type I IFN response comprises a N-terminal fragment of the heterologous proteins involved in induction or regulation of a IFN response or a type I IFN response which contains usually between 25 and 1000 amino acids, preferably between 50 and 600 amino acids, more preferably between 100 and 400 amino acids, even more preferably between 100 and 362 amino acids, in particular between 100 and 246 amino acids or, comprises a N-terminal fragment of the heterologous protein involved in induction or regulation of a IFN response or a type I IFN response which has a deletion of an amino acid sequence containing between amino acid 1 and amino acid 160 of the N-terminal amino acids, preferably a deletion of an amino acid sequence containing N-terminal amino aids 1-59 or N-terminal amino aids 1-160, and wherein the N-terminal fragment of the heterologous protein involved in induction or regulation of a IFN response or a type I IFN response contains usually between 25 and 1000 amino acids, preferably between 50 and 600 amino acids, more preferably between 100 and 400 amino acids, even more preferably between 100 and 362 amino acids.

A fragment of a CARD domain containing heterologous proteins involved in induction or regulation of a IFN response or a type I IFN response contains usually an amino acid sequence from N-terminal amino acid 1 to any of N-terminal amino acid 100-500, preferably an amino acid sequence from N-terminal amino acid 1 to any of N-terminal amino acid 100-400, more preferably an amino acid sequence from N-terminal amino acid 1 to any of N-terminal amino acid 100300, more preferably an amino acid sequence from N-terminal amino acid 1 to any of N-terminal amino acid 100-294, more preferably an amino acid sequence from N-terminal amino acid 1 to any of N-terminal amino acid 100-246.

In some embodiments a fragment of a CARD domain containing heterologous proteins involved in induction or regulation of a IFN response or a type I IFN response contains an amino acid sequence selected from the group consisting of an amino acid sequence comprising at least N-terminal amino acid 1 and no more than N-terminal amino acid 294, an amino acid sequence comprising at least N-terminal amino acid 1 and no more than N-terminal amino acid 246, an amino acid sequence comprising at least N-terminal amino acid 1 and no more than N-terminal amino acid 245, an amino acid sequence comprising at least N-terminal amino acid 1 and no more than N-terminal amino acid 229, an amino acid sequence comprising at least N-terminal amino acid 1 and no more than N-terminal amino acid 228, an amino acid sequence comprising at least N-terminal amino acid 1 and no more than N-terminal amino acid 218, an amino acid sequence comprising at least N-terminal amino acid 1 and no more than N-terminal amino acid 217, an amino acid sequence comprising at least N-terminal amino acid 1 and no more than N-terminal amino acid 100 and an amino acid sequence comprising at least N-terminal amino acid 1 and no more than N-terminal amino acid 101, more particular an amino acid sequence selected from the group consisting of an amino acid sequence comprising at least N-terminal amino acid 1 and no more than N-terminal amino acid 245, an amino acid sequence comprising at least N-terminal amino acid 1 and no more than N-terminal amino acid 228, an amino acid sequence comprising at least N-terminal amino acid 1 and no more than N-terminal amino acid 217 and an amino acid sequence comprising at least N-terminal amino acid 1 and no more than N-terminal amino acid 100 of a human CARD domain.

In some preferred embodiments a fragment of a CARD domain containing heterologous proteins involved in induction or regulation of a IFN response or a type I IFN response contains an amino acid sequence selected from the group consisting of an amino acid sequence from N-terminal amino acid 1 to N-terminal amino acid 294, an amino acid sequence from N-terminal amino acid 1 to N-terminal amino acid 246, an amino acid sequence from N-terminal amino acid 1 to N-terminal amino acid 245, an amino acid sequence from N-terminal amino acid 1 to N-terminal amino acid 229, an amino acid sequence from N-terminal amino acid 1 to N-terminal amino acid 228, an amino acid sequence from N-terminal amino acid 1 to N-terminal amino acid 218, an amino acid sequence from N-terminal amino acid 1 to N-terminal amino acid 217, an amino acid sequence from N-terminal amino acid 1 to N-terminal amino acid 100, an amino acid sequence from N-terminal amino acid 1 to N-terminal amino acid 101, more particular an amino acid sequence selected from the group consisting of an amino acid sequence from N-terminal amino acid 1 to N-terminal amino acid 245, an amino acid sequence from N-terminal amino acid 1 to N-terminal amino acid 228, an amino acid sequence from N-terminal amino acid 1 to N-terminal amino acid 217 and an amino acid sequence from N-terminal amino acid 1 to N-terminal amino acid 100 of a human CARD domain.

A fragment of cyclic dinucleotide generating enzymes such as cyclic-di-AMP, cyclic-di-GMP and cyclic-di-GAMP cyclases contains usually an amino acid sequence from N-terminal amino acid 1 to any of N-terminal amino acid 100-600, preferably an amino acid sequence from N-terminal amino acid 50 to any of N-terminal amino acid 100-550, more preferably an amino acid sequence from N-terminal amino acid 60 to any of N-terminal amino acid 100-530, in particular an amino acid sequence from N-terminal amino acid 60 to N-terminal amino acid 530, an amino acid sequence from N-terminal amino acid 146 to N-terminal amino acid 507 or an amino acid sequence from N-terminal amino acid 161 to N-terminal amino acid 530, more particular an amino acid sequence from N-terminal amino acid 161 to N-terminal amino acid 530 of the human cGAS. In some embodiments a fragment of cGAS contains in particular an amino acid sequence selected from the group consisting of an amino acid sequence comprising at least N-terminal amino acid 60 and no more than N-terminal amino acid N-terminal amino acid 422, an amino acid sequence comprising at least N-terminal amino acid 146 and no more than N-terminal amino acid N-terminal amino acid 507, and an amino acid sequence comprising at least N-terminal amino acid 161 and no more than N-terminal amino acid N-terminal amino acid 522. In some embodiments a fragment of cGAS contains more particular an amino acid sequence selected from the group consisting of an amino acid sequence from N-terminal amino acid 60 to N-terminal amino acid 422, an amino acid sequence from N-terminal amino acid 146 to N-terminal amino acid 507, and an amino acid sequence from N-terminal amino acid 161 to N-terminal amino acid 522.

In a more preferred embodiment the heterologous protein involved in induction or regulation of a type I IFN response is selected from the group consisting of the CARD domain comprising RIG1, MDA5, and MAVS/IPS-1 or a fragment thereof and cGAS and a fragment thereof, in particular selected from the group consisting of the CARD domain comprising RIG1 and a fragment thereof, the CARD domain comprising MAVS/IPS-1 and a fragment thereof, and cGAS and a fragment thereof. Fragments of these proteins are particular preferred. In this more preferred embodiment, the CARD domain comprising RIG1, MDA5, MAVS/IPS-1 comprises the naturally occurring CARD domain(s) and additionally C-terminal amino acids following the naturally occurring CARD domain(s) comprising the naturally occurring helicase domain in case of RIG-1 or a fragment thereof, preferably a fragment containing 1-500, more preferably 1-250, even more preferably 1-150 amino acids wherein the naturally occurring helicase domain or fragment thereof is not functional, i.e. does not bind a CARD domain or, comprises the downstream C-terminal sequence in case of MAVS/IPS-1 or a fragment thereof, preferably a fragment containing 1-500, more preferably 1-250, even more preferably 1-150 amino acids. In these embodiments cGAS and a fragment thereof comprises usually the naturally occurring synthase domain (NTase core and C-terminal domain; amino acids 160-522 of the human cGAS as described in [65] and as Uniprot. Q8N884 for the human protein), preferably cGAS and a fragment thereof comprises the naturally occurring synthase domain, but has a deletion of a part or the complete N-terminal domain, preferably a deletion of the complete N-terminal helical extension (N-terminal helical extension; amino acids 1-160 of the human cGAS as described in [65] and as Uniprot. Q8N884 for the human protein). The deletion of a part or the complete N-terminal domain is preferably a deletion of the amino acids 1-59.

In some embodiments the heterologous proteins involved in induction or regulation of a type I IFN response are selected from the group consisting of the RIG-I-like receptor (RLR) family (as RIG1 and MDA5) and a fragment thereof, other CARD domain containing proteins involved in antiviral signaling and type I IFN induction (as MAVS/IPS-1) and a fragment thereof and cyclic dinucleotide generating enzymes such as cyclic-di-AMP, cyclic-di-GMP and cyclic-di-GAMP cyclases selected from the group consisting of WspR, DncV, DisA and DisA-like, CdaA, CdaS and cGAS, and a fragment thereof, leading to stimulation of STING.

In some embodiments the heterologous proteins involved in induction or regulation of a type I IFN response are selected from the group consisting of RIG1, MDA5, LGP2, MAVS/IPS-1, WspR, DncV, DisA and DisA-like, CdaA, CdaS and cGAS or a fragment thereof, more preferably selected from the group consisting of RIG1, WspR, DncV, DisA-like, and cGAS or a fragment thereof.

In a more preferred embodiment the protein involved in induction or regulation of a type I IFN response is selected from the group consisting of RIG1, MDA5, MAVS/IPS-1, WspR, DncV, DisA and DisA-like, CdaA, and cGAS or a fragment thereof, even more preferably selected from the group consisting of RIG1, MDA5, MAVS/IPS-1, WspR, DncV, DisA-like, CdaA, and cGAS or a fragment thereof, in particular selected from the group consisting of RIG1, MAVS/IPS-1 and cGAS or a fragment thereof. Fragments of these proteins are particular preferred.

In this more preferred embodiment a fragment of RIG1, MDA5, MAVS/IPS-1 usually contains an amino acid sequence from N-terminal amino acid 1 to any of N-terminal amino acid 100-500, preferably an amino acid sequence from N-terminal amino acid 1 to any of N-terminal amino acid 100-400, more preferably an amino acid sequence from N-terminal amino acid 1 to any of N-terminal amino acid 100-300.

In this more preferred embodiment a fragment of RIG1 contains an amino acid sequence selected from the group consisting of an amino acid sequence comprising at least N-terminal amino acid 1 and no more than N-terminal amino acid 246, an amino acid sequence comprising at least N-terminal amino acid 1 and no more than N-terminal amino acid 245, an amino acid sequence comprising at least N-terminal amino acid 1 and no more than N-terminal amino acid 229, an amino acid sequence comprising at least N-terminal amino acid 1 and no more than N-terminal amino acid 228, an amino acid sequence comprising at least N-terminal amino acid 1 and no more than N-terminal amino acid 218, and an amino acid sequence comprising at least N-terminal amino acid 1 and no more than N-terminal amino acid 217; and a fragment of MAVS/IPS-1 contains an amino acid sequence selected from the group consisting of an amino acid sequence comprising at least N-terminal amino acid 1 and no more than N-terminal amino acid 100 and an amino acid sequence comprising at least N-terminal amino acid 1 and no more than N-terminal amino acid 101.

In this more preferred embodiment a fragment of RIG1 contains more particular an amino acid sequence selected from the group consisting of an amino acid sequence from N-terminal amino acid 1 to N-terminal amino acid 246, an amino acid sequence from N-terminal amino acid 1 to N-terminal amino acid 245, an amino acid sequence from N-terminal amino acid 1 to N-terminal amino acid 229, an amino acid sequence from N-terminal amino acid 1 to N-terminal amino acid 228, an amino acid sequence from N-terminal amino acid 1 to N-terminal amino acid 218, and an amino acid sequence from N-terminal amino acid 1 to N-terminal amino acid 217; and a fragment of MAVS/IPS-1 contains more particular an amino acid sequence selected from the group consisting of amino acid sequence from N-terminal amino acid 1 to N-terminal amino acid 100 and an amino acid sequence from N-terminal amino acid 1 to N-terminal amino acid 101.

In this more preferred embodiment a fragment of cGAS contains usually an amino acid sequence from N-terminal amino acid 1 to any of N-terminal amino acid 100-600, preferably an amino acid sequence from N-terminal amino acid 50 to any of N-terminal amino acid 100-550, more preferably an amino acid sequence from N-terminal amino acid 60 to any of N-terminal amino acid 100-530, in particular an amino acid sequence from N-terminal amino acid 60 to N-terminal amino acid 530, an amino acid sequence from N-terminal amino acid 146 to N-terminal amino acid 507 or an amino acid sequence from N-terminal amino acid 161 to N-terminal amino acid 530, more particular an amino acid sequence from N-terminal amino acid 60 to N-terminal amino acid 530, or an amino acid sequence from N-terminal amino acid 161 to N-terminal amino acid 530 of the human cGAS.

In this more preferred embodiment a fragment of cGAS contains in particular an amino acid sequence selected from the group consisting of an amino acid sequence comprising at least N-terminal amino acid 60 and no more than N-terminal amino acid N-terminal amino acid 422, an amino acid sequence comprising at least N-terminal amino acid 146 and no more than N-terminal amino acid N-terminal amino acid 507, and an amino acid sequence comprising at least N-terminal amino acid 161 and no more than N-terminal amino acid N-terminal amino acid 522.

In this more preferred embodiment a fragment of cGAS contains more particular an amino acid sequence selected from the group consisting of an amino acid sequence from N-terminal amino acid 60 to N-terminal amino acid 422, an amino acid sequence from N-terminal amino acid 146 to N-terminal amino acid 507, an amino acid sequence from N-terminal amino acid 161 to N-terminal amino acid 522.

In an even more preferred embodiment the protein involved in induction or regulation of a type I IFN response is selected from the group consisting of human RIG1 CARD domains$_{1-245}$ (SEQ ID NO: 37), human RIG1 CARD domains$_{1-228}$ (SEQ ID NO: 128), human RIG1 CARD domains$_{1-217}$ (SEQ ID NO: 129), murine RIG1 CARD domains$_{1-246}$ (SEQ ID NO: 38), murine RIG1 CARD domains$_{1-229}$ (SEQ ID NO: 110), murine RIG1 CARD domains$_{1-218}$ (SEQ ID NO: 111), human MAVS CARD domain$_{1-100}$ (SEQ ID NO: 116), murine MAVS CARD domain$_{1-101}$ (SEQ ID NO: 130), *N. vectensis* cGAS (SEQ ID NO: 43), human cGAS$_{161-522}$ (SEQ ID NO: 115), murine cGAS$_{146-507}$ (SEQ ID NO: 131) and *N. vectensis* cGAS$_{60-422}$(SEQ ID NO: 117).

In a particular preferred embodiment the protein involved in induction or regulation of a type I IFN response wherein the protein involved in induction or regulation of a type I IFN response is selected from the group consisting of human RIG1 CARD domains$_{1-245}$, (SEQ ID NO: 37), human RIG1 CARD domains$_{1-228}$ (SEQ ID NO: 128), human RIG1 CARD domains$_{1-217}$ (SEQ ID NO: 129), human MAVS CARD domain$_{1-100}$ (SEQ ID NO: 116), and human cGAS$_{161-522}$ (SEQ ID NO: 115).

In a more particular preferred embodiment the protein involved in induction or regulation of a type I IFN response is selected from the group consisting of human RIG1 CARD domains$_{1-245}$, murine RIG1 CARD domains$_{1-246}$, murine RIG1 CARD domains$_{1-229}$, murine RIG1 CARD domains$_{1-218}$, human MAVS$_{1-100}$, *N. vectensis* cGAS, human cGAS$_{161-522}$ and *N. vectensis* cGAS$_{60-422}$.

The RIG-I-like receptor (RLR) family comprises proteins selected from the group consisting of RIG1, MDA5 and LGP2. Preferred heterologous proteins involved in induction or regulation of a type I IFN response are the CARD domain containing proteins RIG1 and MDA5, in particular the CARD domain containing protein RIG1. Other CARD domain containing proteins involved in type I IFN induction comprises proteins selected form the group consisting of MAVS/IPS-1.

In some preferred embodiments the heterologous proteins involved in induction or regulation of a type I IFN response are selected from the group of proteins comprising a CARD domain of RIG1, a CARD domain of MDA5, and/or a CARD domain of MAVS/IPS-1, and WspR, DncV, DisA and DisA-like, CdaA, CdaS and cGAS and a fragment thereof, preferably selected from the group of proteins comprising of a CARD domain of RIG1 and/or a CARD domain of MAVS/IPS-1, and WspR, DncV, DisA and DisA-like, CdaA, and cGAS or a fragment thereof.

In some preferred embodiments the heterologous proteins involved in induction or regulation of a type I IFN response are selected from the group consisting of a CARD domain of RIG1, a CARD domain of MDA5, a CARD domain of MAVS/IPS-1, WspR, DncV, DisA and DisA-like, CdaA, CdaS and cGAS, more preferably selected from the group consisting of a CARD domain of RIG1, WspR, DncV, DisA-like, and cGAS.

In some preferred embodiments the heterologous proteins involved in induction or regulation of a type I IFN response comprises one or more (e.g. two, three or four) CARD domains, preferably comprises one or more (e.g. two, three or four) CARD domains of RIG1, MDA5, and/or MAVS/IPS-1, preferably of RIG1 and/or MAVS/IPS-1. In a more preferred embodiment the heterologous proteins involved in induction or regulation of a type I IFN response comprises both CARD domains of RIG1 or MDA5, in particular RIG1.

In some embodiments the heterologous proteins involved in induction or regulation of a type I IFN response are selected from the group consisting of a type I IFN response inducing protein without enzymatic function or a type I IFN response inducing protein with enzymatic function. A type I IFN response inducing protein without enzymatic function encompassed by the present invention comprise usually at least one CARD domain preferably two CARD domains. A CARD domain is normally composed of a bundle of six to seven alpha-helices, preferably an arrangement of six to seven antiparallel alpha helices with a hydrophobic core and an outer face composed of charged residues. A type I IFN response inducing protein with enzymatic function encompassed by the present invention comprise usually a cyclic dinucleotide generating enzyme (cyclic-di-AMP, cyclic-di-GMP and cyclic-di-GAMP cyclases) or a domain thereof leading to stimulation of STING, preferably a di-adenylate-cyclase (DAC), di-guanylate-cyclase (DGC) or GMP-AMP-cyclase (GAC) or domain thereof.

According to the present invention "proteins involved in apoptosis or apoptosis regulation" include, but are not limited to, Bad, Bcl2, Bak, Bmt, Bax, Puma, Noxa, Bim, Bcl-xL, Apaf1, Caspase 9, Caspase 3, Caspase 6, Caspase 7, Caspase 10, DFFA, DFFB, ROCK1, APP, CAD, ICAD, CAD, EndoG, AIF, HtrA2, Smac/Diablo, Arts, ATM, ATR, Bok/Mtd, Bmf, Mcl-1(S), IAP family, LC8, PP2B, 14-3-3 proteins, PKA, PKC, PI3K, Erk1/2, p90RSK, TRAF2, TRADD, FADD, Daxx, Caspase8, Caspase2, RIP, RAIDD, MKK7, JNK, FLIPS, FKHR, GSK3, CDKs and their inhibitors like the INK4-family (p16(Ink4a), p15(Ink4b), p18 (Ink4c), p19(Ink4d)), and the Cip1/Waf1/Kip1-2-family (p21(Cip1/Waf1), p27(Kip1), p57(Kip2). Preferably Bad, Bmt, Bcl2, Bak, Bax, Puma, Noxa, Bim, Bcl-xL, Caspase9, Caspase3, Caspase6, Caspase7, Smac/Diablo, Bok/Mtd, Bmf, Mcl-1(S), LC8, PP2B, TRADD, Daxx, Caspase8, Caspase2, RIP, RAIDD, FKHR, CDKs and their inhibitors like the INK4-family (p16(Ink4a), p15(Ink4b), p18(Ink4c), p19(Ink4d)), most preferably BIM, Bid, truncated Bid, FADD, Caspase 3 (and subunits thereof), Bax, Bad, Akt, CDKs and their inhibitors like the INK4-family (p16(Ink4a), p15(Ink4b), p18(Ink4c), p19(Ink4d)) are used[11-13]. Additionally proteins involved in apoptosis or apoptosis regulation include DIVA, Bcl-Xs, Nbk/Bik, Hrk/Dp5, Bid and tBid, Egl-1, Bcl-Gs, Cytochrome C, Beclin, CED-13, BNIP1, BNIP3, Bcl-B, Bcl-W, Ced-9, A1, NR13, Bfl-1, Caspase 1, Caspase 2, Caspase 4, Caspase 5, Caspase 8.

Proteins involved in apoptosis or apoptosis regulation are selected from the group consisting of pro-apoptotic proteins, anti-apoptotic proteins, inhibitors of apoptosis-prevention pathways and inhibitors of pro-survival signalling or pathways. Pro-apoptotic proteins comprise proteins selected form the group consisting of Bax, Bak, Diva, Bcl-Xs, Nbk/Bik, Hrk/Dp5, Bmf, Noxa, Puma, Bim, Bad, Bid and tBid, Bok, Apaf1, Smac/Diablo, BNIP1, BNIP3, Bcl-Gs, Beclin 1, Egl-1 and CED-13, Cytochrome C, FADD, the Caspase family, and CDKs and their inhibitors like the INK4-family (p16(Ink4a), p15(Ink4b), p18(Ink4c), p19 (Ink4d)) or selected from the group consisting of Bax, Bak, Diva, Bcl-Xs, Nbk/Bik, Hrk/Dp5, Bmf, Noxa, Puma, Bim, Bad, Bid and tBid, Bok, Egl-1, Apaf1, Smac/Diablo, BNIP1, BNIP3, Bcl-Gs, Beclin 1, Egl-1 and CED-13, Cytochrome C, FADD, and the Caspase family.

Preferred are Bax, Bak, Diva, Bcl-Xs, Nbk/Bik, Hrk/Dp5, Bmf, Noxa, Puma, Bim, Bad, Bid and tBid, Bok, Egl-1, Apaf1, BNIP1, BNIP3, Bcl-Gs, Beclin 1, Egl-1 and CED-13, Smac/Diablo, FADD, the Caspase family, CDKs and their inhibitors like the INK4-family (p16(Ink4a), p15 (Ink4b), p18(Ink4c), p19(Ink4d)). Equally preferred are Bax, Bak, Diva, Bcl-Xs, Nbk/Bik, Hrk/Dp5, Bmf, Noxa, Puma, Bim, Bad, Bid and tBid, Bok, Apaf1, BNIP1, BNIP3, Bcl-Gs, Beclin 1, Egl-1 and CED-13, Smac/Diablo, FADD, the Caspase family.

Anti-apoptotic proteins comprise proteins selected form the group consisting of Bcl-2, Bcl-Xl, Bcl-B, Bcl-W, Mcl-1, Ced-9, A1, NR13, IAP family and Bfl-1. Preferred are Bcl-2, Bcl-Xl, Bcl-B, Bcl-W, Mcl-1, Ced-9, A1, NR13 and Bfl-1. Inhibitors of apoptosis-prevention pathways comprise proteins selected form the group consisting of Bad, Noxa and Cdc25A. Preferred are Bad and Noxa. Inhibitors of pro-survival signalling or pathways comprise proteins selected form the group consisting of PTEN, ROCK, PP2A, PHLPP, JNK, p38. Preferred are PTEN, ROCK, PP2A and PHLPP.

In some embodiments, the heterologous proteins involved in apoptosis or apoptosis regulation are selected from the group consisting of BH3-only proteins, caspases and intracellular signalling proteins of death receptor control of apoptosis. BH3-only proteins are preferred.

BH3-only proteins comprise proteins selected form the group consisting of Bad, BIM, Bid and tBid, Puma, Bik/Nbk, Bod, Hrk/Dp5, BNIP1, BNIP3, Bmf, Noxa, Mcl-1, Bcl-Gs, Beclin 1, Egl-1 and CED-13. Preferred are Bad, BIM, Bid and tBid, in particular tBid.

Caspases comprise proteins selected form the group consisting of Caspase 1, Caspase 2, Caspase 3, Caspase 4, Caspase 5, Caspase 6, Caspase 7, Caspase 8, Caspase 9, Caspase 10. Preferred are Caspase 3, Caspase 8 and Caspase 9.

Intracellular signalling proteins of death receptor control of apoptosis comprise proteins selected form the group consisting of FADD, TRADD, ASC, BAP31, GULP1/CED-6, CIDEA, MFG-E8, CIDEC, RIPK1/RIP1, CRADD, RIPK3/RIP3, Crk, SHB, CrkL, DAXX, the 14-3-3 family, FLIP, DFF40 and 45, PEA-15, SODD. Preferred are FADD and TRADD.

In some embodiments two heterologous proteins involved in apoptosis or apoptosis regulation are comprised by the Gram-negative bacterial strain, wherein one protein is a pro-apoptotic protein and the other protein is an inhibitor of apoptosis-prevention pathways or wherein one protein is a pro-apoptotic protein and the other protein is an inhibitor of pro-survival signalling or pathways.

Pro-apoptotic proteins encompassed by the present invention have usually an alpha helical structure, preferably a hydrophobic helix surrounded by amphipathic helices and usually comprise at least one of BH1, BH2, BH3 or BH4 domaines, preferably comprise at least one BH3 domain. Usually pro-apoptotic proteins encompassed by the present invention have no enzymatic activity.

Anti-apoptotic proteins encompassed by the present invention have usually an alpha helical structure, preferably a hydrophobic helix surrounded by amphipathic helices and comprises a combination of different BH1, BH2, BH3 and BH4 domains, preferably a combination of different BH1, BH2, BH3 and BH4 domains wherein a BH1 and a BH2 domain is present, more preferably BH4-BH3-BH1-BH2, BH1-BH2, BH4-BH1-BH2 or BH3-BH1-BH2 (from N- to the C-terminus). Additionally, proteins containing at least one BIR domain are also encompassed.

Inhibitors of apoptosis-prevention pathways encompassed by the present invention have usually an alpha helical structure, preferably a hydrophobic helix surrounded by amphipathic helices and usually comprise one BH3 domain.

BH1, BH2, BH3 or BH4 domaines are each usually between about 5 to about 50 amino acids in length. Thus in some embodiments the heterologous proteins involved in apoptosis or apoptosis regulation is selected from the group consisting of heterologous proteins involved in apoptosis or apoptosis regulation which are about 5 to about 200, preferably about 5 to about 150, more preferably about 5 to about 100, most preferably about 5 to about 50, in particular about 5 to about 25 amino acids in length.

In some embodiments the Gram-negative bacterial strain of the present invention comprises a nucleotide sequence encoding two domains of a heterologous proteins involved in apoptosis or apoptosis regulation, preferably two repeated, more preferably two identical repeated domains of a protein involved in apoptosis or apoptosis regulation or two domains of different proteins involved in apoptosis or apoptosis regulation, most preferably two identical repeated domains of a protein involved in apoptosis or apoptosis regulation. In some embodiments the Gram-negative bacterial strain of the present invention comprises a nucleotide sequence encoding two domains of a heterologous proteins involved in apoptosis or apoptosis regulation, wherein one is a domain of a pro-apoptotic protein and the other is a domain of a protein which is an inhibitor of apoptosis-prevention pathways or wherein one is a domain of a a pro-apoptotic protein and the other domain is a domain of a protein which is an inhibitor of pro-survival signalling or pathways.

A particular preferred heterologous protein is the BH3 domain of apoptosis inducer tBID, more particular the BH3 domain comprising a sequence selected from the group consisting of SEQ ID NOs: 29-32, preferably SEQ ID NO: 31 or SEQ ID NO: 32. Equally preferred is the BH3 domain of apoptosis regulator BAX, more particular the BAX domain comprising a sequence selected from the group consisting of SEQ ID NOs: 33-36, preferably SEQ ID NO: 35 or SEQ ID NO: 36. The human and murine sequences are given in SEQ ID NOs, but tBID and BAX BH3 domains of all other species are equally included.

In some embodiments the repeated domains of the heterologous proteins are the BH3 domain, preferably repeated BH3 domains of apoptosis inducer tBID, more preferably repeated BH3 domains of the apoptosis inducer tBID comprised by SEQ ID NO: 29-32 or SEQ ID NO: 25 or SEQ ID NO: 19, even more preferably two repeated BH3 domains of apoptosis inducer tBID, most preferably two repeated BH3 domains of the apoptosis inducer tBID comprised by SEQ ID NO: 29-32 or SEQ ID NO: 25 or SEQ ID NO: 19, in particular two repeated BH3 domains of apoptosis inducer tBID comprised by the sequence of SEQ ID NO: 27. Thus in a preferred embodiment the Gram-negative bacterial strain and/or the vector of the present invention comprises a second DNA sequence encoding two repeated domains of a BH3 domain, more preferably two repeated BH3 domains of apoptosis inducer tBID. The two repeated domains may be connected by a linker of 1-30 amino acid length, preferably 2-15 amino acids, more preferred 3-10 amino acids long.

In some embodiments the two or more domains of different heterologous proteins are domains of heterologous proteins which belong to the same functional class of proteins, preferably the different heterologous proteins of the two or more domains are different heterologous proteins from the class of proteins involved in apoptosis or apoptosis regulation. In a preferred embodiment the two or more domains of different heterologous proteins are the BH3 domain of apoptosis inducer tBID and the BH3 domain of apoptosis regulator BAX, in particular the fused BH3 domains comprised by the sequence of SEQ ID NO: 24 and 28. The two domains of different heterologous proteins may be connected by a linker of 1-30 amino acid length, preferably 2-15 amino acids, more preferred 3-10 amino acids long.

Another particular preferred heterologous protein is a domain of a protein involved in induction or regulation of a type I IFN response, more particular a CARD domain of RIG1 comprising a sequence selected from the group consisting of SEQ ID NOs: 37, 38, 110, 111, 128, 129, a CARD domain of MDA5 comprising a sequence selected from the group consisting of SEQ ID NOs: 44-47, 112, 113, preferably SEQ ID NOs: 112 or 113, or a CARD domain of MAVS/IPS-1 comprising a sequence selected from the group consisting of SEQ ID NO: 116, 48-49, preferably SEQ ID NO: 116, full-length cGAS such as *N. vectensis* cGAS (SEQ ID NO: 43), human $cGAS_{161-522}$ (SEQ ID NO: 115), *N. vectensis* $cGAS_{60-422}$(SEQ ID NO: 117) or murine $cGAS_{146-507}$ (SEQ ID NO: 131). Most particular a CARD domain of RIG1 comprising a sequence selected from the group consisting of SEQ ID NOs: 37, 38, 110, 111, 128, 129, a CARD domain protein comprising of MAVS/IPS-1 comprising a sequence selected from the group consisting of SEQ ID NO: 116, 48-49, preferably SEQ ID NO: 116, and full-length cGAS such as *N. vectensis* cGAS (SEQ ID NO: 43), human $cGAS_{161-522}$ (SEQ ID NO: 115), *N. vectensis* $cGAS_{60-422}$(SEQ ID NO: 117) or murine $cGAS_{146-507}$ (SEQ ID NO: 131).

In some embodiments the heterologous proteins is a pro-drug converting enzyme. In these embodiments the recombinant virulence attenuated Gram-negative bacterial strain expresses, preferably expresses and secretes a pro-drug converting enzyme. A prodrug converting enzyme as referred herein comprises enzymes converting non-toxic prodrugs into a toxic drug, preferably enzymes selected from the group consisting of cytosine deaminase, purine nucleoside phosphorylase, thymidine kinase, beta-galactosidase, carboxylesterases, nitroreductase, carboxypeptidases and beta-glucuronidases, more preferably enzymes selected from the group consisting of cytosine deaminase, purine nucleoside phosphorylase, thymidine kinase, and beta-galactosidase.

The term "protease cleavage site" as used herein refers to a specific amino acid motif within an amino acid sequence e.g. within an amino acid sequence of a protein or a fusion protein, which is cleaved by a specific protease, which recognizes the amino acid motif. For review see[14]. Examples of protease cleavage sites are amino acid motifs, which are cleaved by a protease selected from the group consisting of enterokinase (light chain), enteropeptidase, prescission protease, human rhinovirus protease (HRV 3C), TEV protease, TVMV protease, FactorXa protease and thrombin.

The following amino acid motif is recognized by the respective protease:

Asp-Asp-Asp-Asp-Lys: Enterokinase (light chain)/Enteropeptidase

Leu-Glu-Val-Leu-Phe-Gln/Gly-Pro: PreScission Protease/human Rhinovirus protease (HRV 3C)

Glu-Asn-Leu-Tyr-Phe-Gln-Ser and modified motifs based on the Glu-X-X-Tyr-X-Gln-Gly/Ser (where X is any amino acid) recognized by TEV protease (tobacco etch virus)

Glu-Thr-Val-Arg-Phe-Gln-Ser: TVMV protease

Ile-(Glu or Asp)-Gly-Arg: FactorXa protease

Leu-Val-Pro-Arg/Gly-Ser: Thrombin.

Encompassed by the protease cleavage sites as used herein is ubiquitin. Thus in some preferred embodiments ubiquitin is used as protease cleavage site, i.e. a nucleotide sequence encodes ubiquitin as protease cleavage site, which can be cleaved by a specific ubiquitin processing proteases at the N-terminal site, e.g. which can be cleaved by a specific ubiquitin processing proteases called Deubiquitinating enzymes at the N-terminal site endogenously in the cell where the fusion protein has been delivered to. Ubiquitin is processed at its C-terminus by a group of endogenous Ubiquitin-specific C-terminal proteases (Deubiquitinating enzymes, DUBs). The cleavage of Ubiquitin by DUBs is supposed to happen at the very C-terminus of Ubiquitin (after G76).

An "individual," "subject" or "patient" is a vertebrate. In certain embodiments, the vertebrate is a mammal. Mammals include, but are not limited to, primates (including human and non-human primates) and rodents (e.g., mice and rats). In preferred embodiments, a subject is a human.

The term "mutation" is used herein as a general term and includes changes of both single base pair and multiple base pairs. Such mutations may include substitutions, frame-shift mutations, deletions, insertions and truncations.

The term "nuclear localization signal" as used herein refers to an amino acid sequence that marks a protein for import into the nucleus of a eukaryotic cell and includes preferably a viral nuclear localization signal such as the SV40 large T-antigen derived NLS (PPKKKRKV).

The term "multiple cloning site" as used herein refers to a short DNA sequence containing several restriction sites for cleavage by restriction endonucleases such as AclI, HindIII, SspI, MluCI, Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI, EagI, AcuI, PstI, BpmI, DdeI, SfcI, AflII, BpuEI, SmlI, AvaI, BsoBI, MboII, BbsI, XmnI, BsmI, Nb.BsmI, EcoRI, HgaI, AatII, ZraI, Tth111I PflFI, PshAI, AhdI, DrdI, Eco53kI, Sad, BseRI, PleI, Nt.BstNBI, MlyI, HinfI, EcoRV, MboI, Sau3AI, DpnII BfuCI, DpnI, BsaBI, TfiI, BsrDI, Nb.BsrDI, BbvI, BtsI, Nb.BtsI, BstAPI, SfaNI, SphI, NmeAIII, NaeI, NgoMIV, BglI, AsiSI, BtgZI, HinPlI, HhaI, BssHII, NotI, Fnu4HI, Cac8I, MwoI, NheI, BmtI, SapI, BspQI, Nt.BspQI, BlpI, TseI, ApeKI, Bsp1286I, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpy166II, Tsp45I, HpaI, PmeI, HincII, BsiHKAI, ApoI, NspI, BsrFI, BstYI, HaeII, CviKI-1, EcoO109I, PpuMI, I-CeuI, SnaBI, I-SceI, BspHI, BspEI, MmeI, TaqaI, NruI, Hpyl88I, Hpyl88III, XbaI, BclI, HpyCH4V, FspI, PI-PspI, MscI, BsrGI, MseI, Pad, PsiI, BstBI, DraI, PspXI, BsaWI, BsaAI, EaeI, preferably XhoI, XbaI, HindIII, NcoI, NotI, EcoRI, EcoRV, BamHI, NheI, Sad, SalI, BstBI. The term "multiple cloning site" as used herein further refers to a short DNA sequence used for recombination events as e.g in Gateway cloning strategy or for methods such as Gibbson assembly or topo cloning.

The term "wild type strain" or "wild type of the Gram-negative bacterial strain" as used herein refers to a naturally occurring variant or a naturally occurring variant containing genetic modifications allowing the use of vectors, such as deletion mutations in restriction endonucleases or antibiotic resistance genes. These strains contain chromosomal DNA as well as in some cases (e.g. *Y. enterocolitica, S. flexneri*) an unmodified virulence plasmid.

The term "*Yersinia* wild type strain" as used herein refers to a naturally occurring variant (as *Y. enterocolitica* E40) or a naturally occurring variant containing genetic modifications allowing the use of vectors, such as deletion mutations in restriction endonucleases or antibiotic resistance genes (as *Y. enterocolitica* MRS40, the Ampicillin sensitive derivate of *Y. enterocolitica* E40) These strains contain chromosomal DNA as well as an unmodified virulence plasmid (called pYV).

*Y. enterocolitica* subspecies *palearctica* refers to the low-pathogenic *Y. enterocolitica* strains, which are in contrast to the higher virulent strains of subspecies *enterocolitica* 15,16 *Y. enterocolitica* subsp. *palearctica* lack, in comparison to *Y. enterocolitica* subsp. *enterocolitica*, a high-pathogenicity island (HPI). This HPI encodes the iron siderophore called yersiniabactin[17]. The lack of yersiniabactin in *Y. enterocolitica* subsp. *palearctica* renders this subspecies less pathogenic and dependent on induced systemic accessible iron for persistent infection in e.g. liver or spleen[17]. Iron can be made accessible for the bacteria in an individual e.g by pretreatment with deferoxamine, an iron chelator used to treat iron overload in patients[18].

The term "comprise" is generally used in the sense of include, that is to say permitting the presence of one or more features or components.

The term "about" refers to a range of values ±10% of a specified value. For example, the phrase "about 200" includes ±10% of 200, or from 180 to 220.

In one aspect the present invention provides a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a deletion of a chromosomal gene coding for an endogenous protein essential for growth and an endogenous virulence plasmid which comprises a nucleotide sequence comprising a gene coding for said endogenous protein essential for growth operably linked to a promoter.

In a further aspect the present invention provides a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the recombinant virulence attenuated Gram-negative bacterial strain further comprises a modulation within a RNA within a RNA thermosensor region upstream of a gene coding for an endogenous AraC-type DNA binding protein.

In a further aspect the present invention provides a recombinant virulence attenuated Gram-negative bacterial strain which comprises a nucleotide molecule comprising a nucleotide sequence encoding a heterologous protein fused in frame to the 3' end of a nucleotide sequence encoding a delivery signal from a bacterial effector protein, wherein the nucleotide sequence encoding the delivery signal from a bacterial effector protein is operably linked to a promoter, and wherein the heterologous protein is a protein involved in induction or regulation of an interferon (IFN) response.

In a further aspect, the present invention provides a recombinant virulence attenuated Gram-negative bacterial strain as described herein, for use in a method of treating cancer in a subject, the method comprising administering to the subject said recombinant virulence attenuated Gram-negative bacterial strain, wherein the recombinant virulence attenuated Gram-negative bacterial strain is administered in an amount that is sufficient to treat the subject. Preferably the present invention provides a recombinant virulence attenuated Gram-negative bacterial strain as described herein for use in a method of treating a malignant solid tumor cancer in a subject, wherein the recombinant virulence attenuated Gram-negative bacterial strain accumulates in the malignant solid tumor, the method comprising administering to the subject said recombinant virulence attenuated Gram-negative bacterial strain, wherein the recombinant virulence attenuated Gram-negative bacterial strain is administered in an amount that is sufficient to treat the subject.

In some embodiments the recombinant virulence attenuated Gram-negative bacterial strain is deficient in the production of at least one bacterial effector protein which is virulent toward eukaryotic cells.

In one embodiment of the present invention the recombinant virulence attenuated Gram-negative bacterial strain is transformed with a nucleotide molecule e.g. a vector which comprises in the 5' to 3' direction:

a promoter;

a first nucleotide sequence encoding a delivery signal from a bacterial effector protein, operably linked to said promoter;

a second nucleotide sequence encoding a heterologous protein fused in frame to the 3'end of said first nucleotide sequence.

In one embodiment of the present invention the recombinant virulence attenuated Gram-negative bacterial strain is transformed with a nucleotide molecule e.g. a vector which comprises in the 5' to 3' direction:

a first nucleotide sequence encoding a delivery signal or a fragment thereof from a bacterial effector protein;

a second nucleotide sequence encoding a heterologous protein fused in frame to the 3'end of said first nucleotide sequence.

Preferably the nucleotide sequence encoding a heterologous protein is flanked on its 3' end by a nucleotide sequence homologous to the nucleotide sequence of the chromosome or of the endogenous virulence plasmid at the 3' end of a delivery signal from a bacterial effector protein or to a fragment thereof. More preferably, this nucleotide sequence flanking the homologous protein on its 3' end is homologous to a nucleotide sequence lying within 10 kbp on the chromosome or on an endogenous virulence plasmid at the 3' end of the delivery signal from a bacterial effector protein or to a fragment thereof. In particular, this nucleotide sequence flanking the homologous protein on its 3' end is homologous to a nucleotide sequence within the same operon on the chromosome or on an endogenous virulence plasmid as the delivery signal from a bacterial effector protein or a fragment thereof. In this embodiment, transformation is usually performed so that the fused nucleotide sequence is inserted by homologous recombination on an endogenous virulence plasmid or a chromosome, preferably on an endogenous virulence plasmid, of the recombinant virulence attenuated Gram-negative bacterial strain, and the fused nucleotide sequence is operably linked to a promoter of an endogenous virulence plasmid or of a chromosome e.g. of a chromosomal pathogenicity island. Preferably the fused nucleotide sequence is operably linked to a promoter of an endogenous virulence plasmid. In this embodiment the nucleotide sequence comprises a delivery signal or fragment thereof from a bacterial effector protein, preferably a fragment thereof, which provides for homologous recombination at the homologous site at the chromosome or at an endogenous virulence plasmid, preferably on an endogenous virulence plasmid, to result in the nucleotide sequence be placed in frame to the 3'end of the chromosomal or endogenous virulence plasmid delivery signal which is operatively linked to the endogenous promoter.

In a further embodiment of the present invention the recombinant virulence attenuated Gram-negative bacterial strain or the recombinant virulence attenuated Gram-negative bacterial strain, is transformed with a nucleotide molecule, preferably a DNA nucleotide molecule, comprising a nucleotide sequence encoding a heterologous protein and a nucleotide sequence which is homologous or identical to a nucleotide sequence encoding a delivery signal from a bacterial effector protein or which is homologous or identical to a nucleotide sequence encoding a fragment of a delivery signal from a bacterial effector protein, wherein the delivery signal from a bacterial effector protein or a fragment thereof is encoded on the chromosome or on an endogenous virulence plasmid of the recombinant virulence attenuated Gram-negative bacterial strain. Preferably the nucleotide sequence which is homologous or identical to a nucleotide sequence of a delivery signal from a bacterial effector protein or to a fragment thereof is located on the 5' end of the nucleotide sequence encoding a heterologous protein. More preferably the nucleotide sequence encoding a heterologous protein is flanked on its 3' end by a nucleotide sequence homologous to the nucleotide sequence of the chromosome or of the endogenous virulence plasmid at the 3' end of the delivery signal from a bacterial effector protein or to a fragment thereof. Even more preferably, this nucleotide sequence flanking the homologous protein on its 3' end is homologous to the nucleotide sequence lying within 10 kbp on the chromosome or on an endogenous virulence plasmid at the 3' end of the delivery signal from a bacterial effector protein or to a fragment thereof. In particular, this nucleotide sequence flanking the homologous protein on its 3' end is homologous to the nucleotide sequence and is within the same operon on the chromosome or on an endogenous virulence plasmid as the delivery signal from a bacterial effector protein or a fragment thereof. In this embodiment, transformation is usually performed so that the nucleotide sequence encoding a heterologous protein is inserted on an endogenous virulence plasmid or a chromosome of the recombinant virulence attenuated Gram-negative bacterial strain, preferably on an endogenous virulence plasmid, at the 3'end of a delivery signal from a bacterial effector protein encoded by the chromosome or the endogenous virulence plasmid, wherein the heterologous protein fused to the delivery signal is expressed and secreted.

In one embodiment of the present invention the recombinant virulence attenuated Gram-negative bacterial strain comprises a deletion of a chromosomal gene coding for an endogenous protein essential for growth and an endogenous virulence plasmid which comprises a nucleotide sequence comprising a gene coding for said endogenous protein essential for growth operably linked to a promoter. Normally the gene coding for the endogenous protein essential for growth on the endogenous virulence plasmid codes for the same endogenous protein essential for growth as encoded by the deleted chromosomal gene. Preferably the gene coding for an endogenous enzyme essential for growth located on the endogenous virulence plasmid comprises its endogenous promoter and its endogenous transcriptional terminator. In case the recombinant virulence attenuated Gram-negative bacterial strain is a *Yersinia* strain, the gene coding for an endogenous enzyme essential for growth is located on the endogenous virulence plasmid pYV and preferably comprises its endogenous promoter and its endogenous transcriptional terminator. The gene coding for the endogenous enzyme essential for growth, the endogenous promoter and the endogenous transcriptional terminator is preferably located 122 bp upstream of the start of orf155 (SycO) on the endogenous virulence plasmid e.g. on pYV. The gene coding for the endogenous enzyme essential for growth, the endogenous promoter and the endogenous transcriptional terminator usually replaces an insertion sequence found in pYVe40, the virulence plasmid of *Y. enterocolitica* MRS40 and E40 strains, but not in pYVe227, the virulence plasmid of *Y. enterocolitica* W227O3 (Genbank: AF102990.1).

In case the recombinant virulence attenuated Gram-negative bacterial strain is a *Yersinia* strain the endogenous virulence plasmid is pYV (plasmid of *Yersinia* Virulence). In case the recombinant virulence attenuated Gram-negative bacterial strain is a *Salmonella* strain, the endogenous location for insertion is one of the gene clusters called SpiI or SpiII (for *Salmonella* pathogenicity island), a position where an effector protein is elsewhere encoded or alternatively one of the *Salmonella* virulence plasmids (SVPs).

Preferably the nucleotide sequence encoding a heterologous protein fused in frame to the 3'end of a nucleotide sequence encoding a delivery signal from a bacterial effector protein is inserted on an endogenous virulence plasmid at the native site of a bacterial effector protein e.g. at the native site of a virulence factor, preferably in case the recombinant virulence attenuated Gram-negative bacterial strain is a *Yersinia* strain, at the native site of YopE or another Yop (YopH, YopO, YopP, YopM, YopT), preferably at the native site of YopE or in case the recombinant virulence attenuated Gram-negative bacterial strain is a *Salmonella* strain at the native site of an effector protein encoded within SpiI, SpiII or encoded elsewhere, preferably at the native site of an effector protein encoded within SpiI or SpiII, more preferably at the native site of SopE or SteA. Preferably the nucleotide sequence encoding a heterologous protein fused in frame to the 3' end of a nucleotide sequence encoding a delivery signal from a bacterial effector protein is operably linked to a native promoter of a bacterial effector protein present on an endogenous virulence plasmid e.g. in case the recombinant virulence attenuated Gram-negative bacterial strain is a *Yersinia* strain to a native promoter from a *Yersinia* virulon gene as outlined below, more preferably to the native YopE promoter or another Yop (YopH, YopO, YopP, YopM, YopT) promoter, preferably to the native YopE promoter or in case the recombinant virulence attenuated Gram-negative bacterial strain is a *Salmonella* strain to a native promoter from SpiI or SpiII pathogenicity island or from an effector protein elsewhere encoded as outlined below, more preferably to the native SopE, InvB or SteA promoter.

In one embodiment of the present invention the recombinant virulence attenuated Gram-negative bacterial strain comprises a deletion of a chromosomal gene coding for an endogenous protein essential for growth and an endogenous virulence plasmid which comprises a nucleotide sequence comprising a gene coding for said endogenous protein essential for growth operably linked to a promoter, wherein the gene coding for an endogenous protein essential for growth is selected from a gene coding for an enzyme essential for amino acid production, a gene coding for an enzyme involved in peptidoglycan biosynthesis, a gene coding for an enzyme involved in LPS biosynthesis, a gene coding for an enzyme involved in nucleotide synthesis and a gene coding for a translation initiation factor.

In one embodiment of the present invention the recombinant virulence attenuated Gram-negative bacterial strain comprises a deletion of a chromosomal gene coding for an endogenous protein essential for growth and an endogenous virulence plasmid which comprises a nucleotide sequence comprising a gene coding for said endogenous protein essential for growth operably linked to a promoter, and wherein the gene coding for an endogenous enzyme essential for growth is a gene coding for an enzyme essential for amino acid production, wherein the enzyme essential for amino acid production is selected from the group consisting of aspartate-beta-semialdehyde dehydrogenase (asd), glutamine synthetase (glnA), tryptophanyl tRNA synthetase (trpS) or serine hydroxymethyl transferase (glyA), or Transketolase 1 (tktA), Transketolase 2 (tktB), Ribulose-phosphate 3-epimerase (rpe), Ribose-5-phosphate isomerase A (rpiA), Transaldolase A (talA), Transaldolase B (talB), phosphoribosylpyrophosphate synthase (prs), ATP phosphoribosyltransferase (hisG), Histidine biosynthesis bifunctional protein HisIE (hisI), 1-(5-phosphoribosyl)-5-[(5-phosphoribosylamino)methylideneamino] imidazole-4-carboxamide isomerase (hisA), Imidazole glycerol phosphate synthase subunit HisH (hisH), Imidazole glycerol phosphate synthase subunit HisF (hisF), Histidine biosynthesis bifunctional protein HisB (hisB), Histidinol-phosphate aminotransferase (hisC), Histidinol dehydrogenase (hisD), 3-dehydroquinate synthase (aroB), 3-dehydroquinate dehydratase (aroD), Shikimate dehydrogenase (NADP(+)) (aroE), Shikimate kinase 2 (aroL), Shikimate kinase 1 (aroK), 3-phosphoshikimate 1-carboxyvinyltransferase (aroA), Chorismate synthase (aroC), P-protein (pheA), T-protein (tyrA), Aromatic-amino-acid aminotransferase (tyrB), Phospho-2-dehydro-3-deoxyheptonate aldolase (aroG), Phospho-2-dehydro-3-deoxyheptonate aldolase (aroH), Phospho-2-dehydro-3-deoxyheptonate aldolase (aroF), Quinate/shikimate dehydrogenase (ydiB), ATP-dependent 6-phosphofructokinase isozyme 1 (pfkA), ATP-dependent 6-phosphofructokinase isozyme 2 (pfkB), Fructose-bisphosphate aldolase class 2 (fbaA), Fructose-bisphosphate aldolase class 1 (fbaB), Triosephosphate isomerase (tpiA), Pyruvate kinase I (pykF), Pyruvate kinase II (pykA), Glyceraldehyde-3-phosphate dehydrogenase A (gapA), Phosphoglycerate kinase (pgk), 2,3-bisphosphoglycerate-dependent phosphoglycerate mutase (gpmA), 2,3-bisphosphoglycerate-independent phosphoglycerate mutase (gpmM/yibO), Probable phosphoglycerate mutase (ytjC/gpmB), enolase (eno), D-3-phosphoglycerate dehydrogenase (serA), Phosphoserine aminotransferase (serC), Phosphoserine phosphatase (serB), L-serine dehydratase 1 (sdaA), L-serine dehydratase 2 (sdaB), L-threonine dehydratase catabolic (tdcB), L-threonine dehydratase biosynthetic (ilvA), L-serine dehydratase (tdcG), Serine acetyltransferase (cysE), Cysteine synthase A (cysK), Cysteine synthase B (cysM), beta-cystathionase (malY), Cystathionine beta-lyase (metC), 5-methyltetrahydropteroyltriglutamate-homocysteine methyltransferase (metE), Methionine synthase (metH), S-adenosylmethionine synthase (metK), Cystathionine gamma-synthase (metB), Homoserine O-succinyltransferase (metA), 5'-methylthioadenosine/S-adenosylhomocysteine nucleosidase (mtnN), S-ribosylhomocysteine lyase (luxS), cystathione beta lyase, cystathione gamma lyase, Serine hydroxymethyltransferase (glyA), Glycine hydroxymethyltransferase (itaE), 3-isopropylmalate dehydratase small subunit (leuD), 3-isopropylmalate dehydratase large subunit (leuC), 3-isopropylmalate dehydrogenase (leuB), L-threonine dehydratase biosynthetic (ilvA), Acetolactate synthase isozyme 3 large subunit (ilvI), Acetolactate synthase isozyme 3 small subunit (ilvH), Acetolactate synthase isozyme 1 small subunit (ilvN), Acetolactate synthase isozyme 2 small subunit (ilvM), Ketol-acid reductoisomerase (NADP(+)) (ilvC), Dihydroxy-acid dehydratase (ilvD), Branched-chain-amino-acid aminotransferase (ilvE), Bifunctional aspartokinase/homoserine dehydrogenase 1 (thrA), Bifunctional aspartokinase/homoserine dehydrogenase 2 (metL), 2-isopropylmalate synthase (leuA), Glutamate-pyruvate aminotransferase (alaA), Aspartate aminotransferase (aspC), Bifunctional aspartokinase/homoserine dehydrogenase 1 (thrA), Bifunctional aspartokinase/homoserine dehydrogenase 2 (metL), Lysine-sensitive aspartokinase 3 (lysC), Aspartate-semialdehyde dehydrogenase (asd), 2-keto-3-deoxy-galactonate aldolase (yagE), 4-hydroxy-tetrahydrodipicolinate synthase (dapA), 4-hydroxy-tetrahydrodipicolinate reductase (dapB), 2,3,4,5-tetrahydropyridine-2,6-dicarboxylate N-succinyltransferase (dapD), Succinyl-diaminopimelate desuccinylase (dapE), Diaminopimelate epimerase (dapF), Putative lyase (yjhH), Acetylornithine/succinyldiaminopimelate aminotransferase (argD), Citrate synthase (gltA), Aconitate hydratase B (acnB), Aconitate hydratase A (acnA), uncharacterized putative aconitate hydratase (ybhJ), isocitrate dehydrogenase (icd), Aspartate aminotransferase (aspC), Glutamate-pyruvate aminotransferase (alaA), Glutamate synthase [NADPH] large chain (gltB), Glutamate synthase [NADPH] small chain (gltD), Glutamine synthetase (glnA), Amino-acid acetyltransferase (argA), Acetylglutamate kinase (argB), N-acetyl-gamma-glutamyl-phosphate reductase (argC), Acetylornithine/succinyldiaminopimelate aminotransferase (argD), Acetylornithine deacetylase (argE), Ornithine carbamoyltransferase chain F (argF), Ornithine carbamoyltransferase chain I (argI), Argininosuccinate synthase (argG), Argininosuccinate lyase (argH), Glutamate 5-kinase (proB), Gamma-glutamyl phosphate reductase (proA), pyrroline-5-carboxylate reductase (proC), ornithine cyclodeaminase, Leucine-tRNA ligase (leuS), Glutamine-tRNA ligase (glnS), Serine-tRNA ligase (serS), Glycine-tRNA ligase beta subunit (glyS), Glycine-tRNA ligase alpha subunit (glyQ), Tyrosine-tRNA ligase (tyrS), Threonine-tRNA ligase (thrS), Phenylalanine-tRNA ligase alpha subunit (pheS), Phenylalanine-tRNA ligase beta subunit (pheT), Arginine-tRNA ligase (argS), Histidine-tRNA ligase (hisS), Valine-tRNA ligase (valS), Alanine-tRNA ligase (alaS), Isoleucine-tRNA ligase (ileS), Proline-tRNA ligase (proS), Cystein-tRNA ligase (cysS), Asparagine-tRNA ligase (asnS), Aspartate-tRNA ligase (aspS), Glutamate-tRNA ligase (gltX), Tryptophan-tRNA ligase (trpS), Glycine-tRNA ligase beta subunit (glyS), Methionine-tRNA ligase (metG), Lysine-tRNA ligase (lysS). Preferred enzymes essential for amino acid production are tktA, rpe, prs, aroK, tyrB, aroH, fbaA, gapA, pgk, eno, tdcG, cysE, metK, glyA, asd, dapA/B/D/E/F, argC, proC, leuS, glnS, serS, glyS/Q, tyrS, thrS, pheS/T, argS, hisS, valS, alaS, ileS, proS, cysS, asnS, aspS, gltX, trpS, glyS, metG, lysS, more preferred are asd, glyA, leuS, glnS, serS, glyS/Q, tyrS, thrS, pheS/T, argS, hisS, valS, alaS, ileS, proS, cysS, asnS, aspS, gltX, trpS, glyS, metG, lysS, most preferred is asd.

In one embodiment of the present invention the recombinant virulence attenuated Gram-negative bacterial strain further comprises a modulation within a RNA thermosensor region upstream of a gene coding for an endogenous AraC-type DNA binding protein. The modulation within a RNA thermosensor region upstream of a gene coding for an endogenous AraC-type DNA binding protein can be a deletion, an insertion, or a substitution within the RNA thermosensor region. A deletion or an insertion comprises usually a deletion or an insertion of one or several, preferably between about 30 and about 100 nucleotides, more preferably between about 40 and about 60 nucleotides. A substitution comprises usually a substitution of one or several, preferably between about 3 and about 30 nucleotides, more preferably between about 3 and about 15 nucleotides. Preferably, the modulation within a RNA thermosensor region upstream of a gene coding for an endogenous AraC-type DNA binding protein is a deletion, preferably a deletion of between about 30 and about 100 nucleotides, more preferably of between about 40 and about 60 nucleotides within a RNA thermosensor region upstream of a gene coding for an endogenous AraC-type DNA binding protein. The endogenous AraC-type DNA binding protein and the RNA thermosensor region upstream of a gene coding for the AraC-type DNA binding protein are usually located on the endogenous virulence plasmid comprised by the recombinant virulence attenuated Gram-negative bacterial strain. The AraC-type DNA binding protein is preferably selected form the group consisting of VirF, LcrF, MxiE, ExsA, PerA, HrpX, HrpB, GadX, HilC, HilD and InvF. More preferably, the AraC-type DNA binding protein is selected form the group consisting of VirF and LcrF. In some embodiments the recombinant virulence attenuated Gram-negative bacterial strain is *Yersinia enterolitica* the AraC-type DNA binding protein is VirF. Preferably the modulation within a RNA thermosensor region upstream of a gene coding for an endogenous AraC-type DNA binding protein comprises a modulation that interferes with a RNA hairpin, preferably with Hairpin I, upstream of the gene coding for an endogenous AraC-type DNA binding protein. More preferably the modulation within a RNA thermosensor region upstream of a gene coding for an endogenous AraC-type DNA binding protein comprises a deletion which removes a RNA hairpin structure or parts thereof, preferably parts of hairpin I, upstream of the gene coding for an endogenous AraC-type DNA binding protein. A deletion which removes a RNA hairpin structure or parts thereof, comprises usually a deletion of between about 30 and about 100 nucleotides, preferably of between about 40 and about 60 nucleotides. In some embodiments the recombinant virulence attenuated Gram-negative bacterial strain is *Yersinia enterolitica* the deletion comprises a deletion of the nucleotides at position −111 to −57 upstream of the coding sequence of virF (where −1 is 1 base upstream of the A of the ATG start codon of the virF coding sequence).

In one embodiment of the present invention the recombinant virulence attenuated Gram-negative bacterial strain is selected from the group consisting of the genera *Yersinia, Escherichia, Salmonella* and *Pseudomonas*. In one embodiment the recombinant virulence attenuated Gram-negative bacterial strain is selected from the group consisting of the genera *Yersinia* and *Salmonella*. Preferably the recombinant virulence attenuated Gram-negative bacterial strain is a *Yersinia* strain, more preferably a *Yersinia enterocolitica* strain. Most preferred is *Yersinia enterocolitica* E40 (0:9, biotype 2)[19] or Ampicilline sensitive derivates thereof as *Y. enterocolitica* MRS40 (also named *Y. enterocolitica* subsp. *palearctica* MRS40) as described in[20]. *Y. enterocolitica* E40 and its derivate *Y. enterocolitica* MRS40 as described in[20] is identical to *Y. enterocolitica* subsp. *palearctica* E40 and its derivate *Y. enterocolitica* subsp. *palearctica* MRS40 as described in[15,17,21] Also preferably the recombinant virulence attenuated Gram-negative bacterial strain is a *Salmonella* strain, more preferably a *Salmonella enterica* strain. Most preferred is *Salmonella enterica* Serovar *Typhimurium* SL1344 as described by the Public health England culture collection (NCTC 13347).

In some embodiments of the present invention the recombinant virulence attenuated Gram-negative bacterial strain is a strain which does not produce a siderophore e.g. is deficient in the production of a siderophore, preferably does not produce siderophores e.g. is deficient in the production of any siderophore. Such a strain is for example *Y. enterocolitica* subsp. *palearctica* MRS40 as described in [15,17,20,21] which does not produce yersiniabactin and which is preferred.

In one embodiment of the present invention the delivery signal from a bacterial effector protein comprises a bacterial effector protein or a N-terminal fragment thereof, preferably a bacterial effector protein which is virulent toward eukaryotic cells or a N-terminal fragment thereof.

In one embodiment of the present invention the delivery signal from a bacterial effector protein is a bacterial T3SS effector protein comprising a bacterial T3SS effector protein or a N-terminal fragment thereof wherein the T3SS effector protein or a N-terminal fragment thereof may comprise a chaperone binding site. A T3 SS effector protein or a N-terminal fragment thereof which comprises a chaperone binding site is particular useful as delivery signal in the present invention. Preferred T3SS effector proteins or N-terminal fragments thereof are selected from the group consisting of SopE, SopE2, SptP, YopE, ExoS, SipA, SipB, SipD, SopA, SopB, SopD, IpgB1, IpgD, SipC, SifA, SseJ, Sse, SrfH, YopJ, AvrA, AvrBsT, YopT, YopH, YpkA, Tir, EspF, TccP2, IpgB2, OspF, Map, OspG, OspI, IpaH, SspH1, VopF, ExoS, ExoT, HopAB2, XopD, AvrRpt2, HopAO1, HopPtoD2, HopU1, GALA family of proteins, AvrBs2, AvrD1, AvrBS3, YopO, YopP, YopE, YopM, YopT, EspG, EspH, EspZ, IpaA, IpaB, IpaC, VirA, IcsB, OspC1, OspE2, IpaH9.8, IpaH7.8, AvrB, AvrD, AvrPphB, AvrPphC, AvrPphEPto, AvrPpiBPto, AvrPto, AvrPtoB, VirPphA, AvrRpm1, HopPtoE, HopPtoF, HopPtoN, PopB, PopP2, AvrBs3, XopD, and AvrXv3. More preferred T3 SS effector proteins or N-terminal fragments thereof are selected from the group consisting of SopE, SptP, YopE, ExoS, SopB, IpgB1, IpgD, YopJ, YopH, EspF, OspF, ExoS, YopO, YopP, YopE, YopM, YopT, whereof most preferred T3SS effector proteins or N-terminal fragments thereof are selected from the group consisting of IpgB1, SopE, SopB, SptP, OspF, IpgD, YopH, YopO, YopP, YopE, YopM, YopT, in particular YopE or an N-terminal fragment thereof.

Equally preferred T3 S S effector proteins or N-terminal fragments thereof are selected from the group consisting of SopE, SopE2, SptP, SteA, SipA, SipB, SipD, SopA, SopB, SopD, IpgB1, IpgD, SipC, SifA, SifB, SseJ, Sse, SrfH, YopJ, AvrA, AvrBsT, YopH, YpkA, Tir, EspF, TccP2, IpgB2, OspF, Map, OspG, OspI, IpaH, VopF, ExoS, ExoT, HopAB2, AvrRpt2, HopAO1, HopU1, GALA family of proteins, AvrBs2, AvrD1, YopO, YopP, YopE, YopT, EspG, EspH, EspZ, IpaA, IpaB, IpaC, VirA, IcsB, OspC1, OspE2, IpaH9.8, IpaH7.8, AvrB, AvrD, AvrPphB, AvrPphC, AvrPphEPto, AvrPpiBPto, AvrPto, AvrPtoB, VirPphA, AvrRpm1, HopPtoD2, HopPtoE, HopPtoF, HopPtoN, PopB, PopP2, AvrBs3, XopD, and AvrXv3. Equally more preferred T3SS effector proteins or N-terminal fragments thereof are selected from the group consisting of SopE, SptP, SteA, SifB, SopB, IpgB1, IpgD, YopJ, YopH, EspF, OspF, ExoS, YopO, YopP, YopE, YopT, whereof equally most preferred T3SS effector proteins or N-terminal fragments thereof are selected from the group consisting of IpgB1, SopE, SopB, SptP, SteA, SifB, OspF, IpgD, YopH, YopO, YopP, YopE, and YopT, in particular SopE, SteA, or YopE or an N-terminal fragment thereof, more particular SteA or YopE or an N-terminal fragment thereof, most particular YopE or an N-terminal fragment thereof.

In some embodiments the delivery signal from a bacterial effector protein is encoded by a nucleotide sequence comprising the bacterial effector protein or an N-terminal fragment thereof, wherein the N-terminal fragment thereof includes at least the first 10, preferably at least the first 20, more preferably at least the first 100 amino acids of the bacterial T3SS effector protein.

In some embodiments the delivery signal from the bacterial effector protein is encoded by a nucleotide sequence comprising the bacterial T3SS effector protein or an N-terminal fragment thereof, wherein the bacterial T3SS effector protein or the N-terminal fragment thereof comprises a chaperone binding site.

Preferred T3SS effector proteins or a N-terminal fragment thereof, which comprise a chaperone binding site comprise the following combinations of chaperone binding site and T3SS effector protein or N-terminal fragment thereof: SycE-YopE, InvB-SopE, SicP-SptP, SycT-YopT, SycO-YopO, SycN/YscB-YopN, SycH-YopH, SpcS-ExoS, CesF-EspF, SycD-YopB, SycD-YopD. More preferred are SycE-YopE, InvB-SopE, SycT-YopT, SycO-YopO, SycN/YscB-YopN, SycH-YopH, SpcS-ExoS, CesF-EspF.

Most preferred is a YopE or an N-terminal fragment thereof comprising the SycE chaperone binding site such as an N-terminal fragment of a YopE effector protein containing the N-terminal 138 amino acids of the YopE effector protein designated herein as $YopE_{1-138}$ and as shown in SEQ ID NO. 2 or a SopE or an N-terminal fragment thereof comprising the InvB chaperone binding site s as uch an N-terminal fragment of a SopE effector protein containing the N-terminal 81 or 105 amino acids of the SopE effector protein designated herein as $SopE_{1-81}$ or $SopE_{1-105}$ respectively, and as shown in SEQ ID NOs.: 6 and 7.

In one embodiment of the present invention the recombinant virulence attenuated Gram-negative bacterial strain is a *Yersinia* strain and the delivery signal from the bacterial effector protein comprises a YopE effector protein or an N-terminal part, preferably the *Y. enterocolitica* YopE effector protein or an N-terminal part thereof. Preferably the SycE binding site is comprised within the N-terminal part of the YopE effector protein. In this connection an N-terminal fragment of a YopE effector protein may comprise the N-terminal 12, 16, 18, 52, 53, 80 or 138 amino acids[22-24]. Most preferred is an N-terminal fragment of a YopE effector protein containing the N-terminal 138 amino acids of the YopE effector protein e.g. as described in Forsberg and Wolf-Watz[25] designated herein as $YopE_{1-138}$ and as shown in SEQ ID NO.: 2.

In one embodiment of the present invention the recombinant virulence attenuated Gram-negative bacterial strain is a *Salmonella* strain and the delivery signal from the bacterial effector protein encoded by a nucleotide sequence comprises a SopE or SteA effector protein or an N-terminal part thereof, preferably the *Salmonella enterica* SopE or SteA effector protein or an N-terminal part thereof. Preferably the chaperon binding site is comprised within the N-terminal part of the SopE effector protein. In this connection an N-terminal fragment of a SopE effector protein protein may comprise the N-terminal 81 or 105 amino acids. Most preferred is the full length SteA (SEQ ID NO: 5) and an N-terminal fragment of a SopE effector protein containing the N-terminal 105 amino acids of the effector protein e.g. as described in SEQ ID NO.: 7.

One skilled in the art is familiar with methods for identifying the polypeptide sequences of an effector protein that are capable of delivering a protein. For example, one such method is described by Sory et al. [19]. Briefly, polypeptide sequences from e.g. various portions of the Yop proteins can be fused in-frame to a reporter enzyme such as the calmodulin-activated adenylate cyclase domain (or Cya) of the *Bordetella pertussis* cyclolysin. Delivery of a Yop-Cya hybrid protein into the cytosol of eukaryotic cells is indicated by the appearance of cyclase activity in the infected eukaryotic cells that leads to the accumulation of cAMP. By employing such an approach, one skilled in the art can determine, if desired, the minimal sequence requirement, i.e., a contiguous amino acid sequence of the shortest length, that is capable of delivering a protein, see, e.g. [19]. Accordingly, preferred delivery signals of the present invention consists of at least the minimal sequence of amino acids of a T3SS effector protein that is capable of delivering a protein.

In one embodiment, the present invention provides a recombinant virulence attenuated Gram-negative bacterial strain which is deficient in producing at least one bacterial effector protein, more preferably which is deficient in producing at least one bacterial effector protein which is virulent toward eukaryotic cells, even more preferably which is deficient in producing at least one T3 SS effector protein, most preferably which is deficient in producing at least one T3 SS effector protein which is virulent toward eukaryotic cells. In some embodiments the recombinant virulence attenuated Gram-negative bacterial strains are deficient in producing at least one, preferably at least two, more preferably at least three, even more preferably at least four, in particular at least five, more particular at least six, most particular all bacterial effector proteins which are virulent toward eukaryotic cells. In some embodiments the recombinant virulence attenuated Gram-negative bacterial strains are deficient in producing at least one preferably at least two, more preferably at least three, even more preferably at least four, in particular at least five, more particular at least six, most particular all functional bacterial effector proteins which are virulent toward eukaryotic cells such that the resulting recombinant virulence attenuated Gram-negative bacterial strain produces less bacterial effector proteins or produces bacterial effector proteins to a lesser extent compared to the non virulence attenuated Gram-negative bacterial wild type strain i.e. compared to the Gram-negative bacterial wild type strain which normally produces bacterial effector proteins or such that the resulting recombinant virulence attenuated Gram-negative bacterial strain no longer produce any functional bacterial effector proteins which are virulent toward eukaryotic cells.

According to the present invention, such a mutant Gram-negative bacterial strain i.e. such a recombinant virulence attenuated Gram-negative bacterial strain which is deficient in producing at least one bacterial effector protein e.g. which is deficient in producing at least one bacterial effector protein which is virulent toward eukaryotic cells e.g. such a mutant *Yersinia* strain can be generated by introducing at least one mutation into at least one effector-encoding gene. Preferably, such effector-encoding genes include YopE, YopH, YopO/YpkA, YopM, YopP/YopJ and YopT as far as a *Yersinia* strain is concerned. Preferably, such effector-encoding genes include AvrA, CigR, GogB, GtgA, GtgE, PipB, SifB, SipA/SspA, SipB, SipC/SspC, SipD/SspD, SlrP, SopB/SigD, SopA, SpiC/SsaB, SseB, SseC, SseD, SseF, SseG, SseI/SrfH, SopD, SopE, SopE2, SspH1, SspH2, PipB2, SifA, SopD2, SseJ, SseK1, SseK2, SseK3, SseL, SteC, SteA, SteB, SteD, SteE, SpvB, SpvC, SpvD, SrfJ, SptP, as far as a *Salmonella* strain is concerned. Most preferably, all effector-encoding genes are deleted. The skilled artisan may employ any number of standard techniques to generate mutations in these T3SS effector genes. Sambrook et al. describe in general such techniques. See Sambrook et al.[26].

In accordance with the present invention, the mutation can be generated in the promoter region of an effector-encoding gene so that the expression of such effector gene is abolished.

The mutation can also be generated in the coding region of an effector-encoding gene such that the catalytic activity of the encoded effector protein is abolished. The "catalytic activity" of an effector protein refers normally to the anti-target cell function of an effector protein, i.e., toxicity. Such activity is governed by the catalytic motifs in the catalytic domain of an effector protein. The approaches for identifying the catalytic domain and/or the catalytic motifs of an effector protein are well known by those skilled in the art. See, for example, [27,28].

Accordingly, one preferred mutation of the present invention is a deletion of the entire catalytic domain. Another preferred mutation is a frameshift mutation in an effector-encoding gene such that the catalytic domain is not present in the protein product expressed from such "frameshifted" gene. A most preferred mutation is a mutation with the deletion of the entire coding region of the effector protein. Other mutations are also contemplated by the present invention, such as small deletions or base pair substitutions, which are generated in the catalytic motifs of an effector protein leading to destruction of the catalytic activity of a given effector protein.

The mutations that are generated in the genes of the functional bacterial effector proteins may be introduced into the particular strain by a number of methods. One such method involves cloning a mutated gene into a "suicide" vector which is capable of introducing the mutated sequence into the strain via allelic exchange. An example of such a "suicide" vector is described by[29].

In this manner, mutations generated in multiple genes may be introduced successively into a Gram-negative bacterial strain giving rise to polymutant, e.g a sixtuple mutant recombinant strain. The order in which these mutated sequences are introduced is not important. Under some circumstances, it may be desired to mutate only some but not all of the effector genes. Accordingly, the present invention further contemplates polymutant *Yersinia* other than sixtuple-mutant *Yersinia*, e.g., double-mutant, triple-mutant, quadruple-mutant and quintuple-mutant strains. For the purpose of delivering proteins, the secretion and translocation system of the instant mutant strain needs to be intact.

A preferred recombinant virulence attenuated Gram-negative bacterial strain of the present invention is a sixtuple-mutant *Yersinia* strain in which all the effector-encoding genes are mutated such that the resulting *Yersinia* no longer produce any functional effector proteins. Such sixtuple-mutant *Yersinia* strain is designated as ΔyopH$_2$O,P,E,M,T for *Y. enterocolitica*. As an example such a sixtuple-mutant can be produced from the *Y. enterocolitica* MRS40 strain giving rise to *Y. enterocolitica* MRS40 ΔyopH$_2$O,P,E,M,T, (also named *Y. enterocolitica* subsp. *palearctica* MRS40 ΔyopH$_2$O,P,E,M,T or *Y. enterocolitica* ΔyopH$_2$O,P,E,M,T herein) which is preferred. *Y. enterocolitica* MRS40 ΔyopH$_2$O,P,E,M,T which is deficient in the production of Yersiniabactin has been described in WO02077249 and was deposited on 24$^{th}$ of September, 2001, according to the Budapest Treaty on the International Recognition of the Deposit of Microorganisms for the Purposes of Patent Procedure with the Belgian Coordinated Collections of Microorganisms (BCCM) and was given accession number LMG P-21013.

More preferred is *Y. enterocolitica* MRS40 ΔyopH$_2$O,P,E,M,T which comprises a deletion on the endogenous virulence plasmid pYV which removes a RNA hairpin structure or parts thereof such as a deletion of Hairpin I upstream of the gene coding for an endogenous AraC-type DNA binding protein (ΔHairpinI-virF) such as *Y. enterocolitica* MRS40 ΔyopH$_2$O,P,E,M,T ΔHairpinI-virF (also named *Y. enterocolitica* ΔyopH$_2$O,P,E,M,T ΔHairpinI-virF). Equally preferred is *Y. enterocolitica* MRS40 ΔyopH$_2$O,P,E,M,T which comprises a deletion of a chromosomal gene coding for asd and the endogenous virulence plasmid pYV which comprises a nucleotide sequence comprising a gene coding for asd operably linked to a promoter (pYV-asd) such as *Y. enterocolitica* MRS40 ΔyopH$_2$O,P,E,M,T Δasd pYV-asd (also named *Y. enterocolitica* ΔyopH$_2$O,P,E,M,T Δasd pYV-asd herein). Particular preferred is *Y. enterocolitica* MRS40 ΔyopH$_2$O,P,E,M,T Δasd ΔHairpinI-virF pYV-asd which comprises both modifications as described above (also named *Y. enterocolitica* ΔyopH$_2$O,P,E,M,T Δasd ΔHairpinI-virF pYV-asd herein). Particular preferred strains are *Y. enterocolitica* MRS40 ΔyopH$_2$O,P,E,M,T ΔHairpinI-virF (also named *Y. enterocolitica* ΔyopH$_2$O,P,E,M,T ΔHairpinI-virF), *Y. enterocolitica* MRS40 ΔyopH$_2$O,P,E,M,T Δasd pYV-asd (also named *Y. enterocolitica* ΔyopH$_2$O,P,E,M,T Δasd pYV-asd herein) or *Y. enterocolitica* MRS40 ΔyopH$_2$O,P,E,M,T Δasd ΔHairpinI-virF pYV-asd (also named *Y. enterocolitica* ΔyopH$_2$O,P,E,M,T Δasd ΔHairpinI-virF pYV-asd herein) which are deficient in the production of a siderophore, preferably does not produce siderophores e.g. are deficient in the production of any siderophore, as is the case for all *Y. enterocolitica* subsp. *palearctica* strains. Thus, equally particular preferred strains are *Y. enterocolitica* subsp. *palearctica* ΔyopH$_2$O,P,E,M,T ΔHairpinI-virF (also named *Y. enterocolitica* subsp. *palearctica* ΔyopH$_2$O,P,E,M,T ΔHairpinI-virF), *Y. enterocolitica* subsp. *palearctica* ΔyopH$_2$O,P,E,M,T Δasd pYV-asd also named *Y. enterocolitica* ΔyopH$_2$O,P,E,M,T Δasd pYV-asd herein) or *Y. enterocolitica* subsp. *palearctica* ΔyopH$_2$O,P,E,M,T Δasd ΔHairpinI-virF pYV-asd (also named *Y. enterocolitica* ΔyopH$_2$O,P,E,M,T Δasd ΔHairpinI-virF pYV-asd herein).

Nucleotide molecules like vectors which can be used according to the invention to transform a Gram-negative bacterial strain may depend on the Gram-negative bacterial strains used as known to the skilled person. Nucleotide molecules which can be used according to the invention include expression vectors (including synthetic or otherwise generated modified versions of endogenous virulence plasmids), vectors for chromosomal or virulence plasmid insertion and nucleotide sequences such as e.g.

DNA fragments for chromosomal or virulence plasmid insertion. Expression vectors which are useful in e.g. *Yersinia, Escherichia, Salmonella* or *Pseudomonas* strain are e.g pUC, pBad, pACYC, pUCP20 and pET plasmids. Vectors for chromosomal or virulence plasmid insertion which are useful in e.g. *Yersinia, Escherichia, Salmonella* or *Pseudomonas* strain are e.g pKNG101. DNA fragments for chromosomal or virulence plasmid insertion refer to methods used in e.g. *Yersinia, Escherichia, Salmonella* or *Pseudomonas* strain as e.g. lambda-red genetic engineering. Vectors for chromosomal or virulence plasmid insertion or DNA fragments for chromosomal or virulence plasmid insertion may insert the nucleotide sequences of the present invention so that e.g. the nucleotide sequence encoding a heterologous protein fused in frame to the 3' end of a nucleotide sequence encoding a delivery signal from a bacterial effector protein is operably linked to an endogenous promoter of the recombinant virulence attenuated Gram-negative bacterial strain. Thus if a vector for chromosomal or virulence plasmid insertion or a DNA fragment for chromosomal or virulence plasmid insertion is used, an endogenous promoter can be encoded on the endogenous bacterial DNA (chromosomal or plasmid DNA) and only the respective nucleotide sequence will be provided by the engineered vector for chromosomal or virulence plasmid insertion or DNA fragment for chromosomal or virulence plasmid insertion. Alternatively, if a vector for chromosomal or virulence plasmid insertion or a nucleotide molecule such as e.g. a nucleotide sequence for chromosomal or virulence plasmid insertion is used, an endogenous promoter and the delivery signal from a bacterial effector protein can be encoded on the endogenous bacterial DNA (chromosomal or plasmid DNA) and only the nucleotide molecule such as e.g. a nucleotide sequence encoding the heterologous protein will be provided by a vector for chromosomal or virulence plasmid insertion or by a nucleotide molecule such as e.g. a nucleotide sequence for chromosomal or virulence plasmid insertion. Thus a promoter is not necessarily needed to be comprised by the vector used for transformation of the recombinant virulence attenuated Gram-negative bacterial strains i.e. the recombinant virulence attenuated Gram-negative bacterial strains of the present invention may be transformed with a vector which dose not comprise a promoter.

In a preferred embodiment the nucleotide molecule e.g. the vector of the present invention comprises in the 5' to 3' direction:

a first nucleotide sequence encoding a delivery signal or a fragment thereof from a bacterial effector protein;

a second nucleotide sequence encoding a heterologous protein fused in frame to the 3'end of said first nucleotide sequence.

A preferred vector e.g. a preferred expression vector for *Yersinia* is selected from the group consisting of pBad_Si_1 and pBad_Si_2. pBad_Si2 was constructed by cloning of the SycE-YopE$_{1-138}$ fragment containing endogenous promoters for YopE and SycE from purified pYV40 into KpnI/HindIII site of pBad-MycHisA (Invitrogen). Additional modifications include removal of the NcoI/BglII fragment of pBad-MycHisA by digest, Klenow fragment treatment and religation. Further at the 3' end of YopE$_{1-138}$ the following cleavage sites were added: XbaI-XhoI-BstBI-(HindIII). pBad_Si1 is equal to pBad_Si2 but encodes EGFP amplified from pEGFP-C1 (Clontech) in the NcoI/BglII site under the Arabinose inducible promoter. Equally preferred is the use of modified versions of the endogenous *Yersinia* virulence plasmid pYV encoding heterologous proteins as fusions to a T3SS signal sequence.

A preferred vector e.g. a preferred expression vector for *Salmonella* is selected from the group consisting of pSi_266, pSi_267, pSi_268 and pSi_269. Plasmids pSi_266, pSi_267, pSi_268 and pSi_269 containing the corresponding endogenous promoter and the SteA$_{1-20}$ fragment (pSi_266), the full length SteA sequence (pSi_267), the SopE$_{1-81}$ fragment (pSi_268) or the SopE$_{1-105}$ fragment (pSi_269) were amplified from *S. enterica* SL1344 genomic DNA and cloned into NcoI/KpnI site of pBad-MycHisA (Invitrogen).

The nucleotide molecules e.g. the vectors of the instant invention may include other sequence elements such as a 3' termination sequence (including a stop codon and a poly A sequence), or a gene conferring a drug resistance which allows the selection of transformants having received the instant vector.

The nucleotide molecules e.g. the vectors of the present invention may be transformed by a number of known methods into the recombinant virulence attenuated Gram-negative bacterial strains. For the purpose of the present invention, the methods of transformation for introducing a vector include, but are not limited to, electroporation, calcium phosphate mediated transformation, conjugation, or combinations thereof. For example, a nucleotide molecules e.g. a vector can be transformed into a first bacteria strain by a standard electroporation procedure. Subsequently, such a nucleotide molecules e.g. a vector can be transferred from the first bacteria strain into the desired strain by conjugation, a process also called "mobilization". Transformant (i.e., Gram-negative bacterial strains having taken up the vector) may be selected, e.g., with antibiotics. These techniques are well known in the art. See, for example, [19].

In accordance with the present invention, the promoter operably linked to the bacterial effector protein of the recombinant virulence attenuated Gram-negative bacterial strain of the invention can be a native promoter of a T3SS effector protein of the respective strain or a compatible bacterial strain or a promoter used in expression vectors which are useful in e.g. *Yersinia, Escherichia, Salmonella* or *Pseudomonas* strain e.g pUC and pBad. Such promoters are the T7 promoter, Plac promoter or the arabinose inducible Ara-bad promoter.

If the recombinant virulence attenuated Gram-negative bacterial strain is a *Yersinia* strain the promoter can be from a *Yersinia* virulon gene. A "*Yersinia* virulon gene" refers to genes on the *Yersinia* pYV plasmid, the expression of which is controlled both by temperature and by contact with a target cell. Such genes include genes coding for elements of the secretion machinery (the Ysc genes), genes coding for translocators (YopB, YopD, and LcrV), genes coding for the control elements (YopN, TyeA and LcrG), genes coding for T3SS effector chaperones (SycD, SycE, SycH, SycN, SycO and SycT), and genes coding for effectors (YopE, YopH, YopO/YpkA, YopM, YopT and YopP/YopJ) as well as other pYV encoded proteins as VirF and YadA.

In a preferred embodiment of the present invention, the promoter is the native promoter of a T3SS functional effector encoding gene. If the recombinant virulence attenuated Gram-negative bacterial strain is a *Yersinia* strain the promoter is selected from any one of YopE, YopH, YopO/YpkA, YopM and YopP/YopJ. More preferably, the promoter is from YopE or SycE. Most preferred is the YopE promoter.

If the recombinant virulence attenuated Gram-negative bacterial strain is a *Salmonella* strain the promoter can be from SpiI or SpiII pathogenicity island or from an effector protein elsewhere encoded. Such genes include genes coding for elements of the secretion machinery, genes coding for translocators, genes coding for the control elements, genes coding for T3SS effector chaperones, and genes coding for effectors as well as other proteins encoded by SPI-1 or SPI-2. In a preferred embodiment of the present invention, the promoter is the native promoter of a T3SS functional effector encoding gene. If the recombinant virulence attenuated Gram-negative bacterial strain is a *Salmonella* strain the promoter is selected from any one of the effector proteins. More preferably, the promoter is from SopE, InvB or SteA.

In some embodiments the promoter is an artificially inducible promoter, as e.g. the arabinose inducible promoter, which is preferred. In this case, arabinose is usually provided to the bacteria and will then induce the bacterial expression of the protein to be delivered.

In one embodiment of the present invention the recombinant virulence attenuated Gram-negative bacterial strain comprises a nucleotide sequence encoding a protease cleavage site. The protease cleavage site is usually located on the nucleotide molecule comprising a nucleotide sequence encoding a heterologous protein fused in frame to the 3'end of a nucleotide sequence encoding a delivery signal from a bacterial effector protein between the nucleotide sequence encoding a heterologous protein and the nucleotide sequence encoding a delivery signal. Generation of a functional and generally applicable cleavage site allows cleaving off the delivery signal after translocation. As the delivery signal can interfere with correct localization and/or function of the translocated protein within the target cells the introduction of a protease cleavage site between the delivery signal and the protein of interest provides delivery of almost native proteins into eukaryotic cells. Preferably the protease cleavage site is an amino acid motif which is cleaved by a protease or the catalytic domains thereof selected from the group consisting of enterokinase (light chain), enteropeptidase, prescission protease, human rhinovirus protease 3C, TEV protease, TVMV protease, FactorXa protease and thrombin, more preferably an amino acid motif which is cleaved by TEV protease. Equally preferable the protease cleavage site is an amino acid motif which is cleaved by a protease or the catalytic domains thereof selected from the group consisting of enterokinase (light chain), enteropeptidase, prescission protease, human rhinovirus protease 3C, TEV protease, TVMV protease, FactorXa protease, ubiquitin processing protease, called Deubiquitinating enzymes, and thrombin. Most preferred is an amino acid motif which is cleaved by TEV protease or by an ubiquitin processing protease.

Thus in a further embodiment of the present invention, the heterologous protein is cleaved from the delivery signal from a bacterial effector protein by a protease.

Preferred methods of cleavage are methods wherein:
a) the protease is translocated into the eukaryotic cell by a recombinant virulence attenuated Gram-negative bacterial strain as described herein which expresses a fusion protein which comprises the delivery signal from the bacterial effector protein and the protease as heterologous protein; or
b) the protease is expressed constitutively or transiently in the eukaryotic cell.

Usually the recombinant virulence attenuated Gram-negative bacterial strain used to deliver a desired protein into a eukaryotic cell and the recombinant virulence attenuated Gram-negative bacterial strain translocating the protease into the eukaryotic cell are different.

In one embodiment of the present invention the recombinant virulence attenuated Gram-negative bacterial strain comprises a further nucleotide sequence encoding a labelling molecule or an acceptor site for a labelling molecule. The further nucleotide sequence encoding a labelling molecule or an acceptor site for a labelling molecule is usually fused to the 5' end or to the 3' end of the nucleotide sequence encoding a heterologous protein. A preferred labelling molecule or an acceptor site for a labelling molecule is selected from the group consisting of enhanced green fluourescent protein (EGFP), coumarin, coumarin ligase acceptor site, resorufin, resurofin ligase acceptor site, the tetra-Cysteine motif in use with FlAsH/ReAsH dye (life technologies). Most preferred is resorufin and a resurofin ligase acceptor site or EGFP. The use of a labelling molecule or an acceptor site for a labelling molecule will lead to the attachment of a labelling molecule to the heterologous protein of interest, which will then be delivered as such into the eukaryotic cell and enables tracking of the protein by e.g. live cell microscopy.

In one embodiment of the present invention the recombinant virulence attenuated Gram-negative bacterial strain comprises a further nucleotide sequence encoding a peptide tag. The further nucleotide sequence encoding a peptide tag is usually fused to the 5' end or to the 3' end of the nucleotide sequence encoding a heterologous protein. A preferred peptide tag is selected from the group consisting of Myc-tag, His-tag, Flag-tag, HA tag, Strep tag or V5 tag or a combination of two or more tags out of these groups. Most preferred is Myc-tag, Flag-tag, His-tag and combined Myc- and His-tags. The use of a peptide tag will lead to traceability of the tagged protein e.g by immunofluorescence or Western blotting using anti-tag antibodies. Further, the use of a peptide tag allows affinity purification of the desired protein either after secretion into the culture supernatant or after translocation into eukaryotic cells, in both cases using a purification method suiting the corresponding tag (e.g. metal-chelate affinity purification in use with a His-tag or anti-Flag antibody based purification in use with the Flag-tag).

In one embodiment of the present invention the recombinant virulence attenuated Gram-negative bacterial strain comprises a further nucleotide sequence encoding a nuclear localization signal (NLS). The further nucleotide sequence encoding a nuclear localization signal (NLS) is usually fused to the 5'end or to the 3'end of the nucleotide sequence encoding a heterologous protein wherein said further nucleotide sequence encodes a nuclear localization signal (NLS). A preferred NLS is selected from the group consisting of SV40 large T-antigen NLS and derivates thereof[30] as well as other viral NLS. Most preferred is SV40 large T-antigen NLS and derivates thereof.

In one embodiment of the present invention the recombinant virulence attenuated Gram-negative bacterial strain comprises a multiple cloning site. The multiple cloning site is usually located at the 3'end of the nucleotide sequence encoding a delivery signal from a bacterial effector protein and/or at the 5'end or 3'end of the nucleotide sequence encoding a heterologous protein. One or more than one multiple cloning sites can be comprised by the vector. A preferred multiple cloning site is selected from the group of restriction enzymes consisting of XhoI, XbaI, HindIII, NcoI, NotI, EcoRI, EcoRV, BamHI, NheI, Sad, SalI, BstBI. Most preferred is XbaI, XhoI, BstBI and HindIII.

The fused protein expressed by the recombinant virulence attenuated Gram-negative bacterial strain of the present invention is also termed as a "fusion protein" or a "hybrid protein", i.e., a fused protein or hybrid of delivery signal and a heterologous protein. The fusion protein can also comprise e.g. a delivery signal and two or more different heterologous proteins.

The present invention contemplates methods for treating cancer in a subject e.g. treating malignant solid tumors including delivering heterologous proteins as hereinabove described into cancer cells e.g. to cells of a malignant solid tumor. The proteins may be delivered i.e. translocated into the cancer cell e.g. to cells of a malignant solid tumor at the time of administering the recombinant virulence attenuated Gram-negative bacterial strain to a subject or may be delivered i.e. translocated into the cancer cell e.g. to cells of a malignant solid tumor at a later time e.g. after the recombinant virulence attenuated Gram-negative bacterial strain has reached a cancer cell e.g. the site of the malignant solid tumor and/or has reached a cancer cell e.g. the site of the malignant solid tumor and has replicated as described above. The time of delivery can be regulated e.g by the promoter used to express the heterologous proteins in the recombinant virulence attenuated Gram-negative bacterial strain. In the first case, either a constitutive promoter or, more preferred, an endogenous promoter of a bacterial effector protein might drive the heterologous protein. In the case of delayed protein delivery, an artificially inducible promoter, as the arabinose inducible promoter, might drive the heterologous protein. In this case, arabinose will be administered to a subject once bacteria have reached and accumulated at the desired site. Arabinose will then induce the bacterial expression of the protein to be delivered.

Thus in one embodiment the method of treating cancer comprises i) culturing the recombinant virulence attenuated Gram-negative bacterial strain as described herein;

ii) administering to the subject said recombinant virulence attenuated Gram-negative bacterial strain by contacting a cancer cell with the recombinant virulence attenuated Gram-negative bacterial strain of i) wherein a fusion protein which comprises a delivery signal from a bacterial effector protein and the heterologous protein is expressed by the recombinant virulence attenuated Gram-negative bacterial strain and is translocated into the cancer cell; and optionally iii) cleaving the fusion protein so that the heterologous protein is cleaved from the delivery signal from the bacterial effector protein inside of the cancer cell, wherein the recombinant virulence attenuated Gram-negative bacterial strain is administered in an amount that is sufficient to treat the subject.

The cancer cells for delivering heterologous proteins are usually cancer cells from cancers selected from non-solid tumors selected from the group consisting of Sarcoma, Leukemia, Lymphoma, multiple myeloma, Central nervous system cancers, and malignant solid tumors, which include, but are not limited to, abnormal mass of cells which may stem from different tissue types such as liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung and thus include malignant solid liver, colon, colorectum, skin, breast, pancreas, cervix uteri, corpus uteri, bladder, gallbladder, kidney, larynx, lip, oral cavity, oesophagus, ovary, prostate, stomach, testis, thyroid gland or lung tumors. Preferably the cancer cells for delivering heterologous proteins are malignant solid tumors.

Thus in one preferred embodiment the cancer is a malignant solid tumor and the method r comprises i) culturing the recombinant virulence attenuated Gram-negative bacterial strain as described herein;

ii) administering to the subject said recombinant virulence attenuated Gram-negative bacterial strain by contacting a cell of a malignant solid tumor with the recombinant virulence attenuated Gram-negative bacterial strain of i) wherein a fusion protein which comprises a delivery signal from a bacterial effector protein and the heterologous protein is expressed by the recombinant virulence attenuated Gram-negative bacterial strain and is translocated into the cell of a malignant solid tumor;

and optionally iii) cleaving the fusion protein so that the heterologous protein is cleaved from the delivery signal from the bacterial effector protein inside of the cell of a malignant solid tumor, wherein the recombinant virulence attenuated Gram-negative bacterial strain is administered in an amount that is sufficient to treat the subject.

In some embodiments at least two fusion proteins which comprise each a delivery signal from a bacterial effector protein and a heterologous protein are expressed by the recombinant virulence attenuated Gram-negative bacterial strain and are translocated into the eukaryotic cell e.g the cancer cell by the methods of the present inventions.

The recombinant virulence attenuated Gram-negative bacterial strain can be cultured so that a fusion protein is expressed which comprises the delivery signal from the bacterial effector protein and the heterologous protein according to methods known in the art (e.g. FDA, Bacteriological Analytical Manual (BAM), chapter 8: *Yersinia enterocolitica*). Preferably the recombinant virulence attenuated Gram-negative bacterial strain can be cultured in Brain Heart infusion broth e.g. at 28° C. For induction of expression of T3SS and e.g. YopE/SycE promoter dependent genes, bacteria can be grown at 37° C.

In one embodiment, the cancer cell e.g the cell of a malignant solid tumor is contacted with two recombinant virulence attenuated Gram-negative bacterial strains of i), wherein the first recombinant virulence attenuated Gram-negative bacterial strain expresses a first fusion protein which comprises the delivery signal from the bacterial effector protein and a first heterologous protein and the second recombinant virulence attenuated Gram-negative bacterial strain expresses a second fusion protein which comprises the delivery signal from the bacterial effector protein and a second heterologous protein, so that the first and the second fusion protein are translocated into the cell of a malignant solid tumor. This embodiment provided for co-infection of a cancer cell e.g a cell of a malignant solid tumor with two bacterial strains as a valid method to deliver e.g. two different hybrid proteins into single cells to address their functional interaction.

Those skilled in the art can also use a number of assays to determine whether the delivery of a fusion protein is successful. For example, the fusion protein may be detected via immunofluorescence using antibodies recognizing a fused tag (like Myc-tag). The determination can also be based on the enzymatic activity of the protein being delivered, e.g., the assay described by [19].

The present invention also provides a pharmaceutical composition comprising a recombinant virulence attenuated Gram-negative bacterial strain as described herein optionally comprising a suitable pharmaceutically acceptable carrier. Thus the present invention also provides a pharmaceutical composition comprising a recombinant virulence attenuated Gram-negative bacterial strain as described herein for use in a method of treating cancer e.g. a malignant solid tumor in a subject.

The recombinant virulence attenuated Gram-negative bacteria can be compounded for convenient and effective administration in an amount that is sufficient to treat the subject as pharmaceutical composition with a suitable pharmaceutically acceptable carrier. A unit dosage form of the recombinant virulence attenuated Gram-negative bacteria or of the pharmaceutical composition to be administered can, for example, contain the recombinant virulence attenuated Gram-negative bacteria in an amount from about $10^5$ to about $10^9$ bacteria per ml, preferably about $10^6$ to about $10^8$ bacteria per ml, more preferably about $10^7$ to about $10^8$ bacteria per ml, most preferably about $10^8$ bacteria per ml.

By "amount that is sufficient to treat the subject" or "effective amount" which are used herein interchangeably is meant to be an amount of a bacterium or bacteria, high enough to significantly positively modify the condition to be treated but low enough to avoid serious side effects (at a reasonable benefit/risk ratio), within the scope of sound medical judgment. An effective amount of a bacterium will vary with the particular goal to be achieved, the age and physical condition of the subject being treated, the duration of treatment, the nature of concurrent therapy and the specific bacterium employed. The effective amount of a bacterium will thus be the minimum amount, which will provide the desired effect. Usually an amount from about $10^5$ to about $10^9$ bacteria e.g. from about $10^5$ to about $10^9$ bacteria/$m^2$ body surface, preferably from about $10^6$ to about $10^8$ bacteria e.g. from about $10^6$ to about $10^8$ bacteria/$m^2$ body surface, more preferably from about 10' to about $10^8$ bacteria e.g. from about 10' to about $10^8$ bacteria/$m^2$ body surface, most preferably $10^8$ bacteria e.g. $10^8$ bacteria/$m^2$ body surface are administered to the subject.

A single dose of the recombinant virulence attenuated Gram-negative bacterial strain to administer to a subject, e.g. to a human to treat cancer e.g. a malignant solid tumor is usually from about $10^4$ to about $10^{10}$ bacteria e.g. from about $10^4$ bacteria/$m^2$ body surface to about $10^{10}$ bacteria/$m^2$ body surface, preferably from about $10^5$ to about 109 bacteria e.g. from about $10^5$ to about $10^9$ bacteria/$m^2$ body surface, more preferably from about $10^6$ to about $10^8$ bacteria e.g. from about $10^6$ to about $10^8$ bacteria/$m^2$ body surface, even more preferably from about $10^7$ to about $10^8$ bacteria e.g. from about $10^7$ to about $10^8$ bacteria/$m^2$ body surface, most preferably $10^8$ bacteria e.g. $10^8$ bacteria/$m^2$ body surface of total recombinant virulence attenuated Gram-negative bacteria.

Examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present.

Modes of administration of the recombinant virulence attenuated Gram-negative bacteria to a subject may be selected from the group consisting of intravenous, intratumoral, intraperitoneal and per-oral administration. Although this invention is not intended to be limited to any particular mode of application, intravenous or intratumoral administration of the bacteria or the pharmaceutical compositions is preferred.

Depending on the route of administration, the active ingredients which comprise bacteria may be required to be coated in a material to protect said organisms from the action of enzymes, acids and other natural conditions which may inactivate said organisms. In order to administer bacteria by other than parenteral administration, they should be coated by, or administered with, a material to prevent inactivation. For example, bacteria may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport bacteria, such as *Lactobacillus*, or their by-products to an internal target of a host subject. One bacterium may be administered alone or in conjunction with a second, different bacterium. Any number of different bacteria may be used in conjunction. By "in conjunction with" is meant together, substantially simultaneously or sequentially. The compositions may be also administered in the form of tablet, pill or capsule, for example, such as a freeze-dried capsule comprising the bacteria or the pharmaceutical compositions of the present invention or as frozen solution of bacteria or the pharmaceutical compositions of the present invention containing DMSO or glycerol. Another preferred form of application involves the preparation of a lyophilized capsule of the bacteria or the pharmaceutical compositions of the present invention. Still another preferred form of application involves the preparation of a heat dried capsule of the bacteria or the pharmaceutical compositions of the present invention.

The recombinant virulence attenuated Gram-negative bacteria or the pharmaceutical composition to be administered can be administered by injection. Forms suitable for injectable use include monoseptic or sterile aqueous solutions (where water soluble) or dispersions and sterile powders for the extemporaneous preparation of sterile injectable solutions or dispersion. In all cases the form must be monoseptic or sterile and must be fluid to the extent that easy syringability exists. It must be stable under the conditions of manufacture and storage. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments of the present invention the recombinant virulence attenuated Gram-negative bacterial strain is co-administered with a siderophore to the subject.

These embodiments are preferred. Siderophores which can be co-administered are siderophores including hydroxamate, catecholate and mixed ligand siderophores. Preferred siderophores are Deferoxamine (also known as desferrioxamine B, desferoxamine B, DFO-B, DFOA, DFB or desferal), Desferrioxamine E, Deferasirox (Exjade, Desirox, Defrijet, Desifer) and Deferiprone (Ferriprox), more preferred is Deferoxamine. Deferoxamine is a bacterial siderophore produced by the Actinobacteria *Streptomyces pilosus* and is commercially available from e.g. Novartis Pharma Schweiz AG (Switzerland).

Co-administration with a siderophore can be before, simultaneous to or after administration of the recombinant virulence attenuated Gram-negative bacterial strain.

Preferably a siderophore is administered before the administration of recombinant virulence attenuated Gram-negative bacterial strain, more preferably is administered at least 1 hour, preferably at least 6 hours, more preferably at least 12, hours, in particular at least 24 hours before the administration of the recombinant virulence attenuated Gram-negative bacterial strain to the subject. In a particular embodiment the subject is pretreated with desfreoxamine 24 h prior to infection with the recombinant virulence attenuated Gram-negative bacterial strain in order to allow bacterial growth. Usually a siderophore is co-administered at a single dose from about $0.5\times10^{-5}$ Mol to about $1\times10^{-3}$ Mol, more preferably from about $1\times10^{-5}$ Mol to about $1\times10^{-4}$ Mol preferably from about $3.5\times10^{-5}$ Mol to about $1.1\times10^{-4}$ Mol per kg of body weight. Usually desferoxamine is co-administered at single dose from about 20 mg to about 60 mg preferably from about 20 mg to about 60 mg per kg of body weight.

Dosis regimens of the administration of the recombinant virulence attenuated Gram-negative bacterial strain or the pharmaceutical composition described herein will vary with the particular goal to be achieved, the age and physical condition of the subject being treated, the duration of treatment, the nature of concurrent therapy and the specific bacterium employed, as known to the skilled person. The recombinant virulence attenuated Gram-negative bacterial strain is usually administered to the subject according to a dosing regimen consisting of a single dose every 1-20 days, preferably every 1-10 days, more preferably every 1-7 days. The period of administration is usually about 20 to about 60 days, preferably about 30-40 days. Alternatively the period of administration is usually about 8 to about 32 weeks, preferably about 8 to about 24 weeks, more preferably about 12 to about 16 weeks.

In a further embodiment the present invention provides a kit for treating cancer e.g. such as malignant solid tumors, preferably in human. Such kits generally will comprise the recombinant virulence attenuated Gram-negative bacterial strain or the pharmaceutical composition described herein, and instructions for using the kit. In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

EXAMPLES

Example 1

A) Materials and Methods

Bacterial strains and growth conditions. The strains used in this study are listed in FIGS. 3A to M. *E. coli* Top10, used for plasmid purification and cloning, and *E. coli* Sm10λ pir, used for conjugation, as well as *E. coli* BW19610[31], used to propagate pKNG101, were routinely grown on LB agar plates and in LB broth at 37° C. Ampicillin was used at a concentration of 200 μg/ml (*Yersinia*) or 100 μg/ml (*E. coli*) to select for expression vectors. Streptomycin was used at a concentration of 100 μg/ml to select for suicide vectors. *Y. enterocolitica* MRS40 (0:9, biotype 2)[20] a non Ampicillin resistant E40-derivate[19] and strains derived thereof were routinely grown on Brain Heart Infusion (BHI; Difco) at RT. To all *Y. enterocolitica* strains Nalidixic acid was added (35 μg/ml) and all *Y. enterocolitica* asd strains were additionally supplemented with 100 μg/ml meso-2,6-Diaminopimelic acid (mDAP, Sigma Aldrich). *S. enterica* SL1344 were routinely grown on LB agar plates and in LB broth at 37° C. Ampicillin was used at a concentration of 100 μg/ml to select for expression vectors in *S. enterica*.

Genetic manipulations of *Y. enterocolitica*. Genetic manipulations of *Y. enterocolitica* has been described[32,33] Briefly, mutators for modification or deletion of genes in the pYV plasmids or on the chromosome were constructed by 2-fragment overlapping PCR using purified pYV40 plasmid or genomic DNA as template, leading to 200-250 bp of flanking sequences on both sides of the deleted or modified part of the respective gene. Resulting fragments were cloned in pKNG101[29] in *E. coli* BW19610[31]. Sequence verified plasmids were transformed into *E. coli* Sm10λ pir, from where plasmids were mobilized into the corresponding *Y. enterocolitica* strain. Mutants carrying the integrated vector were propagated for several generations without selection pressure. Then sucrose was used to select for clones that have lost the vector. Finally mutants were identified by colony PCR. Specific mutators (pSi_408, pSi_419) are listed in Table III.

Construction of plasmids. Plasmid pBad_Si2 or pBad_Si1 (FIG. 2) were used for cloning of fusion proteins with the N-terminal 138 amino acids of YopE (SEQ ID No. 2). pBad_Si2 was constructed by cloning of the SycE-$YopE_{1-138}$ fragment containing endogenous promoters for YopE and SycE from purified pYV40 into KpnI/HindIII site of pBad-MycHisA (Invitrogen). Additional modifications include removal of the NcoI/BglII fragment of pBad-MycHisA by digestion, Klenow fragment treatment and religation. A bidirectional transcriptional terminator (BBa_B1006; iGEM foundation) was cloned into KpnI cut and Klenow treated (pBad_Si2) or BglII cut site (pBad_Si1). Further at the 3' end of $YopE_{1-138}$ the following cleavage sites were added: XbaI-XhoI-BstBI-(HindIII) (FIG. 2 B). pBad_Si1 is equal to pBad_Si2 but encodes EGFP amplified from pEGFP-C1 (Clontech) in the NcoI/BglII site under the Arabinose inducible promoter. Plasmids pSi_266, pSi_267, pSi_268 and pSi_269 containing the corresponding endogenous promoter and the $SteA_{1-20}$ fragment (pSi_266), the full length SteA sequence (pSi_267), the $SopE_{1-81}$ fragment (pSi_268) or the $SopE_{1-105}$ fragment (pSi_269) were amplified from *S. enterica* SL1344 genomic DNA and cloned into NcoI/KpnI site of pBad-MycHisA (Invitrogen).

Full length genes or fragments thereof were amplified with the specific primers listed in Table I below and cloned as fusions to $YopE_{1-138}$ into plasmid pBad_Si2 or in case of z-BIM (SEQ ID No. 16) into pBad_Si1 (see Table II below). For fusion to SteA or SopE, synthetic DNA constructs were cleaved by KpnI/HindII and cloned into pSi_266, pSi_267, pSi_268 or pSi_269 respectively. In case of genes of bacterial species, purified genomic DNA was used as template (*S. flexneri* M9OT, *Salmonella enterica* subsp. *enterica* serovar *Typhimurium* SL1344, *Bartonella henselae* ATCC 49882). For human genes a universal cDNA library (Clontech) was used if not otherwise stated (FIGS. 3A to M, zebrafish genes were amplified from a cDNA library (a kind gift of M. Affolter). Ligated plasmids were cloned in *E. coli* Top10. Sequenced plasmids were electroporated into the desired *Y. enterocolitica* or *S. enterica* strain using settings as for standard *E. coli* electroporation.

TABLE I

| (Primer Nr. Si: Sequence) |
|---|
| Seq_Id_No_51: Primer No.: Si_285<br>CATACCATGGGAGTGAGCAAGGGCGAG |
| Seq_Id_No_52: Primer No.: Si_286<br>GGAAGATCTTtACTTGTACAGCTCGTCCAT |
| Seq_Id_No_53: Primer No.: Si_287<br>CGGGGTACCTCAACTAAATGACCGTGGTG |
| Seq_Id_No_54: Primer No.: Si_288<br>GTTAAAGCTTttcgaatctagactcgagCGTGGCGAACTGGTC |
| Seq_Id_No_55: Primer No.: Si_387<br>CGTAtctagaATGGACTGTGAGGTCAACAA |
| Seq_Id_No_56: Primer No.: Si_391<br>CGTAtctagaGGCAACCGCAGCA |
| Seq_Id_No_57: Primer No.: Si_389<br>GTTAAAGCTTTCAGTCCATCCCATTTCTg |
| Seq_Id_No_58: Primer No.: Si_436<br>CGTAtctagaATGCCCCGCCCC |
| Seq_Id_No_59: Primer No.: Si_437<br>GTTAAAGCTTCTACCCACCGTACTCGTCAAT |
| Seq_Id_No_60: Primer No.: Si_438<br>CGTAtctagaATGTCTGACACGTCCAGAGAG |
| Seq_Id_No_61: Primer No.: Si_439<br>GTTAAAGCTTTCATCTTCTTCGCAGGAAAAAG |
| Seq_Id_No_62: Primer No.: Si_463<br>CAGTctcgaggaaagcttgtttaaggggc |
| Seq_Id_No_63: Primer No.: Si_464<br>cagtTTCGAAttagcgacggcgacg |
| Seq_Id_No_64: Primer No.: Si_476<br>GTTAAAGCTTttACTTGTACAGCTCGTCCAT |
| Seq_Id_No_65: Primer No.: Si_494<br>CGTAtctagaATGGCCGAGCCTTG |
| Seq_Id_No_66: Primer No.: Si_495<br>GTTAAAGCTTttaTTGAAGATTTGTGGCTCC |
| Seq_Id_No_67: Primer No.: Si_504<br>CGTAtctagaGAAAATCTGTATTTTCAAAGTGAAAATCTGTATTTTCAAA<br>GTATGCCCCGCCCC |
| Seq_Id_No_68: Primer No.: Si_505<br>GTTAAAGCTTCCCACCGTACTCGTCAATtc |
| Seq_Id_No_69: Primer No.: Si_508<br>CGTAtctagaGAAAATCTGTATTTTCAAAGTGAAAATCTGTATTTTCAAA<br>GTATGGCCGAGCCTTG |

TABLE I-continued

| (Primer Nr. Si: Sequence) |
|---|
| Seq_Id_No_70: Primer No.: Si_509<br>GTTAAAGCTTTTGAAGATTTGTGGCTCCc |
| Seq_Id_No_71: Primer No.: Si_511<br>CGTAtctagaGAAAATCTGTATTTTCAAAGTGAAAATCTGTATTTTCAAA<br>GTGTGAGCAAGGGCGAG |
| Seq_Id_No_72: Primer No.: Si_512<br>CGTAtctagaGAAAATCTGTATTTTCAAAGTGAAAATCTGTATTTTCAAA<br>GTCCGCCGAAAAAAAAACGTAAAGTTGTGAGCAAGGGCGAG |
| Seq_Id_No_73: Primer No.: Si_513<br>GTTAAAGCTTttAAACTTTACGTTTTTTTTTCGGCGGCTTGTACAGCTCG<br>TCCAT |
| Seq_Id_No_74: Primer No.: 55 15<br>CGTAtctagaGAAAATCTGTATTTTCAAAGTGAAAATCTGTATTTTCAAA<br>GTGATTATAAAGATGATGATGATAAAATGGCCGAGCCTTG |
| Seq_Id_No_75: Primer No.: Si_677<br>TTACTATTCGAAGAAATTATTCATAATATTGCCCGCCATCTGGCCCAAAT<br>TGGTGATGAAATGGATCATTAAGCTTGGAGTA |
| Seq_Id_No_76: Primer No.: Si_678<br>TACTCCAAGCTTAATGATCCATTTCATCACCAATTTGGGCCAGATGGCGG<br>GCAATATTATGAATAATTTCTTCGAATAGTAA |
| Seq_Id_No_77: Primer No.: Si_682<br>TTACTACTCGAGAAAAAACTGAGCGAATGTCTGCGCCGCATTGGTGATGA<br>ACTGGATAGCTAAGCTTGGAGTA |
| Seq_Id_No_78: Primer No.: Si_683<br>TACTCCAAGCTTAGCTATCCAGTTCATCACCAATGCGGCGCAGACATTCG<br>CTCAGTTTTTTCTCGAGTAGTAA |
| Seq_Id_No_79: Primer No.: Si_580<br>catgccatggatttatggtcatagatatgacctc |
| Seq_Id_No_80: Primer No.: Si_612<br>CGGGGTACCatgaggtagcttatttcctgataaag |
| Seq_Id_No_81: Primer No.: Si_613<br>CGGGGTACCataattgtccaaatagttatggtagc |
| Seq_Id_No_82: Primer No.: Si_614<br>catgccatggCGGCAAGGCTCCTC |
| Seq_Id No_83: Primer No.: Si_615<br>cggggtaccTTTATTTGTCAACACTGCCC |
| Seq_Id No_84: Primer No.: Si_616<br>cggggtaccTGCGGGGTCTTTACTCG |
| Seq_Id No_85: Primer No.: Si_585<br>CAGTctcgagATGCAGATCTTCGTCAAGAC |
| Seq_Id No_86: Primer No.: Si_586<br>GTTAAAGCTTgctagcttcgaaACCACCACGTAGACGTAAGAC |
| Seq_Id_No_87: Primer No.: Si_588<br>cagtTTCGAAGATTATAAAGATGATGATGATAAAATGGCCGAGCCTTG |
| Seq_Id No_88: primer No. 733<br>TTACTACTCGAGGGTGCCATCGATGCCGAAGAAATTATTCATAATATTGC<br>CCG |
| Seq_Id No_89: primer No. 735<br>TACTCCTTCGAATTAATGATCCATTTCATCACCAATTTG |
| Seq_Id No_90: primer No. 736<br>TTACTACTCGAGGGTGCCATCGATGCCAAAAAACTGAGCGAATGTCTGCG |
| Seq_Id No_91: primer No. 738<br>TACTCCTTCGAATTAGCTATCCAGTTCATCACCAATG |
| Seq_Id No_92: primer No. 734<br>TACTCCTTCGAAGGCACCATGATCCATTTCATCACCAATTTGG |

TABLE I-continued

| (Primer Nr. Si: Sequence) |
|---|
| Seq_ID No_93: primer No. 725: TTACTATTCGAAGAAATTATTCATAATATTGCC |
| Seq_ID No_94: primer No. 726: TACTCCAAGCTTACGGTTGAATATTATGATCCATTTCATCACCAATTTGG |
| Seq_ID No_95: primer No. 727: TTACTATTCGAAGCCGGTGGTGCCGAAGAAATTATTCATAATATTGCCC |
| Seq_ID No_96: primer No. 728: TACTCCAAGCTTAATGATCCATTTCATCA |
| Seq_ID No_97: primer No. 737: TACTCCTTCGAAGGCACCGCTATCCAGTTCATCACCAATG |
| Seq_ID No_101: primer No. 869: gatcgtcgacTTAAGTTCAATGGAGCGTTTAATATC |
| Seq_ID_No_102: primer No. 870: ctttgactggcgagaaacgcTCTTAACATGAGGCTGAGCTC |
| Seq_ID_No_103: primer No. 871: GAGCTCAGCCTCATGTTAAGAgcgtttctcgccagtcaaag |
| Seq_ID_No_104: primer No. 872: gatagcccccgagcctgtGCACTTTGTCATTAACCTCAGC |
| Seq_ID_No_105: primer No. 873: GCTGAGGTTAATGACAAAGTGCacaggctcgggggctatc |
| Seq_ID_No_106: primer No. 874: catgtctagaCCCTCAGCATAATAACGACTC |

TABLE I-continued

| (Primer Nr. Si: Sequence) |
|---|
| Seq_ID_No_107: primer No. 600: catgacatgtTGGCGTTTCTCGCC |
| Seq_ID_No_108: primer No. 601: catgacatgtATTAACCTCAGCCCTGACTATAAG |
| Seq_ID_No_119: primer No. 1010: cacatgtctagaCAACCGTTTCCGAAAGGTGATCTG |
| Seq_ID_No_120: primer No. 1012: atccCAagctTATTGGCGTTGGGTGGTAAAAATTTTG |
| Seq_ID_No_121: primer No. 1021: cacatgtctagaATGACCGCCGAACAACGC |
| Seq_ID_No_122: primer No. 1022: catgaagcttaCGGACCCGGATTTTGGCTC |
| Seq_ID_ No_123: primer No. 1023: catgaagcttaCGGTTCTTCTTGAATAAAAATTTGAATG |
| Seq_ID_No_124: primer No. 1024: catgaagcttaTTGCAGCACTTTCGGCCAATTT |
| Seq_ID_No_125: primer No. 1025: cacatgtctagaATGAGCATTGTGTGTAGCGC |
| Seq_ID_No_126: primer No. 1026: catgaagcttaGCTTTCATCCACGGCCGG |
| Seq_ID_No_127: primer No. 1027: catgaagcttaATTACCGGTTTGGCGCAGC |

TABLE II

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| YopE1-138-MycHis | 3 | pBad-MycHisA (Invitrogen) | pBad_Si_1 | 285/286 (EGFP), 287/288 (sycE-YopE1-138) | 51/52 and 53/54 |
| YopE1-138-MycHis | 3 | pBad-MycHisA (Invitrogen) | pBad_Si_2 | 287/288 (sycE-YopE1-138) | 53/54 |
| YopE1-138- human Bid | 16 | pBad_Si_2 | pSi_85 | 387/391 | 55/56 |
| YopE1-138- human t-Bid | 17 | pBad_Si_2 | pSi_87 | 389/391 | 55/57 |
| YopE1-138-ET1 | 9 | pBad_Si_2 | pSi_120 | 436/437 | 58/59 |
| YopE1-138-z-BIM | 16 | pBad_Si_1 | pSi_121 | 438/439 | 60/61 |
| YopE1-138-TEV protease S219V | 12 | pBad_Si_2 | pSi_132 | 463/464 | 62/63 |
| YopE1-138-Ink4C | 8 | pBad_Si_2 | pSi_151 | 494/495 | 65/66 |
| YopE1-138-2x TEVsite - ET1 | 11 | pBad_Si_2 | pSi_156 | 504/505 | 67/68 |
| YopE1-138-2xTEVsite- EGFP | 98 | pBad_Si_2 | pSi_158 | 511/476 | 71/64 |
| YopE1-138-2xTEVsite - EGFP - NLS | 99 | pBad_Si_2 | pSi_159 | 511/513 | 71/73 |
| YopE1-138-2xTEVsite - NLS - EGFP | 100 | pBad_Si_2 | pSi_160 | 512/476 | 72/64 |
| YopE1-138-2x TEVsite - INK4C | 10 | pBad_Si_2 | pSi_161 | 508/509 | 69/70 |
| YopE1-138-2x TEVsite - Flag - INK4C | 13 | pBad_Si_2 | pSi_164 | 515/509 | 74/70 |

TABLE II-continued

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| YopE1-138-*Y. enterocolitica* codon optimized murine tBid BH3 part | 19 | pBad_Si_2 | pSi_318 | 677/678 | 75/76 |
| YopE1-138-*Y. enterocolitica* codon optimized murine Bax BH3 part | 20 | pBad_Si_2 | pSi_322 | 682/683 | 77/78 |
| SteA1-20 | 5 | pBad-MycHisA (Invitrogen) | pSi_266 | 580/612 | 79/80 |
| SteA | 4 | pBad-MycHisA (Invitrogen) | pSi_267 | 580/613 | 79/81 |
| SopE1-81 | 6 | pBad-MycHisA (Invitrogen) | pSi_268 | 614/615 | 82/83 |
| SopE1-105 | 7 | pBad-MycHisA (Invitrogen) | pSi_269 | 614/616 | 82/84 |
| YopE1-138-*Y. enterocolitica* codon optimized murine tBid | 21 | pBad_Si_2 | pSi_315 | synthetic construct | / |
| YopE1-138-Ubiquitin | 14 | pBad_Si_2 | pSi_236 | 585/586 | 85/86 |
| YopE1-138-Ubiquitin-Flag-INK4C-MycHis | 15 | pSi_236 | pSi_237_II | 588/509 | 87/70 |
| YopE1-138-(*Y. enterocolitica* codon optimized murine tBid BH3 part) ready for insertion of further domains | 25 | pBad_Si_2 | pSi_357 | 733/735 | 88/89 |
| YopE1-138-(*Y. enterocolitica* codon optimized murine BAχ BH3 part) ready for insertion of further domains | 26 | pBad_Si_2 | pSi_358 | 736/738 | 90/91 |
| YopE1-138-(*Y. enterocolitica* codon optimized murine tBid BH3 part)$_2$ | 27 | pSi_357 | pSi_371 | 733/734 | 88/92 |
| YopE1-(138-*Y. enterocolitica* codon optimized murine tBid BH3 part- *Y. enterocolitica* codon optimized murine BAχ BH3 part | 28 | pSi_358 | pSi_373 | 733/734 | 88/92 |
| YopE$_{1-138}$- codon optimized murine tBid BH3 extended part | 22 | pBad_Si_2 | pSi_353 | 725/726 | 93/94 |
| YopE$_{1-138}$-10 Aa linker - *Y. enterocolitica* codon optimized murine tBid BH3 part | 23 | pBad_Si_2 | pSi_354 | 727/728 | 95/96 |
| YopE$_{1-138}$-*Y. enterocolitica* codon optimized murine Bax BH3 part- *Y. enterocolitica* codon optimized murine tBid BH3 part | 24 | pSi_357 | pSi_374 | 736/737 | 90/97 |
| YopE$_{1-138}$- *Y. enterocolitica* codon optimized human RIG-1 two CARD domains (Aa. 1-245) | 37 | pBad_Si_2 | pSi_453 | synthetic construct | / |

TABLE II-continued

| Cloned fusion proteins | | | | | |
|---|---|---|---|---|---|
| Protein to be delivred by T3SS | Protein Seq. ID. No. | Backbone plasmid | Resulting plasmid name | Primers. Si_Nr.: | Primer Seq. ID No. |
| $YopE_{1-138}$- *Y. enterocolitica* codon optimized murine RIG-1 two CARD domains (Aa. 1-246) | 38 | pBad_Si_2 | pSi_454 | synthetic construct | / |
| $YopE_{1-138}$- *Y. enterocolitica* codon optimized *S. cerevisiae* GCN4 (Aa. 249-278) - *Y. enterocolitica* codon optimized *P. aeruginosa* WspR (Aa. 172-347) | 39 | pBad_Si_2 | pSi_452 | synthetic construct | / |
| $YopE_{1-138}$- *Y. enterocolitica* codon optimized murine IRF3 S397D | 40 | pBad_Si_2 | pSi_428 | synthetic construct | / |
| $YopE_{1-138}$- *Y. enterocolitica* codon optimized *V. Cholerae* DncV (M3toL413) | 41 | pBad_Si_2 | pSi_482 | synthetic construct | / |
| $YopE_{1-138}$- *Y. enterocolitica* codon optimized *B. cereus*_DisA-like (PDB: 2FB5; Aa. 76-205) | 42 | pBad_Si_2 | pSi_483 | synthetic construct | / |
| $YopE_{1-138}$- *Y. enterocolitica* codon optimized Anemonae (*N. vectensis*) cGAS (Ensembl: A7SFB5.1) | 43 | pBad_Si_2 | pSi_484 | synthetic construct | / |
| YopE1-138 - *Y. enterocolitica* codon optimized murine RIG1 CARD domains (Aa. 1-229) | 110 | pBad_Si_2 | pSi_521 | 1021/1022 | 122/123 |
| YopE1-138 - *Y. enterocolitica* codon optimized murine RIG1 CARD domains (Aa. 1-218) | 111 | pBad_Si_2 | pSi_522 | 1021/1023 | 122/124 |
| YopE1-138 - *Y. enterocolitica* codon optimized murine MDA5 (Aa. 1-294) | 112 | pBad_Si_2 | pSi_517 | synthetic construct | / |
| YopE1-138 - *Y. enterocolitica* codon optimized murine MDA5 (Aa. 1-231) | 113 | pBad_Si_2 | pSi_524 | 1025/1026 | 126/127 |
| YopE1-138- *Y. enterocolitica* codon optimized human cGAS (Aa. 161-522) | 115 | pBad_Si_2 | pSi_515 | synthetic construct | / |
| YopE1-138- *Y. enterocolitica* codon optimized human MAVS CARD (Aa. 1-100) | 116 | pBad_Si_2 | pSi_539 | synthetic construct | / |
| YopE1-138- *Y. enterocolitica* codon optimized *Anemonae* (*N. vectensis*) cGAS (Aa. 60-422) (Ensembl: A7SFB5.1) | 117 | pBad_Si_2 | pSi_503 | 1010/1012 | 120/121 |
| YopE1-138- *Y. enterocolitica* codon optimized *Listeria* CdaA (Aa. 101-273) | 118 | pBad_Si_2 | pSi_518 | synthetic construct | / |

TABLE III

Mutators for genetic modification

| Mutator/ Construct | To be inserted onto: | Backbone plasmid | Resulting plasmid name | Primers Si_Nr.: | Primers Seq. Id No. | used with special parent strain |
|---|---|---|---|---|---|---|
| $YopE_{1-138}$-murine tBID BH3 | pYV | pKNG101 | pSi_408 | Synthetic gene | / | / |
| $YopE_{1-138}$-(murine tBID $BH3)_2$ | pYV | pKNG101 | pSi_437 | Synthetic gene | / | Strain mutated with pSi_408 |
| $YopE_{1-138}$-*Y. enterocolitica* codon optimized murine RIG-1 two CARD domains (Aa. 1-246) | pYV | pKNG101 | pSi_456 (Seq ID No 50) | Synthetic gene | / | / |
| pYV-asd | pYV | pKNG101 | pSi_417 | PCR1: 869/870; PCR2: 871/872; PCR3: 873/874; overlapping PCR 869/874 | PCR1: 101/102; PCR2: 103/104; PCR3: 105/106; overlapping PCR 101/106 | Δasd |
| pYV-virF-hairpinI | pYV | pKNG101 | pSi_441 | Synthetic gene | / | / |
| pYV-pAra-VirF | pYV | pKNG101 | pSi_439 | Synthetic gene | / | / |

Yop secretion. Induction of the yop regulon was performed by shifting the culture to 37° C. in BHI-Ox (secretion-permissive conditions)[34]. As carbon source glucose was added (4 mg/ml).

Total cell and supernatant fractions were separated by centrifugation at 20 800 g for 10 min at 4° C. The cell pellet was taken as total cell fraction. Proteins in the supernatant were precipitated with trichloroacetic acid 10% (w/v) final for 1 h at 4° C. After centrifugation (20 800 g for 15 min) and removal of the supernatant, the resulting pellet was washed in ice-cold Acetone over-night. The samples were centrifuged again, the supernatant was discarded and the pellet was air-dried and resuspended in 1× SDS loading dye.

Secreted proteins were analysed by SDS—PAGE; in each case, proteins secreted by $3\times10^8$ bacteria were loaded per lane. Detection of specific secreted proteins by immunoblotting was performed using 12.5% SDS—PAGE gels. For detection of proteins in total cells, $2\times10^8$ bacteria were loaded per lane, if not stated otherwise, and proteins were separated on 12.5% SDS—PAGE gels before detection by immunoblotting.

Immunoblotting was carried out using rat monoclonal antibodies against YopE (MIPA193-13A9; 1:1000, [35]). The antiserum was preabsorbed twice overnight against *Y. enterocolitica* ΔHOPEMT asd to reduce background staining. Detection was performed with secondary antibodies directed against rat antibodies and conjugated to horseradish peroxidase (1:5000; Southern biotech), before development with ECL chemiluminescent substrate (LumiGlo, KPM).

Cell culture and infections. HeLa Ccl2 and B16F10 cells were cultured in Dulbecco's modified Eagle's medium (DMEM) supplemented with 10% FCS and 2 mM L-Glutamine (cDMEM). 4T1 cells were cultured in RPMI 1640 supplemented with 10% FCS and 2 mM L-Glutamine. *Y. enterocolitica* were grown in BHI with additives overnight at RT, diluted in fresh BHI to an $OD_{600}$ of 0.2 and grown for 2 h at RT before a temperature shift to a 37° C. water bath shaker for further 30 min or for 1 h in case of delivery of EGFP. Finally, the bacteria were collected by centrifugation (6000 rcf, 30 sec) and washed once with DMEM supplemented with 10 mM HEPES and 2 mM L-glutamine. Finally, the bacteria were collected by centrifugation (6000 rcf, 30 sec) and washed once with DMEM supplemented with 10 mM HEPES and 2 mM L-glutamine. Cells seeded in 96-well (for Immunofluorescence) or 6-well (for Western blotting) plates were infected at indicated MOIs in DMEM supplemented with 10 mM HEPES and 2 mM L-glutamine. After adding bacteria, plates were centrifuged for 1 min at 1750 rpm and placed at 37° C. for indicated time periods. Extracellular bacteria were killed by gentamicin (100 mg/ml) if indicated. In case of immunofluorescence analysis, infection assays were stopped by 4% PFA fixation. For Western blot analysis cells were washed twice with ice-cold PBS and Phospho-safe lysis buffer (Novagen) was added to lyse the cells. After incubation on ice, the cells were centrifuged (16 000 rcf, 25 min, 4° C.). Supernatants were collected and analyzed for total protein content by Bradford BCA assay (Pierce) before SDS PAGE and Western blotting using anti-Actin (Millipore), Anti-Bid (Cell Signaling), anti-Myc (Santa Cruz), anti-Caspase-3 p17 (Cell Signaling) and anti-Ink4C (Cell Signaling) antibody.

Western blotting of T3SS translocated proteins from infected cells. HeLa cells in 6-well plates were infected at an MOI of 100 as described above. In case of coinfection with the TEV protease translocating *Y. enterocolitica* strain, the $OD_{600}$ of the strains was set and the two bacterial suspensions were mixed in a tube at a ratio of 1:1 (if not otherwise indicated) before addition to the cells. At the end of the infection, the cells were washed twice with ice-cold PBS and collected by scraping in a small volume of ice-cold PBS. After centrifugation (16 000 rcf, 5 min, 4° C.) the pellet was dissolved in 0.002% digitonin supplemented with a protease inhibitor cocktail (Roche complete, Roche). The dissolved pellets were incubated for 5 minutes on ice and then centrifuged (16 000 rcf, 25 min, 4° C.). Supernatants were collected and analyzed for total protein content by Bradford BCA assay (Pierce) before SDS PAGE and Western blotting using an anti-Myc (Santa Cruz, 9E11) or anti-Ink4C (Cell Signaling) antibody.

Automated Microscopy and Image Analysis. Images were automatically acquired with an ImageXpress Micro (Molecular devices, Sunnyvale, USA). Quantification of anti-Myc staining intensities was performed using MetaXpress (Molecular devices, Sunnyvale, USA). Regions within cells excluding nuclear regions and regions containing bacteria were manually chosen (circles with an area of 40 pixels) and average intensity was recorded.

Biodistribution in B16-F10 and 4T1 Tumor Allograft Mouse Models

All animal experiments were approved (license 1908; Kantonales Veterinäramt Basel-Stadt) and performed according to local guidelines (Tierschutz-Verordnung, Basel-Stadt) and the Swiss animal protection law (Tierschutz-Gesetz). 6 week old C57B1/6 and BALB/c mice were ordered from Janvier Labs. After at least one week of accommodation, mice were anesthetized using isoflurane and 100 ul B16-F10 or 4T1 cells ($1\times10^5$-$1\times10^6$ cells) were subcutaneously injected into the flank of C57B1/6 and BALB/c, respectively. Throughout the experiment, mice were scored for behavior and physical appearance, and surface temperature, as well as body weight was measured.

Once tumors had developed, mice were administered an 8 mg/ml desferal solution (10 ml/kg) through i.p. injection. On the following day, mice were infected with *Y. enterocolitica* MRS40 or *Y. enterocolitica* MRS40 ΔHOPEMT ($2\times10^5$, $1\times10^6$ or $1\times10^7$ bacteria) by injection into the tail vein. The inoculum i.v. administered to the mice was validated by dilution plating. In some experiments, tumor progression was followed by daily measurements of tumor length and width with digital calipers. Tumor volume was determined as $0.523\times\text{lenght}\times\text{width}^2$. On respective days postinfection, mice were sacrificed by $CO_2$ inhalation. A blood sample was immediately isolated through aspiration from the heart. Liver, spleen, lung and the tumor were isolated and their weight determined. The organs and the tumor were homogenized. CFU in each sample was determined by spotting of serial dilutions onto LB agar plates containing nalidixic acid (35 ug/ml).

Direct type I Interferon activation assay. Murine B16F10 melanoma cells, murine RAW264.7 wildtype or MAVS knockout macrophages stably expressing secreted embryonic alkaline phosphatase (SEAP) or secreted Lucia luciferase under the control of the I-ISG54 promoter which is comprised of the IFN-inducible ISG54 promoter enhanced by a multimeric ISRE were purchased from InvivoGen (B16-Blue ISG, RAW-Blue ISG, RAW-Lucia ISG and RAW-Lucia ISG-KO-MAVS). Growth conditions and type I IFN assay were adapted from the protocols provided by InvivoGen. Briefly, 12'500 B16-Blue ISG cells or 30'000 RAW-Blue, RAW-Lucia or RAW-Lucia KO-MAVS ISG cells in 150 µl test medium (RPMI+2 mM L-glutamine+10% FCS for B16-Blue ISG cells; DMEM+2 mM L-glutamine+10% FCS for RAW-Blue, RAW-Lucia and RAW-Lucia KO-MAVS ISG cells) per well were seeded in a flat-bottom 96-well plate (NUNC or Corning). The next day, the cells were infected with the bacterial strains to be assessed by adding 15 µl per well of the desired multiplicity of infection (MOI, diluted in test medium). After 2 hours of incubation (37° C. and 5% $CO_2$) the bacteria were killed by adding test medium containing penicillin (100 U/ml) and streptomycin (100 ug/ml). The incubation was continued for 20-24 h. Detection of SEAP and luciferase followed the QUANTI-Blue™ and QUANTI-Luc™ protocol (InvivoGen), respectively. For SEAP detection: 20 µl of the cell supernatant was incubated with 180 µl detection reagent (QUANTI-Blue™, InvivoGen). The plate was incubated at 37° C. and SEAP activity was measured by reading the OD at 650 nm using a microplate reader (Molecular Devices). As a positive control murine IFN γ (stock: 1'000'000 U/ml) diluted to the respective concentrations in test medium was used. For luciferase detection: To 20 µl of the cell supernatant 50 µl detection reagent (QUANTI-Luc™, InvivoGen) was added in opaque plates (ThermoScientific). Luminescence was measured immediately using a plate reader (BioTek).

Indirect type I Interferon activation assay. Murine B16F10 or 4T1 cells were infected with indicated multiplicities of infection (MOI) of the bacterial strains to be assessed for a total of 4 h as described above. Cell supernatant was then transferred onto murine B16F10 melanoma cells stably expressing secreted embryonic alkaline phosphatase (SEAP) under the control of the I-ISG54 promoter (comprised of the IFN-inducible ISG54 promoter enhanced by a multimeric ISRE; purchased from InvivoGen, B16-Blue ISG cells). Growth conditions and type I IFN assay were adapted from the protocols provided by InvivoGen. Briefly, 12'500 B16-Blue ISG cells in 150 µl test medium (RPMI+2 mM L-glutamine+10% FCS) per well were seeded in a flat-bottom 96-well plate (NUNC). The next day, the entire medium was removed and 100 ul of the cell supernatant of previously infected B16F10 or 4T1 was added. The plate was incubated for 20-24 h at 37° C. and 5% $CO_2$. Detection of SEAP followed the QUANTI-Blue™ protocol (InvivoGen). 20 µl of the cell supernatant was incubated with 180 u 1 detection reagent (QUANTI-Blue™, InvivoGen). The plate was incubated at 37° C. and SEAP activity was measured by reading the OD at 650 nm using a microplate reader (Molecular Devices).

Study of tumor progression in the B16F10 tumor allograft mouse model upon intratumoral treatment. All animal experiments were approved by the responsible authorities and performed according to local guidelines and animal protection laws. 5-7 weeks old female C57B1/6 mice were ordered from Charles River (L'Arbresles). After at least one week of accommodation, mice were anesthetized using isoflurane and $1\times10^6$ B16-F10 cells in 200 µL of RPMI 1640 were subcutaneously injected into the right flank of the mice. At regular intervals, mice were monitored for behaviour and physical appearance and the body weight was measured.

Treatments started once tumors had reached a volume of 60-130 $mm^3$ (defined as day 0). Mice were administered with the bacterial strains to be assessed on days 0, 1, 2, 3, 6 and 9 by intratumoral injection ($7.5\times10^7$ bacteria in 50 ul PBS per administration) under isoflurane anaesthesia. The inoculum intratumorally administered to the mice was validated by dilution plating. As control, mice were injected with endotoxin-free PBS only. 24 hours before the last bacterial treatment (day 8) mice were administered an 8 mg/ml desferal solution (10 ml/kg) through i.p. injection. Tumor progression was followed by measurements of tumor length and width with digital calipers. Tumor volume was determined as 0.5×lenght×width$^2$. A tumor volume exceeding 1500 mm$^3$ was defined as humane endpoint.

Study of tumor progression and rechallenge in the EMT-6 tumor allograft mouse models upon intratumoral treatment. All animal experiments were approved by the responsible authorities and performed according to local guidelines and animal protection laws. 5-7 weeks old female BALB/c (BALB/cByJ) mice were ordered from Charles River (L'Arbresles). After at least one week of accommodation, mice were anesthetized using isoflurane and 1×10$^6$ EMT-6 cells in 200 μL of RPMI 1640 were subcutaneously injected into the right flank of the mice. At regular intervals, mice were monitored for behaviour and physical appearance and the body weight was measured.

Treatments started once tumors had reached a volume of 60-130 mm$^3$ (defined as day 0). Mice were administered with the bacterial strains to be assessed on days 0, 1, 5, 6, 10 and 11 by intratumoral injection (7.5x10$^7$ bacteria in 50 ul PBS per administration) under isoflurane anaesthesia. The inoculum intratumorally administered to the mice was validated by dilution plating. As control, mice were injected with endotoxin-free PBS only. 24 hours before the last bacterial treatment (day 10) mice were administered an 8 mg/ml desferal solution (10 ml/kg) through i.p. injection. Tumor progression was followed by measurements of tumor length and width with digital calipers. Tumor volume was determined as 0.5×lenght×width$^2$. A tumor volume exceeding 1500 mm$^3$ was defined as humane endpoint. Mice displaying a complete tumor regression at day 54 after treatment start, were anesthetized using isoflurane and 1x10$^6$ EMT-6 cells in 200 μL of RPMI 1640 were subcutaneously injected into the contralateral (left) flank in relation to the first tumor cell injection. As control group, naïve mice that have not been grafted with EMT-6 cells before were included. Tumor progression was followed by measurements of tumor length and width with digital calipers. Tumor volume was determined as 0.5×lenght×width$^2$. A tumor volume exceeding 1500 mm$^3$ was defined as humane endpoint.

Study of tumor progression in the EMT-6 tumor allograft mouse models upon intravenous treatment. All animal experiments were approved by the responsible authorities and performed according to local guidelines and animal protection laws. 5-6 weeks old female BALB/c (BALB/cByJ) mice were ordered from Charles River (L'Arbresles). After at least one week of accommodation, mice were anesthetized using isoflurane and 1×10$^6$ EMT-6 cells in 200 μL of RPMI 1640 were subcutaneously injected into the right flank of the mice. At regular intervals, mice were monitored for behaviour and physical appearance and the body weight was measured.

Mice were randomized into treatment groups once tumors had reached a volume of 80-250 mm$^3$ (defined as day 0). 24 hours before randomization (D-1) mice were administered an 8 mg/ml desferal solution (10 ml/kg) through i.p. injection. On day 0, mice were administered with the bacterial strains to be assessed by intravenous injection (5×10$^6$ bacteria in 100 ul PBS per administration) under isoflurane anaesthesia. The inoculum intravenously administered to the mice was validated by dilution plating. As control, mice were injected with endotoxin-free PBS only. Tumor progression was followed by measurements of tumor length and width with digital calipers. Tumor volume was determined as 0.5×lenght×width$^2$. A tumor volume exceeding 1500 mm$^3$ was defined as humane endpoint.

Measurement of IFNβ secretion upon infection of tumor cell isolates. All animal experiments were approved (license 1908; Kantonales Veterinäramt Basel-Stadt) and performed according to local guidelines (Tierschutz-Verordnung, Basel-Stadt) and the Swiss animal protection law (Tierschutz-Gesetz). 6 week old BALB/c mice were ordered from Janvier Labs. After one week of accommodation, mice were anesthetized using isoflurane and 100 ul EMT-6 cells (1×10$^6$ cells) were subcutaneously injected into the flank of the mice. Throughout the experiment, mice were scored for behavior and physical appearance, and surface temperature, and the body weight was measured. Tumor progression was followed by measurements of tumor length and width with digital calipers. Tumor volume was determined as 0.5×lenght×width$^2$. On the day of the assay, tumors were isolated, cut to small pieces of 1-2 mm, digested for 1-1.5 hours and passed through a 70 μm nylon mesh to obtain a single cell suspension. Cell count of this crude cell isolate was determined and 300'000 cells per well were seeded in a flat-bottom 24-well plate (Corning) in growth medium (DMEM+L-Glutamine+non-essential amino acids+10% FCS). After 1 hour of incubation at 37° C. and 5% $CO_2$, the cells were infected with the bacterial strains to be assessed by adding 100 μl per well of a titration of bacteria (different MOI, diluted in growth medium). After 1 hour of incubation (37° C. and 5% $CO_2$) the bacteria were killed by adding growth medium containing penicillin (100 U/ml) and streptomycin (100 ug/ml). The incubation was continued for another 3 hours. The plate was centrifuged to collect all cells at the well bottom and the supernatant was analyzed for IFNβ concentration by the LumiKine™ Xpress murine IFN-β ELISA (Invivogen) according to manufacturer's instructions.

B) Results

A Protein Delivery System Based on Type 3 Secretion of YopE Fusion Proteins

Figure 2:
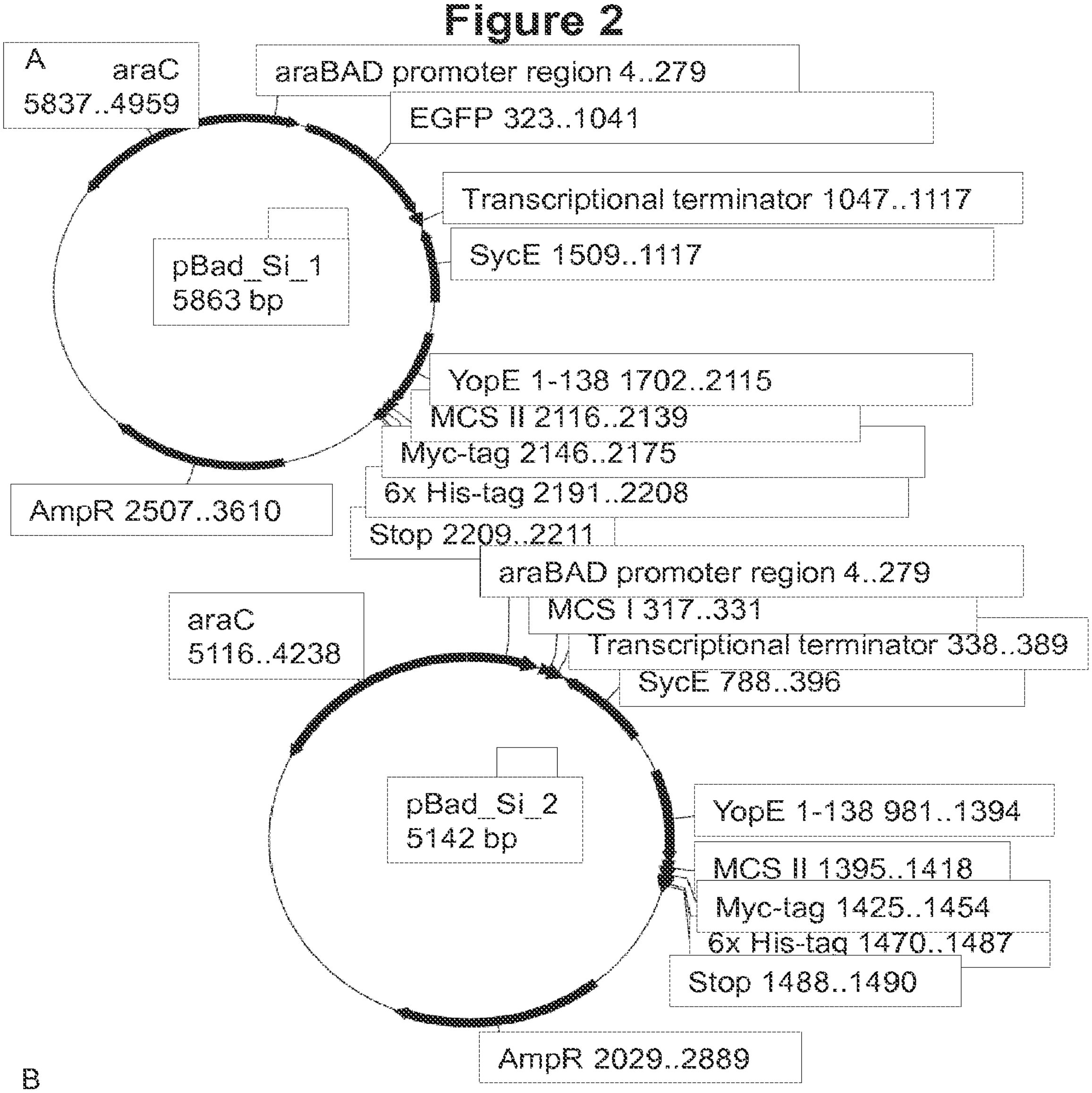
FIG. 2: Description of the type III secretion-based delivery toolbox. (A) Vector maps of the cloning plasmids pBad_Si1 and pBad_Si2 used to generate fusion constructs with $YopE_{1-138}$. The chaperone SycE and the $YopE_{1-138}$-fusion are under the native *Y. enterocolitica* promoter. The two plasmids only differ in presence of an arabinose inducible EGFP present on pBad_Si1 (B) Multiple cloning site directly following the $yopE_{1-138}$ fragment on pBad_Si1 and pBad_Si2 plasmids.

While the very N-terminus of the *Y. enterocolitica* T3SS effector YopE (SEQ ID No. 1) contains the secretion signal sufficient to translocate heterologous proteins[22], the chaperone-binding site (CBS) for its chaperone (SycE) is not included[36]. We selected the N-terminal 138 amino acids of YopE (SEQ ID No. 2) to be fused to proteins to be delivered, as this had been shown to give best results for translocation of other heterologous T3S substrates[24]. As these N-terminal 138 amino acids of YopE contain the CBS, we further decided to coexpress SycE. The SycE-YopE$_{1-138}$ fragment cloned from purified *Y. enterocolitica* pYV40 virulence plasmid contains the endogenous promoters of YopE and of its chaperone SycE (FIG. 2). Therefore, SycE and any YopE$_{1-138}$ fusion protein are induced by a rapid temperature shift from growth at RT to 37° C. Culture time at 37° C. will affect fusion protein amount present in bacteria. A multiple cloning site (MCS) was added at the 3' end of YopE$_{1-138}$ (FIG. 2 B) followed by a Myc and a 6×His tag and a Stop codon.

The background strain was carefully selected. First, to limit the translocation of endogenous effectors, we used a *Y. enterocolitica* strain that was deleted for all known effectors, Yop H, O, P, E, M and T (named ΔHOPEMT)[37]. In addition, we occasionally used an auxotroph mutant that cannot grow in absence of exogenous meso-2,6-diaminopimelic acid[38]. This strain was deleted for the aspartate-beta-semialdehyde dehydrogenase gene (Δasd), and classified as biosafety level 1 by the Swiss safety agency (amendment to A010088/2). In addition, we deleted the adhesion proteins YadA and/or InvA to offer a larger choice of background strains. While the use of the yadA or yadA/invA strains reduce the background signalling induced[39], the delivered protein amount is affected as well [40].

Removal of the $YopE_{1-138}$ Appendage after Translocation of the Fusion Protein to the Eukaryotic Cell While for bacterial delivery the $YopE_{1-138}$ fragment is of great benefit, it might hamper the fusion proteins function and/or localization. Therefore, its removal after protein delivery would be optimal. To this end, we introduced two TEV cleavage sites (ENLYFQS)[41-43] in between $YopE_{1-138}$ and a fusion partner (the transcriptional regulator ET1-Myc (SEQ ID No. 9 and 11)[44] and human INK4C (SEQ ID No. 8 and SEQ ID No. 10)). To keep the advantages of the presented method, we further fused the TEV protease (S219V variant; [45]) to $YopE_{1-138}$ (SEQ ID No. 12) in another *Y. enterocolitica* strain. HeLa cells were infected with both strains at once. To allow analysis of the translocated fraction of proteins only, infected HeLa cells were lysed at 2 h p.i. with Digitonin, which is known not to lyse the bacteria ([46];). Western blot analysis revealed the presence of the $YopE_{1-138}$-2×TEV-cleavage-site-ET1-Myc or $YopE_{1-138}$-2× TEV-cleavage-site-Flag-INK4C-Myc only when cells had been infected with the corresponding strain. Upon overnight digestion of this cell-lysate with purified TEV protease, a shifted band could be observed. This band corresponds to ET1-Myc or Flag-INK4C with the N-terminal remnants of the TEV cleavage site, most likely only one Serine. Upon coinfection of cells with the strain delivering the TEV protease, the same cleaved ET1-Myc or Flag-INK4C fragment became visible, indicating that the TEV protease delivered via T3 SS is functional and that single cells had been infected by both bacterial strains. While cleavage is not complete, the majority of translocated protein is cleaved already 2 h post infection and even over-night digestion with purified TEV protease did not yield better cleavage rates. As reported, TEV protease dependent cleavage might need optimization dependent on the fusion protein[47,48]. TEV protease dependent removal of the $YopE_{1-138}$ appendage after translocation hence provides for the first time a T3SS protein delivery of almost native heterologous proteins, changing the amino acid composition by only one N-terminal amino acid.

An alternative approach to the TEV protease dependent cleavage of the YopE fragment consisted in incorporating Ubiquitin into the fusion protein of interest. Indeed, Ubiquitin is processed at its C-terminus by a group of endogenous Ubiquitin-specific C-terminal proteases (Deubiquitinating enzymes, DUBs). As the cleavage is supposed to happen at the very C-terminus of Ubiquitin (after G76), the protein of interest should be free of additional amino acid sequence. This method was tested on the $YopE_{1-138}$-Ubiquitin-Flag-INK4C-MycHis fusion protein. In control cells infected by $YopE_{1-138}$-Flag-INK4C-MycHis-expressing bacteria, a band corresponding to $YopE_{1-138}$-Flag-INK4C-MycHis was found, indicative of efficient translocation of the fusion protein. When cells were infected for 1 h with $YopE_{1-138}$-Ubiquitin-Flag-INK4C-MycHis-expressing bacteria, an additional band corresponding to the size of Flag-INK4C-MycHis was visible, indicating that part of the fusion protein was cleaved. This result shows that the introduction of Ubiquitin into the fusion protein enables to cleave off the $YopE_{1-138}$ fragment without a need for an exogenous protease.

Figure 4:
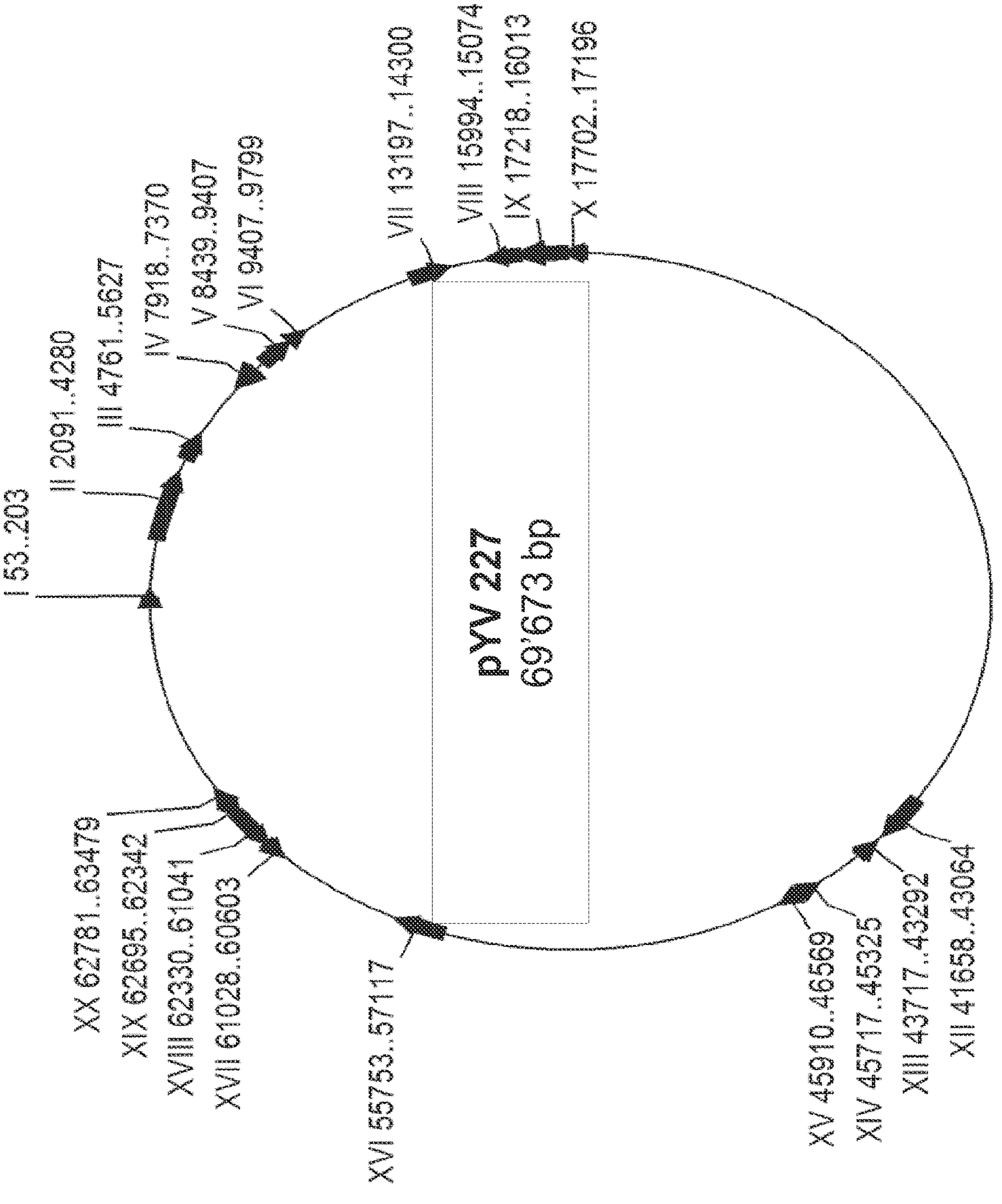
FIG. 4: The *Yersinia enterocolitica* W227 virulence plasmid, pYV. The 69'673 bp plasmid of *Yersinia* virulence (pYV) of strain W227 drawn to scale. T3 SS effector proteins, origin of replication and the arsenic resistance (encoded by genes arsC, B, R and H) are indicated: I: origin of replication, II: yopO, III: yopP, IV: yopQ, V: yopT, VI: sycT, VII: yopM, VIII: yopD, IX: yopB, X: sycD, XII: yopH, XIII: sycH, XIV: sycE, XV: yopE, XVI: yadA, XVII-XVXX: arsC, B, R and H.

Virulence Attenuation by Deletion/Mutation of Bacterial Effector Proteins with Virulence Activity Towards Eukaryotic Cells In case of *Y. enterocolitica*, the virulence was reduced by deletion of the six endogenous effector proteins, called "*Yersinia* outer proteins" (Yops), in detail YopH, O, P, E, M, T (MRS40 pIML421 [yopHΔ1-352, yopOΔ465-558, yopP23, yopE21, yopM23, yopT135])[37]. These Yops are encoded on the "*Yersinia* virulence plasmid" (pYV), a about 70 kbp sized plasmid, on which the complete type 3 secretion system (T3SS) as well as other virulence players are encoded (FIG. 4). YopH, O, P, E, M and T are the six effector proteins, which are delivered to host cells by the bacterial type three secretion system in order to modulate and dampen the immune system. Each Yop has a specific biochemical activity in the host cell. YopT cleaves off the C-terminal Cysteine of Rho GTPases and thus removes the isoprenyl group anchoring the GTPases to the membrane. This inactivation of the Rho due to mislocalization avoids phagocytosis by immune cells as macrophages and neutrophils[49]. In the same pathway, YopE acts as GTPase activating protein (GAP) for Rho GTPases, deactivating them. This results in decreased phagocytosis and inhibition of release of IL-1 beta by immune cells[49]. Furthermore, YopO acts as guanidine nucleotide dissociation inhibitor (GDI), deactivating Rho GTPases. YopO further has a serine/threonine kinase domain acting in a not yet defined way on the actin cytoskeleton[49]. YopH is a tyrosine phosphatase acting on focal adhesion proteins as Focal adhesion kinase (Fak), paxillin and others, thus strongly preventing phagocytosis by macrophages and neutrophils[49]. YopP, termed YopJ in *Y. pseudotuberculosis* or *Y. pestis*, was found to inactivate the MAPK/NFkB pathway in immune cells, preventing TNFa and IL-8 release from immune cells stimulated by the presence of the bacteria. Furthermore, YopP was found to induce apoptosis in immune cells, which might be related to the effect sin the MAPK pathway, which in its activated state protects cells from apoptosis[49]. The role of YopM is not yet completely clear, but it was found associated with ribosomal S6 kinase 1 (RSK1) and protein kinase C-like 2 (PRK2). It seems as if YopM could stimulate phosphorylation of RSK1 and thus affects downstream targets, as e.g cell cycle progression[49]. By deleting one or several of these Yops, the defense mechanism of the bacteria against the immune system are dramatically affected[50]. Mutation of respective yops was confirmed by PCR on the respective region, and by in vitro secretion assay. Analysis of in vitro secretion by SDS-PAGE and Coomassie-blue staining confirmed absence of full-length YopH, O, M and YopE.

Furthermore, a *Y. enterocolitica* strain with deletions in asd (aspartate semialdehyde dehydrogenase) was constructed. The mutation in asd leads to a complete loss of growth capability without addition of meso-diamino-pimelic acid. This allows generating antibiotic free plasmid maintenance systems based on the presence of asd on the respective plasmid. In a similar way, other auxotroph mutants might be used.

Generation of Enhanced Pro-Apoptotic Bacteria

In order to optimize the delivery or pro-apoptotic proteins, strains transformed with different pro-apoptotic proteins have been generated according to Table IV.

TABLE IV

| Strains transformed with different pro-apoptotic proteins | | | | | | |
|---|---|---|---|---|---|---|
| Strain Name | Background strain | Protein to be delivred by T3SS | Backbone plasmid | Resulting plasmid name | Primers. Si_Nr.: | resistances |
| YopE1-138-(*Y. enterocolitica* codon optimized murine tBid BH3 extended part) | *Y. enterocolitica* ΔyopH, O, P, E, M, T Δasd | YopE1-138-*Y. enterocolitica* codon optimized murine tBid BH3 extended (by 4 Aa) | pBad_Si_2 | pSi_353 | | Nal Amp |
| YopE1-138-10 Aa linker-(*Y. enterocolitica* codon optimized murine tBid BH3 part) | *Y. enterocolitica* ΔyopH, O, P, E, M, T Δasd | YopE1-138-10 Aa linker-*Y. enterocolitica* codon optimized murine tBid BH3 | pBad_Si_2 | pSi_354 | 727/728 | Nal Amp |
| YopE1-(138-*Y. enterocolitica* codon optimized murine Bax BH3 part-*Y. enterocolitica* codon optimized murine tBid BH3 part | *Y. enterocolitica* ΔyopH, O, P, E, M, T Δasd | YopE1-138-*Y. enterocolitic* codon optimized murine Bax BH3-. *enterocolitica* codon optimized murine tBid BH3 | pSi_357 | pSi_374 | 736/737 | Nal Amp |

Figure 5:
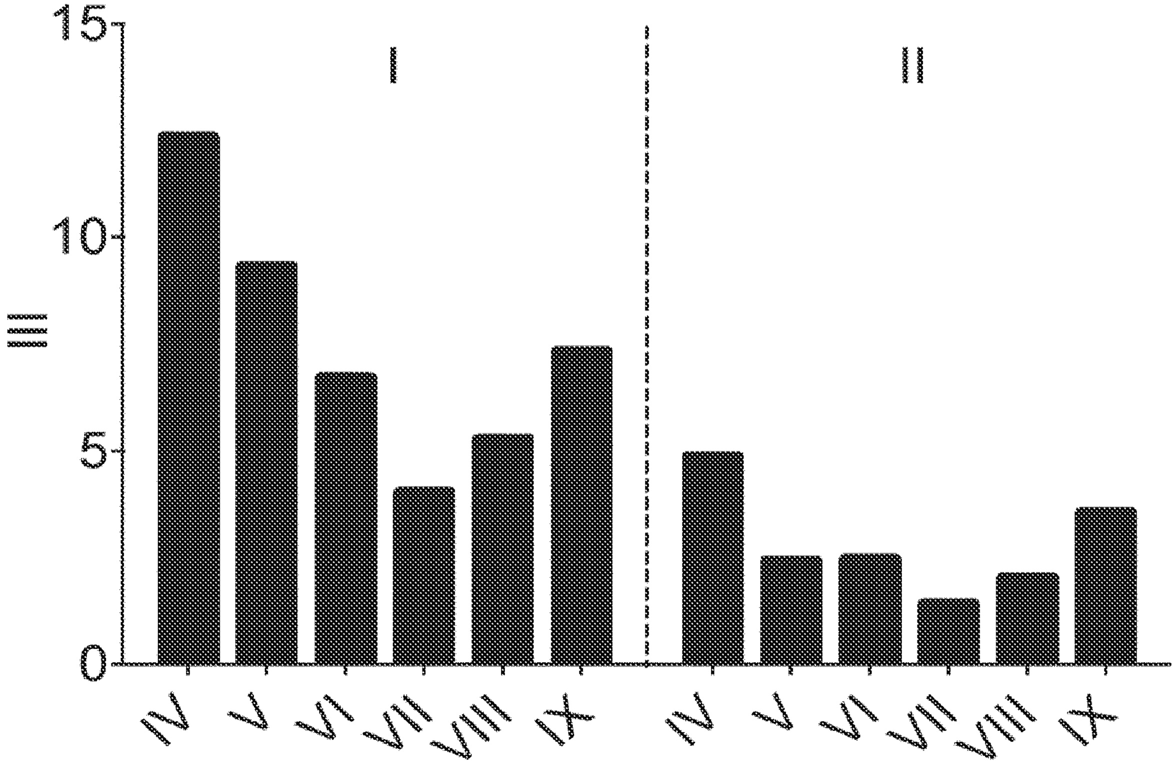
FIG. 5: Delivery of synthetic increased pro-apoptotic proteins. Delivery of single synthetic proteins consisting of single or tandem repeats of BH3 domains originating from pro-apoptotic proteins t-BID or BAX leads to enhanced apoptosis induction in 4T1 and B16F10 cancerous cells. 4T1 (I) or B16F10 (II) cells were infected with *Y. enterocolitica* ΔyopHOPEMT encoding on pBad-MycHisA IV: $YopE_{1-138}$-tBID BH3 extended domain, V: $YopE_{1-138}$-linker-tBID BH3, VI: $YopE_{1-138}$-tBID BH3, VII: $YopE_{1-138}$-$(tBID\ BH3)_2$, VIII: $YopE_{1-138}$-tBID BH3—BAX BH3 or IX: $YopE_{1-138}$-BAX BH3—tBID BH3. A titration of the bacteria added to the cells (MOI) was performed for each strain, cell counts determined and IC50 calculated using non-linear regression. IC50 MOI is indicated as (III).

Shortening the delivered proteins to the essential domains required for signaling (e.g. the BH3 domain of t-BID (SEQ ID No. 19)) could increase the efficiency of cell killing (FIG. 5). Without being bound by theory, this increase in efficacy is likely to be related to increased amount of protein production and following delivery via T3SS due to smaller size of the delivered protein. Introduction of a linker between the YopE part and the BH3 domain of tBID (SEQ ID No. 23) decreased efficacy, as well as extending the BH3 domain by 4 further amino acids (SEQ ID No. 22) (FIG. 5). Additionally, synthetic cargos with repeats of such essential domains (e.g. the BH3 domain of t-BID (SEQ ID No. 27)) or combinations of these essential domains (e.g. the BH3 domain of t-BID and the BH3 domain of BAX (SEQ ID No. 24 and 28)) were generated. Surprisingly, tandem repeats of the same or different BH3 domains were found to result in enhanced apoptosis induction on cancerous cell lines (including 4T1 and B16F10 cells, FIG. 5). The IC50 (half maximal inhibitory concentration), referring to the number of bacteria per eukaryotic cell (MOI) needed in order to kill 50% of such cells, was found to be decreased upon delivery of tandem repeats of tBID BH3 domain as compared to a single tBID BH3 domain (FIG. 5). This finding was surprising, as the protein size is increased by fusing as second BH3 domain of t-BID. Due to this, decreased expression and delivery levels of $YopE_{1-138}$-(tBID BH3)$_2$ (SEQ ID No. 27) as compared to $YopE_{1-138}$-tBID BH3 (SEQ ID No. 19 and 25) would be expected, and might maximally reach equivalent levels. In order to reach an increase in cell killing activity, the fused tBID BH3 domains must simultaneously act side by side upon delivery by the T3SS into eukaryotic cells. In case only one tBID BH3 domain in the $YopE_{1-138}$-(tBID BH3)$_2$ construct would be functional, at best the same efficiency as with $YopE_{1-138}$-tBID BH3 might be expected.

Figure 6:
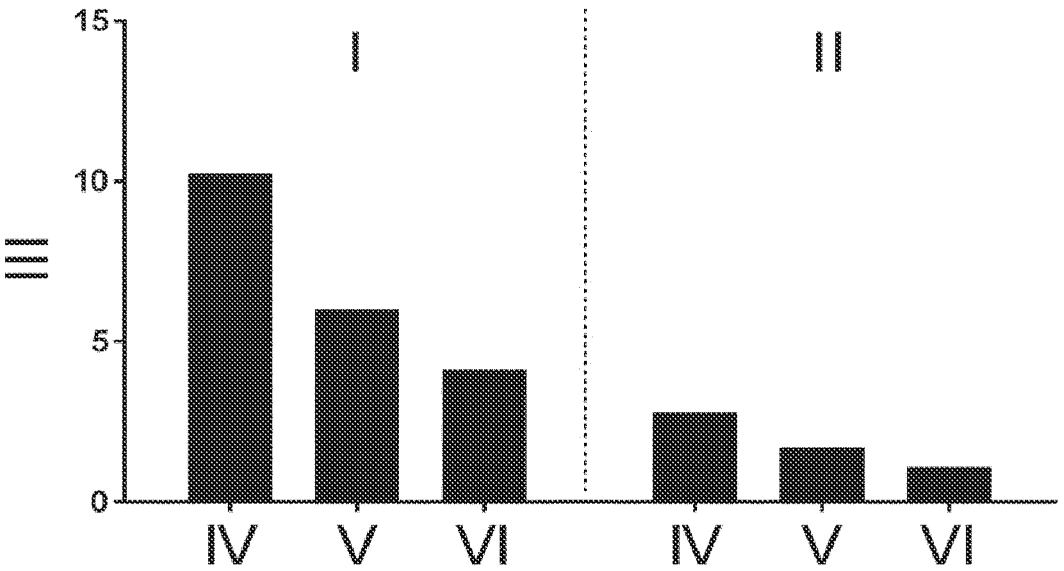
FIG. 6: Induction of apoptosis by pYV-encoded synthetic pro-apoptotic proteins. Delivery of a single or a tandem repeat of BID BH3 domain encoded on the pYV leads to apoptosis induction in 4T1 and B16F10 cancerous cells. 4T1 (I) or B16F10 (II) cells were infected with *Y. enterocolitica* ΔHOPEMT+IV: pYV-$YopE_{1-138}$-BH3-Bid, or V: +pYV-$YopE_{1-138}$-$(BH3\text{-}Bid)_2$ or VI: with *Y. enterocolitica* ΔHOPEMT pBad-MycHisA-$YopE_{1-138}$-$(BH3\text{-}Bid)_2$ for 3 hours. A titration of the bacteria added to the cells (MOI) was performed for each strain, cell counts determined and IC50 (III) calculated using non-linear regression.

In order to increase the genetic stability of $YopE_{1-138}$-(tBID BH3)$_2$ (SEQ ID No. 27) for in vivo studies, we cloned $YopE_{1-138}$-(tBID BH3)$_2$ (SEQ ID No. 27) by homologous recombination on the *Yersinia* virulence plasmid pYV at the native site of YopE and under the native YopE promoter (using mutator plamids pSI_408 and pSI_419). Such mutators contain the DNA sequence coding for the desired protein, flanked by 200-250 bp of sequences on both sides corresponding to the site of the respective gene, where the integration shall take place. These plasmids are transformed into *E. coli* Sm10λ pir, from where plasmids were mobilized into the corresponding *Y. enterocolitica* strain. Mutants carrying the integrated vector were propagated for several generations without selection pressure. Then sucrose was used to select for clones that have lost the vector. Finally mutants were identified by colony PCR. The endogenous proteins for the transport by the T3SS (called "*Yersinia* outer proteins", Yops) are encoded by *Y. enterocolitica* on this 70 kb plasmid, named plasmid of *Yersinia* Virulence (pYV), which further encodes the T3SS apparatus. *Yersinia* strains encoding $YopE_{1-138}$-(tBID BH3) (SEQ ID No. 19 and 25) or $YopE_{1-138}$-(tBID BH3)$_2$ (SEQ ID No. 27) on the *Yersinia* virulence plasmid pYV at the native site of YopE and under the native YopE promoter were assessed for their capacity of inducing apoptosis in cancerous cells (including 4T1 and B16F10 cells, FIG. 6). The IC50 (half maximal inhibitory concentration), referring to the number of bacteria per eukaryotic cell (MOI) needed in order to kill 50% of such cells, was found to be decreased upon delivery of tandem repeats of tBID BH3 domain as compared to a single tBID BH3 domain, when both proteins are encoded on the *Yersinia* virulence plasmid pYV at the native site of YopE and under the native YopE promoter (FIG. 6). This is in agreement with findings from expression plasmid borne delivery of these proteins (FIG. 5). Again, this finding was surprising, as the protein size is increased by fusing a second BH3 domain of t-BID. Due to this, decreased expression and delivery levels of $YopE_{1-138}$-(tBID BH3)$_2$ (SEQ ID No. 27) as compared to $YopE_{1-138}$-tBID BH3 (SEQ ID No. 19 and 25) would be expected, and might maximally reach equivalent levels. In order to reach an increase in cell killing activity, the fused tBID BH3 domains must simultaneously act side by side upon delivery by the T3SS into eukaryotic cells. In case only one tBID BH3 domain in the $YopE_{1-138}$-$(tBID\ BH3)_2$ construct would be functional, at best the same efficiency as with $YopE_{1-138}$-tBID BH3 might be expected. Furthermore, *Yersinia* strains encoding $YopE_{1-138}$-$(tBID\ BH3)_2$ (SEQ ID No. 27) on the *Yersinia* virulence plasmid pYV at the native site of YopE and under the native YopE promoter were compared for their capacity of inducing apoptosis in cancerous cells to expression plasmid (pBad-MycHisA based) derived delivery of $YopE_{1-138}$-$(tBID\ BH3)_2$. In agreement with the higher copy number of pBad-MycHisA (20-25 copies) as compared to the pYV (1-6 copies are reported), pBad-MycHisA based delivery of $YopE_{1-138}$-$(tBID\ BH3)_2$ (SEQ ID No. 27) resulted in a slightly decreased IC50 value on 4T1 and B16F10 cells (FIG. 6).

Biodistribution Studies in a Murine Model of Melanoma

Figure 47:
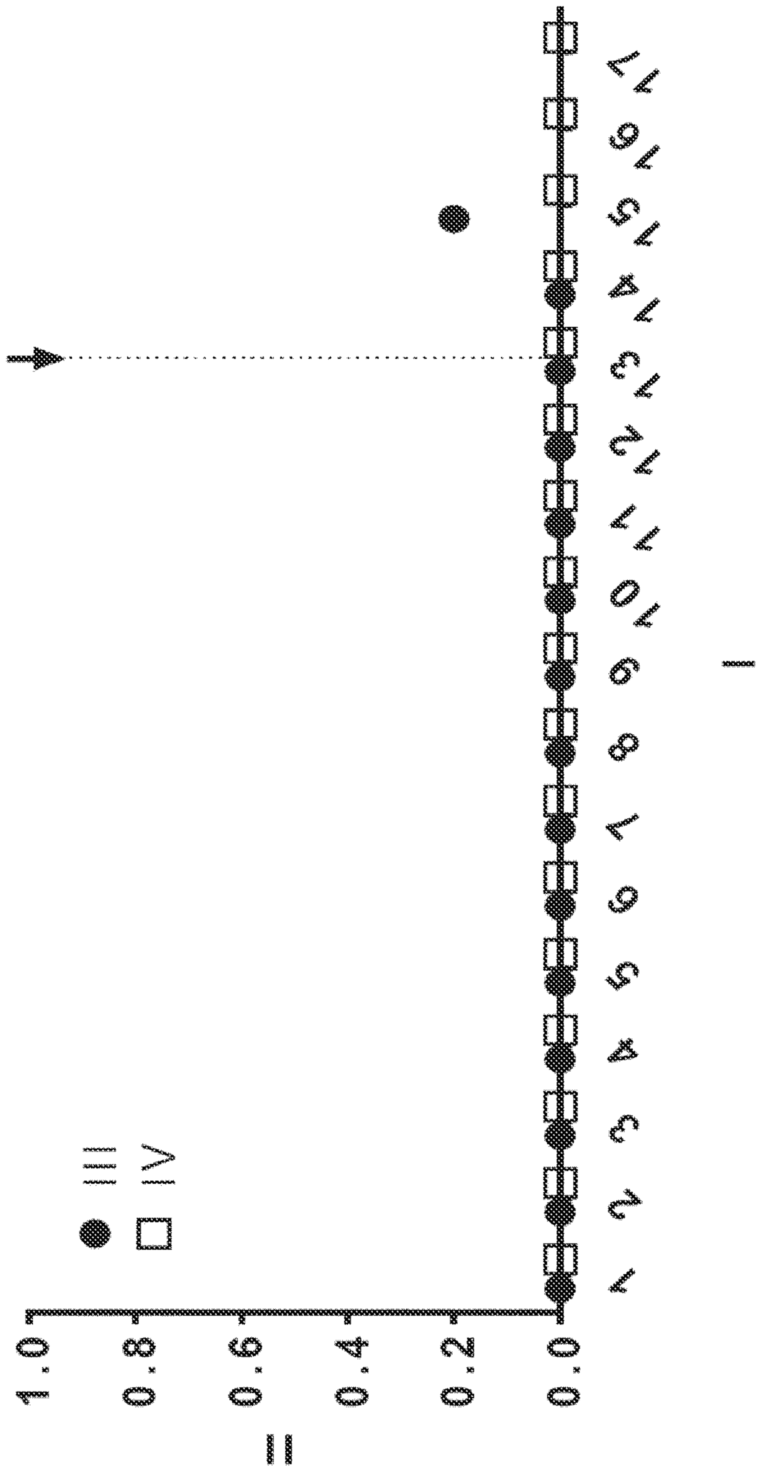
FIG. 47: Biodistribution of *Y. enterocolitica* subsp. *palearctica* in the B16F10 melanoma mouse allograft model: scoring for physical appearance. I: Days, II: fraction of mice with a score, III: *Y. enterocolitica* MRS40 wt, IV: *Y. enterocolitica* $\Delta yopH_2O$,P,E,M,T. The arrow indicates the day of i.v. injection of $2\times10^5$ bacteria.
Figure 48:
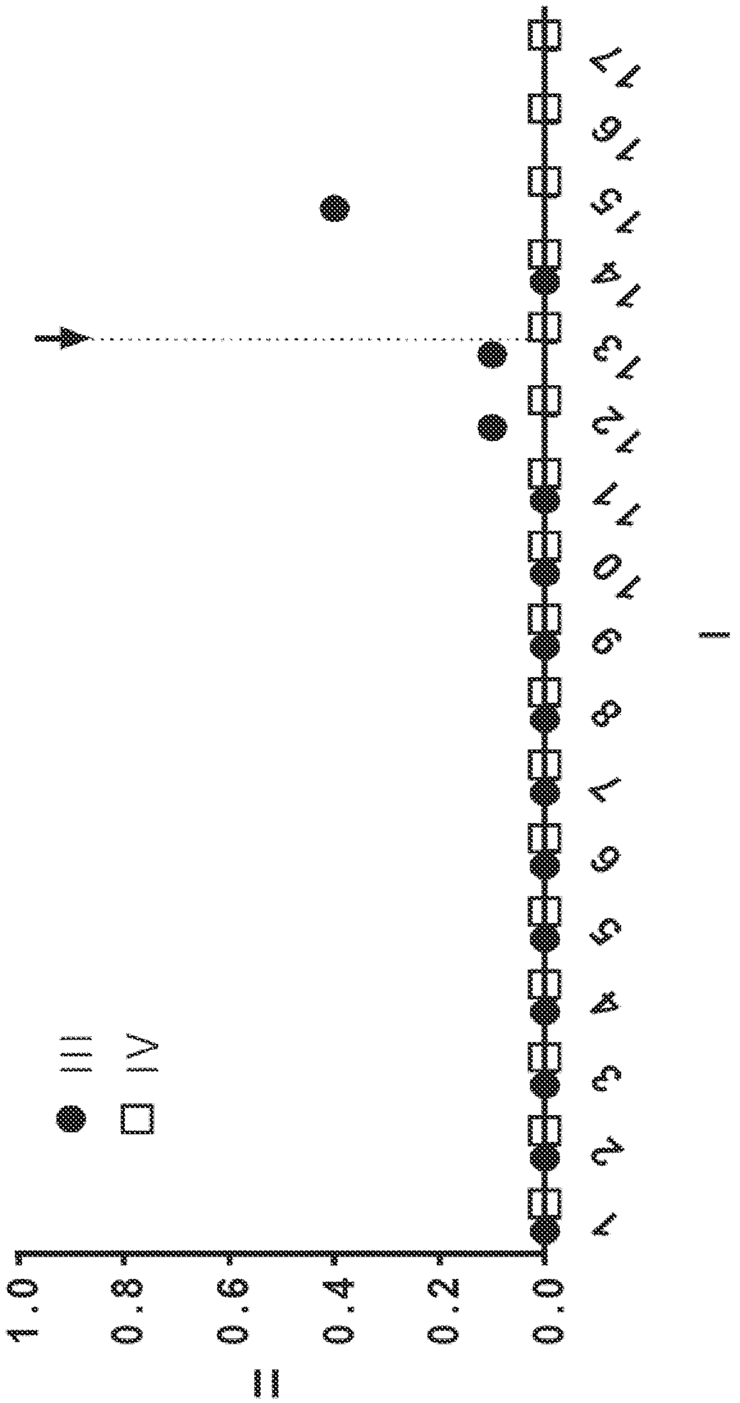
FIG. 48: Biodistribution of *Y. enterocolitica* subsp. *palearctica* in the B16F10 melanoma mouse allograft model: scoring for behavior. I: Days, II: fraction of mice with a score, III: *Y. enterocolitica* MRS40 wt, IV: *Y. enterocolitica* $\Delta yopH_2O$,P,E,M,T. The arrow indicates the day of i.v. infection with $2\times10^5$ bacteria.
Figure 49:
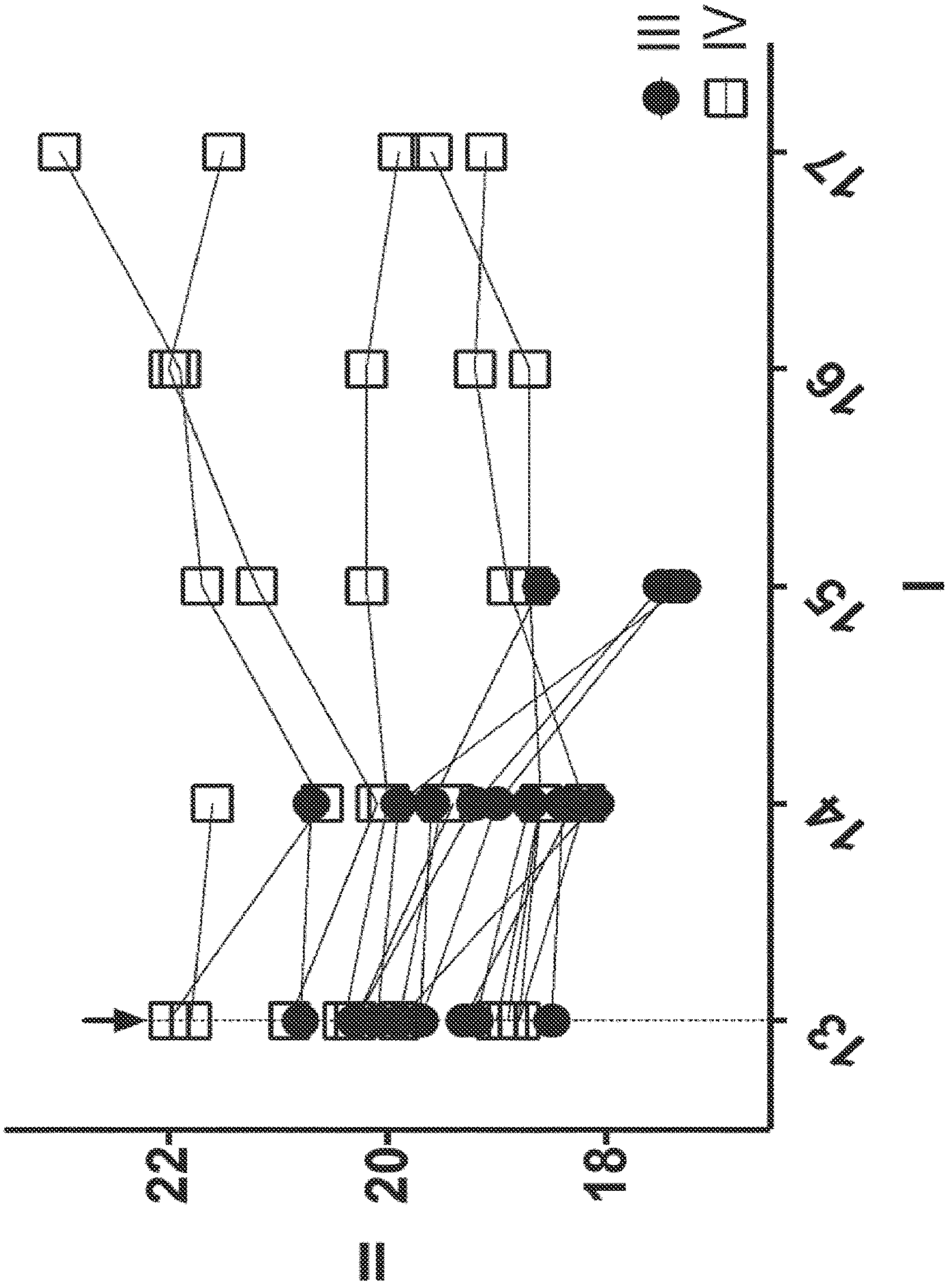
FIG. 49: Biodistribution of *Y. enterocolitica* subsp. *palearctica* in the B16F10 melanoma mouse allograft model: weights of mice. Weight of mice was assessed daily following i.v. infection with bacteria. I: Days, II: body weight in gram, III: *Y. enterocolitica* MRS40 wt, IV: *Y. enterocolitica* $\Delta yopH_2O$,P,E,M,T. The arrow indicates the day of i.v. infection with $2\times10^5$ bacteria.
Figure 50:
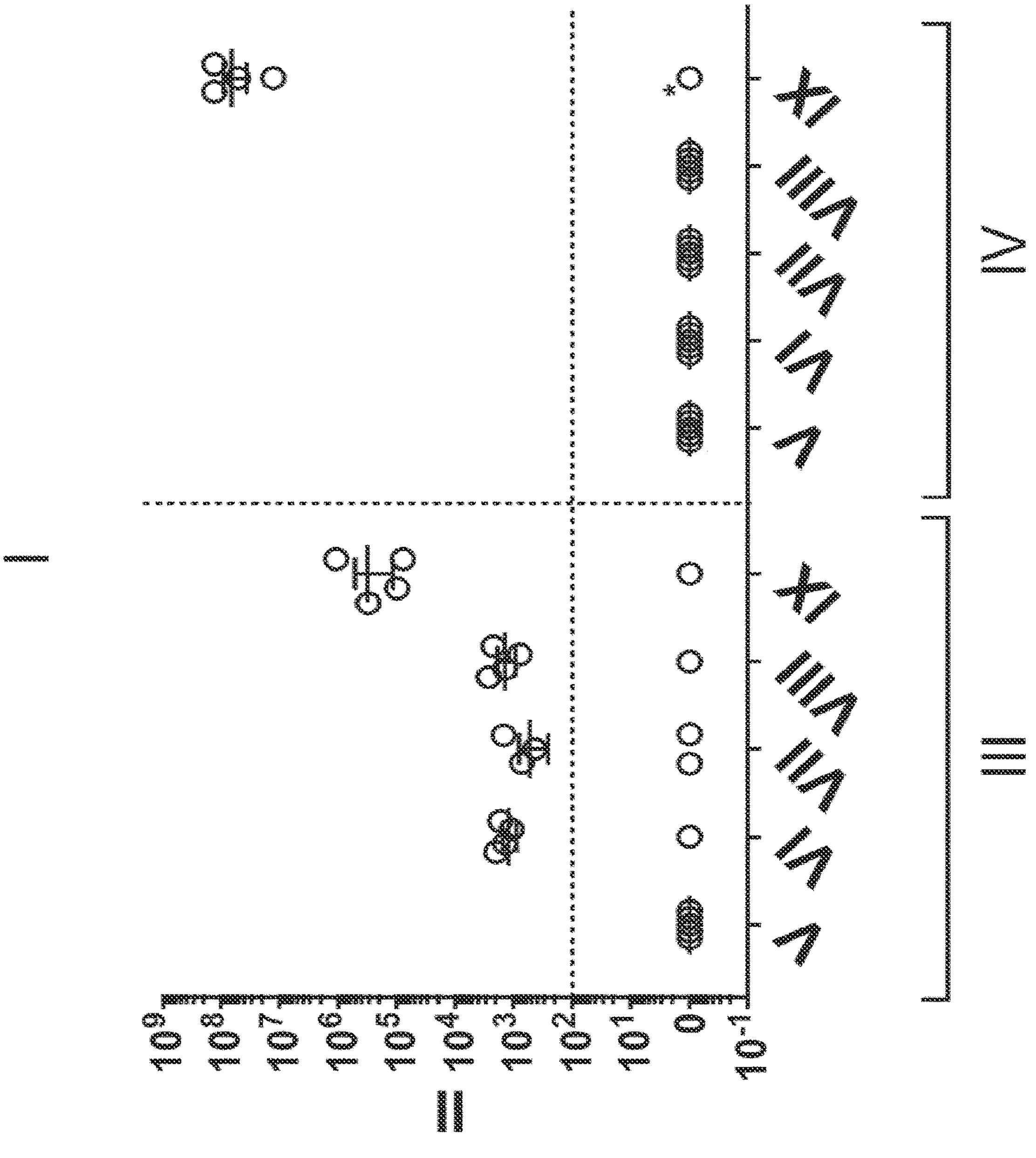
FIG. 50: Biodistribution of *Y. enterocolitica* subsp. *palearctica* in the B16F10 melanoma mouse allograft model: biodistribution of *Y. enterocolitica* $\Delta yopH_2O$,P,E,M, T. Counts in the organs at the time indicated were assessed by organ homogenization, serial dilution and counting of resulting colony forming units (CFU). The day of the i.v. injection of bacteria was defined as day 0, all mice were treated i.p ith Desferal at d-1. I: *Y. enterocolitica* $\Delta yopH_2O$, P,E,M,T, II: CFU per gram tissue or ml of blood, III: day 1, IV: day 4, V: blood, VI: spleen, VII: liver, VIII: lung, IX: tumor. * indicates a mouse with no visible tumor.
Figure 51:
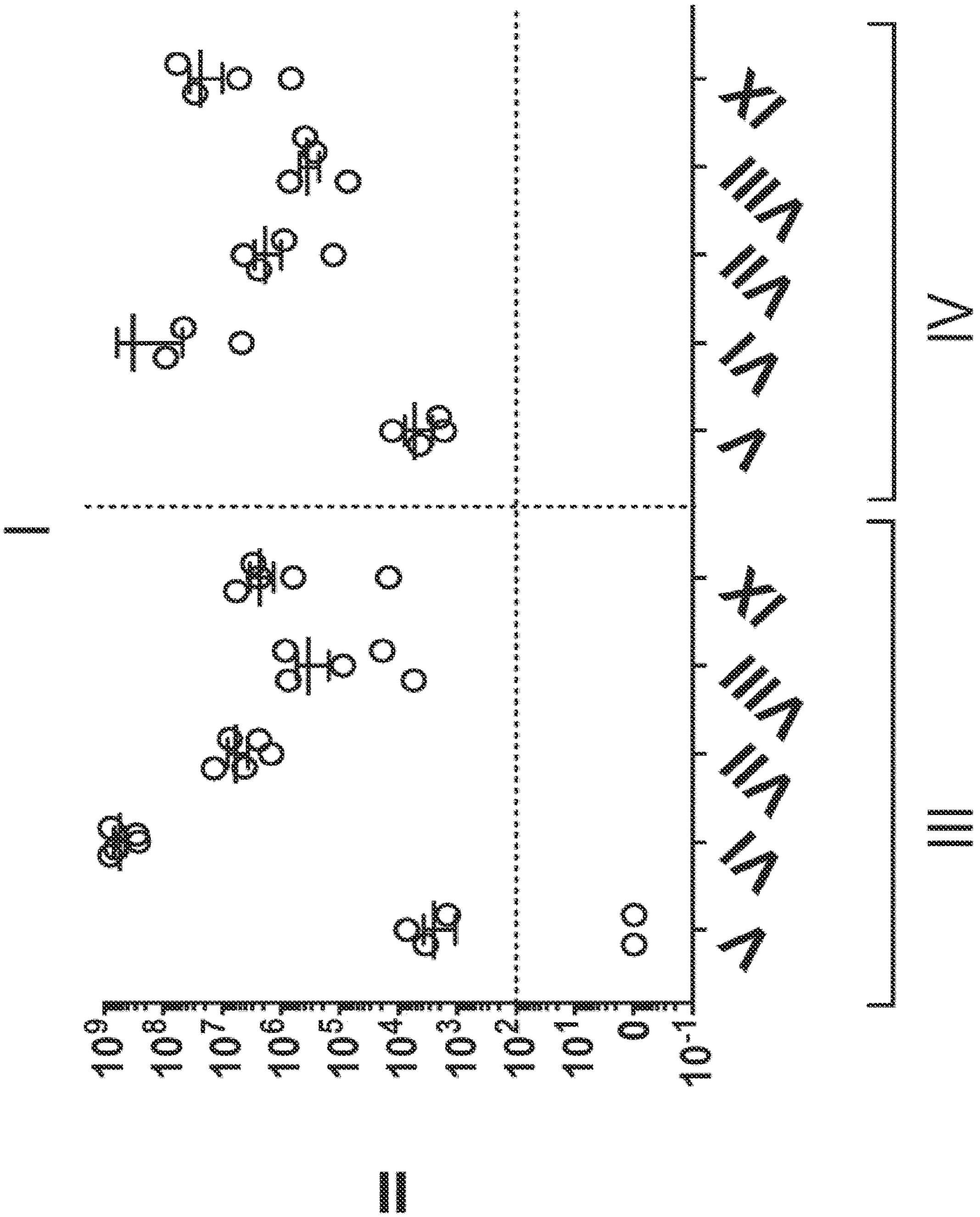
FIG. 51: Biodistribution of *Y. enterocolitica* subsp. *palearctica* in the B16F10 melanoma mouse allograft model: biodistribution of *Y. enterocolitica* MRS40 wt. Counts in the organs at the time indicated were assessed by organ homogenization, serial dilution and counting of resulting colony forming units (CFU). The day of the i.v. injection of bacteria was defined as day 0, all mice were treated i.p ith Desferal at d-1. I: *Y. enterocolitica* MRS40 wt, II: CFU per gram tissue or ml of blood, III: day 1, IV: day 4, V: blood, VI: spleen, VII: liver, VIII: lung, IX: tumor.

In order to validate gram-negative bacteria with mutation(s) in key virulence determinants like the T3SS effectors as tumor specific vehicle, murine allograft tumor studies using the well-established B16F10 melanoma model (ATCC No. CRL-6475) were performed. When s.c. tumors had reached a certain size (about 100-200 $mm^3$), mice were i.v. infected with $2\times10^5$ cfu *Y. enterocolitica* subsp. *palearctica* MRS40 or *Y. enterocolitica* subsp. *palearctica* MRS40 $\Delta yopH_2O$,P,E,M,T. In order to allow bacterial growth, mice were pretreated 24 h prior to infection with desfreoxamine. Mice infected with the wt *Y. enterocolitica* subsp. *palearctica* MRS40 strain had increased scoring for physical appearance and behavior (FIG. 47-48) and exhibited significant weight loss over the first 48 h of infection (FIG. 49), which urged us to sacrifice all of the mice in this group already at day 2 post infection. In contrast, mice infected with the virulence attenuated *Y. enterocolitica* subsp. *palearctica* MRS40 $\Delta yopH_2O$,P,E,M,T strain did not show significant weight loss and scored normally for physical appearance and behavior (FIG. 47-49) still at day 4 post infection. In mice infected with the wt strain (*Y. enterocolitica* subsp. *palearctica* MRS40) living bacteria were detected in all organs assessed, and furthermore in the blood (FIG. 51). While wt bacteria were found present in the malignant solid tumor, equally high or higher counts were found in other organs, highest in the spleen (FIG. 51). In sharp contrast, in mice infected with *Y. enterocolitica* subsp. *palearctica* MRS40 $\Delta yopH_2O$,P,E,M,T living bacteria were mainly found in the malignant solid tumor at day 1 post infection, with low bacterial counts observed in spleen, liver and lung. Notably, at day 4 post infection, the bacterial count in the malignant solid tumor had increased by some orders of magnitude (reaching more than $10^8$ cfu/g of tumor tissue), while in all other organs assessed the bacterial counts dropped below the detection limit (FIG. 50). *Y. enterocolitica* subsp. *palearctica* MRS40 $\Delta yopH_2O$,P,E,M,T thus accumulated at day 4 post infection with a ration of about (minimally) one million fold at the site of the malignant solid tumor as compared to spleen or liver (when calculating the ration against the detection limit).

Figure 26:
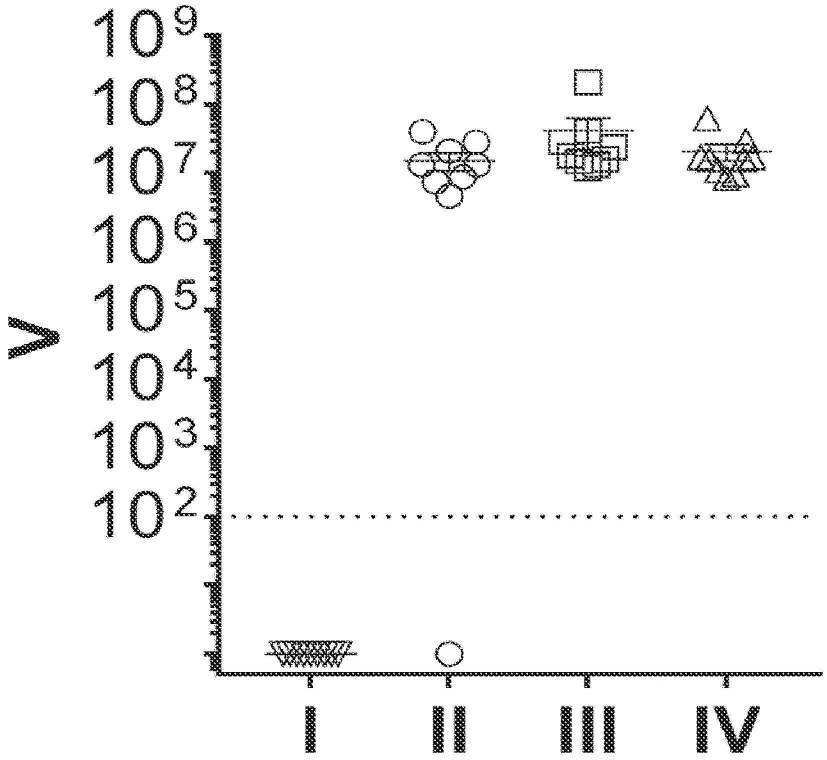
FIG. 26: Tumor colonization of i.v. injected *Y. enterocolitica* strains in the B16F10 breast cancer allograft model. Wildtype C57BL/6 mice allografted s.c. with B16F10 melanoma cancer cells were i.v. injected with I: PBS, II: $1*10^7$ *Y. enterocolitica* dHOPEMT, III: *Y. enterocolitica* dHOPEMT+pYV-$YopE_{1-138}$—murine RIG1 $CARDs_{1-246}$ or IV: *Y. enterocolitica* dHOPEMT ΔHairpinI-VirF+pYV-$YopE_{1-138}$-murine RIG1 $CARDs_{1-246}$ once the tumor had reached a size of 100-315 $mm^3$. Bacterial counts in tumors are indicated as colony forming units (CFU) per gram of tissue (V). Counts were assessed in tumors at day 5 or 8 post infection. Each dot represents an individual mouse. The horizontal dashed line indicates the detection limit.

Similar high numbers of bacteria per gram of solid tumors at day 5 or 8 after intravenous administration into the lateral tail vein of B16F10 melanoma bearing mice were measured for *Y. enterocolitica* dHOPEMT, Y *Y. enterocolitica* dHOPEMT +pYV-$YopE_{1-138}$-murine RIG1 CARDs or *Y. enterocolitica* dHOPEMT ΔHairpinI-VirF+pYV-$YopE_{1-138}$—murine RIG1 CARDs (FIG. 26). These validates, that heterologous protein cargo and further mutations affecting T3SS regulation (VirF) do not influence bacterial colonization of solid tumors in murine models.

These results validate this strategy for virulence attenuation by mutation of key virulence determinants to generate a bacterial vehicle specifically targeting the malignant solid tumor.

Figure 7:
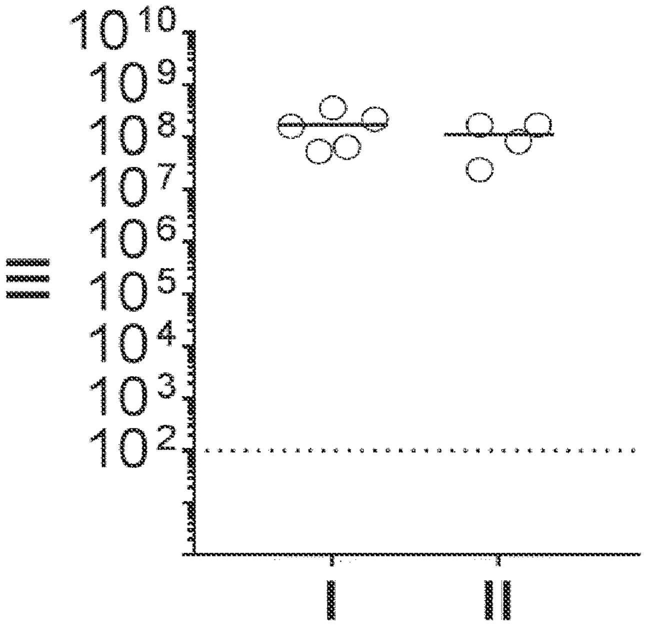
FIG. 7: Tumor colonization of i.v. injected *Y. enterocolitica* Δ$yopH_2O$,P,E,M,T in the 4T1 breast cancer allograft model. Bacterial counts in tumors are indicated as colony forming units (CFU) per gram of tissue (III). Counts were assessed in tumors at day 8 (I) and 14 (II) post infection. Each dot represents an individual mouse. The horizontal dashed line indicates the detection limit.
Figure 8:
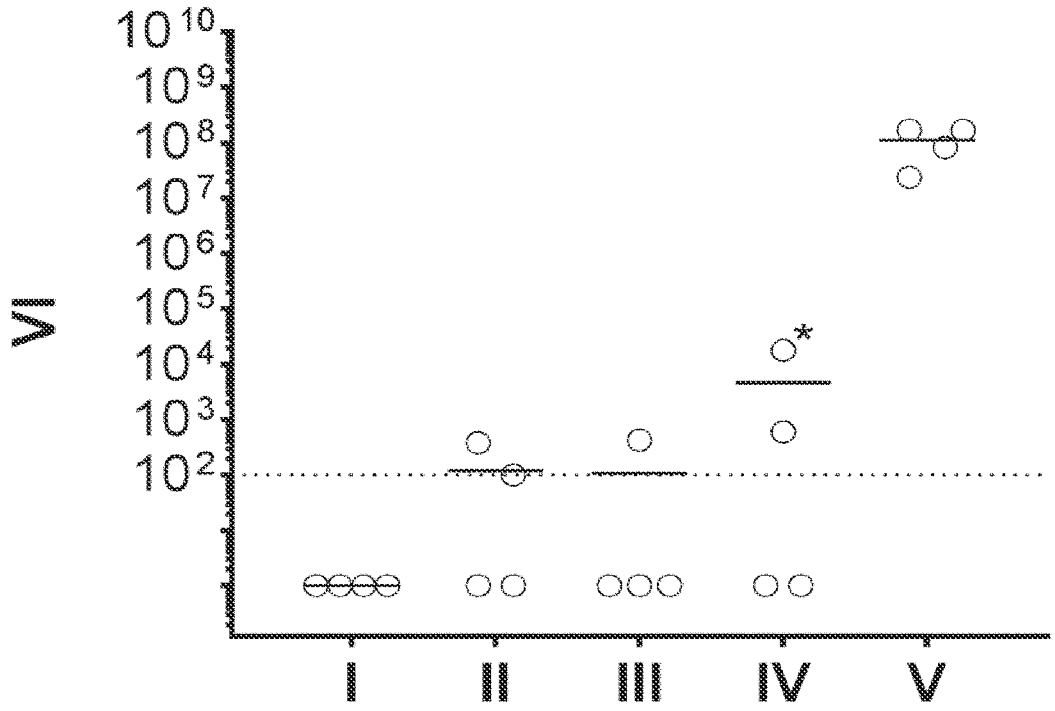
FIG. 8: Biodistribution of i.v. injected *Y. enterocolitica* Δ$yopH_2O$,P,E,M,T in the 4T1 breast cancer allograft model. Bacterial counts in blood (I), spleen (II), liver (III), lung (IV) and tumor (V) are indicated as colony forming units (CFU) per gram of tissue or per ml of blood (VI). Counts were assessed at day 14 post infection. Each dot represents an individual mouse. The horizontal dashed line indicates the detection limit. * indicates a mouse with large metastases found on lung.

Validation of Tumor Specific Growth In Vivo Up to Day 14 Post Bacterial Administration The experiment of tumor colonization by genetically modified *Y. enterocolitica* was repeated in a syngeneic murine allograft model (4T1 breast cancer model) and bacterial colonization was followed over two weeks. This time, mice were infected with $1*10^6$ colony forming units (CFU) of *Y. enterocolitica* ΔyopH,O,P,E,M,T. While obtaining similar results to the B16F10 model at early days post infection, we could further show that the tumor colonization is consistently found at day 8 and up to day 14 after infection (FIG. 7). Furthermore, the colonization remains highly specific with only low counts of bacteria detected in all other organs assessed (FIG. 8). These findings indicate that *Y. enterocolitica* $\Delta yopH_2O$,P,E,M,T is able to establish a persistent colonization of the tumor thereby preventing clearance by the immune system.

Efficacy of *Y. enterocolitica* ΔHOPEMT in Delaying Tumor Progression

Figure 9:
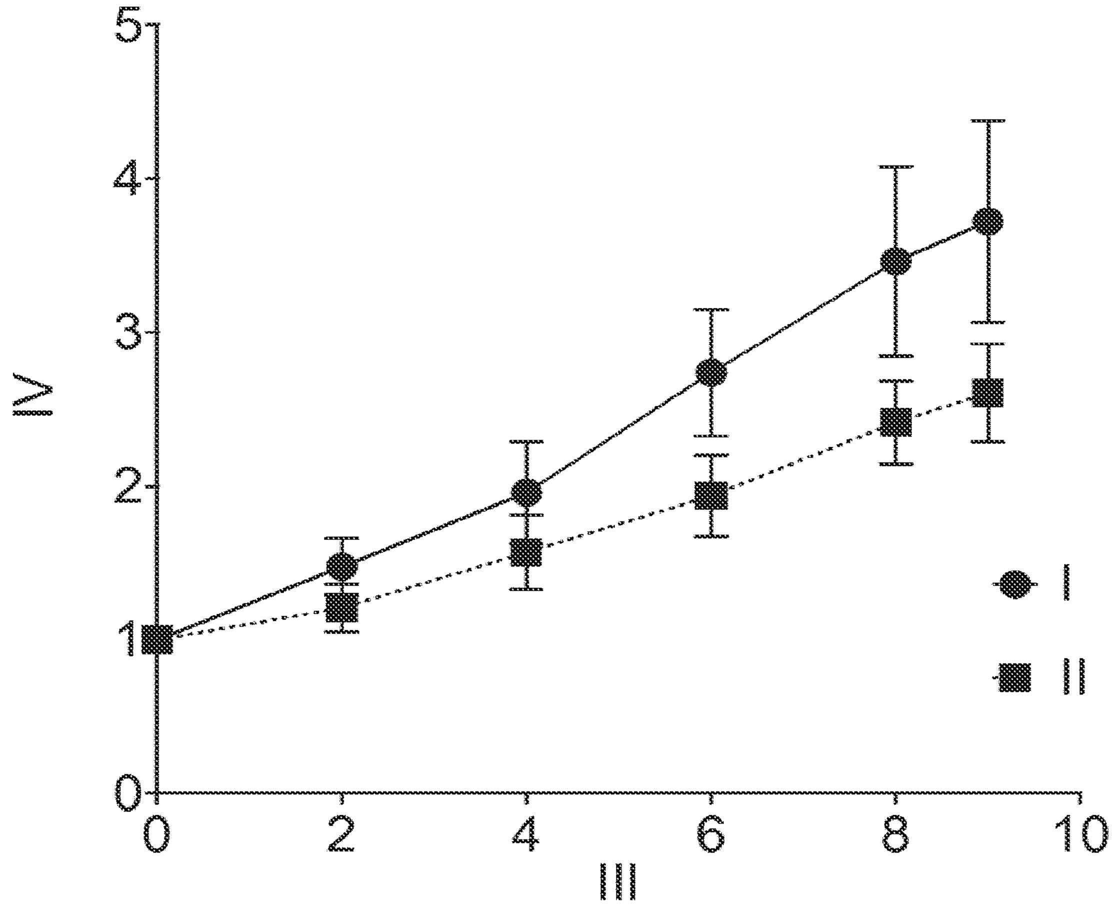
FIG. 9: Delay of tumor progression in wildtype Balb/C mice allografted s.c. with 4T1 breast cancer cells. Wildtype Balb/C mice allografted s.c. with 4T1 breast cancer cells were i.v. injected with I: PBS or II: 1*$10^7$ *Y. enterocolitica* dHOPEMT ΔHairpinI-VirF+pYV-$YopE_{1-138}$(BH3-Bid$)_2$, once the tumor had reached a size of 150-250 mm3. The day of the i.v. injection of bacteria was defined as day 0. Tumor volume was measured over the following days (III; day 0 to day 9 post i.v. injection of bacteria) with calipers. The relative tumor volume, normalized to the tumor volume at day 0, is indicated (IV) as $mm^3$. The mean is indicated with symbols, error bars depicted show the standard error of the mean. Statistical significance is measured with a 2way ANOVA, * indicates p value <0.05, ** a p value <0.005.
Figure 10:
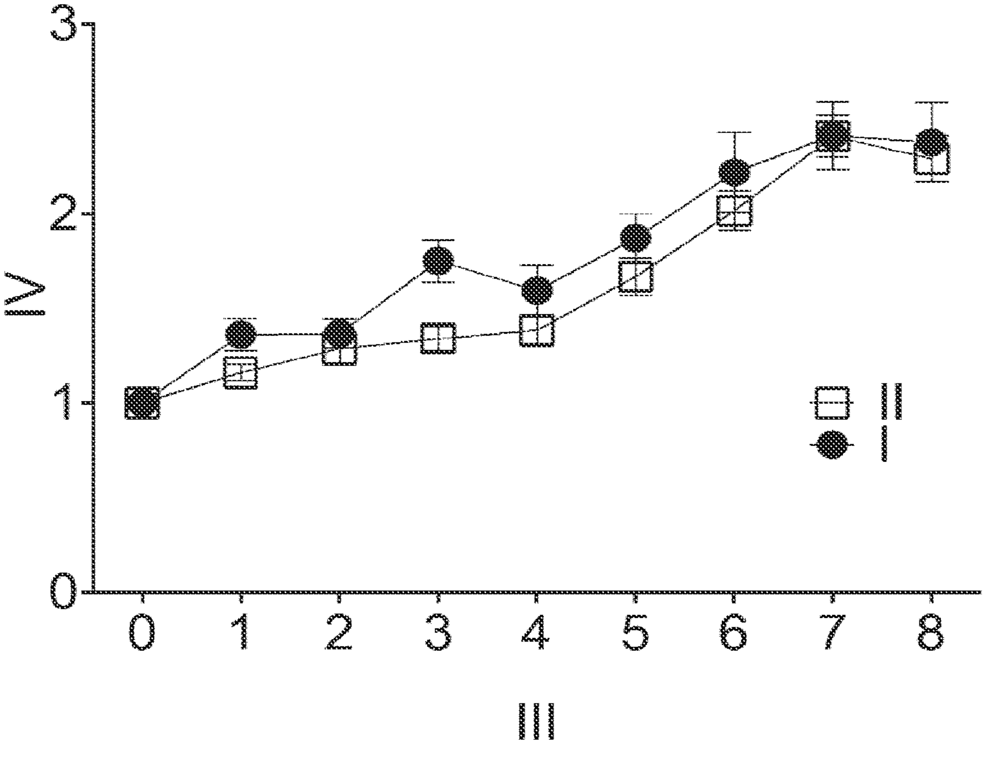
FIG. 10: Tumor progression in wildtype Balb/C mice allografted s.c. with 4T1 breast cancer cells. Wildtype Balb/C mice allografted s.c. with 4T1 breast cancer cells were i.v. injected with I: PBS or II: 1*$10^7$ *Y. enterocolitica* dHOPEMT, once the tumor had reached a size of 150-250 mm3. The day of the i.v. injection of bacteria was defined as day 0. Tumor volume was measured over the following days (III; day 0 to day 9 post i.v. injection of bacteria) with calipers. The relative tumor volume, normalized to the tumor volume at day 0, is indicated (IV) as $mm^3$. The mean is indicated with symbols, error bars depicted show the standard error of the mean

In order to assess the impact of $YopE_{1-138}$-$(tBID\ BH3)_2$ delivered to tumor cells in vivo, we performed studies in wildtype Balb/C mice allografted s.c. with 4T1 breast cancer cells. We aimed at assessing the *Y. enterocolitica* ΔHOPEMT strain encoding $YopE_{1-138}$-$(tBID\ BH3)_2$ on the *Yersinia* virulence plasmid pYV at the native site of YopE and under the native YopE promoter, which is further optimized by deletion of hairpin I region upstream of VirF in order to increase amount of proteins delivered. Mice were i.v. injected with PBS or $1*10^7$ *Y. enterocolitica* ΔHOPEMT ΔHairpinI-virF pYV-$YopE_{1-138}$-$(tBID\ BH3)_2$, once the tumor had reached a size of 150-250 mm3. The day of the i.v. injection of bacteria was defined as day 0. Tumor volume was measured over the following days (day 0 to day 9 post i.v. injection of bacteria) with calipers. The tumor volume was normalized to the tumor volume at day 0 to compensate for any initial heterogeneity in tumor size. Treatment with *Y. enterocolitica* ΔHOPEMT ΔHairpinI-VirF pYV-$YopE_{1-138}$-$(tBID\ BH3)_2$ showed an impact on tumor volume progression, with statistically significant tumor reduction at day 8, 9 and 10 post bacterial administration (FIG. 9). Importantly, *Y. enterocolitica* ΔHOPEMT alone was found not to impact tumor progression in the 4T1 murine cancer model (FIG. 10). These findings highlight that such bacteria and their T3SS can be employed for interference with tumor progression.

*Y. enterocolitica* ΔHOPEMT with Deletion within a RNA Thermosensor Region Upstream of a Gene Coding for a AraC-Type DNA Binding Protein Most known *Yersinia* virulence genes are not expressed outside the eukaryotic host and are only induced after entry into the host environment. Expression of these virulence genes is induced by the sudden increase in temperature related to the entry into the host. Especially, pYV encoded virulence factors as the T3SS and its effector proteins (the Yop's) are regulated this way. At room temperature (20-25° C.) the genes required for regulation of the T3SS, the T3SS formation itself and the delivered effectors are not expressed and only upon such a temperature increase to 37° C., expression is induced. Expression of the majority of pYV-encoded virulence genes (yadA and T3SS related genes) is induced by temperature and requires the AraC-type DNA-binding protein VirF in *Y. enterocolitica* (LcrF in other *Yersinia* species). Thermoregulation of the expression of LcrF is thought to happen via the melting of a RNA stem-loop in the mRNA at higher temperatures, which when not melted is sequestering the ribosomal binding site, thus preventing translation[51]. In contrast, in *Y. enterocolitica* the transcription of VirF has mainly been shown to be dependent on temperature[52]. More recent studies show a more complex picture with implication of a thermolabile regulator called YmoA[51], while the RNA thermosensor upstream of LcrF was found to be mainly responsible for temperature regulation of LcrF a thus the temperature dependent virulence genes.

In order to increase the secretion levels of a heterologous cargo expressed from the pYV under the native YopE promoter, we aimed at deleting one of these RNA hairpin structures in *Y. enterocolitica* upstream of VirF. While the importance of such RNA stem-loops was not clearly shown in *Y. enterocolitica* and the temperature induction was rather attributed to changes in transcription, we could identify hairpin I[51] upstream of *Y. enterocolitica* VirF. By homologous recombination we then removed parts of hairpin I (−111 to −57 as in[51]) and assessed secretion capacity of pYV encoded $YopE_{1-138}$-(tBID $BH3)_2$ (SEQ ID NO: 27) or $YopE_{1-138}$— murine RIG-1 $CARD_2$ protein (SEQ ID NO: 38) (each at the native site of YopE) in an in vitro secretion assay (FIG. 11). Surprisingly, deletion of part of hairpin region I upstream of VirF in *Y. enterocolitica* increased secretion of the heterologous proteins in vitro (FIGS. 11 A and B), which is in contrast to previous reports on *Y. enterocolitica*[52], where transcription of VirF was thought to be the main driver of thermoregulation.

In order to be able to artificially induce the expression of the T3 SS and the delivery of proteins by the T3 SS, we replaced in another strain the endogenous promoter of VirF on the pYV by an Arabinose inducible promoter as known from pBad-MycHisA. In addition to replacing the promoter of VirF, we introduced upstream (in inverted orientation) the complete araC gene. We then assessed secretion capacity of $YopE_{1-138}$-(tBID $BH3)_2$ (SEQ ID NO: 27) (pYV encoded; at the native site of YopE) in absence or presence of Arabinose in an in vitro secretion assay (FIG. 11A). Only upon addition of Arabinose the heterologous protein was found to be secreted by the T3 SS, which is in agreement with a regulation of the expression of VirF by Arabinose.

*Y. enterocolitica* ΔHOPEMT with Increased Stability of Heterologous Cargo (In Vitro and In Vivo)

Figure 12:
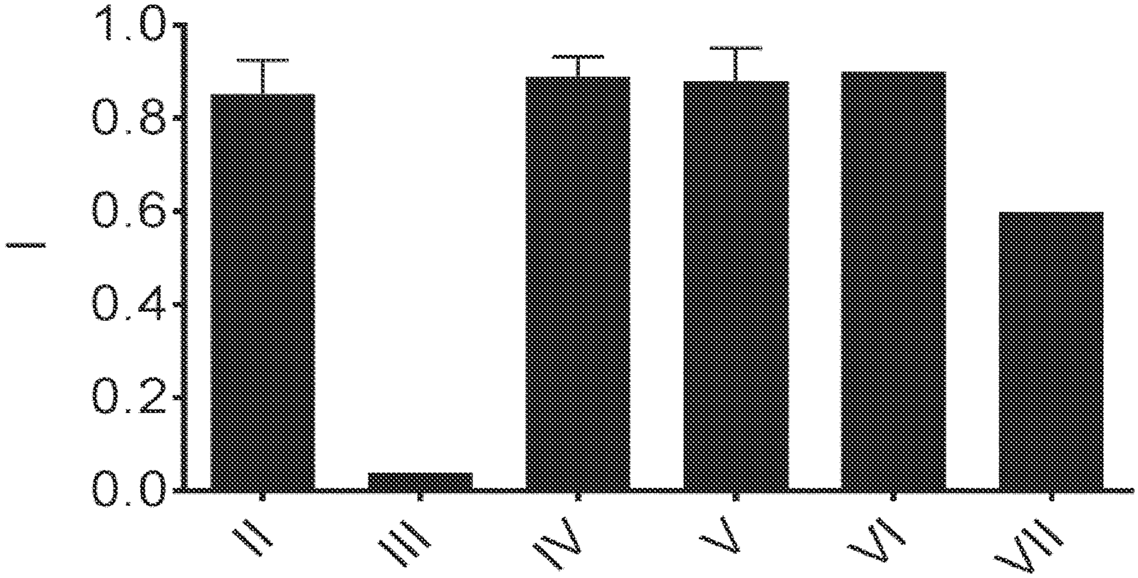
FIG. 12: Comparison of in vitro growth: Comparison of in vitro growth for II: *Y. enterocolitica* ΔHOPEMT, III: *Y. enterocolitica* ΔHOPEMT Δasd, IV: *Y. enterocolitica* ΔHOPEMT Δasd+pBAD-MycHisA-asd, V: *Y. enterocolitica* ΔHOPEMT Δasd+pBAD-MycHisA-asd (reverse orientation), VI: *Y. enterocolitica* ΔHOPEMT encoding $YopE_{1-138}$-(tBID BH3$)_2$ on the pYV and VII: *Y. enterocolitica* ΔHOPEMT Δasd+pYV-asd-$YopE_{1-138}$-(tBID BH3$)_2$. Bacteria were inoculated in liquid culture and grown for 3 hours. Subsequently, the OD600 (I) was determined for all strains.
Figure 13:
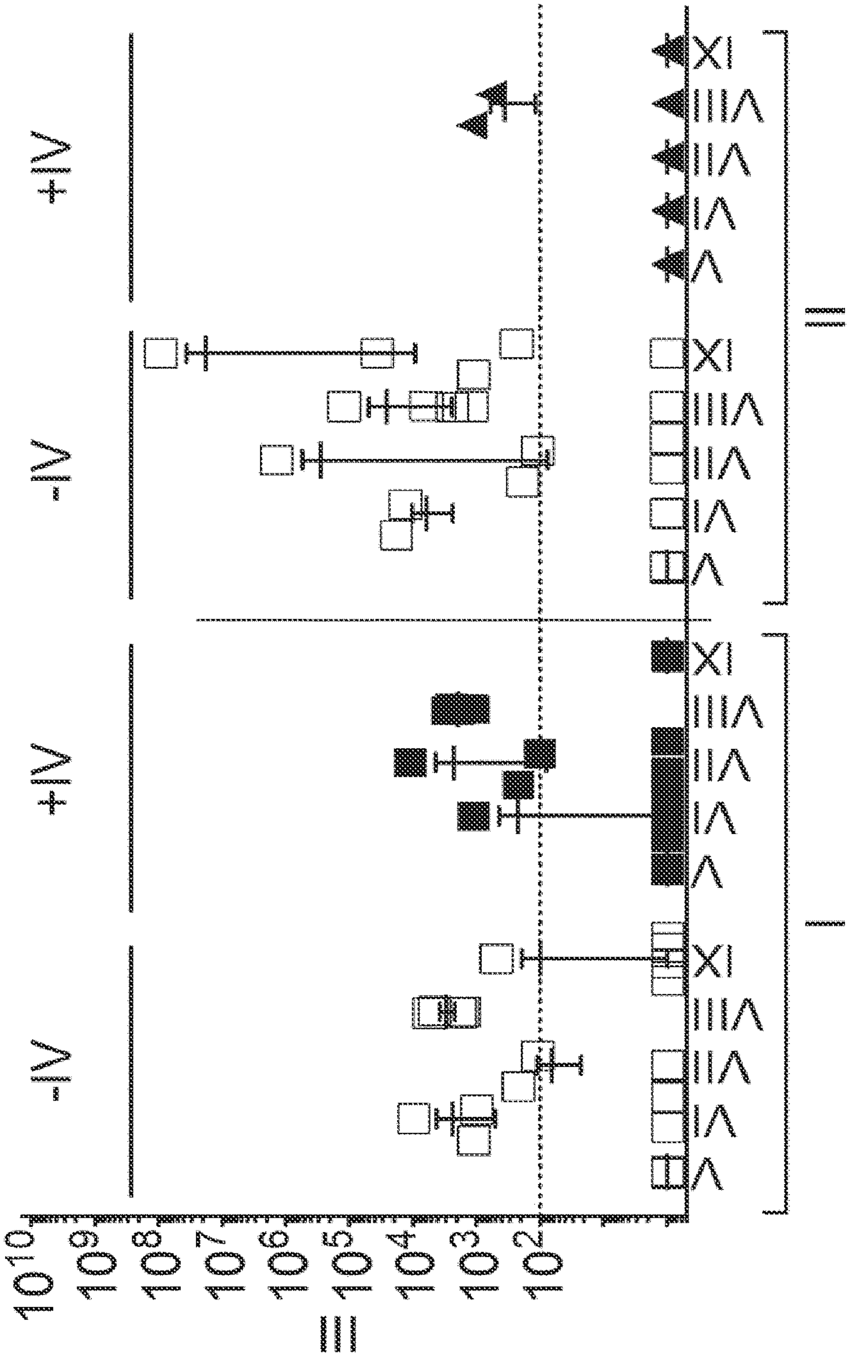
FIG. 13: Tumor colonization with *Y. enterocolitica* ΔHOPEMT Δasd+pBad-MycHisA-asd and stability of pBad-MycHisA-asd: Wildtype C57BL/6 mice allografted s.c. with B16F10 melanoma cells were i.v. injected with 1*$10^6$ *Y. enterocolitica* ΔHOPEMT Δasd+pBad-MycHisA-asd. At day 1 (I) or day 4 (II) post i.v. injection of bacteria, blood (V), spleen (VI), liver (VII), lung (VIII) and tumor (IX) were isolated, homogenized, serially diluted and plated on LB-agar plates containing Nalidixic acid (and no Ampicillin, -IV) or on LB-agar plates with Ampicillin (+IV), selective for pBad-MycHisA-asd. Bacterial counts in the respective samples are indicated as colony forming units (CFU) per gram of tissue or ml of blood (III). Each dot represents an individual mouse. The horizontal dashed line indicates the detection limit.
Figure 14:
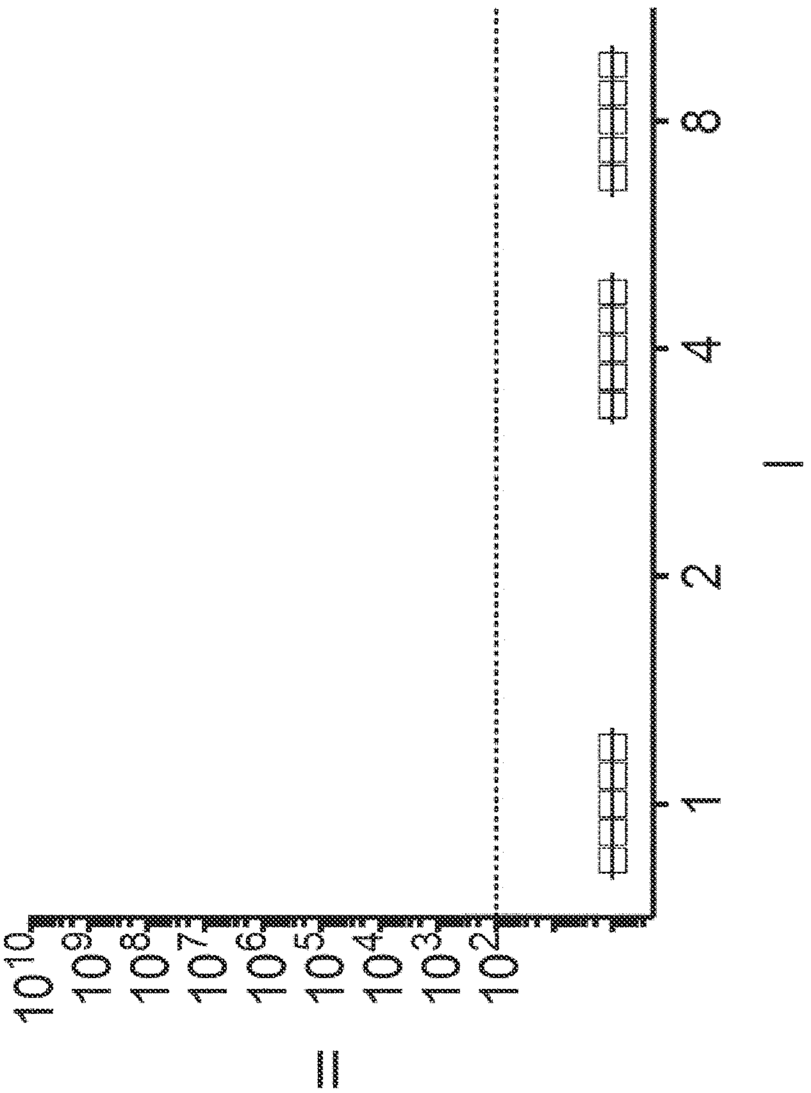
FIG. 14: Tumor colonization with *Y. enterocolitica* ΔHOPEMT Δasd+pBad-MycHisA-asd: Wildtype Balb/C mice allografted s.c. with 4T1 breast cancer cells were i.v. injected with 1*$10^6$ *Y. enterocolitica* ΔHOPEMT Δasd+pBad-MycHisA-asd. At the indicated days post i.v. injection of bacteria (I), tumors were isolated, homogenized, serially diluted and plated on LB-agar plates containing Nalidixic acid. Bacterial counts in tumors are indicated as colony forming units (CFU) per gram of tissue (II). Each dot represents an individual mouse. The horizontal dashed line indicates the detection limit.

*Y. enterocolitia* Δyop$H_2$O,P,E,M,T showed to be a highly specific strain to target solid tumors in our murine experiments, while the T3SS-dependent delivery of cytotoxic proteins was found efficacious in cell culture on cancer cells. In order to combine these two traits, solid tumor-colonizing bacteria need optimally to be engineered in order to stably encode the cytotoxic cargo over several days, or even weeks, in vivo. Due to regulatory requirements, the use of classical antibiotic resistances to maintain a foreign plasmid in bacteria is disfavored. In murine allograft studies we have thus assessed an antibiotic-resistance-free plasmid-maintenance system. This system is based on chromosomal deletion of an essential gene (such as the aspartate-semialdehyde dehydrogenase, asd) and coding for the same gene on a heterologous plasmid to maintain bacterial growth. The complementation of an asd deletion for plasmid maintenance has been shown before[53], while difficulties in reproducibility and persistence over several days have been reported[54]. We adapted this system for use in *Y. enterocolitica* Δyop$H_2$O,P,E,M,T, where we additionally deleted the chromosomally encoded asd (resulting in *Y. enterocolitica* Δyop$H_2$O,P,E,M,T Δasd), which was then brought back on a medium copy number plasmid, pBad-MycHisA (pBad-MycHisA-asd). The asd gene was cloned from *Y. enterocolitica* 8081 and inserted into the PciI site of pBad-MycHisA in forward and reverse orientation, respectively, with its endogenous promoter and transcriptional terminator. Growth behavior of the resulting strains *Y. enterocolitica* Δyop$H_2$O,P,E,M,T Δasd+pBad-MycHisA-asd (forward or reverse asd orientation) was compared in culture flasks in vitro (BHI medium) to wt and parent *Y. enterocolitica* Δyop$H_2$O,P,E,M,T Δasd strains (FIG. 12). In both orientations, pBad-MycHisA-asd rescued the phenotype observed upon deletion of asd (FIG. 12). In contrast, in the B16F10 melanoma mouse model as well as the 4T1 model, we found *Y. enterocolitica* Δyop$H_2$O,P,E,M,T Δasd+pBad-MycHisA-asd not to colonize solid tumors sufficiently (FIGS. 13 and 14) and from the few colonies isolated we were not able to recover the pBad-MycHisA-asd plasmid. Furthermore, the colonies isolated from the B16F10 melanoma mouse model were verified for growth on Ampicillin containing plates, which would be in favor of the presence of the pBad-MycHisA-asd plasmid coding for an Ampicillin resistance. At day 4 after i.v. injection, only a minor fraction of isolated colonies exhibited Ampicillin resistance (FIG. 13). This might reflect a of loss of pBad-MycHisA-asd, but could as well be related to loss of the Ampicillin resistance gene only or difficulties in re-starting the expression of the Ampicillin resistance gene rapid enough to avoid killing by Ampicillin. In any case, the tumor colonization with *Y. enterocolitica* Δyop$H_2$O,P,E,M,T Δasd+pBad-MycHisA-asd observed in the B16F10 melanoma mouse model as well as the 4T1 model show a rapid decrease of bacterial counts within the solid tumor, which is in contrast to *Y. enterocolitica* Δyop$H_2$O,P,E,M,T. Thus, the deletion of chromosomal asd and complementation on pBad-MycHisA leads to a drastic reduction on bacterial fitness in vivo. This observation is in agreement with reports on reduced viability upon misbalanced levels of asd[54].

Figure 15:
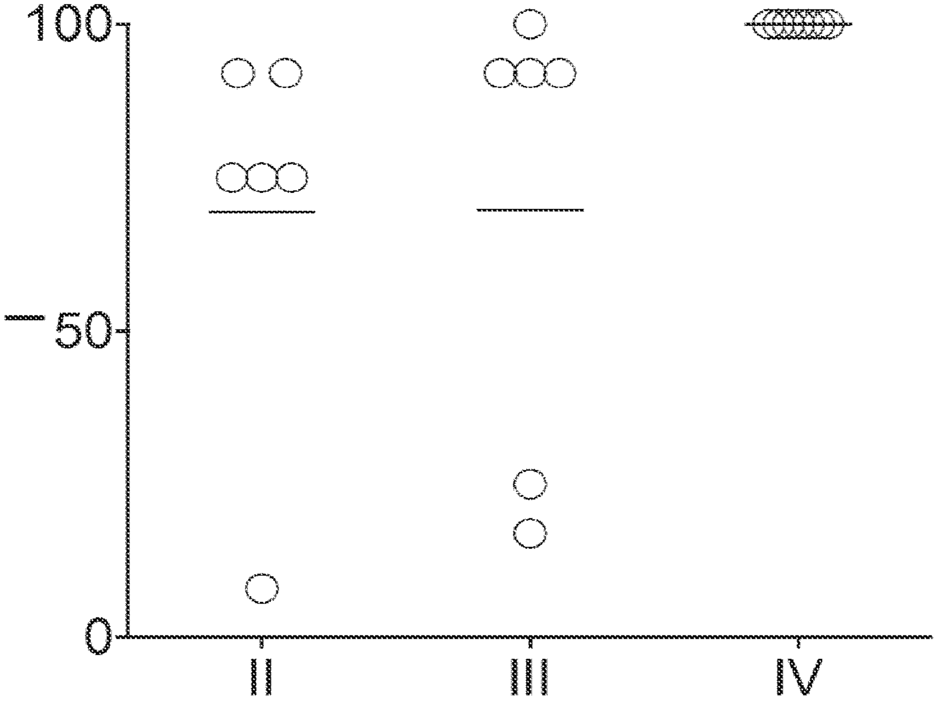
FIG. 15: Genetic stability of the pYV: Stability of native pYV or pYV-asd in solid tumors in vivo. Wildtype Balb/C mice allografted s.c. with 4T1 breast cancer cells were i.v. injected with 1*$10^7$ II: *Y. enterocolitica* ΔHOPEMT+pYV-$YopE_{1-138}$-(tBID BH3$)_2$, *enterocolitica* ΔHOPEMT ΔhairpinI-virF+pYV-$YopE_{1-138}$-(tBID BH3$)_2$ or IV: *Y. enterocolitica* ΔHOPEMT Δasd+pYV-asd-$YopE_{1-138}$-(tBID BH3$)_2$. At day 9 post i.v. injection of bacteria, tumors were isolated, homogenized, serially diluted and plated on LB-agar plates containing Nalidixic acid. After growth on these plates, single colonies from individual mice were re-picked on LB-agar plates with and without Sodium Arsenite, selective for the pYV. For each mouse, the percentage of colonies growing on the agar plates containing Arsenite to the number of colonies growing of plates not containing Arsenite is indicates (I: as %). 100% indicates, that all isolated colonies from a solid tumor still contain the pYV plasmid.

The endogenous proteins for the transport by the T3SS (called "*Yersinia* outer proteins", Yops) are encoded by *Y. enterocolitica* on a 70 kb plasmid. This plasmid, named plasmid of *Yersinia* Virulence (pYV), further encodes the T3SS apparatus. We have assessed the stability of the pYV plasmid in the 4T1 murine allograft model. We have successfully isolated the pYV from strains collected at day 9 or 10 after infection of the mice (FIG. 15). We have further performed tests confirming presence and functionality of the T3SS of isolated bacterial strains after eight days of growth in a solid tumor in vivo. We thus consider the pYV as a vector of choice to encode heterologous cargo for in vivo delivery. Nevertheless, we found the percentage of bacterial colonies carrying the pYV plasmid to be heterogeneous after growth for 9-10 das in 4T1 solid tumors in mice (FIG. 15). In addition to the intrinsic instability of the pYV, the strain *Y. enterocolitica* Δyop$H_2$O,P,E,M,T has lost the selective advantage of the virulence increasing Yop's in vivo.

In order to stabilize the pYV and thus the heterologous cargo encoded on the pYV, we adapted the "asd"-system for use in *Y. enterocolitica* Δyop$H_2$O,P,E,M,T on the pYV. We deleted the chromosomally encoded asd (resulting in *Y. enterocolitica* Δyop$H_2$O,P,E,M,T Δasd), which was then brought back on the pYV (called pYV-asd). The asd gene was cloned from *Y. enterocolitica* 8081 (*Y. enterocolitica* subsp. *enterocolitica* 8081; NCBI Reference Sequence: NC 008800.1) and inserted by homologous recombination onto the pYV (in to the natural insertion region before SycO) with its endogenous promoter and transcriptional terminator.

Figure 16:
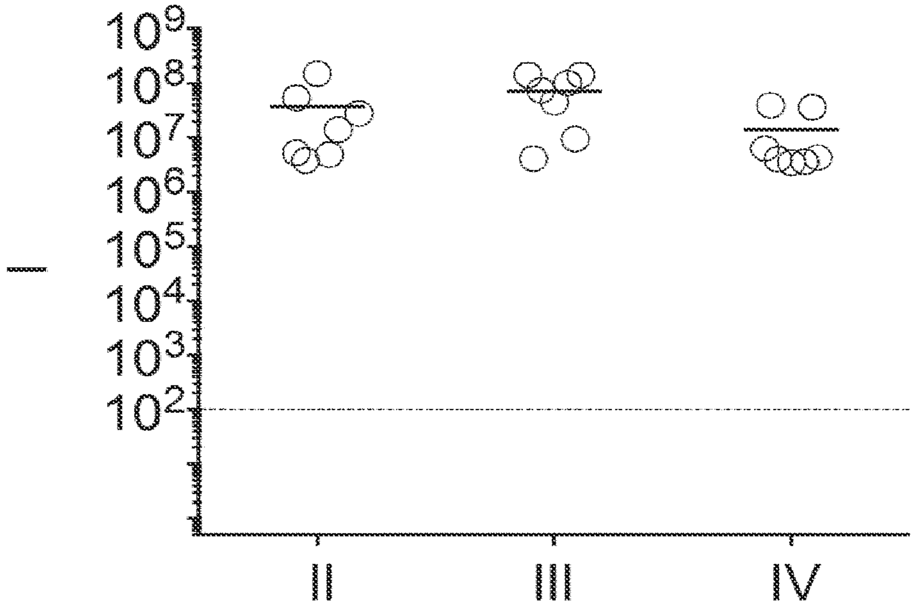
FIG. 16: Tumor colonization: Wildtype Balb/C mice allografted s.c. with 4T1 breast cancer cells were i.v. injected with 1*$10^7$ II: *Y. enterocolitica* ΔHOPEMT+pYV-$YopE_{1-138}$-(tBID BH3$)_2$, III:*Y. enterocolitica* ΔHOPEMT ΔhairpinI-virF+pYV-$YopE_{1-138}$-(tBID BH3$)_2$ or IV: *Y. enterocolitica* ΔHOPEMT Δasd+pYV-asd-$YopE_{1-138}$-(tBID BH3$)_2$. At day 9 post i.v. injection of bacteria, tumors were isolated, homogenized, serially diluted and plated on LB-agar plates containing Nalidixic acid. Bacterial counts in tumors are indicated as colony forming units (CFU) per gram of tissue (I). Each dot represents an individual mouse. The horizontal dashed line indicates the detection limit.

Growth behavior of the resulting strains *Y. enterocolitica* ΔyopH$_2$O,P,E,M,T Δasd+pYV-asd was compared in culture flasks in vitro (BHI medium) to wt and parent *Y. enterocolitica* ΔyopH$_2$O,P,E,M,T Δasd strains (FIG. 12). pYV-asd was able to rescue the phenotype observed upon deletion of asd (FIG. 12), while the rescue was not complete and a slight growth reduction in vitro could be observed. In contrast, in the in vivo syngeneic 4T1 murine cancer model, we found *Y. enterocolitica* ΔyopH$_2$O,P,E,M,T Δasd+pYV-asd to colonize solid tumors efficiently (FIG. 16). Strikingly, all the colonies isolated at day 9-10 post injection from the solid tumor were found to still contain the pYV plasmid (selection on Arsenite containing growth plates; Arsenite resistance is related to presence of arsRBC genes on the pYV[55]) (FIG. 15). Hence, pYV-asd surprisingly showed to be an in vivo stable vector for encoding heterologous proteins to be expressed in solid tumors by colonizing bacteria over several days and weeks in a *Y. enterocolitica* ΔyopH$_2$O,P,E,M,T Δasd strain background.

Figure 45:
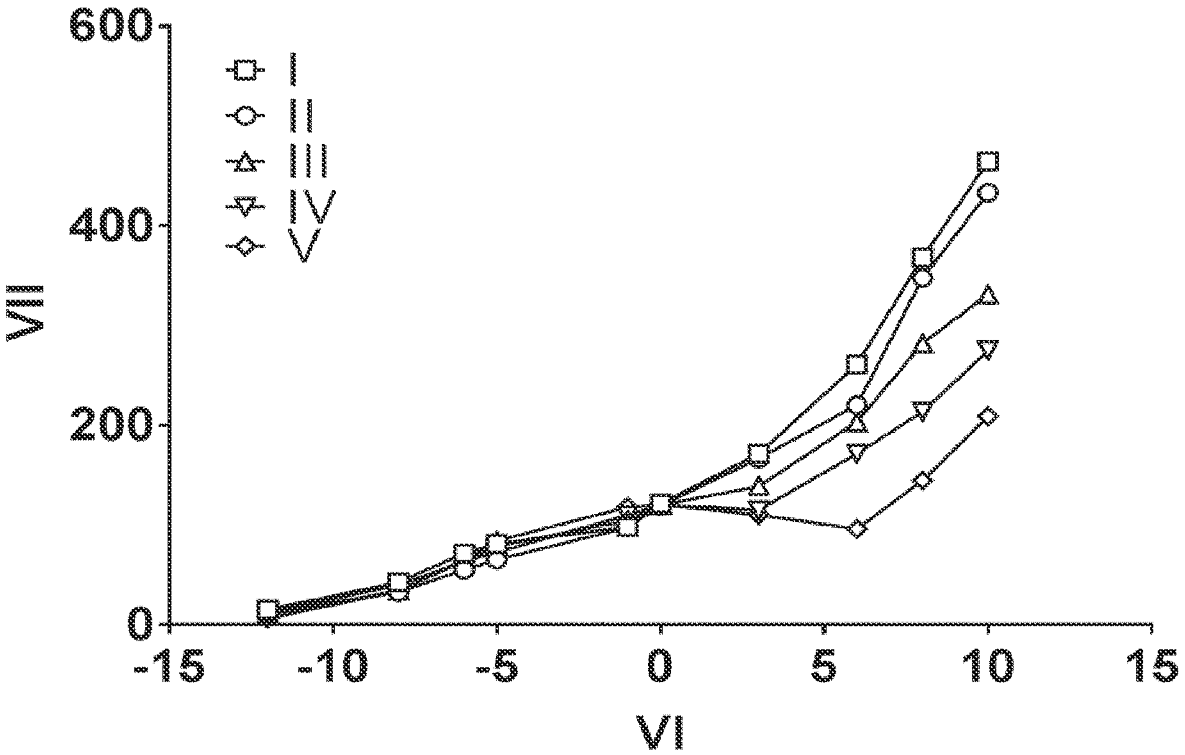
FIG. 45: Tumor progression in wildtype Balb/C mice allografted s.c. with EMT6 breast cancer cells. Wildtype Balb/C mice allografted s.c. with EMT6 breast cancer cells were i.v. injected with I: PBS, or $5*10^6$ II: *Y. enterocolitica* dHOPEMT, III: *Y. enterocolitica* dHOPEMT pYV-$YopE_{1-138}$-(tBID BH3)$_2$, IV: *Y. enterocolitica* dHOPEMT ΔHairpinI-VirF pYV-$YopE_{1-138}$-(tBID BH3)$_2$, V: *Y. enterocolitica* dHOPEMT ΔHairpinI-VirF Δasd pYV-asd-$YopE_{1-138}$-(tBID BH3)$_2$ once the tumor had reached a size of 80-250 mm3. The day of the i.v. injection of bacteria was defined as day 0, all mice were treated i.p with Desferal at d-1. Tumor volume was measured over the following days (VI: day 0 to day 15 post first injection of bacteria) with calipers. The median tumor volume is indicated (VII) as $mm^3$.

Efficacy of *Y. enterocolitica* ΔHOPEMT in Delaying Tumor Progression and Impact of Altering VirF Activity as Well as Increasing Stability Similar experiments as with 4T1 cells (FIGS. 9 and 10) were performed in the EMT6 breast cancer mouse model, in which wildtype Balb/C mice were allografted s.c. with EMT6 breast cancer cells and treated with a single i.v. administration of bacteria once the tumor had reached a size of about 80-250 mm3. The day of the i.v. injection of bacteria was defined as day 0, all mice had an i.p injection of Desferal one ay before d0. Treatment with *Y. enterocolitica* ΔHOPEMT did not impact tumor progression as compared to saline solution. *Y. enterocolitica* ΔHOPEMT pYV-YopE$_{1-138}$-(tBID BH3)$_2$ showed slight impact on tumor progression, which was reinforced by using *Y. enterocolitica* ΔHOPEMT pYV-YopE$_{1-138}$-(tBID BH3)$_2$ (FIG. 45).

These findings highlight that such bacteria and their T3SS can be employed for interference with tumor progression and that manipulation of VirF activity can be used to modulate bacterial T3SS activity upon administration in vivo. Furthermore, using *Y. enterocolitica* ΔHOPEMT ΔHairpinI-VirF Δasd pYV-asd-YopE$_{1-138}$-(tBID BH3)$_2$ further strengthened the impact on tumor progression (FIG. 45), highlighting benefits of increased genetic stability upon systemic administration.

Delivery of RIG-1-Like Receptor Pathway Triggering Proteins Via the Bacterial T3SS for Induction of a Type I IFN Response Cytosolic nucleic acids are sensed by receptor as the RIG-1-like receptor (RLR) family members that detect pathogen-derived RNA in the cytosol[56]. RIG-1 and MDA5 consist of two N-terminal CARD domains and a central (DExD/H) helicase domain sensing specific nucleotides[56]. Binding to stimulatory RNA induces a structural rearrangement in RIG-I (and MDA5) that liberates its CARDs for subsequent association with unanchored K63-linked ubiquitin chains to form oligomers[56] (and in case of MDA5 to filament formation[56]). Oligomerized CARD domains of RIG-I and MDA5 interact with the CARD domain of MAVS. This interaction promotes the polymerization of the single CARD domain of MAVS, which induces downstream signaling ultimately leading to induction of type I IFN genes[56].

Figure 17:
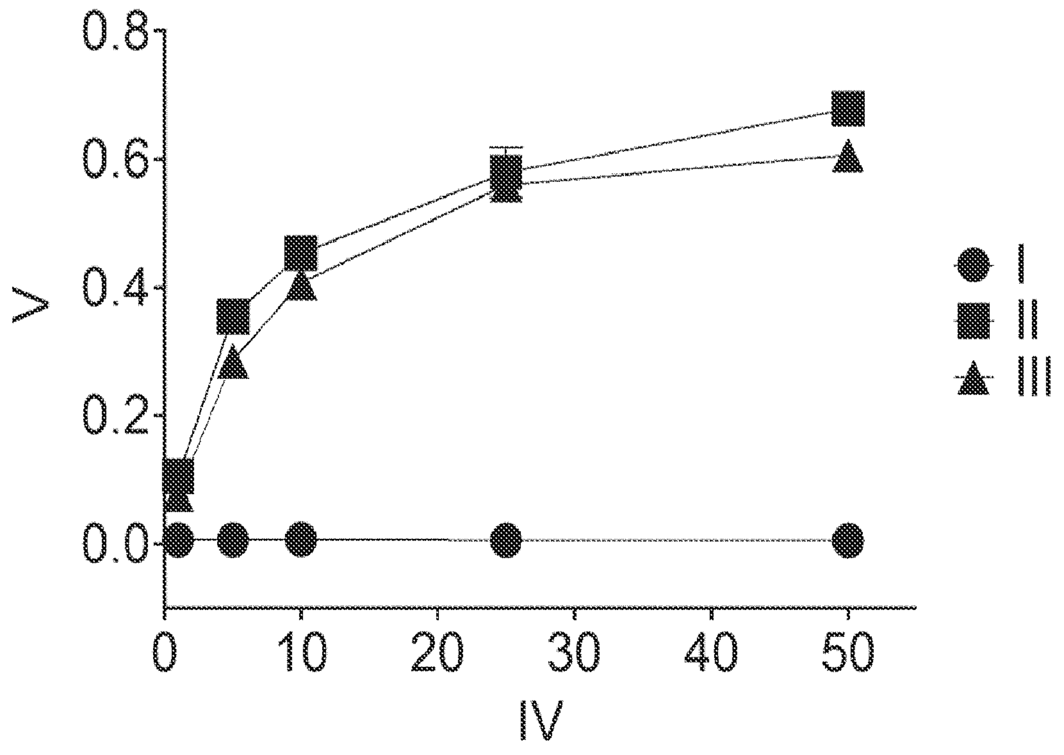
FIG. 17: Delivery of type I Interferon response inducing proteins via the bacterial T3SS-Rig1 pathway. Delivery of human and murine Rig1 CARD domains lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-human Rig1 CARD domains, III: $YopE_{1-138}$-murine Rig1 CARD domains. A titration of the bacteria added to the cells (IV: indicated as MOI) was performed for each strain, and IFN stimulation was assessed based on activity of secreted alkaline phosphatase (V: OD650) which is under the control of the I-ISG54 promoter which is comprised of the IFN-inducible ISG54 promoter enhanced by a multimeric ISRE.

We generated bacterial strains expressing the two N-terminal CARD domains of RIG-1 of human or murine origin fused to a N-terminal bacterial secretion signal for delivery by the T3SS, specifically YopE$_{1-138}$ (SEQ ID NO: 37 and 38). Delivery of the fusion protein YopE$_{1-138}$-RIG-1 CARD$_2$ was assessed by a standard in vitro secretion assay and functionality of delivered proteins were assessed on a reporter cell line for type I IFN induction. Murine B16F10 melanoma reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the YopE$_{1-138}$-RIG-1 CARD$_2$ protein. Murine and human N-terminal CARD domains of RIG-1 showed to induce a dose-dependent type I IFN response in the reporter cell line (FIG. 17), while the bacterial background strain (*Y. enterocolitica* ΔHOPEMT) was not capable of inducing such a response (FIG. 17). Human and murine RIG-1 CARD domains induced a similar type I IFN response in the murine reporter cell line (FIG. 17), which is in agreement with the high sequence identity (76%) and similarity (88.5%).

Thus, the fusion to the N-terminal secretion signal of bacteria has lead to successful delivery of bacterially expressed human and murine YopE$_{1-138}$-RIG-1 CARD$_2$ proteins and has not prevented the folding and function of the RIG-1 CARD domains within the eukaryotic cell. This implies, that the YopE-fused RIG1 CARD domains are still able to multimerize themselves and induce multimerization of MAVS, which is surprising.

Figure 18:
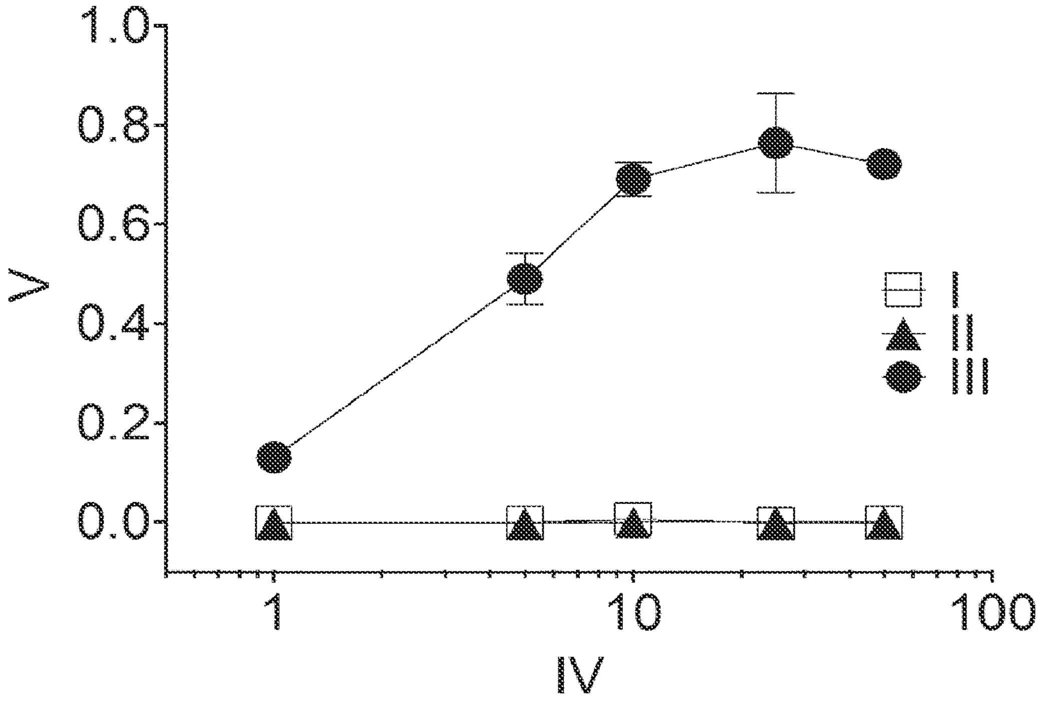
FIG. 18: Delivery of type I Interferon response inducing proteins via the bacterial T3SS-Rig1 pathway. Delivery of human Rig1 CARD domains lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-MycHis, III: $YopE_{1-138}$-human Rig1 CARD domains. A titration of the bacteria added to the cells (IV: indicated as MOI) was performed for each strain, and IFN stimulation was assessed based on activity of secreted alkaline phosphatase (V: OD650) which is under the control of the I-ISG54 promoter which is comprised of the IFN-inducible ISG54 promoter enhanced by a multimeric ISRE.
Figure 19:
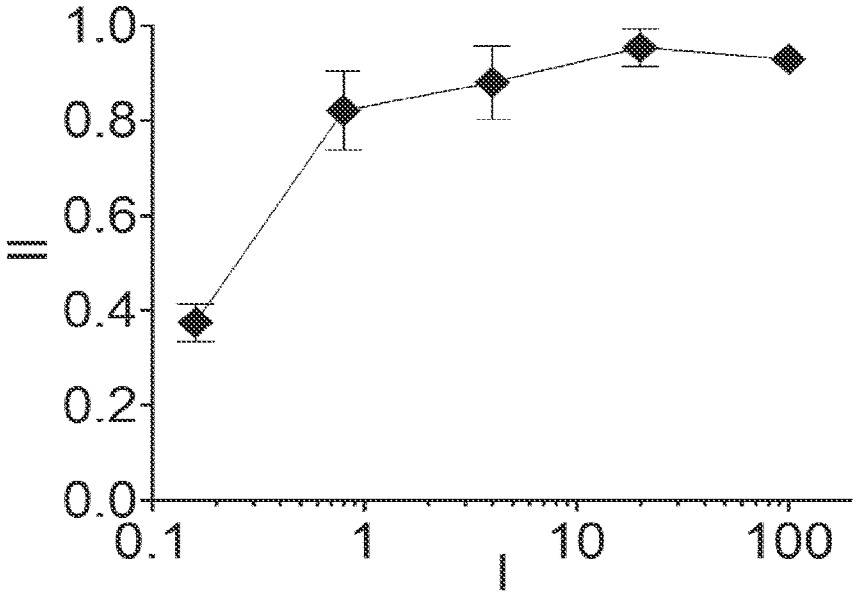
FIG. 19: Delivery of type I Interferon response inducing proteins via the bacterial T3SS-Rig1 pathway: positive control. Positive control in same experiment as FIG. 18 using IFN gamma to stimulate the B16F10 IFN-reporter cell line. B16F10 reporter cells were stimulated with murine IFN gamma. A titration of IFN gamma was added to the cells (I: indicated as U/ml), and IFN stimulation was assessed based on activity of secreted alkaline phosphatase (II: OD650) which is under the control of the I-ISG54 promoter which is comprised of the IFN-inducible ISG54 promoter enhanced by a multimeric ISRE.

In further experiments using this B16F10 type I IFN reporter cell line, we compared *Y. enterocolitica* ΔHOPEMT, to *Y. enterocolitica* ΔHOPEMT encoding on a pBadMycHisA derived plasmid (pBad_Si2) YopE$_{1-138}$-MycHis or YopE$_{1-138}$-human Rig1 CARD$_2$. Again, delivery of human RIG-1 CARD domains induced a dose dependent type I IFN response, while *Y. enterocolitica* ΔHOPEMT or *Y. enterocolitica* ΔHOPEMT delivering YopE$_{1-138}$-MycHis had no effect on type I IFN response (FIG. 18). In the same assay we compared the type I IFN inducing potential of bacteria delivering RIG-1 CARD domains to a positive control, murine Interferon gamma (IFNγ). Very surprisingly, bacterial delivery of RIG-1 CARD domains was able to induce a maximal response of the reporter cell line similar to the response obtained by the positive control for type I IFN induction, IFNy (FIGS. 18 and 19).

Figure 20:
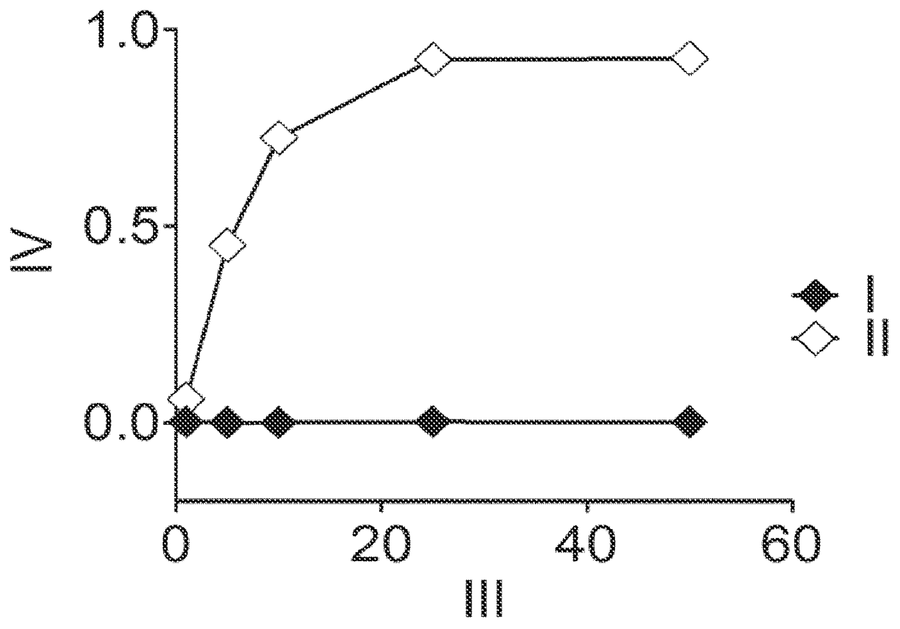
FIG. 20: Delivery of type I Interferon response inducing proteins via the bacterial T3SS-Rig1 pathway. Delivery of pYV encoded murine Rig1 CARD domains lead to type I IFN induction in theB16F10 cancer cell line.B16F10 cells were infected with I: *Y. enterocolitica* ΔHOPEMT, or *Y. enterocolitica* ΔHOPEMT encoding on the pYV II: $YopE_{1-138}$-murine Rig1 CARD domains. A titration of the bacteria added to the cells (III: indicated as MOI) was performed for each strain, and IFN stimulation was assessed by adding cellular supernatant to a IFN reporter cell line based on activity of secreted alkaline phosphatase (IV: OD650) which is under the control of the I-ISG54 promoter which is comprised of the IFN-inducible ISG54 promoter enhanced by a multimeric ISRE.
Figure 21:
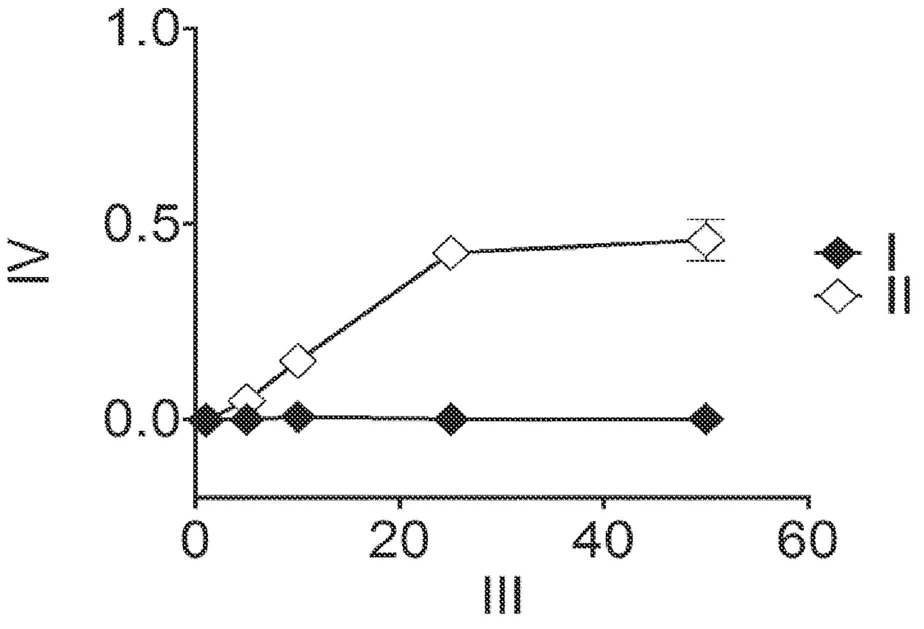
FIG. 21: Delivery of type I Interferon response inducing proteins via the bacterial T3SS-Rig1 pathway. Delivery of pYV encoded murine Rig1 CARD domains lead to type I IFN induction in the 4T1 cancer cell line. 4T1 cells were infected with I: *Y. enterocolitica* ΔHOPEMT, or *Y. enterocolitica* ΔHOPEMT encoding on the pYV II: $YopE_{1-138}$-murine Rig1 CARD domains. A titration of the bacteria added to the cells (III: indicated as MOI) was performed for each strain, and IFN stimulation was assessed by adding cellular supernatant to a IFN reporter cell line based on activity of secreted alkaline phosphatase (IV: OD650) which is under the control of the I-ISG54 promoter which is comprised of the IFN-inducible ISG54 promoter enhanced by a multimeric ISRE.

In further experiments we infected 4T1 murine breast cancer cells or wt B16F10 melanoma cells, and transferred the supernatant possibly containing IFN after 4 h onto the B16F10 type I IFN reporter cell line. This way, we compared *Y. enterocolitica* ΔHOPEMT, to *Y. enterocolitica* ΔHOPEMT encoding on the endogenous virulence plasmid (pYV) YopE$_{1-138}$-murine Rig1 CARD$_2$. Delivery of pYV encoded murine RIG-1 CARD domains induced a dose dependent type I IFN response, while *Y. enterocolitica* ΔHOPEMT had no effect on type I IFN response in wt B16F10 (FIG. 20) or 4T1 cells (FIG. 21).

Figure 27:
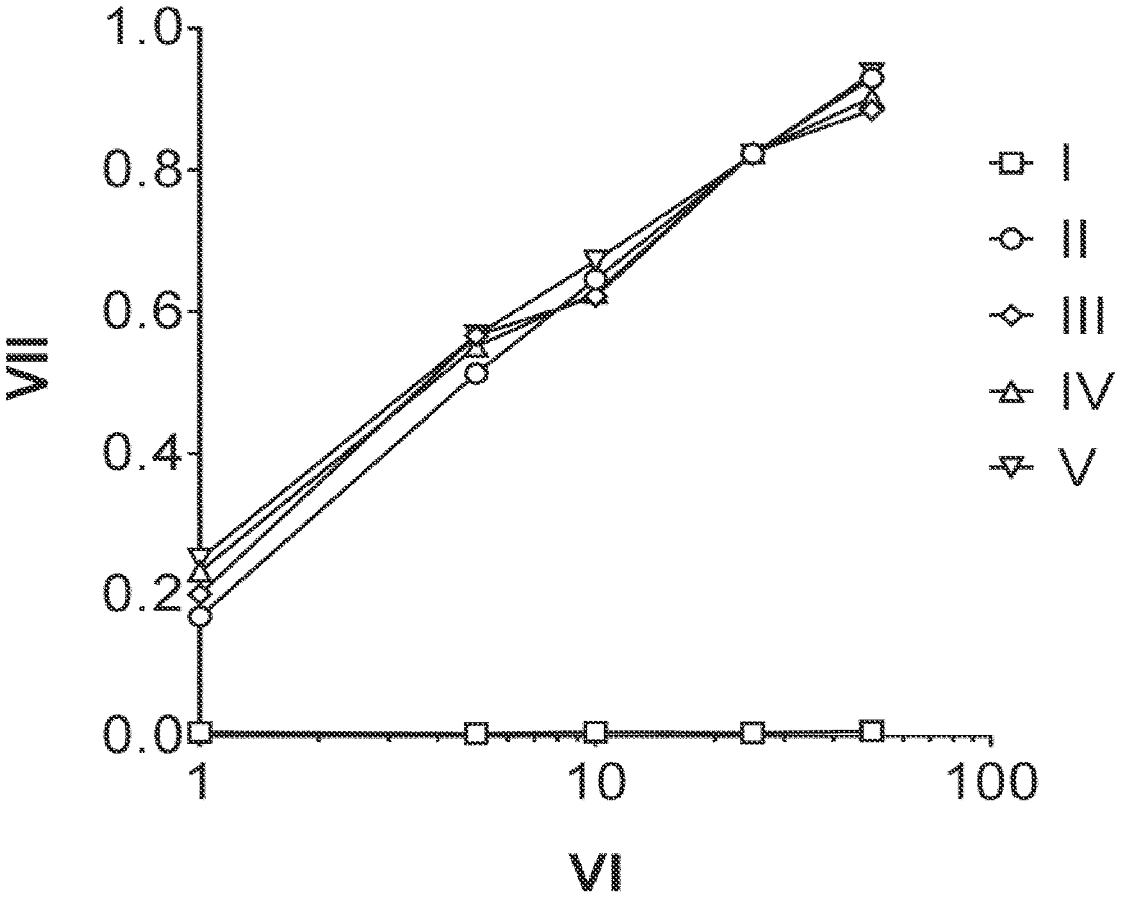
FIG. 27: Delivery of type I Interferon response inducing proteins via the bacterial T3SS-RIG1. Delivery of human and murine RIG1 CARD domains lead to type I IFN induction in a B16F10 IFN-reporter cell line. B16F10 cells were infected with I: *Y. enterocolitica* ΔHOPEMT, or *Y. enterocolitica* ΔHOPEMT encoding on a pBadMycHisA derived plasmid II: $YopE_{1-138}$-human RIG1 CARD $domains_{1-245}$, III: $YopE_{1-138}$-murine RIG1 CARD $domains_{1-246}$, $YopE_{1-138}$-murine RIG1 CARD $domains_{1-229}$, V: $YopE_{1-138}$-murine RIG1 CARD $domains_{1-218}$. A titration of the bacteria added to the cells (VI: indicated as MOI) was performed for each strain, and IFN stimulation was assessed based on activity of secreted alkaline phosphatase (VII: OD650) which is under the control of the I-ISG54 promoter which is comprised of the IFN-inducible ISG54 promoter enhanced by a multimeric ISRE.
Figure 28:
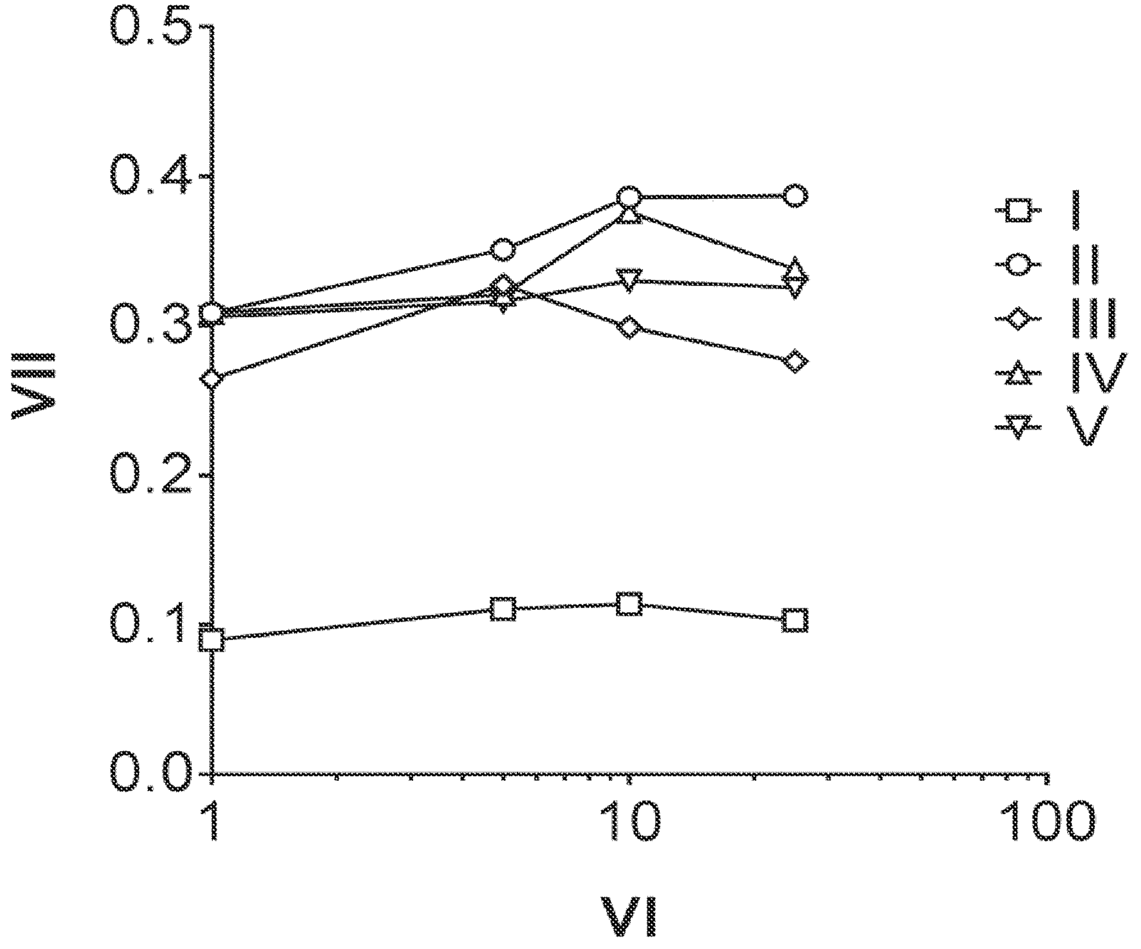
FIG. 28: Delivery of type I Interferon response inducing proteins via the bacterial T3SS-RIG1. Delivery of human and murine RIG1 CARD domains lead to type I IFN induction in a RAW IFN-reporter cell line. RAW reporter cells were infected with I: *Y. enterocolitica* ΔHOPEMT, or *Y. enterocolitica* ΔHOPEMT encoding on a pBadMycHisA derived plasmid II: $YopE_{1-138}$-human RIG1 CARD $domains_{1-245}$, III: $YopE_{1-138}$-murine RIG1 CARD $domains_{1-246}$, $YopE_{1-138}$-murine RIG1 CARD $domains_{1-229}$, V: $YopE_{1-138}$-murine RIG1 CARD $domains_{1-218}$. A titration of the bacteria added to the cells (VI: indicated as MOI) was performed for each strain, and IFN stimulation was assessed based on activity of secreted alkaline phosphatase (VII: OD650) which is under the control of the I-ISG54 promoter which is comprised of the IFN-inducible ISG54 promoter enhanced by a multimeric ISRE.

In a further experiment, several versions consisting of different length of murine RIG-1 CARDs have been assessed for their potential in inducing a type I IFN response. The CARD domains of RIG-1 are predicted to be encoded by amino acids 1-172 (murine sequence, Uniprot Nr. Q6Q899). We assessed YopE$_{1-138}$-murine RIG1 CARD domains$_{1-246}$, YopE$_{1-138}$-murine RIG1 CARD domains$_{1-229}$, and YopE$_{1-138}$-murine RIG1 CARD domains$_{1-218}$ on B16F10 melanoma IFN reporter cells as well as RAW macrophage IFN reporter cells (FIG. 27-28). YopE$_{1-138}$-murine RIG1 CARD domains$_{1-246}$, YopE$_{1-138}$-murine RIG1 CARD domains$_{1-229}$ and YopE$_{1-138}$-murine RIG1 CARD domains$_{1-218}$ were found equally active.

Figure 29:
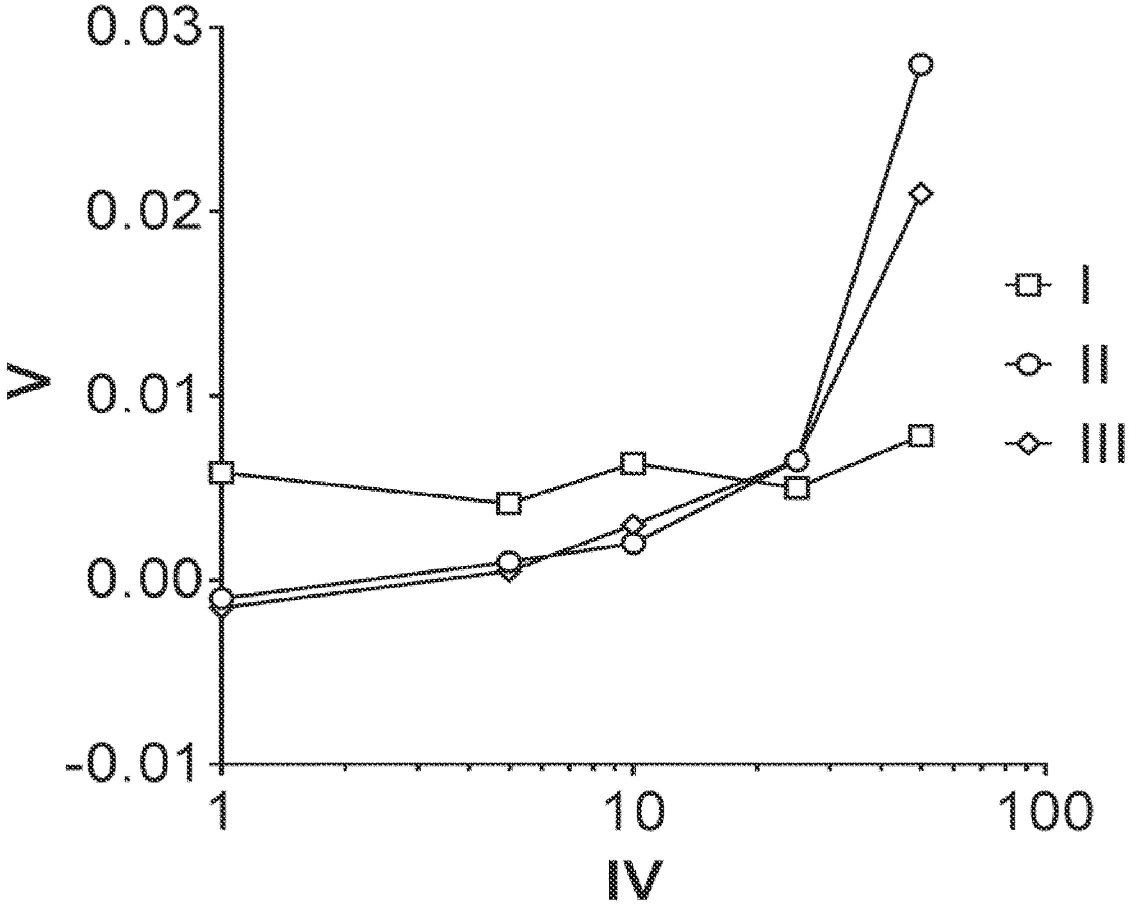
FIG. 29: Delivery of type I Interferon response inducing proteins via the bacterial T3SS—MDA5 pathway. Delivery of murine MDA5 lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-murine MDA51-294, III: $YopE_{1-138}$-murine MDA51-231. A titration of the bacteria added to the cells (IV: indicated as MOI) was performed for each strain, and IFN stimulation was assessed based on activity of secreted alkaline phosphatase (V: OD650) which is under the control of the I-ISG54 promoter which is comprised of the IFN-inducible ISG54 promoter enhanced by a multimeric ISRE.

In a follow—on experiment we assessed potency of bacterially delivered MDA5. We cloned several versions consisting of different length of murine MDA5 CARDs and assessed them for their potential in inducing a type I IFN response on B16F10 IFN reporter cells. The CARD domains of MDA5 are predicted to be encoded by amino acids 1-190 (murine sequence, Uniprot Nr. Q8R5F7). We assessed $YopE_{1-138}$-murine MDA5 CARD $domains_{1-294}$ and $YopE_{1-138}$-murine MDA5 CARD $domains_{1-231}$, on B16F10 melanoma IFN reporter cells. All variants were found active (FIG. 29). Surprisingly, activity of delivered MDA5 CARDs was found being by far less strong as RIG-1 CARDs, even though the proteins share very similar biological function and protein structure consisting of two N-terminal CARD domains and a central (DExD/H) helicase domain sensing specific nucleotides[56].

Delivery of cGAS/STING Pathway Triggering Proteins Via the Bacterial T3SS for Induction of a Type I IFN Response In the cGAS/STING pathway, cytosolic double-stranded DNA is detected by binding to the enzyme cyclic GMP-AMP synthase (cGAS). Upon dsDNA binding, cGAS is activated and produces a cyclic CDN second messenger, cyclic GMP-AMP (cGAMP). cGAMP then directly binds to the endoplasmic reticulum receptor protein STING (Stimulator of IFN Genes). Upon binding of cGAMP, STING is activated and induces a signaling pathway leading to transcription of type I IFN and other co-regulated genes[57]. Human cGAS produces 2',3' cGAMP (containing 2'-5' and 3'-5' phosphodiester bonds), but other CDNs have been shown to be able to induce murine or human STING at various levels. This includes 3',3' cGAMP (e.g. produced by *Vibrio cholera* DncV or some eukaryotic cGAS), cyclic di-AMP (e.g. produced by CdaA or DisA of different gram-positive species) or cyclic di-GMP (e.g. produced by *Pseudomonas aeruginosa* WspR)[57,58]. While the wt human STING (and murine STING) recognize 2',3' cGAMP, 3',3' cGAMP, cyclic di-AMP and cyclic di-GMP, several natural human STING variants respond differently to these agonists[59].

In order to activate the cGAS/STING pathway upon delivery of proteins by bacteria, we cloned *P. aeruginosa* WspR producing cyclic di-GMP to be expressed and delivered by *Y. enterocolitica* via the T3SS. In order to increase activity of WspR, only its GGDEF domain (diguanylate cyclased domain) was used and the upstream stalk domain was replaced with the leucin-zipper motif of GCN4 from yeast. Dimerization of WspR is know to be required for its activity and the leucine zipper of GCN4 has been shown to form parallel coiled-coils and, thus to serve as a strong dimerization module. The GCN4 motif was fused to the GGDEF domain of WspR including the natural linker between the GGDEF and helical stalk to allow for inter-domain flexibility comparable to wild-type WspR[60].

Figure 22:
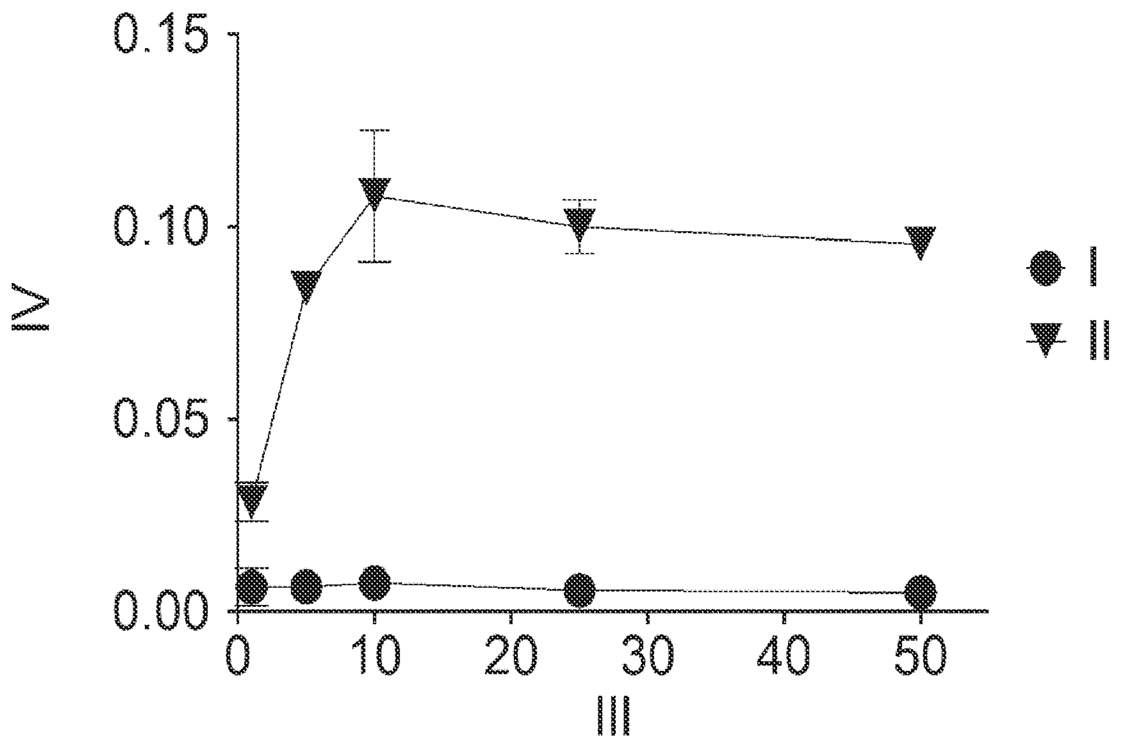
FIG. 22: Delivery of type I Interferon response inducing proteins via the bacterial T3SS-STING pathway. Delivery of cyclic dinucleotide generating enzymes lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-*P. aeruginosa* WspR (with adapted stalk domain). A titration of the bacteria added to the cells (III: indicated as MOI) was performed for each strain, and IFN stimulation was assessed based on activity of secreted alkaline phosphatase (IV: OD650) which is under the control of the I-ISG54 promoter which is comprised of the IFN-inducible ISG54 promoter enhanced by a multimeric ISRE.

Delivery of the fusion protein $YopE_{1-138}$-GCN4 leucin zipper—WspR GGDEF domain (short: $YopE_{1-138}$-WspR) (SEQ ID NO: 39) was assessed on a reporter cell line for type I IFN induction. Murine B16F10 melanoma reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the $YopE_{1-138}$-WspR protein. *P. areuginosa* WspR GGDEF domain fused to GCN4 leucin zipper motif showed to dose-dependently induce a type I IFN response in the reporter cell line (FIG. 22), while the bacterial background strain (*Y. enterocolitica* ΔHOPEMT) was not capable of inducing such a response (FIG. 22).

Thus, the fusion to the N-terminal secretion signal of bacteria has lead to successful delivery of bacterially expressed $YopE_{1-138}$-GCN4 leucin zipper (yeast)—WspR GGDEF (*P. areuginosa*) protein and has not prevented the folding and function of the this tri-partite protein within the eukaryotic cell. This implies, that the YopE-fused GCN4 leucin zipper—WspR GGDEF is still able to dimerize and thus lead to active GGDEF domains, which is surprising.

For further experiments, we cloned *V. cholerae* DncV (producing 3',3' cGAMP)[57], a *Bacillus cereus* DisA-like protein (producing cyclic di-AMP)[61] and the eukaryotic Anemonae (*Nematostella vectensis*) cGAS (producing 3',3' cGAMP)[57], which has been reported to be active in absence of external stimuli, for expression and translocation by bacteria. DisA type cyclases usually form octamers[61], which might not be compatible with the N-terminal YopE fusion and bacterial delivery. *B. cereus* DisA-like (PDB code 2fb5) was identified based on structural similarity to the diadenylate cyclase (DAC) domain of classical DisA proteins[61], but it interestingly lacks all helices known from other DisA proteins to be required for multimerization. We thus decided to take advantage of the possibly monomerical active DisA-like protein from *B. cereus* (PDB code 2fb5; residues 76-205).

Figure 23:
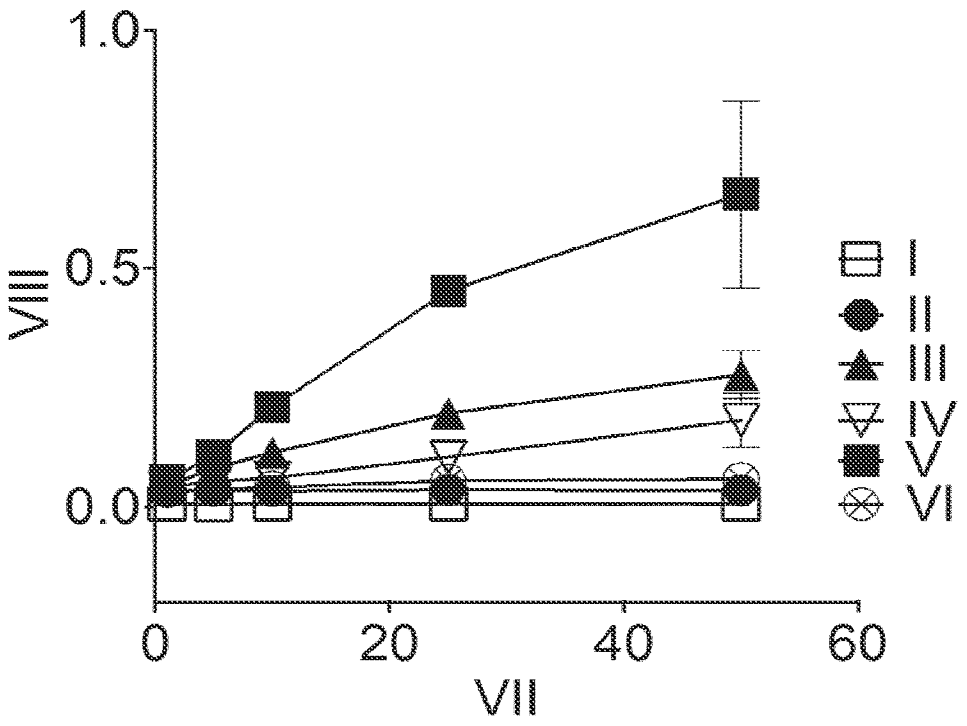
FIG. 23: Delivery of type I Interferon response inducing proteins via the bacterial T3SS-STING pathway. Delivery of cyclic dinucleotide generating enzymes lead to type I IFN induction in a B16F10 IFN-reporter cell line. B16F10 reporter cells were either left untreated (I), or infected with II: *Y. enterocolitica* ΔHOPEMT, or *Y. enterocolitica* ΔHOPEMT encoding on a pBadMycHisA derived plasmid III: $YopE_{1-138}$—*V. cholerae* DncV, IV: $YopE_{1-138}$-*B. cereus* DisA-like protein, V: $YopE_{1-138}$-Anemonae cGAS or VI: $YopE_{1-138}$-MycHis. A titration of the bacteria added to the cells (VII: indicated as MOI) was performed for each strain, and IFN stimulation was assessed based on activity of secreted alkaline phosphatase (VIII: OD650) which is under the control of the I-ISG54 promoter which is comprised of the IFN-inducible ISG54 promoter enhanced by a multimeric ISRE.

Delivery of the fusion protein $YopE_{1-138}$—*V. cholerae* DncV (SEQ ID NO: 41), $YopE_{1-138}$—*B. cereus* DisA-like protein (SEQ ID NO: 42) and $YopE_{1-138}$-Anemonae cGAS (SEQ ID NO: 43) was assessed on a reporter cell line for type I IFN induction. Murine B16F10 melanoma reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the $YopE_{1-138}$—*V. cholerae* DncV, $YopE_{1-138}$—*B. cereus* DisA-like protein and $YopE_{1-138}$-Anemonae cGAS. $YopE_{1-138}$—*V. cholerae* DncV, $YopE_{1-138}$—*B. cereus* DisA-like protein and $YopE_{1-138}$-Anemonae cGAS all showed to dose-dependently induce a type I IFN response in the reporter cell line (FIG. 23), while the bacterial background strain (*Y. enterocolitica* ΔHOPEMT) or *Y. enterocolitica* ΔHOPEMT delivering $YopE_{1-138}$-MycHis were not capable of inducing such a response (FIG. 23). The 3',3' cGAMP producing Anemonae (*Nematostella vectensis*) cGAS showed highest activity, while *V. cholerae* DncV (producing 3',3' cGAMP) and *Bacillus cereus* DisA-like protein (producing cyclic di-AMP) were found to be similarly activating a type I IFN response.

Thus, the fusion to the N-terminal secretion signal of bacteria has lead to successful deliver of bacterially expressed $YopE_{1-138}$—*V. cholerae* DncV, $YopE_{1-138}$—*B. cereus* DisA-like protein and $YopE_{1-138}$-Anemonae cGAS proteins and has not prevented the folding and function of these proteins within the eukaryotic cell, which could not have been predicted.

Alternatively, murine IRF3, a central transcription factor downstream of RLR or cGAS/STING dependent signalling[62], was cloned for expression and transport by bacteria. In the absence of activation, IRF-3 is in a latent conformation in the cytoplasm. Only upon activation of upstream receptors as RIG-1, MDA5 or STING, IRF-3 is phosphorylated via TBK1 and IKKε and thus activated. Phosphorylation of IRF-3 leads to dimerization, translocation to the nucleus, and association with co-activators[62]. In order to reach a constitutive active version of IRF3, we replaced one of the most important phosphorylation sites (Ser397 in murine IRF3) by Asp[62].

Figure 24:
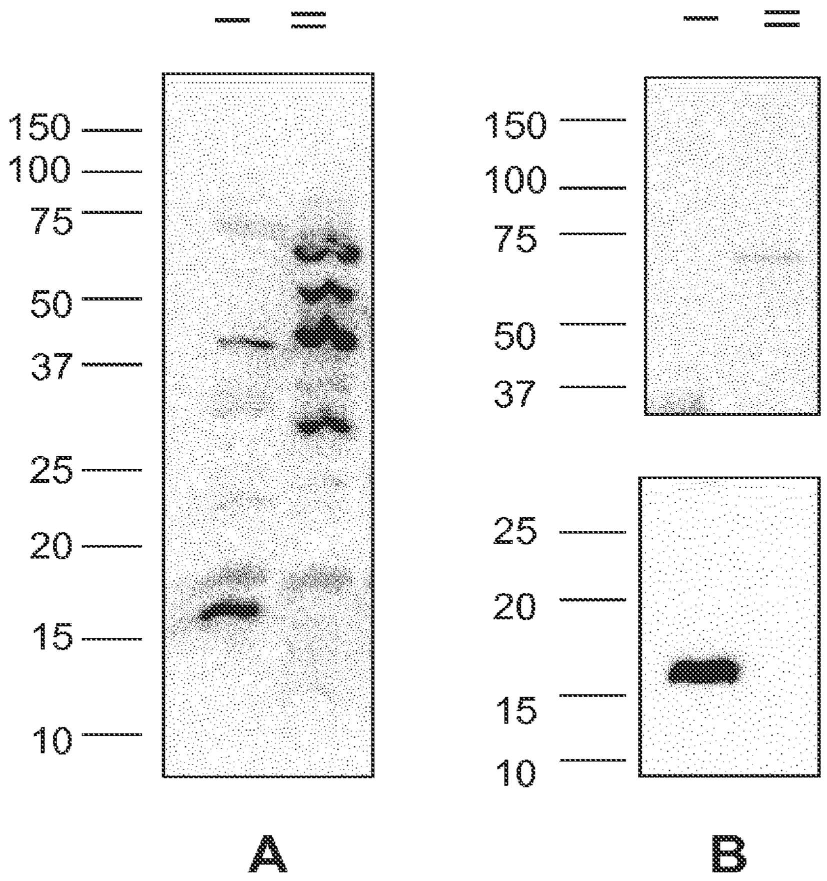
FIG. 24: T3SS dependent secretion of IRF3 into the culture supernatant. In-vitro secretion experiment of I: *Y. enterocolitica* ΔHOPEMT+$YopE_{1-138}$-murine tBID BH3 and II: *Y. enterocolitica* ΔHOPEMT+$YopE_{1-138}$-murine IRF3 Ser397Asp. Protein content of total bacterial lysates ("A") and precipitated culture supernatants ("B") was analyzed by Western blotting using an anti-YopE antibody. Numbers written indicate molecular weight in kDa at the corresponding height.

Delivery of the fusion protein $YopE_{1-138}$—murine IRF3 Ser397Asp (SEQ ID NO: 40) was assessed in an in-vitro secretion assay, where protein secretion into the surrounding liquid is artificially induced. After TCA based protein precipitation, Western blot analysis with anti-YopE antibody was used to determine protein amounts secreted (FIG. 24). While a ΔHOPEMT strains encoding $YopE_{1-138}$-murine tBID BH3 resulted in a strong band in the secreted fraction (at 15-20 kDa), $YopE_{1-138}$—murine IRF3 Ser397Asp (at 50-75 Da) was found to be secreted as well, albeit to a lesser extent (FIG. 24). Total bacterial cell fraction analysis revealed that expression levels of $YopE_{1-138}$—murine tBID BH3 and $YopE_{1-138}$—murine IRF3 Ser397Asp are comparable, while $YopE_{1-138}$—murine IRF3 Ser397Asp showed a pattern of degradation bands (FIG. 24).

Delivery of cGAS/STING and RIG-1-like receptor pathway triggering proteins via the bacterial T3SS for induction of a type I IFN response in immune cells.

Figure 25:
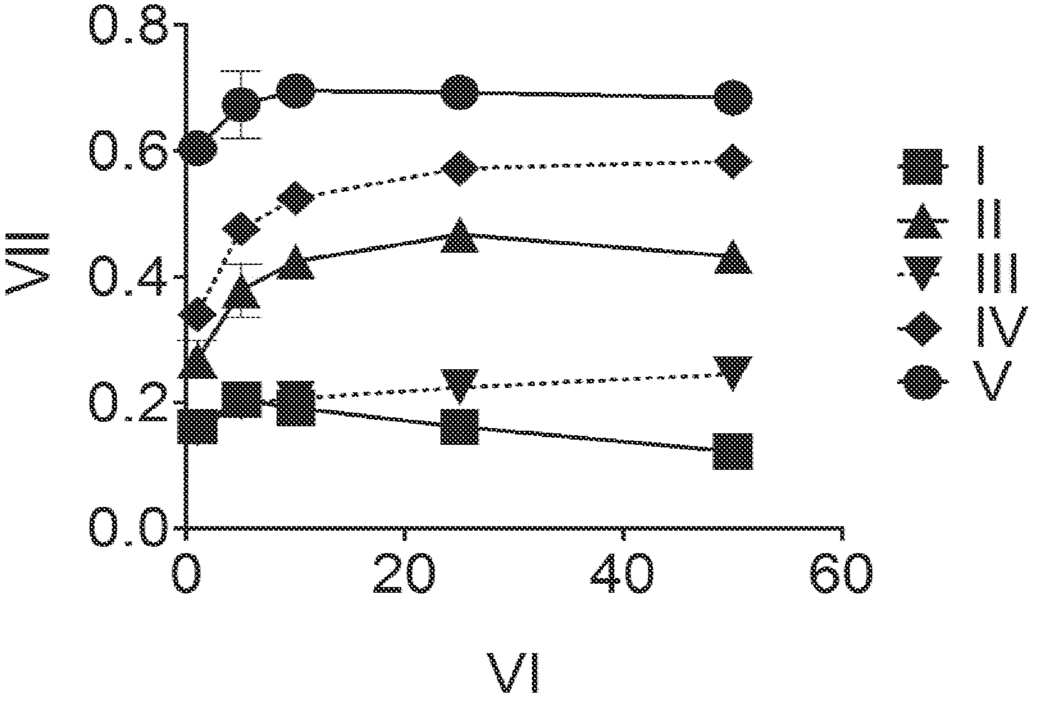
FIG. 25: Delivery of type I Interferon response inducing proteins via the bacterial T3SS to immune cells—Rig1 and STING pathway. Delivery of murine Rig1 CARD domains and cyclic dinucleotide generating enzymes lead to type I IFN induction in a RAW264.7 IFN-reporter cell line. RAW264.7 reporter cells were infected with I: *Y. enterocolitica* ΔHOPEMT, or *Y. enterocolitica* ΔHOPEMT encoding on a pBadMycHisA derived plasmid II: $YopE_{1-138}$-*V. cholerae* DncV, III: $YopE_{1-138}$-*B. cereus* DisA-like protein, IV: $YopE_{1-138}$-Anemonae cGAS or V: $YopE_{1-138}$—murine Rig1 CARD domains. A titration of the bacteria added to the cells (VI: indicated as MOI) was performed for each strain, and IFN stimulation was assessed based on activity of secreted alkaline phosphatase (VII: OD650) which is under the control of the I-ISG54 promoter which is comprised of the IFN-inducible ISG54 promoter enhanced by a multimeric ISRE.

Delivery of the fusion protein $YopE_{1-138}$—murine RIG-1 $CARD_2$, $YopE_{1-138}$—*V. cholerae* DncV, $YopE_{1-138}$—*B. cereus* DisA-like protein and $YopE_{1-138}$-Anemonae cGAS was assessed on a immune reporter cell line for type I IFN induction. Murine RAW264.7 macrophage reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the $YopE_{1-138}$—murine RIG-1 $CARD_2$, $YopE_{1-138}$—*V. cholerae* DncV, $YopE_{1-138}$—*B. cereus* DisA-like protein and $YopE_{1-138}$—Anemonae cGAS. $YopE_{1-138}$—murine RIG-1 $CARD_2$, $YopE_{1-138}$—*V. cholerae* DncV, and $YopE_{1-138}$-Anemonae cGAS all showed to dose-dependently induce a type I IFN response in this immune reporter cell line (FIG. 25), while the bacterial background strain (*Y. enterocolitica* ΔHOPEMT) was not capable of inducing such a response (FIG. 25). $YopE_{1-138}$—murine RIG-1 $CARD_2$ showed highest activity, followed by the 3',3' cGAMP producing Anemonae (*Nematostella vectensis*) cGAS and *V. cholerae* DncV (producing 3',3' cGAMP). *Bacillus cereus* DisA-like protein (producing cyclic di-AMP) was found to be only weakly activating a type I IFN response.

Figure 32:
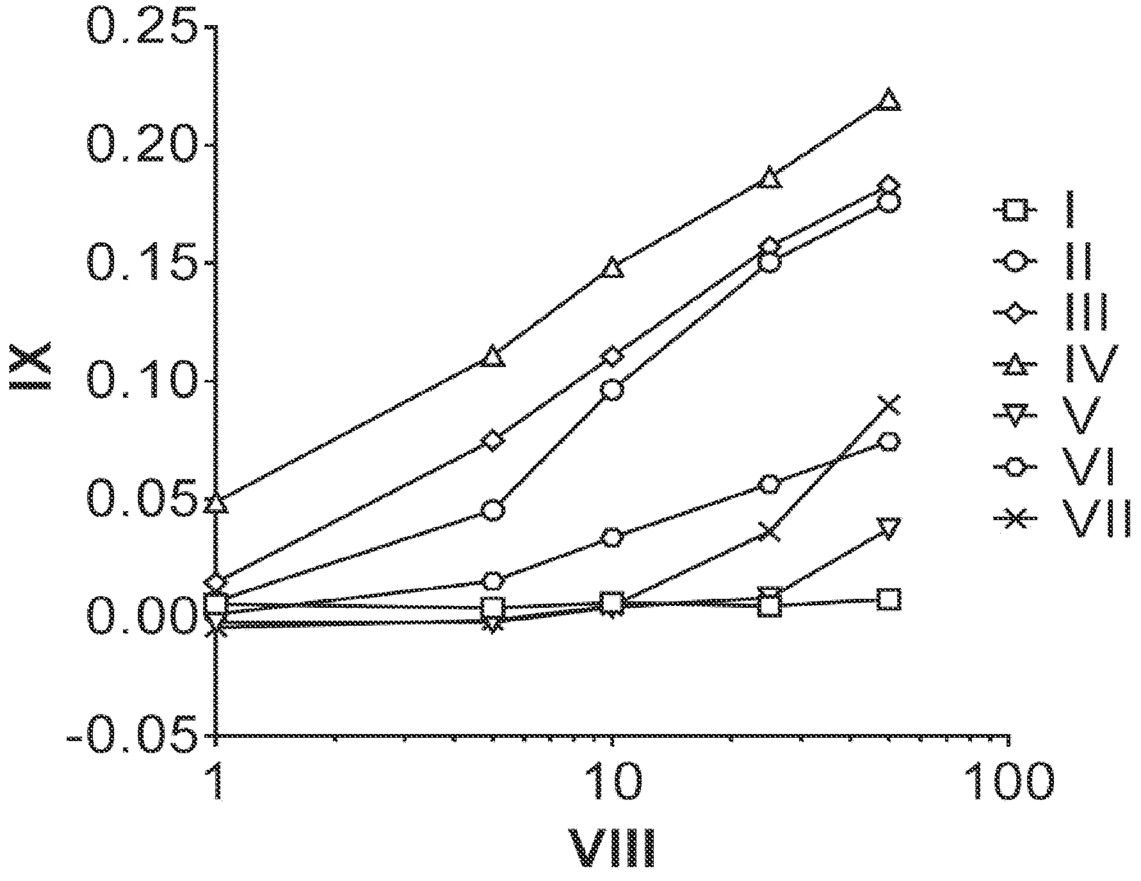
FIG. 32: Delivery of type I Interferon response inducing proteins via the bacterial T3SS-STING pathway. Delivery of cyclic dinucleotide generating enzymes lead to type I IFN induction in a B16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-Anemonae cGAS, III: $YopE_{1-138}$-Anemonae $cGAS_{60-422}$, $YopE_{1-138}$-human $cGAS_{161-522}$, V: $YopE_{1-138}$-*Listeria* $CdaA_{101-273}$, VI: $YopE_{1-138}$-*V. cholerae* DncV, VII: $YopE_{1-138}$-*B. cereus* DisA-like protein. A titration of the bacteria added to the cells (VIII: indicated as MOI) was performed for each strain, and IFN stimulation was assessed based on activity of secreted alkaline phosphatase (IX: OD650) which is under the control of the I-ISG54 promoter which is comprised of the IFN-inducible ISG54 promoter enhanced by a multimeric ISRE.
Figure 33:
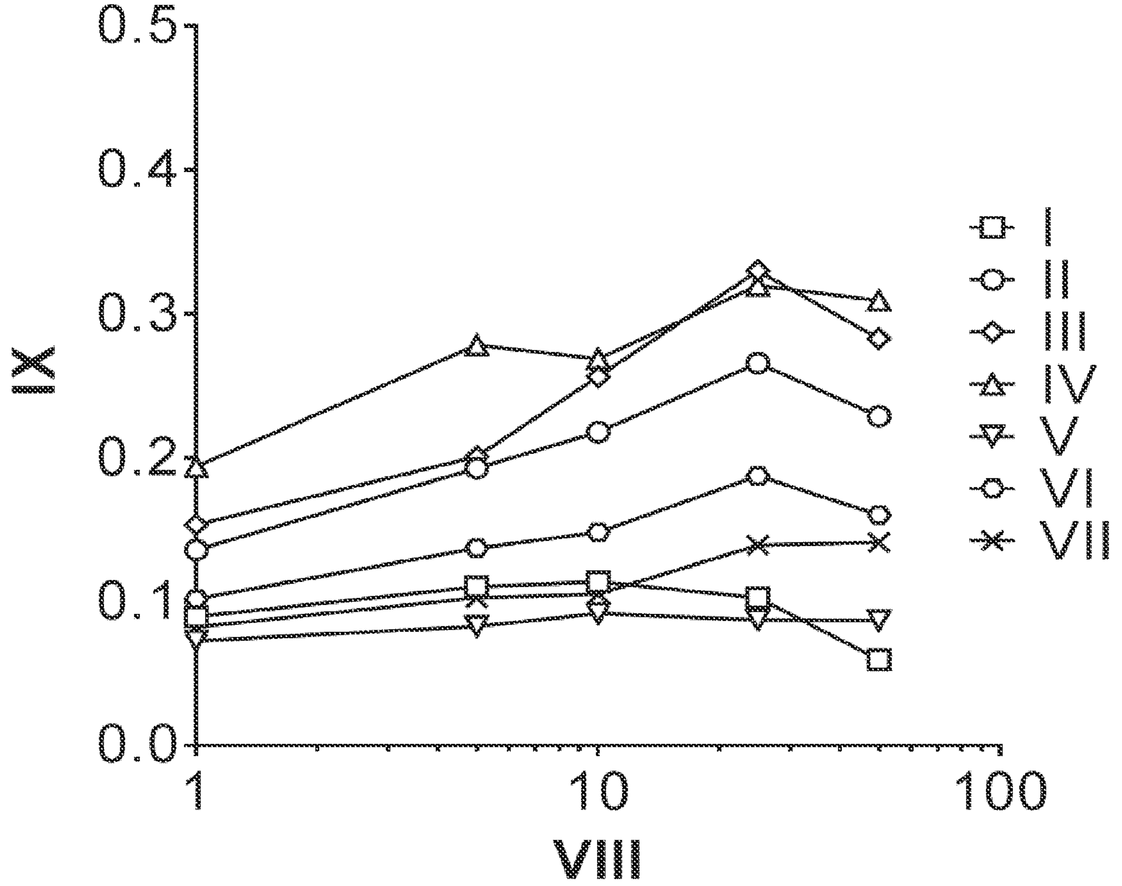
FIG. 33: Delivery of type I Interferon response inducing proteins via the bacterial T3SS-STING pathway. Delivery of cyclic dinucleotide generating enzymes lead to type I IFN induction in a RAW macrophage IFN-reporter cell line. RAW macrophage reporter cells were infected with I: *Y. enterocolitica* ΔHOPEMT, or *Y. enterocolitica* ΔHOPEMT encoding on a pBadMycHisA derived plasmid II: $YopE_{1-138}$-Anemonae cGAS, III: $YopE_{1-138}$-Anemonae $cGAS_{60-422}$, $YopE_{1-138}$-human $cGAS_{161-522}$, V: $YopE_{1-138}$-*Listeria* $CdaA_{101-273}$, VI: $YopE_{1-138}$-*V. cholerae* DncV, VII: $YopE_{1-138}$-*B. cereus* DisA-like protein. A titration of the bacteria added to the cells (VIII: indicated as MOI) was performed for each strain, and IFN stimulation was assessed based on activity of secreted alkaline phosphatase (IX: OD650) which is under the control of the I-ISG54 promoter which is comprised of the IFN-inducible ISG54 promoter enhanced by a multimeric ISRE.
Figure 34:
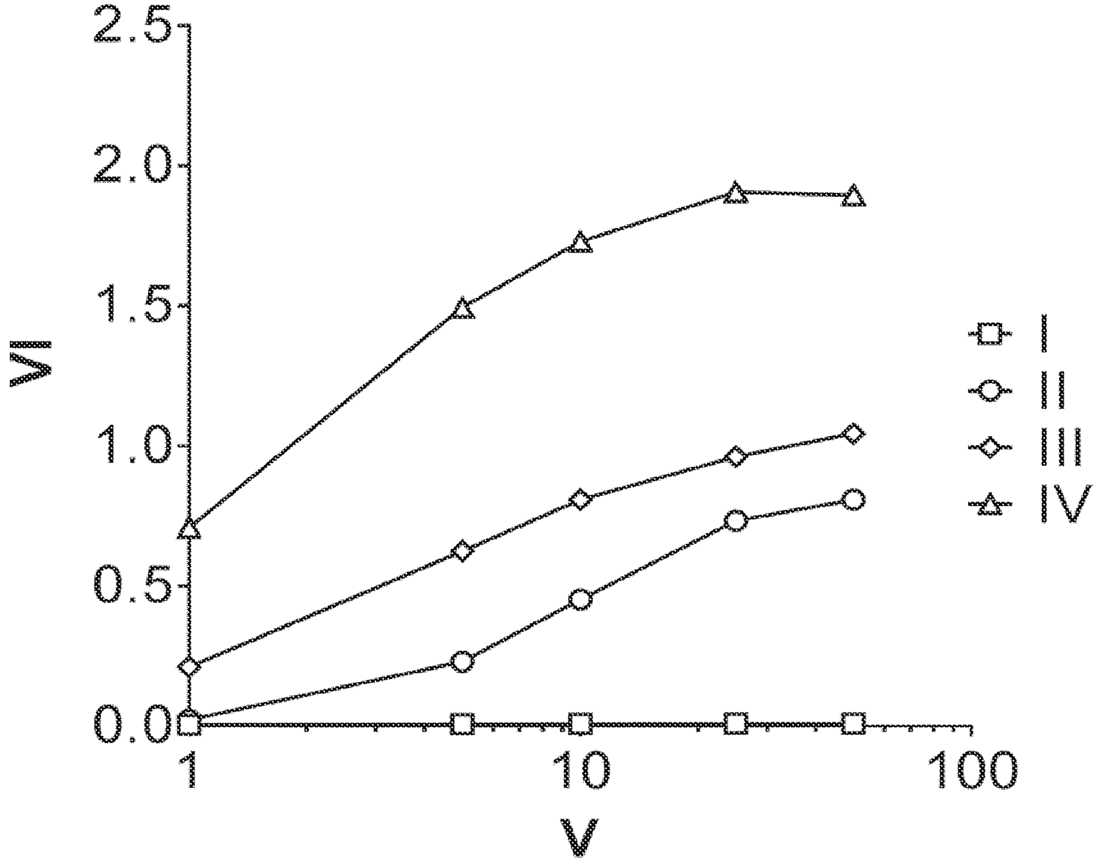
FIG. 34: Delivery of type I Interferon response inducing proteins via the bacterial T3SS and comparison to small molecular agonists of STING. Delivery of cyclic dinucleotide generating enzymes lead to type I IFN induction in aB16F10 IFN-reporter cell line. B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-Anemonae cGAS, III: $YopE_{1-138}$-human $cGAS_{161-522}$, IV: $YopE_{1-138}$-murine RIG1 CARD $domains_{1-218}$. A titration of the bacteria added to the cells (V: indicated as MOI) was performed, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.
Figure 35:
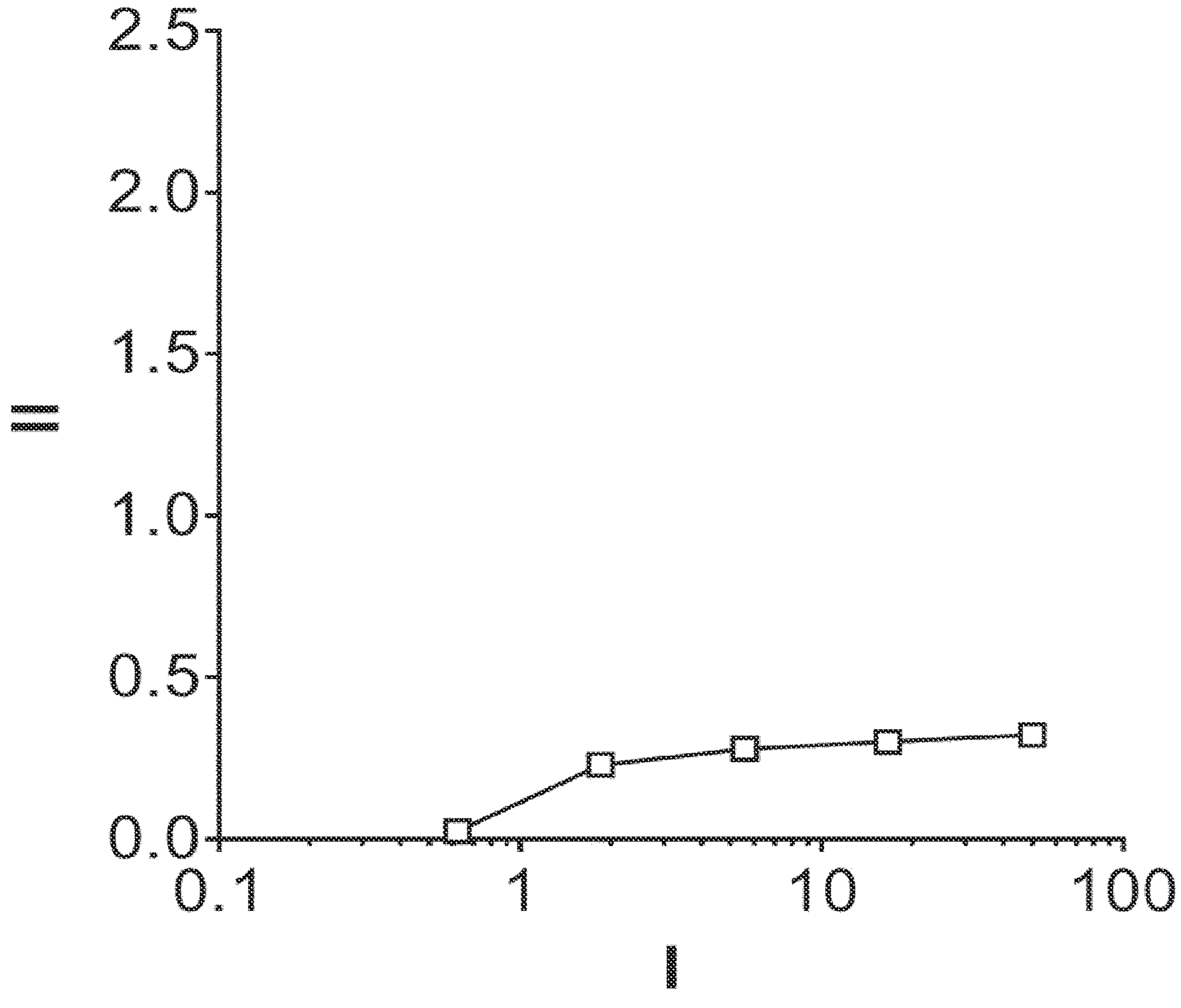
FIG. 35: Delivery of type I Interferon response inducing proteins via the bacterial T3SS and comparison to small molecular agonists of STING. Delivery of a cyclic dinucleotide lead to type I IFN induction in a B16F10 IFN-reporter cell line. B16F10 reporter cells treated with small molecular STING agonist 2'3'-c-di-AM$(PS)_2$ (Rp,Rp). A titration of the compound (I: indicated as micromolar) was performed, and IFN stimulation was assessed based on activity of secreted alkaline phosphatase (II: OD650) which is under the control of the I-ISG54 promoter which is comprised of the IFN-inducible ISG54 promoter enhanced by a multimeric ISRE.
Figure 36:
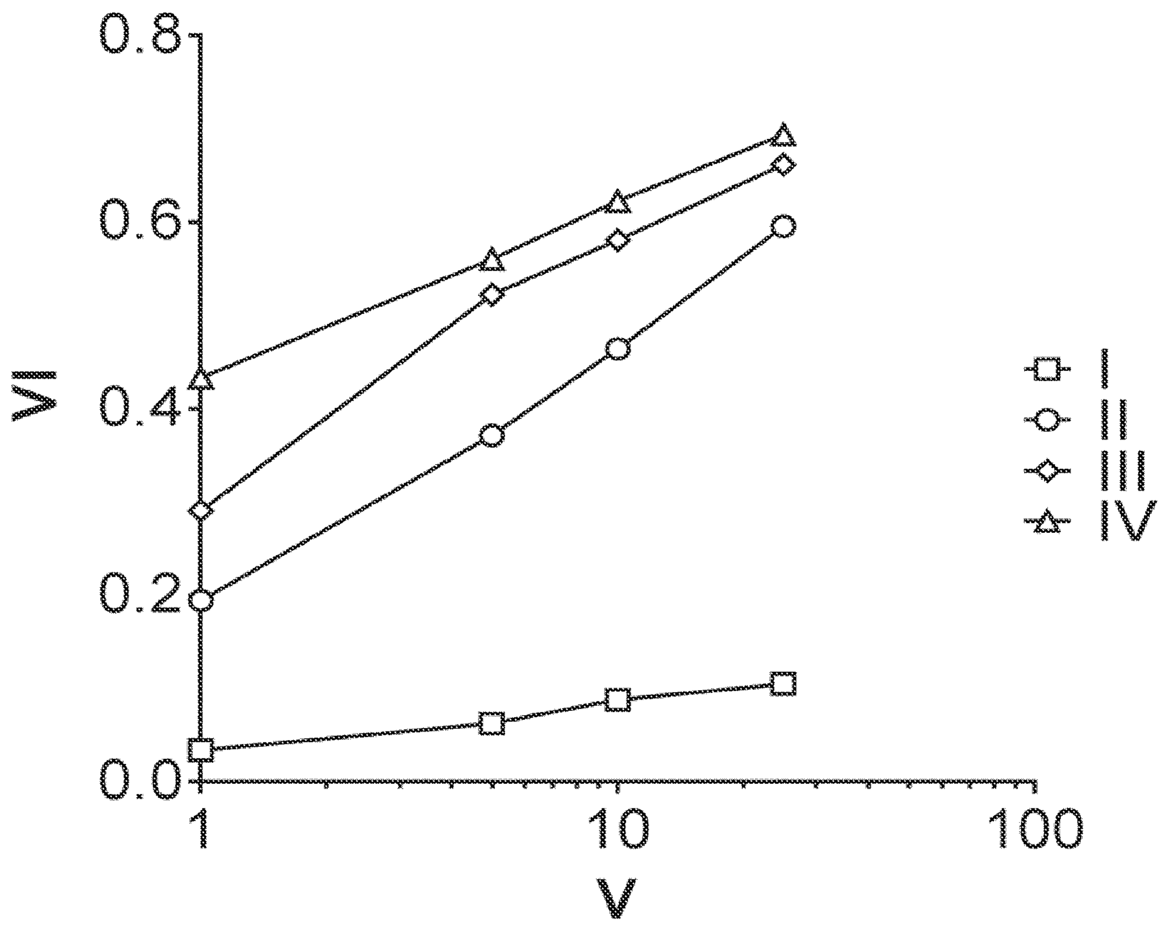
FIG. 36: Delivery of type I Interferon response inducing proteins via the bacterial T3SS and comparison to small molecular agonists of STING. Delivery of cyclic dinucleotide generating enzymes lead to type I IFN induction in a RAW IFN-reporter cell line. RAW reporter cells were infected with I: *Y. enterocolitica* ΔHOPEMT, or *Y. enterocolitica* ΔHOPEMT encoding on a pBadMycHisA derived plasmid II: $YopE_{1-138}$-Anemonae cGAS, III: $YopE_{1-138}$-human $cGAS_{161-522}$, IV: $YopE_{1-138}$-murine RIG1 CARD $domains_{1-218}$). A titration of the bacteria added to the cells (V: indicated as MOI) was performed, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.
Figure 37:
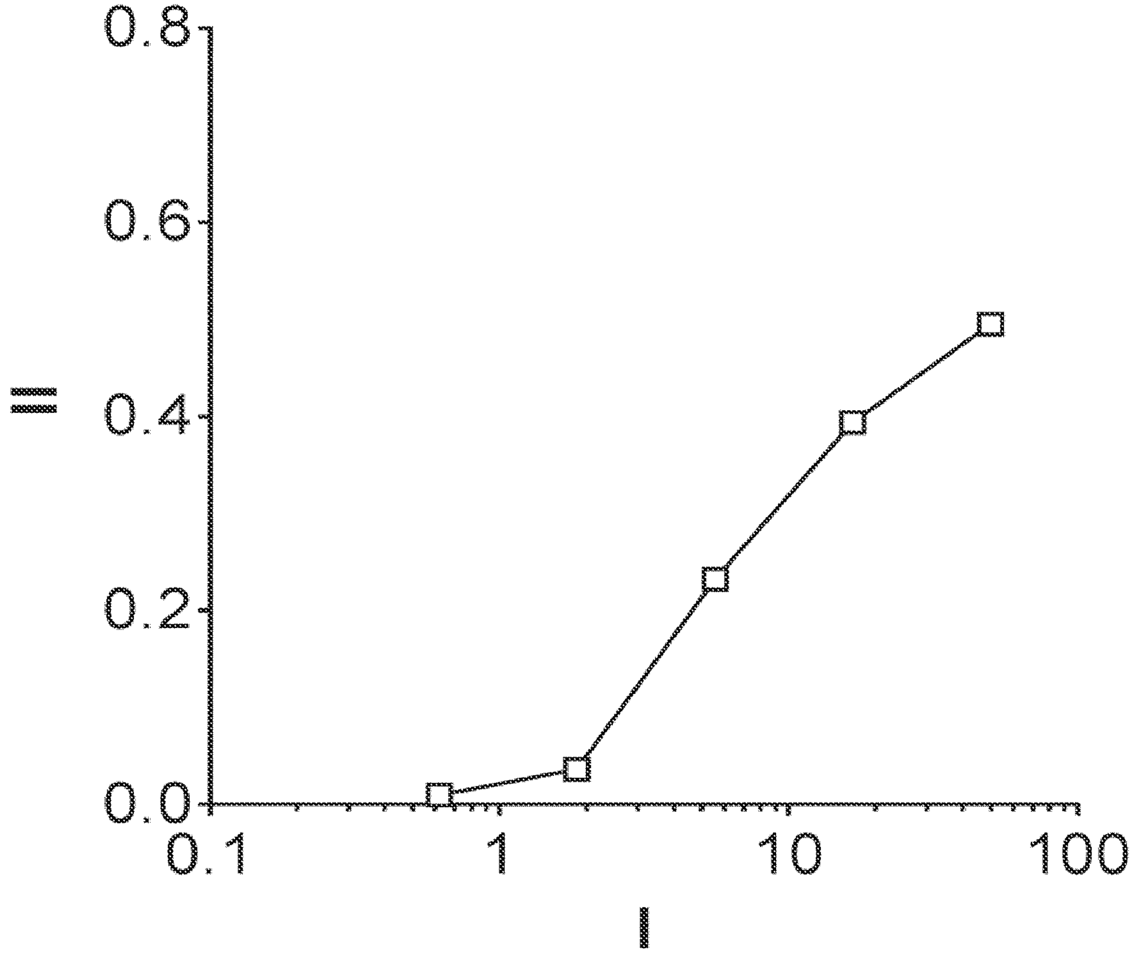
FIG. 37: Delivery of type I Interferon response inducing proteins via the bacterial T3SS and comparison to small molecular agonists of STING. Delivery of a cyclic dinucleotide lead to type I IFN induction in a RAW IFN-reporter cell line. RAW reporter cells were treated with the small molecular STING agonist 2'3'-c-di-AM(PS)2 (Rp,Rp). A titration of the compound (I: indicated as micromolar) was performed, and IFN stimulation was assessed based on activity of secreted alkaline phosphatase (II: OD650) which is under the control of the I-ISG54 promoter which is comprised of the IFN-inducible ISG54 promoter enhanced by a multimeric ISRE.

For further experiments, we cloned human cGAS amino acids 161-522 (Uniprot Nr. Q8N884 and SEQ ID No. 115; producing 2',3' cGAMP)[57], for expression and translocation by bacteria. Murine B16F10 melanoma and murine RAW macrophage reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of bacterial strains expressing from a pBadMycHisA derived plasmid (pBad_Si2) and translocating the $YopE_{1-138}$—human $cGAS_{161-522}$ and showed to dose-dependently induce a type I IFN response in the reporter cell line, as well as a bacterial strain expressing from a pBadMycHisA derived plasmid (pBad_Si2) and translocating $YopE_{1-138}$-Anemonae cGAS, $YopE_{1-138}$—Anemonae $cGAS_{60-422}$, $YopE_{1-138}$-*Listeria* $CdaA_{101-273}$, $YopE_{1-138}$-*V. cholerae* DncV or $YopE_{1-138}$-*B. cereus* DisA-like protein (FIG. 32-33). Strongest activation was observed with $YopE_{1-138}$—human $cGAS_{161-522}$, followed by $YopE_{1-138}$-Anemonae cGAS, $YopE_{1-138}$-Anemonae $cGAS_{60-422}$. Interestingly, the shorter Anemonae $cGAS_{60-422}$ variant was slightly more active. $YopE_{1-138}$-*Listeria* $CdaA_{101-273}$, $YopE_{1-138}$—*V. cholerae* DncV or $YopE_{1-138}$—*B. cereus* DisA-like protein as well exhibited dose-dependent IFN activation, albeit to a lesser extend than cGAS proteins (FIG. 32-33).

Delivery of MAVS Via the Bacterial T3SS for Induction of a Type I IFN Response

Cytosolic nucleic acids are sensed by receptor as the RIG-1-like receptor (RLR) family members that detect pathogen-derived RNA in the cytosol[56]. RIG-1 and MDA5 consist of two N-terminal CARD domains and a central (DExD/H) helicase domain sensing specific nucleotides[56]. Binding to stimulatory RNA induces a structural rearrangement in RIG-I (and MDA5) that liberates its CARDs for subsequent association with unanchored K63-linked ubiquitin chains to form oligomers[56] (and in case of MDA5 to filament formation[56]). Oligomerized CARD domains of RIG-I and MDA5 interact with the CARD domain of MAVS. This interaction promotes the polymerization of the single CARD domain of MAVS, which induces downstream signaling ultimately leading to induction of type I IFN genes[56].

Figure 30:
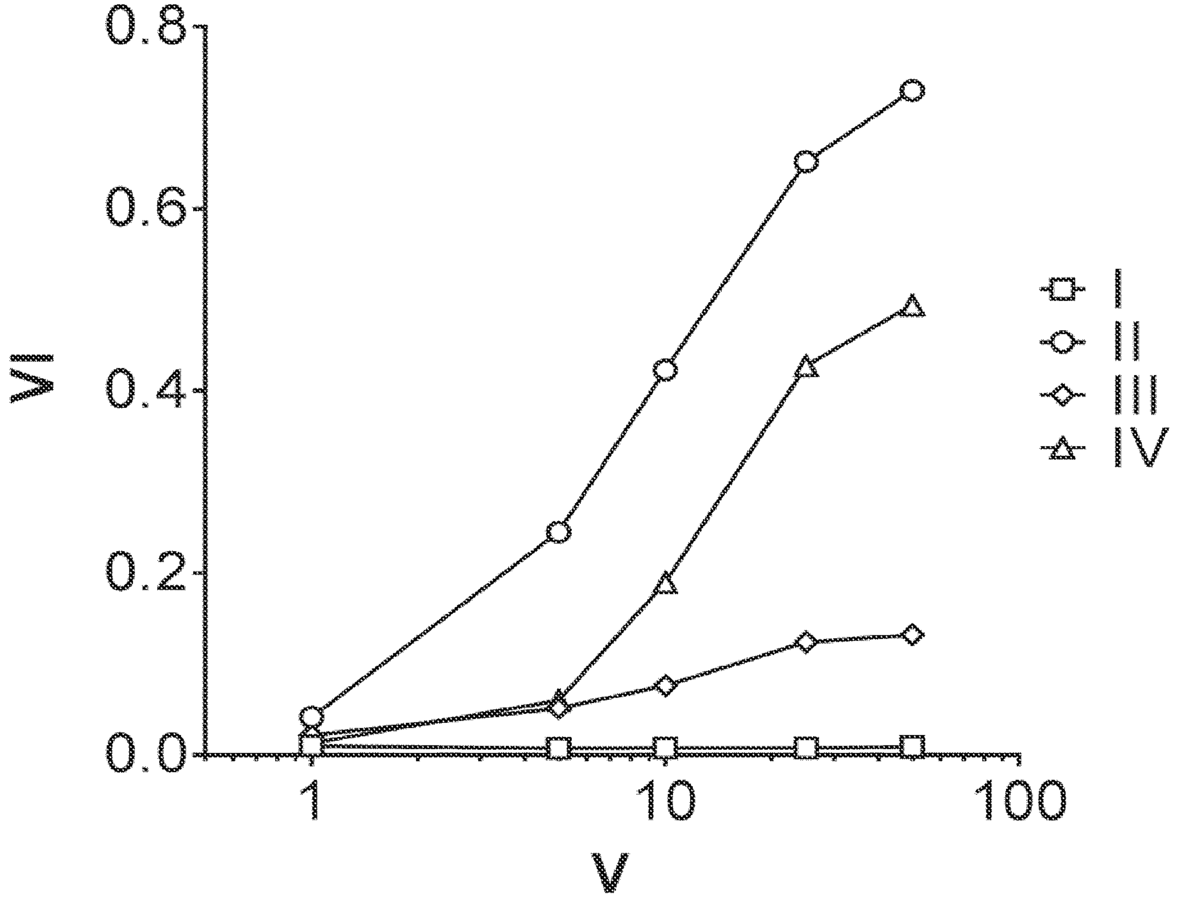
FIG. 30: Delivery of type I Interferon response inducing proteins via the bacterial T3SS-MAVS. Delivery of MAVS CARD lead to type I IFN induction in a B16F10 IFN-reporter cell line.B16F10 reporter cells were infected with I: *Y. enterocolitica* ΔHOPEMT, or *Y. enterocolitica* ΔHOPEMT encoding on a pBadMycHisA derived plasmid II: $YopE_{1-138}$-murine RIG1 CARD $domains_{1-246}$, III: $YopE_{1-138}$-human $cGAS_{161-522}$, $YopE_{1-138}$-human MAVS $CARD_{1-100}$. A titration of the bacteria added to the cells (V: indicated as MOI) was performed for each strain, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.
Figure 31:
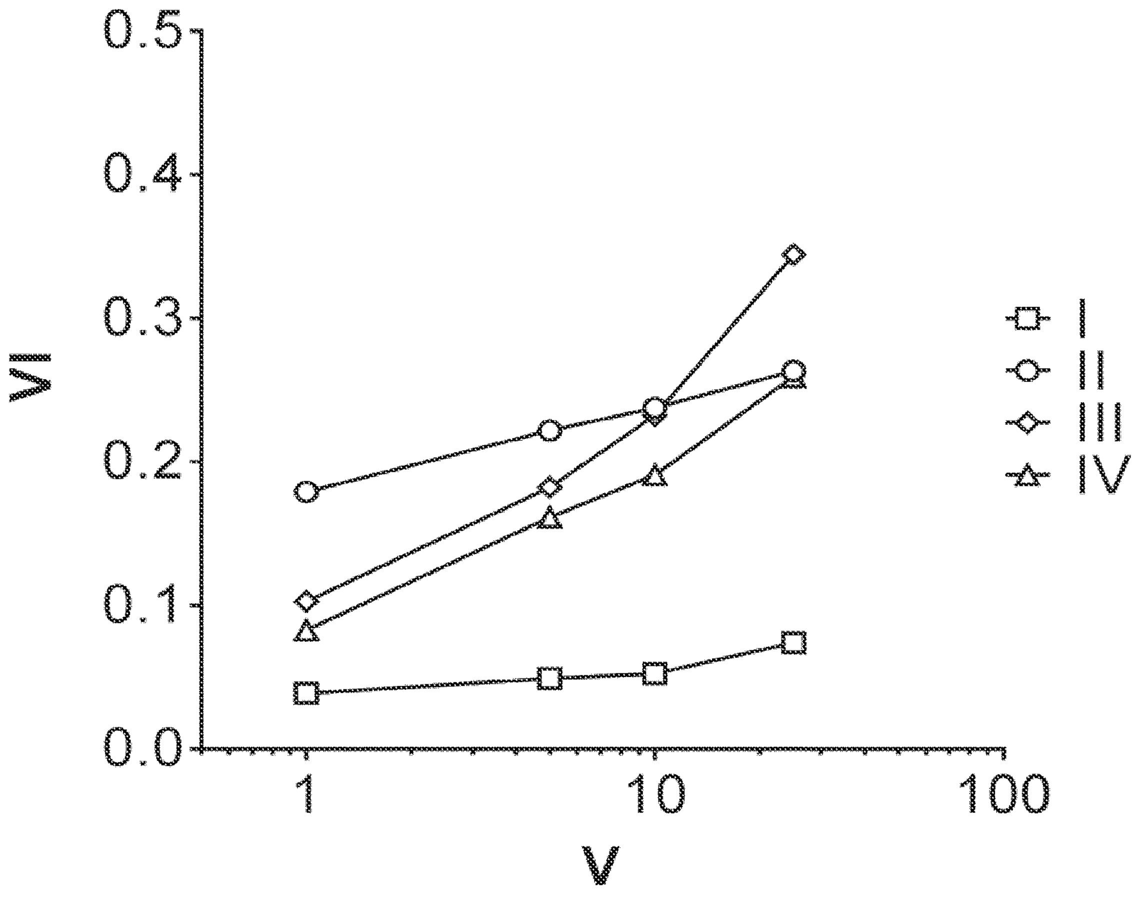
FIG. 31: Delivery of type I Interferon response inducing proteins via the bacterial T3SS-MAVS. Delivery of MAVS CARD lead to type I IFN induction in a RAW macrophage IFN-reporter cell line. RAW macrophage reporter cells were infected with I: *Y. enterocolitica* ΔHOPEMT, or *Y. enterocolitica* ΔHOPEMT encoding on a pBadMycHisA derived plasmid II: $YopE_{1-138}$-murine RIG1 CARD $domains_{1-246}$, III: $YopE_{1-138}$-human $cGAS_{161-522}$, $YopE_{1-138}$-human MAVS $CARD_{1-100}$. A titration of the bacteria added to the cells (V: indicated as MOI) was performed for each strain, and IFN stimulation was assessed based on activity of secreted alkaline phosphatase (VI: OD650) which is under the control of the I-ISG54 promoter which is comprised of the IFN-inducible ISG54 promoter enhanced by a multimeric ISRE.

We generated bacterial strains (based on *Y. enterocolitica* ΔHOPEMT) expressing the N-terminal CARD domains of MAVS of human origin fused to a N-terminal bacterial secretion signal for delivery by the T3SS, specifically $YopE_{1-138}$. Delivery of the fusion protein $YopE_{1-138}$—MAVS CARD was assessed by a standard in vitro secretion assay and functionality of delivered proteins were assessed on a reporter cell line for type I IFN induction. Murine B16F10 melanoma or murine RAW macrophage reporter cells for type I IFN stimulation are based on activity of secreted alkaline phosphatase, which is under the control of the I-ISG54 promoter, which is comprised of the IFN-inducible ISG54 promoter enhanced by a multimeric ISRE. Reporter cells were infected with various amounts (MOI) of *Y. enterocolitica* ΔHOPEMT expressing from a pBadMycHisA derived plasmid (pBad_Si2) and translocating the $YopE_{1-138}$—human MAVS CARD protein. Murine N-terminal CARD domain of MAVS showed to dose-dependently induce a type I IFN response in the reporter cell line (FIG. 30-31), while the bacterial background strain (*Y. enterocolitica* ΔHOPEMT) was not capable of inducing such a response (FIG. 30-31). Human cGAS and murine RIG-1 CARD domains induced a type I IFN response in a similar way in the murine reporter cell lines (FIG. 30-31), with RIG-1 showing highest activation potential, followed by MAVS and cGAS.

Thus, the fusion to the N-terminal secretion signal of bacteria has led to successful deliver of bacterially expressed human $YopE_{1-138}$-MAVS CARD protein and has not prevented the folding and function of the MAVS CARD domain within the eukaryotic cell. This implies, that the YopE-fused MAVS CARD domain is still able to multimerize themselves and induce multimerization of MAVS, which is surprizing. Even more surprisingly, MAVS CARD only had been shown to fail to induce IFN downstream signalling[64], whereat we found YopE-fused MAVS CARD domain to activate the type I IFN pathway strongly.

Figure 52:
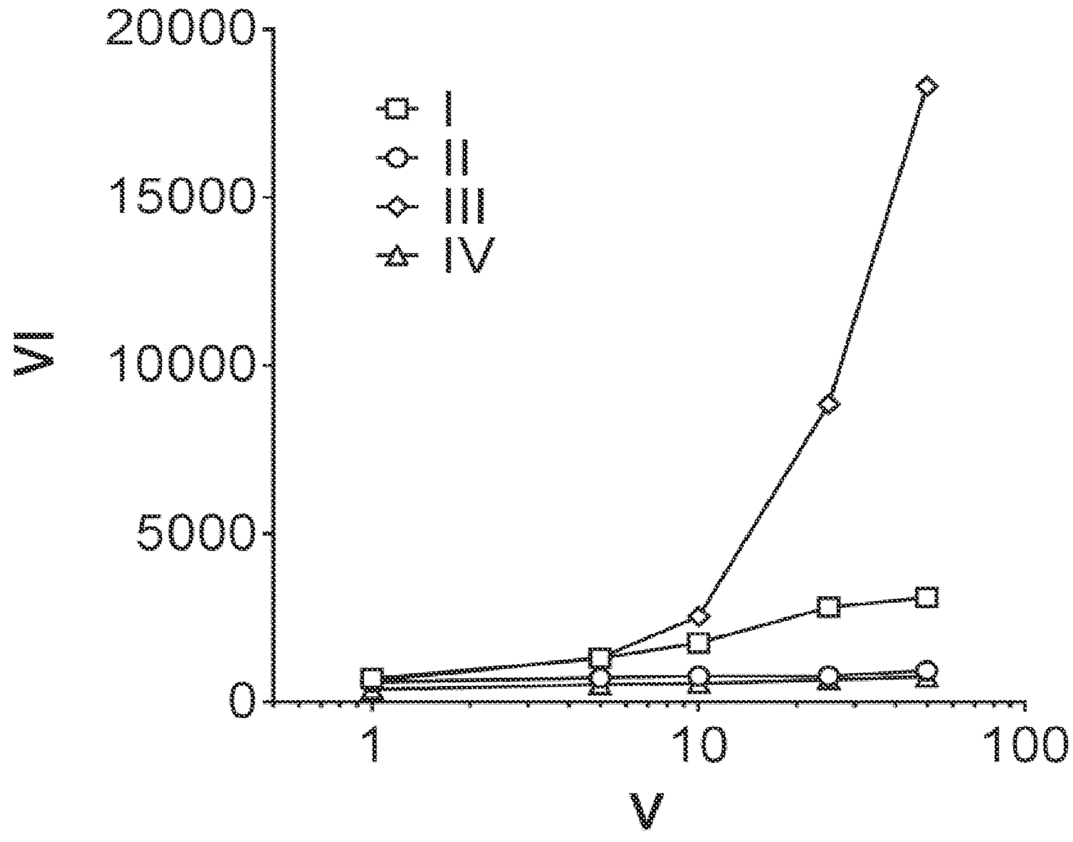
FIG. 52: Delivery of type I Interferon response inducing proteins via the bacterial T3SS—bacterially T3SS delivered MAVS works independent of endogenous MAVS. Delivery of via T3SS of MAVS CARD lead to type I IFN induction in a $MAVS^{KO}$ RAW macrophage IFN-reporter (luciferase) cell line. $MAVS^{KO}$ RAW macrophage reporter cells were infected with I: *Y. enterocolitica* ΔHOPEMT, or II: *Y. enterocolitica* ΔHOPEMT-yopB, III: *Y. enterocolitica* ΔHOPEMT encoding on a pBadMycHisA derived plasmid $YopE_{1-138}$-human MAVS $CARD_{1-100}$ or IV: *Y. enterocolitica* ΔHOPEMT-yopB encoding on a pBadMycHisA derived plasmid $YopE_{1-138}$-human MAVS $CARD_{1-100}$. A titration of the bacteria added to the cells (V: indicated as MOI) was performed for each strain, and IFN stimulation was assessed based on activity of luciferase (VI: RLU—relative luminescence units) which is under the control of the I-ISG54 promoter which is comprised of the IFN-inducible ISG54 promoter enhanced by a multimeric ISRE.

Furthermore, the C-terminal transmembrane domain of MAVS has been shown to be essential for MAVS function upon DNA transfection and MAVS CARD domain alone had been shown to be inactive when expressed from transfected DNA constructs[66]. Even more, MAVS CARD fused to the transmembrane region, which has the capacity when expressed from transfected DNA or as purified protein to activate a type I IFN response[64,66], was shown to rely on endogenous MAVS, which it started aggregating and thus activating[64]. We could show by using a MAVS KO cell line (FIG. 52), that bacterially delivered YopE-fused MAVS CARD is active without endogenous MAVS present on mitochondria. That YopE-fused MAVS CARD is able to multimerize and activate downstream partners without transmembrane domain and furthermore without endogenous MAVS is surprizing.

Benchmarking to Small Molecular STING Agonist for Induction of a Type I IFN Response In Vitro Cyclic dinucleotides are well-known agonists of the STING pathway, lading to downstream induction of type I IFN signaling. STING agonists have been described in literature[59] and have been found to mainly act on immune cells, with highest activity shown on dendritic cells[59]. In contrast, RLR signaling was found to be more ubiquitously expressed[63]. We thus compared *Y. enterocolitica* ΔHOPEMT bacteria delivering cyclic dinucleotide generating enzymes (YopE$_{1-138}$-Anemonae cGAS and YopE$_{1-138}$-human cGAS) or bacteria delivering YopE$_{1-138}$-murine RIG1 CARD domains$_{1-218}$ to the small molecular STING agonist 2'3'-c-di-AM(PS)2 (Rp,Rp) (similar to ADU-S100 from Aduro Biotech) on immune cells (RAW macrophage IFN reporter cells) and non-immune cells (B16F1 melanoma IFN reporter cells) for the Interferon inducing potential. On immune cells, a similar activating potential was observed for the small molecular STING agonist 2'3'-c-di-AM(PS)2 (Rp, Rp) and all three tested bacterial strains delivering a protein (YopE1_138-Anemonae cGAS, YopE$_{1-138}$-human cGAS or YopE$_{1-138}$-murine RIG1 CARD domains$_{1-218}$) while the *Y. enterocolitica* ΔHOPEMT bacteria not delivering a protein showed a very weak activating potential (FIG. 34-37). On non-immune cells (cancer cells, melanoma), bacterially delivered YopE$_{1-138}$-murine RIG1 CARD domains$_{1-218}$,bacterially delivered YopE$_{1-138}$-Anemonae cGAS and YopE$_{1-138}$-human cGAS worked equally well and almost outperformed small-molecular STING agonist, highlighting more ubiquitous presence of RLR as compared to STING (FIG. 34-37).

Strict T355-Dependency of Bacterially Delivered RIG1 CARD Domains or MAVS CARD

Figure 38:
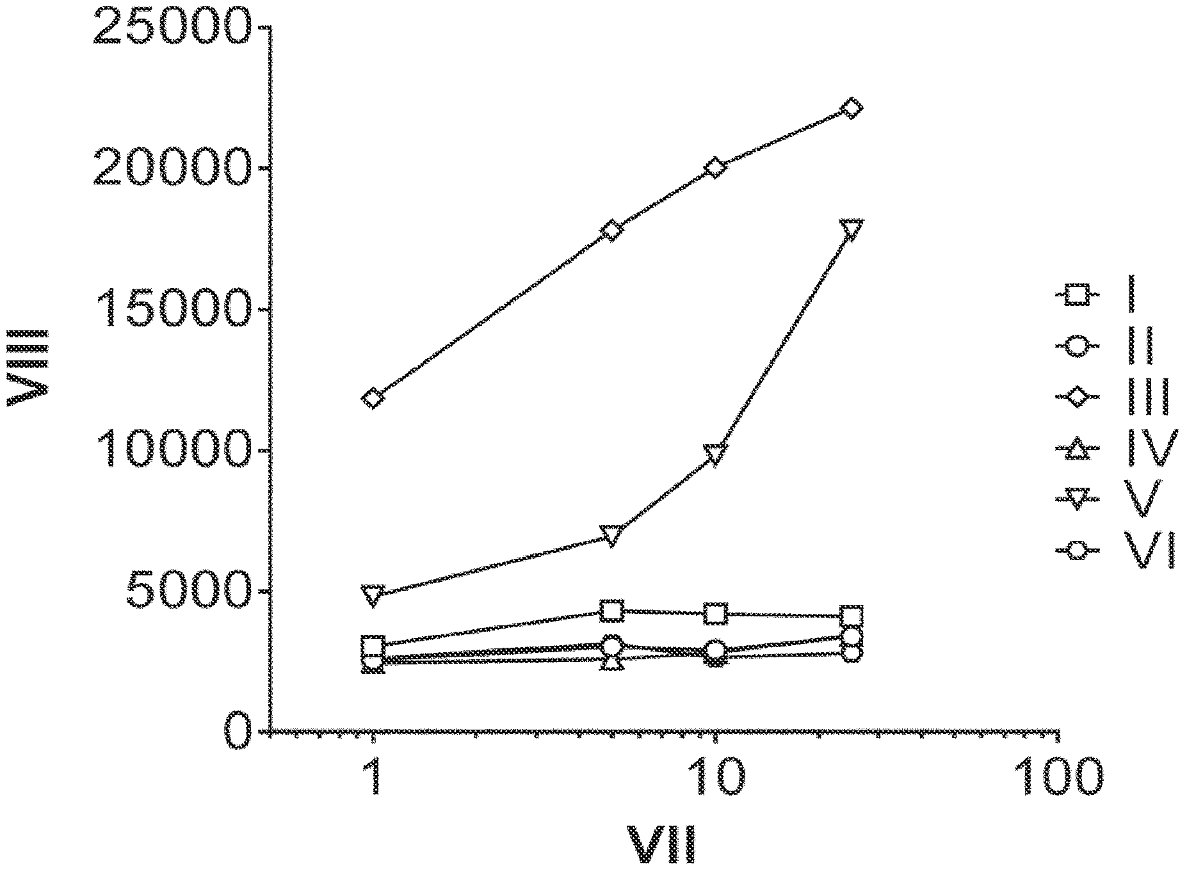
FIG. 38: Delivery of type I Interferon response inducing proteins via the bacterial T3SS and proof of T3SS dependency—RIG1 and MAVS. Delivery of RIG1 CARD domains or MAVS CARD fused to $YopE_{1-138}$ lead to type I IFN induction in a RAW IFN-reporter cell line, which is strictly T3SS dependent. RAW reporter cells were infected with I: *Y. enterocolitica* ΔHOPEMT, or II: *Y. enterocolitica* ΔHOPEMT-yopB, or *Y. enterocolitica* ΔHOPEMT encoding on a pBadMycHisA derived plasmid III: $YopE_{1-138}$-murine RIG1 CARD $domains_{1-246}$, V: $YopE_{1-138}$-human MAVS $CARD_{1-100}$ or *Y. enterocolitica* ΔHOPEMT-yopB encoding on a pBadMycHisA derived plasmid IV: $YopE_{1-138}$-murine RIG1 CARD $domains_{1-246}$, VI: $YopE_{1-138}$-human MAVS $CARDs_{1-100}$. A titration of the bacteria added to the cells (VII: indicated as MOI) was performed for each strain, and IFN stimulation was assessed based on activity of secreted lucia luciferase (VIII: OD650) which is under the control of the I-ISG54 promoter which is comprised of the IFN-inducible ISG54 promoter enhanced by a multimeric ISRE.

In order to proof strict T3SS dependent transport, one of the T3SS proteins forming the translocation pore into the eukaryotic cell membrane was deleted (YopB). Potential of such yopB deleted bacteria (called *Y. enterocolitica* ΔHOPEMT-yopB) expressing YopE$_{1-138}$-murine RIG1 CARD domains$_{1-246}$ or YopE$_{1-138}$-human MAVS CARD moo was assessed on a RAW macrophage IFN reporter cell line and compared to yopB expressing *Y. enterocolitica* ΔHOPEMT bacteria expressing as well YopE$_{1-138}$-murine RIG1 CARD domains$_{1-246}$ or YopE$_{1-138}$—human MAVS CARD$_{1-100}$ (FIG. 38). While yopB-wildtype bacteria expressing YopE$_{1-138}$-murine RIG1 CARD domains$_{1-246}$ or YopE$_{1-138}$—human MAVS CARD$_{1-100}$ exhibited dose-dependent activation of a type I IFN response, yopB-deleted strains expressing the same proteins failed to induce such a response above the background level induced by the background abacterial strain not expressing a protein to be delivered (FIG. 38). This validates, that YopE$_{1-138}$-murine RIG1 CARD domains$_{1-246}$ or YopE$_{1-138}$—human MAVS CARD$_{1-100}$ are both transported through the T3SS needle into target eukaryotic cells.

Induction of Type I IFN Response in Crude Tumor Isolate

Figure 39:
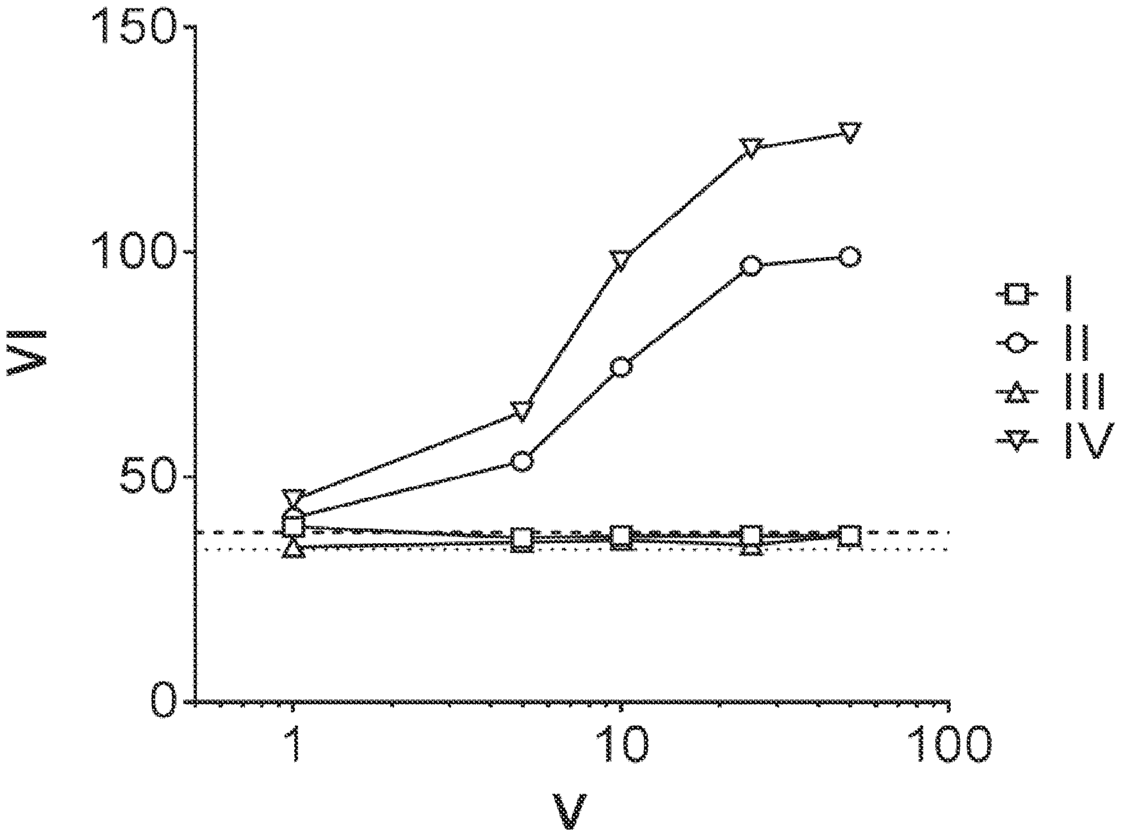
FIG. 39: Delivery of type I Interferon response inducing proteins via the bacterial T3SS in crude cell mixture from tumor isolate—RIG1. Delivery of RIG1 CARD domains fused to $YopE_{1-138}$ lead to type I IFN induction in crude tumor isolate. Wildtype Balb/C mice allografted s.c. with EMT6 breast cancer cells were sacrificed when tumor had reached a volume of >200 $mm^3$. Tumors were mashed, digested and seeded as single-cell suspension into 24-well plates. Such cells from two different tumors were infected with I and III: *Y. enterocolitica* ΔHOPEMT, or II and IV: *Y. enterocolitica* ΔHOPEMT encoding on a pBadMycHisA derived plasmid $YopE_{1-138}$-murine RIG1 CARD $domains_{1-246}$. A titration of the bacteria added to the cells (V: indicated as MOI) was performed for each strain, and IFN stimulation was assessed using an ELISA on Interferon beta (VI: picogram/millilitre). Dashed lines indicated untreated corresponding tumors, I/II and III/IV are each cells derived from the same tumor.

In order to verify that type I IFN response can be initiated within the tumor microenvironment, we performed analysis on crude tumor isolates infected ex vivo with bacterial strains followed by ELISA on Interferon beta. Wildtype Balb/C mice allografted s.c. with EMT6 breast cancer cells were sacrificed when tumor had reach a volume of. Tumors were mashed, digested and seeded as single-cell suspension into 24-well plates. Such cells from two different tumors were ledt uninfected (dashed lines in FIG. 39) or infected with *Y. enterocolitica* ΔHOPEMT, or *Y. enterocolitica* ΔHOPEMT encoding on a pBadMycHisA derived plasmid YopE$_{1-138}$-murine RIG1 CARD domains$_{1-246}$. IFN stimulation was assessed using an ELISA on Interferon beta and showed that while *Y. enterocolitica* ΔHOPEMT failed to induce Interferon beta secretion, infection with *Y. enterocolitica* ΔHOPEMT encoding YopE$_{1-138}$-murine RIG1 CARD domains$_{1-246}$ resulted in dose-dependent Interferon beta secretion by the crude tumor isolate of two different tumors (FIG. 39). This validates, that bacterially delivered RIG1 CARD domains are capable of inducing Interferon production in a mixed cell population consisting of cancer cells, immune cells and all other cells within the tumor microenvironment.

Figure 40:
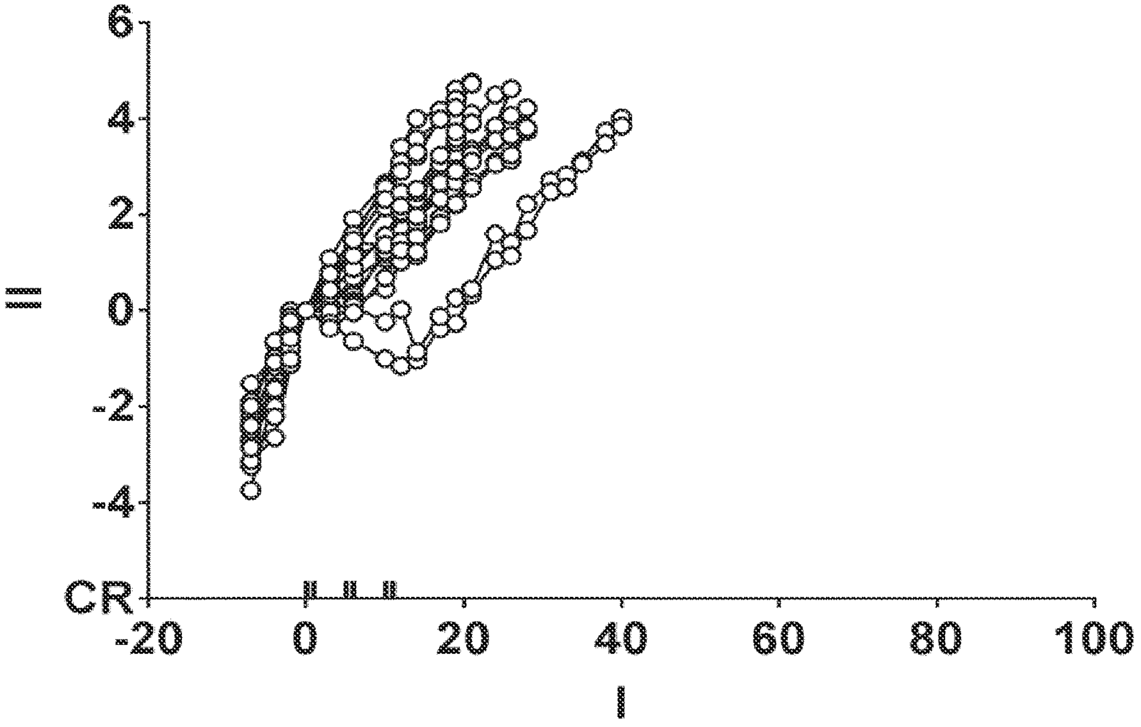
FIG. 40: Tumor progression in wildtype Balb/C mice allografted s.c. with EMT6 breast cancer cells. Wildtype Balb/C mice allografted s.c. with EMT6 breast cancer cells were intratumorally injected with PBS once the tumor had reached a size of 60-130 mm3. The day of the first intratumoral injection of PBS was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as $mm^3$, is indicated log-2 transformed (II) for each mouse. CR is complete remission.
Figure 41:
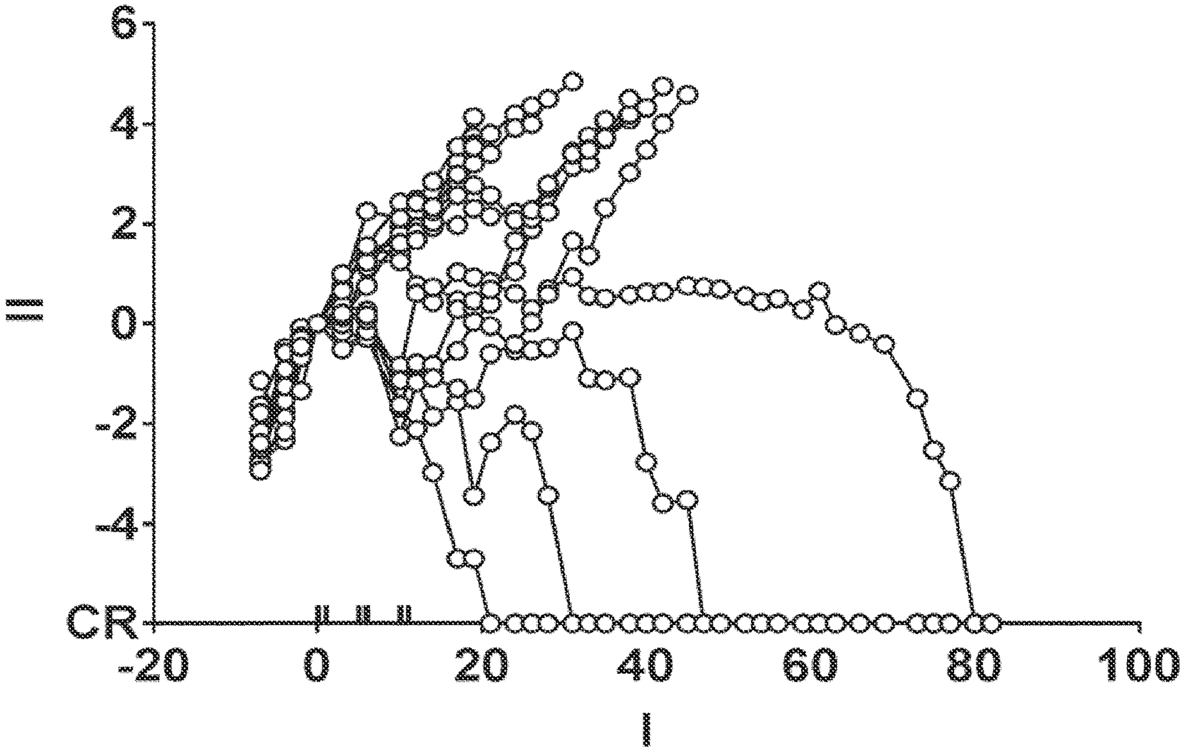
FIG. 41: Tumor progression in wildtype Balb/C mice allografted s.c. with EMT6 breast cancer cells. Wildtype Balb/C mice allografted s.c. with EMT6 breast cancer cells were intratumorally injected with $7.5*10^7$ *Y. enterocolitica* dHOPEMT once the tumor had reached a size of 60-130 mm3. The day of the first intratumoral injection of bacteria was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as $mm^3$, is indicated log-2 transformed (II) for each mouse. CR is complete remission.
Figure 42:
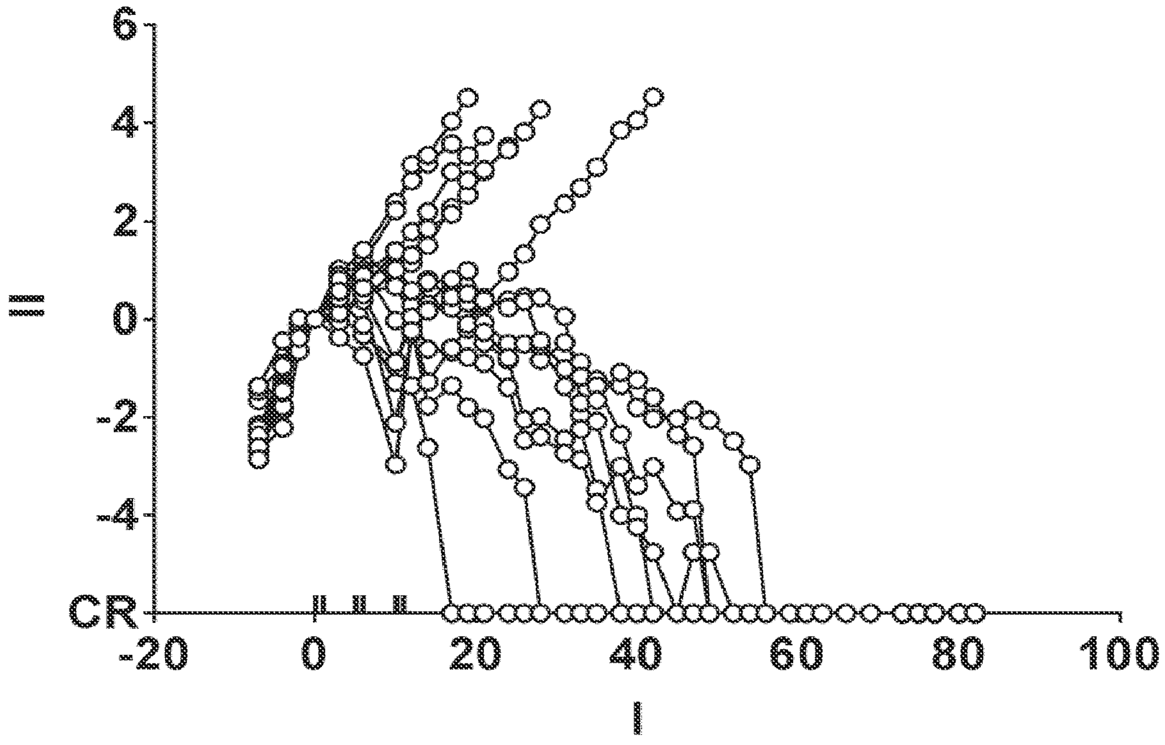
FIG. 42: Tumor progression in wildtype Balb/C mice allografted s.c. with EMT6 breast cancer cells. Wildtype Balb/C mice allografted s.c. with EMT6 breast cancer cells were intratumorally injected with $7.5*10^7$ *Y. enterocolitica* dHOPEMT encoding on a pBadMycHisA derived plasmid $YopE_{1-138}$-murine RIG1 CARD $domains_{1-246}$ once the tumor had reached a size of 60-130 mm3. The day of the first intratumoral injection of bacteria was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as $mm^3$, is indicated log-2 transformed (II) for each mouse. CR is complete remission.
Figure 43:
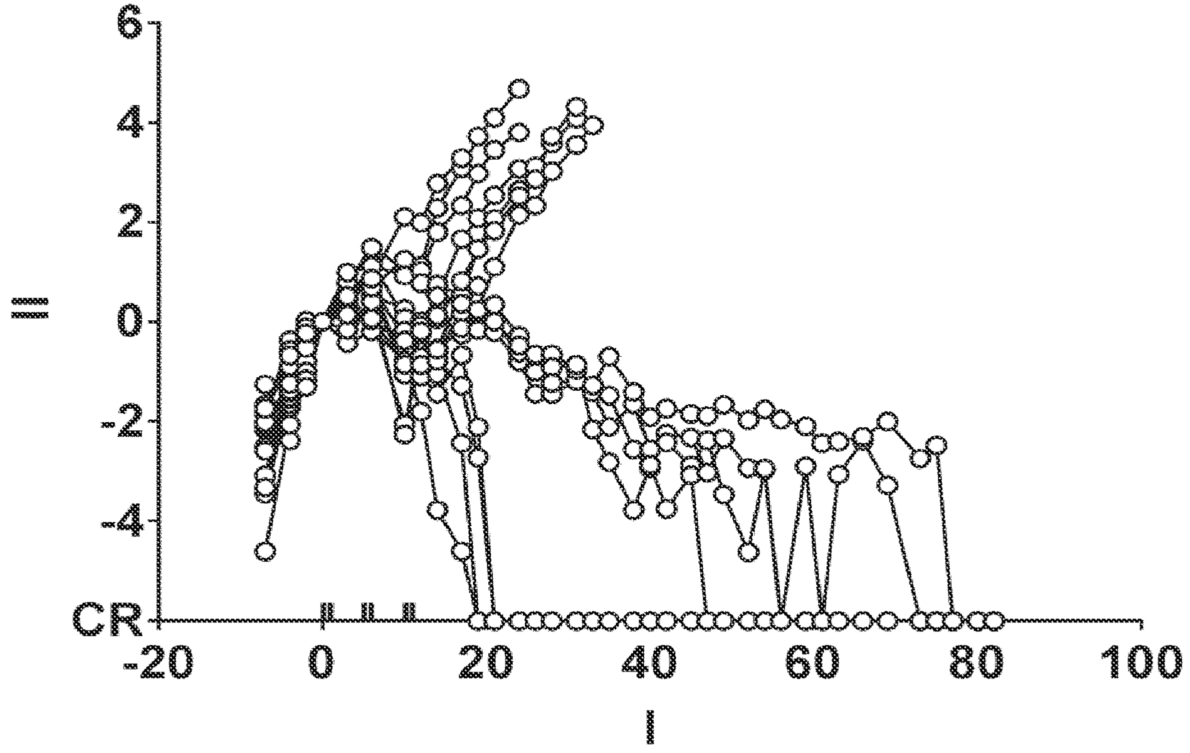
FIG. 43: Tumor progression in wildtype Balb/C mice allografted s.c. with EMT6 breast cancer cells. Wildtype Balb/C mice allografted s.c. with EMT6 breast cancer cells were intratumorally injected with $7.5*10^7$ *Y. enterocolitica* dHOPEMT encoding on a pBadMycHisA derived plasmid $YopE_{1-138}$-human $cGAS_{161-522}$ once the tumor had reached a size of 60-130 mm3. The day of the first intratumoral injection of bacteria was defined as day 0, treatments were performed on d0, d1, d5, d6, d10 and d11. Tumor volume was measured over the following days (I: day −11 to day 80 post first injection of bacteria) with calipers. The relative tumor volume (tumor volume at corresponding day divided by tumor volume at d0) as $mm^3$, is indicated log-2 transformed (II) for each mouse. CR is complete remission.

Efficacy of *Y. enterocolitica* ΔHOPEMT Delivering RIG1 CARDs or cGAS in Delaying Tumor Progression In order to assess the impact of YopE$_{1-138}$-murine RIG1 CARD domains$_{1-246}$ and YopE$_{1-138}$-human cGAS delivered to tumor cells in vivo, we performed studies in wildtype Balb/C mice allografted s.c. with EMT6 breast cancer cells. Mice were intratumorally (it) injected with PBS (FIG. 40) or 7.5*10$^7$ *Y. enterocolitica* ΔHOPEMT, *Y. enterocolitica* ΔHOPEMT+YopE$_{1-138}$ murine RIG1 CARD domains$_{1-246}$ or *Y. enterocolitica* ΔHOPEMT+YopE$_{1-138}$ human cGAS once the tumor had reached a size of about 60-130 mm3. The day of the first it injection of bacteria was defined as day 0. Mice were it injected on d0, d1, d5, d6, d10 and d11. Tumor volume was measured over the following days with calipers. Treatment with *Y. enterocolitica* ΔHOPEMT alone showed an impact on tumor volume progression, with 4/14 mice exhibiting complete tumor regression (FIG. 41). *Y. enterocolitica* ΔHOPEMT delivering a protein inducing a type I IFN response, being it RIG1 CARDS or cGAS, was found to lead to a more pronounced impact on tumor progression with each 8/14 (RIG1 CARDs) or 8/15 (cGAS) mice showing complete and durable tumor regression (FIG. 42-43). These findings highlight that such bacteria and their T3SS can be employed for very significant interference with tumor progression and that delivery type I IFN inducing proteins is well-suited to induce regression of primary tumor.

Figure 44:
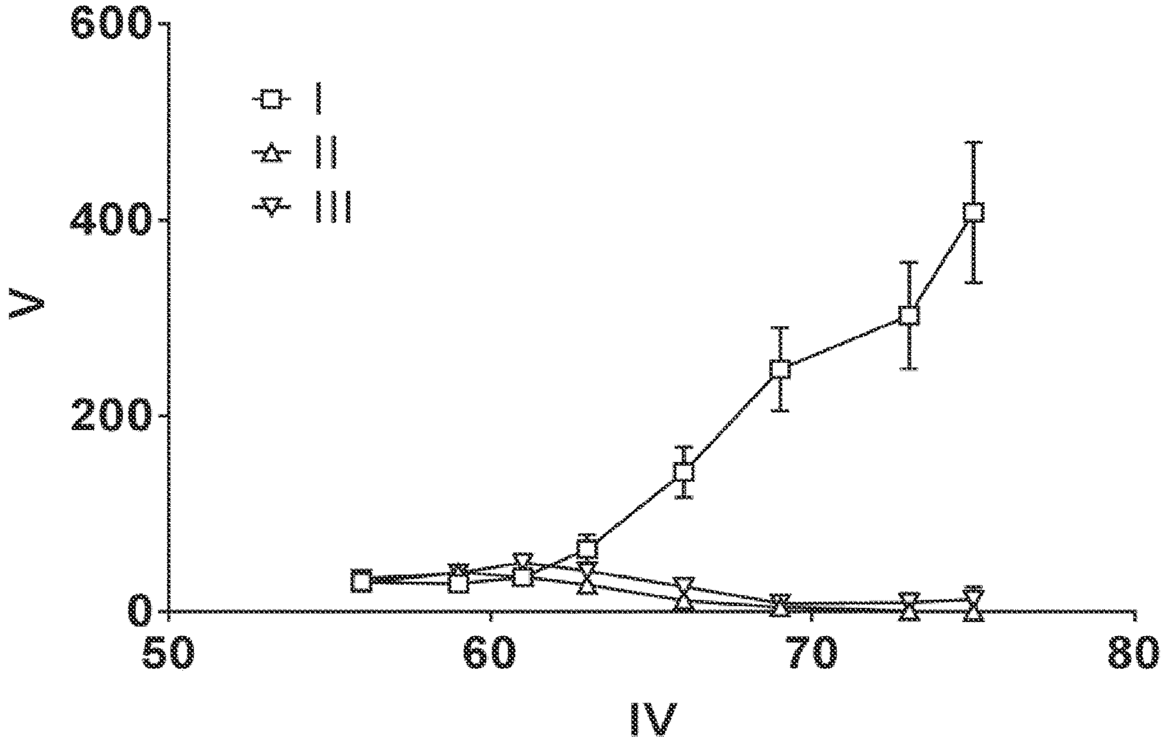
FIG. 44: Tumor progression in wildtype Balb/C mice rechallenged s.c. on the contralateral side with EMT6 breast cancer cells after a first complete remission. Wildtype Balb/C mice allografted s.c. with EMT6 breast cancer cells were treated as described above (FIG. 40-43) intratumorally with $7.5*10^7$ II: *Y. enterocolitica* dHOPEMT encoding on a pBadMycHisA derived plasmid $YopE_{1-138}$-murine RIG1 CARD $domains_{1-246}$, III: *Y. enterocolitica* dHOPEMT encoding on a pBadMycHisA derived plasmid $YopE_{1-138}$-human $cGAS_{161-522}$, once the tumor had reached a size of 60-130 mm3. The day of the intratumoral injection of bacteria was defined as day 0. Mice with a complete tumor regression (or I: naïve mice as control) were allografted s.c. with EMT6 breast cancer cells on the contralateral flank. Tumor volume was measured over the following days (IV: up to day 80 post first injection of bacteria) with calipers. The absolute tumor volume is indicated (V) as $mm^3$ for each mouse.

Mice with complete tumor regression were further observed up to day 65 after initial tumor allografting, followed on day 65 by a rechallenge with EMT6 breast cancer cells on the contralateral flank to assess immune-mediated memory and systemic activity towards these cancer cells. In this rechallenge study no additional treatment was administered and mice were simply observed for tumor progression on contralater flank and compared to naïve mice (mice without previous exposure to EMT6 breast cancer cells, but all other parameters as age being identical). While in naïve mice tumor cells s.c. allografted resulted in tumor growth, all mice with a previously treated EMT6 tumor on the opposite flank with complete regression were found to be protected from tumor growth (FIG. 44). Remarkably, tumors in mice with a previous complete regression induced by bacterial treatment on contralater flank started growing for several days and reached volumes of up to >100 mm3 (with peak volume at around day 10 after second grafting) and shrinkage thereafter (FIG. 44). This lag-period may be indicative of an adaptive immune system response needing several days before being fully mounted.

Figure 46:
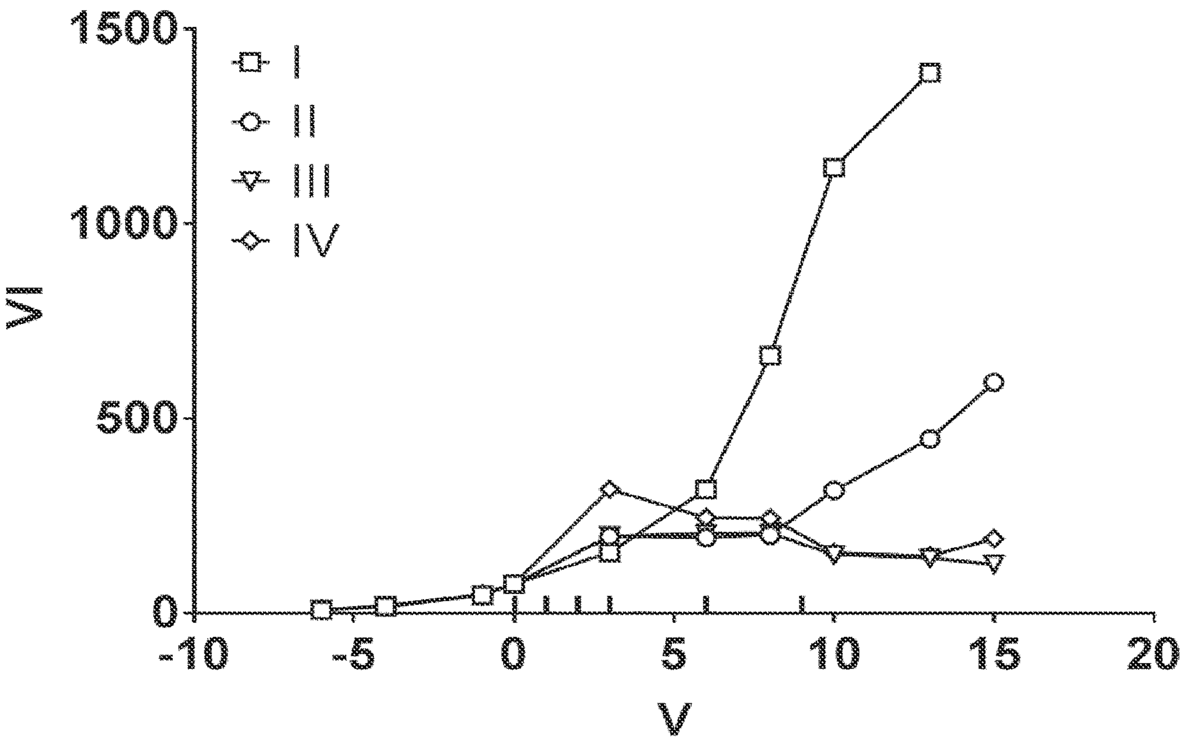
FIG. 46: Tumor progression in wildtype C57BL/6 mice allografted s.c. with B16F10 melanoma cells. Wildtype C57BL/6 mice allografted s.c. with B16F10 melanoma cells were intratumorally injected with I: PBS, or 7.5*$10^7$ II: *Y. enterocolitica* dHOPEMT, III: encoding on a pBadMycHisA derived plasmid $YopE_{1-138}$-murine RIG1 CARD $domains_{1-246}$, IV: *Y. enterocolitica* dHOPEMT encoding on a pBadMycHisA derived plasmid $YopE_{1-138}$-human $cGAS_{161-522}$ once the tumor had reached a size of 60-130 $mm^3$. The day of the first intratumoral injection of bacteria was defined as day 0, treatments were performed on d0, d1, d2, d3, d6 and d9. Tumor volume was measured over the following days (V: days) with calipers. The mean tumor volume is indicated (VI) as $mm^3$.

In further experiments to assess the impact of YopE$_{1-138}$-murine RIG1 CARD domains$_{1-246}$ and YopE$_{1-138}$-human cGAS delivered to tumor cells in vivo, we performed studies in wildtype C57BL/6 mice allografted s.c. with B16F10 melanoma cancer cells. Mice were intratumorally (it) injected with PBS or 7.5*10$^7$ *Y. enterocolitica* ΔHOPEMT, *Y. enterocolitica* ΔHOPEMT+YopE$_{1-138}$ murine RIG1 CARD domains$_{1-246}$ or *Y. enterocolitica* ΔHOPEMT+YopE$_{1-138}$ human cGAS once the tumor had reached a size of about 75 mm3. The day of the first it injection of bacteria was defined as day 0. Mice were it injected on d0, d1, d2, d3, d6 and d9. Tumor volume was measured over the following days with calipers. Treatment with *Y. enterocolitica* ΔHOPEMT alone showed an impact on tumor volume progression, with 1/15 mice exhibiting complete tumor regression (FIG. 46). *Y. enterocolitica* ΔHOPEMT delivering a protein inducing a type I IFN response, being it RIG1 CARDS or cGAS, was found to lead to a very pronounced impact on tumor progression with each 5/15 (RIG1 CARDs) or 8/15 (cGAS) mice showing complete and durable tumor regression (FIG. 46). These findings highlight that such bacteria and their T3SS can be employed for very significant interference with tumor progression and that delivery type I IFN inducing proteins is well-suited to induce regression of primary tumor. Remarkably, especially in case of bacteria delivering YopE$_{1-138}$-human cGAS, an increase in tumor volume shortly after first administrations was observed comparing to PBS treated control, which may be induced by leukocyte influx into the tumor (pseudo-progression) induced by the intracellular delivery of the type I IFN inducing cGAS protein.

LIST OF REFERENCES

1 Hayes, C. S., Aoki, S. K. & Low, D. A. Bacterial contact-dependent delivery systems. *Annu Rev Genet* 44, 71-90, doi:10.1146/annurev.genet.42.110807.091449 (2010).

2 Cornelis, G. R. The type III secretion injectisome. *Nat Rev Microbiol* 4, 811-825, doi:nrmicro1526 [pii]10.1038/nrmicro1526 (2006).

3 Blanco-Toribio, A., Muyldermans, S., Frankel, G. & Fernandez, L. A. Direct injection of functional single-domain antibodies from *E. coli* into human cells. *PLoS One* 5, e15227, doi:10.1371/journal.pone.0015227 (2010).

4 Bichsel, C. et al. Direct reprogramming of fibroblasts to myocytes via bacterial injection of MyoD protein. *Cell Reprogram* 15, 117-125, doi:10.1089/cell.2012.0058 (2013).

5 Bichsel, C. et al. Bacterial delivery of nuclear proteins into pluripotent and differentiated cells. *PLoS One* 6, e16465, doi:10.1371/journal.pone.0016465 (2011).

6 Chamekh, M. et al. Delivery of biologically active anti-inflammatory cytokines IL-10 and IL-1ra in vivo by the *Shigella* type III secretion apparatus. *J Immunol* 180, 4292-4298 (2008).

7 Skurnik, M. & Wolf-Watz, H. Analysis of the yopA gene encoding the Yopl virulence determinants of *Yersinia* spp. *Mol Microbiol* 3, 517-529 (1989).

8 Isberg, R. R., Voorhis, D. L. & Falkow, S. Identification of invasin: a protein that allows enteric bacteria to penetrate cultured mammalian cells. *Cell* 50, 769-778 (1987).

9 Mota, L. J. & Cornelis, G. R. The bacterial injection kit: type III secretion systems. *Ann Med* 37, 234-249, doi: R673752030212825 [pii]10.1080/07853890510037329 (2005).

10 Trosky, J. E., Liverman, A. D. & Orth, K. *Yersinia* outer proteins: Yops. *Cell Microbiol* 10, 557-565, doi:10.1111/j.1462-5822.2007.01109.x (2008).

11 Brenner, D. & Mak, T. W. Mitochondrial cell death effectors. *Curr Opin Cell Biol* 21, 871-877, doi:S0955-0674(09)00160-4 [pii]10.1016/j.ceb.2009.09.004 (2009).

12 Chalah, A. & Khosravi-Far, R. The mitochondrial death pathway. *Adv Exp Med Biol* 615, 25-45, doi:10.1007/978-1-4020-6554-5_3 (2008).

13 Fuchs, Y. & Steller, H. Programmed cell death in animal development and disease. *Cell* 147, 742-758, doi:S0092-8674(11)01283-9 [pii]10.1016/j.cell.2011.10.033 (2011).

14 Waugh, D. S. An overview of enzymatic reagents for the removal of affinity tags. *Protein Expr Purif* 80, 283-293, doi:S1046-5928(11)00203-8 [pii]10.1016/j.pep.2011.08.005 (2011).

15 Howard, S. L. et al. Application of comparative phylogenomics to study the evolution of *Yersinia enterocolitica* and to identify genetic differences relating to pathogenicity. *J Bacteriol* 188, 3645-3653, doi:10.1128/JB.188.10.3645-3653.2006 (2006).

16 Thomson, N. R. et al. The complete genome sequence and comparative genome analysis of the high pathogenicity *Yersinia enterocolitica* strain 8081. *PLoS Genet* 2, e206, doi:10.1371/journal.pgen.0020206 (2006).

17 Pelludat, C., Hogardt, M. & Heesemann, J. Transfer of the core region genes of the *Yersinia enterocolitica* WA-C serotype O:8 high-pathogenicity island to *Y. enterocolitica* MRS40, a strain with low levels of pathogenicity, confers a yersiniabactin biosynthesis phenotype and enhanced mouse virulence. *Infect Immun* 70, 1832-1841 (2002).

18 Mulder, B., Michiels, T., Simonet, M., Sory, M. P. & Cornelis, G. Identification of additional virulence determinants on the pYV plasmid of *Yersinia enterocolitica* W227. *Infect Immun* 57, 2534-2541 (1989).

19 Sory, M. P. & Cornelis, G. R. Translocation of a hybrid YopE-adenylate cyclase from *Yersinia enterocolitica* into HeLa cells. *Mol Microbiol* 14, 583-594 (1994).

20 Sarker, M. R., Neyt, C., Stainier, I. & Cornelis, G. R. The *Yersinia* Yop virulon: LcrV is required for extrusion of the translocators YopB and YopD. *J Bacteriol* 180, 1207-1214 (1998).

21 Neubauer, H., Aleksic, S., Hensel, A., Finke, E. J. & Meyer, H. *Yersinia enterocolitica* 16S rRNA gene types belong to the same genospecies but form three homology groups. *Int J Med Microbiol* 290, 61-64, doi:10.1016/S1438-4221(00)80107-1 (2000).

22 Feldman, M. F., Muller, S., Wuest, E. & Cornelis, G. R. SycE allows secretion of YopE-DHFR hybrids by the *Yersinia enterocolitica* type III Ysc system. *Mol Microbiol* 46, 1183-1197, doi:3241 [pii] (2002).

23 Ramamurthi, K. S. & Schneewind, 0. A synonymous mutation in *Yersinia enterocolitica* yopE affects the function of the YopE type III secretion signal. *J Bacteriol* 187, 707-715, doi:10.1128/JB.187.2.707-715.2005 (2005).

24 Wolke, S., Ackermann, N. & Heesemann, J. The *Yersinia enterocolitica* type 3 secretion system (T3SS) as toolbox for studying the cell biological effects of bacterial Rho GTPase modulating T3SS effector proteins. *Cell Microbiol* 13, 1339-1357, doi:10.1111/j.1462-5822.2011.01623.x (2011).

25 Forsberg, A. & Wolf-Watz, H. Genetic analysis of the yopE region of *Yersinia* spp.: identification of a novel conserved locus, yerA, regulating yopE expression. *J Bacteriol* 172, 1547-1555 (1990).
26 Sambrook, J. (ed David W. Russell) (Cold Spring Harbor Laboratory Press, Cold Spring Harbor, N.Y., 2001).
27 Alto, N. M. & Dixon, J. E. Analysis of Rho-GTPase mimicry by a family of bacterial type III effector proteins. *Methods Enzymol* 439, 131-143, doi:S0076-6879(07)00410-7 [pii]10.1016/S0076-6879(07)00410-7 (2008).
28 Alto, N. M. et al. Identification of a bacterial type III effector family with G protein mimicry functions. *Cell* 124, 133-145, doi:S0092-8674(05)01229-8 [pii]10.1016/j.cell.2005.10.031 (2006).
29 Kaniga, K., Delor, I. & Cornelis, G. R. A wide-host-range suicide vector for improving reverse genetics in gram-negative bacteria: inactivation of the blaA gene of *Yersinia enterocolitica. Gene* 109, 137-141, doi:0378-1119(91)90599-7 [pii] (1991).
30 Yoneda, Y. et al. A long synthetic peptide containing a nuclear localization signal and its flanking sequences of SV40 T-antigen directs the transport of IgM into the nucleus efficiently. *Exp Cell Res* 201, 313-320 (1992).
31 Metcalf, W. W., Jiang, W. & Wanner, B. L. Use of the rep technique for allele replacement to construct new *Escherichia coli* hosts for maintenance of R6K gamma origin plasmids at different copy numbers. *Gene* 138, 1-7 (1994).
32 Diepold, A. et al. Deciphering the assembly of the *Yersinia* type III secretion injectisome. *Embo J* 29, 1928-1940, doi:emboj201084 [pii]10.1038/emboj.2010.84 (2010).
33 Iriarte, M., Stainier, I. & Cornelis, G. R. The rpoS gene from *Yersinia enterocolitica* and its influence on expression of virulence factors. *Infect Immun* 63, 1840-1847 (1995).
34 Cornelis, G., Vanootegem, J. C. & Sluiters, C. Transcription of the yop regulon from *Y. enterocolitica* requires trans acting pYV and chromosomal genes. *Microb Pathog* 2, 367-379, doi:0882-4010(87)90078-7 [pii] (1987).
35 Grosdent, N., Maridonneau-Parini, I., Sory, M. P. & Cornelis, G. R. Role of Yops and adhesins in resistance of *Yersinia enterocolitica* to phagocytosis. *Infect Immun* 70, 4165-4176 (2002).
36 Boyd, A. P., Lambermont, I. & Cornelis, G. R. Competition between the Yops of *Yersinia enterocolitica* for delivery into eukaryotic cells: role of the SycE chaperone binding domain of YopE. *J Bacteriol* 182, 4811-4821 (2000).
37 Iriarte, M. & Cornelis, G. R. YopT, a new *Yersinia* Yop effector protein, affects the cytoskeleton of host cells. *Mol Microbiol* 29, 915-929 (1998).
38 Kudryashev, M. et al. In situ structural analysis of the *Yersinia enterocolitica* injectisome. *Elife* 2, e00792, doi:10.7554/eLife.0079200792 [pii] (2013).
39 Schulte, R. et al. *Yersinia enterocolitica* invasin protein triggers IL-8 production in epithelial cells via activation of Rel p65-p65 homodimers. *FASEB J*14, 1471-1484 (2000).
40 Mota, L. J., Journet, L., Sorg, I., Agrain, C. & Cornelis, G. R. Bacterial injectisomes: needle length does matter. *Science* 307, 1278, doi:307/5713/1278 [pii]10.1126/science.1107679 (2005).
41 Carrington, J. C. & Dougherty, W. G. A viral cleavage site cassette: identification of amino acid sequences required for tobacco etch virus polyprotein processing. *Proc Natl Acad Sci USA* 85, 3391-3395 (1988).
42 Kapust, R. B., Tozser, J., Copeland, T. D. & Waugh, D. S. The P1' specificity of tobacco etch virus protease. *Biochem Biophys Res Commun* 294, 949-955, doi:10.1016/S0006-291X(02)00574-0S0006-291X(02)00574-0 [pii] (2002).
43 Liang, H., Gao, H., Maynard, C. A. & Powell, W. A. Expression of a self-processing, pathogen resistance-enhancing gene construct in *Arabidopsis. Biotechnol Lett* 27, 435-442, doi:10.1007/s10529-005-1884-9 (2005).
44 Weber, W. et al. Macrolide-based transgene control in mammalian cells and mice. *Nat Biotechnol* 20, 901-907, doi:10.1038/nbt731nbt731 [pii] (2002).
45 Kapust, R. B. et al. Tobacco etch virus protease: mechanism of autolysis and rational design of stable mutants with wild-type catalytic proficiency. *Protein Eng* 14, 993-1000 (2001).
46 Lee, V. T., Anderson, D. M. & Schneewind, O. Targeting of *Yersinia* Yop proteins into the cytosol of HeLa cells: one-step translocation of YopE across bacterial and eukaryotic membranes is dependent on SycE chaperone. *Mol Microbiol* 28, 593-601 (1998).
47 Gray, D. C., Mahrus, S. & Wells, J. A. Activation of specific apoptotic caspases with an engineered small-molecule-activated protease. *Cell* 142, 637-646, doi:S0092-8674(10)00783-X [pii]10.1016/j.cell.2010.07.014 (2010).
48 Henrichs, T. et al. Target-directed proteolysis at the ribosome. *Proc Natl Acad Sci USA* 102, 4246-4251, doi:102/12/4246 [pii]10.1073/pnas.0408520102 (2005).
49 Aepfelbacher, M., Trasak, C. & Ruckdeschel, K. Effector functions of pathogenic *Yersinia* species. *Thromb Haemost* 98, 521-529 (2007).
50 Trulzsch, K., Sporleder, T., Igwe, E. I., Russmann, H. & Heesemann, J. Contribution of the major secreted yops of *Yersinia enterocolitica* 0:8 to pathogenicity in the mouse infection model. *Infect Immun* 72, 5227-5234, doi:10.1128/IAI.72.9.5227-5234.2004 (2004).
51 Bohme, K. et al. Concerted actions of a thermo-labile regulator and a unique intergenic RNA thermosensor control *Yersinia* virulence. *PLoS Pathog* 8, e1002518, doi:10.1371/journal.ppat.1002518 (2012).
52 Rohde, J. R., Luan, X. S., Rohde, H., Fox, J. M. & Minnich, S. A. The *Yersinia enterocolitica* pYV virulence plasmid contains multiple intrinsic DNA bends which melt at 37 degrees C. *J Bacteriol* 181, 4198-4204 (1999).
53 Curtiss, R., 3rd, Galan, J. E., Nakayama, K. & Kelly, S. M. Stabilization of recombinant avirulent vaccine strains in vivo. *Res Microbiol* 141, 797-805 (1990).
54 Spreng, S. & Viret, J. F. Plasmid maintenance systems suitable for GMO-based bacterial vaccines. *Vaccine* 23, 2060-2065, doi:10.1016/j.vaccine.2005.01.009 (2005).
55 Neyt, C., Iriarte, M., Thi, V. H. & Cornelis, G. R. Virulence and arsenic resistance in Yersiniae. *J Bacteriol* 179, 612-619 (1997).
56 Wu, J. & Chen, Z. J. Innate immune sensing and signaling of cytosolic nucleic acids. *Annu Rev Immunol* 32, 461-488, doi:10.1146/annurev-immunol-032713-120156 (2014).
57 Kranzusch, P. J. et al. Ancient Origin of cGAS-STING Reveals Mechanism of Universal 2',3' cGAMP Signaling. *Mol Cell* 59, 891-903, doi:10.1016/j.molcel.2015.07.022 (2015).
58 Commichau, F. M., Dickmanns, A., Gundlach, J., Ficner, R. & Stulke, J. A jack of all trades: the multiple roles of the unique essential second messenger cyclic di-AMP. *Mol Microbiol* 97, 189-204, doi:10.1111/mmi.13026 (2015).

59 Corrales, L. et al. Direct Activation of STING in the Tumor Microenvironment Leads to Potent and Systemic Tumor Regression and Immunity. *Cell Rep* 11, 1018-1030, doi:10.1016/j.celrep.2015.04.031 (2015).
60 De, N., Navarro, M. V., Raghavan, R. V. & Sondermann, H. Determinants for the activation and autoinhibition of the diguanylate cyclase response regulator WspR. *J Mol Biol* 393, 619-633, doi:10.1016/j.jmb.2009.08.030 (2009).
61 Witte, G., Hartung, S., Buttner, K. & Hopfner, K. P. Structural biochemistry of a bacterial checkpoint protein reveals diadenylate cyclase activity regulated by DNA recombination intermediates. *Mol Cell* 30, 167-178, doi: 10.1016/j.molcel.2008.02.020 (2008).
62 Panne, D., McWhirter, S. M., Maniatis, T. & Harrison, S. C. Interferon regulatory factor 3 is regulated by a dual phosphorylation-dependent switch. *J Biol Chem* 282, 22816-22822, doi:10.1074/jbc.M703019200 (2007).
63 Engel, C., G. Brugmann, S. Lambing, L. H. Muhlenbeck, S. Marx, C. Hagen, D. Horvath, M. Goldeck, J. Ludwig, A. M. Herzner, J. W. Drijfhout, D. Wenzel, C. Coch, T. Tuting, M. Schlee, V. Hornung, G. Hartmann, and J. G. Van den Boom. 2017. RIG-I Resists Hypoxia-Induced Immunosuppression and Dedifferentiation. *Cancer Immunol Res.* 5:455-467.
64 Hou, F., L. Sun, H. Zheng, B. Skaug, Q. X. Jiang, and Z. J. Chen. 2011. MAVS forms functional prion-like aggregates to activate and propagate antiviral innate immune response. *Cell.* 146:448-461.
65 Kranzusch, P. J., A. S. Lee, J. M. Berger, and J. A. Doudna. 2013. Structure of human cGAS reveals a conserved family of second-messenger enzymes in innate immunity. *Cell Rep.* 3:1362-1368.
66 Seth, R. B., L. Sun, C. K. Ea, and Z. J. Chen. 2005. Identification and characterization of MAVS, a mitochondrial antiviral signaling protein that activates NF-kappaB and IRF 3. *Cell.* 122:669-682.

The invention claimed is:

1. A recombinant virulence attenuated Gram-negative bacterial strain which comprises a nucleotide molecule comprising:

a nucleotide sequence encoding a fusion protein comprising a delivery signal from a bacterial effector protein and a heterologous protein, wherein the nucleotide sequence comprises a nucleotide sequence encoding the heterologous protein fused in frame to the 3' end of a nucleotide sequence encoding the delivery signal from a bacterial effector protein, and a promoter sequence operably linked to the nucleotide sequence encoding the delivery signal from a bacterial effector protein, wherein the fusion protein comprises the amino acid sequence set forth in SEQ ID NO: 37-48, 110-118, or 128-131, and wherein the recombinant virulence attenuated Gram-negative bacterial strain is *Yersinia enterocolitica.*

2. The recombinant virulence attenuated Gram-negative bacterial strain of claim 1, wherein the recombinant virulence attenuated Gram-negative bacterial strain further comprises:

a deletion of a chromosomal gene coding for an endogenous protein essential for growth; and an endogenous virulence plasmid which comprises a nucleotide sequence comprising a gene coding for said endogenous protein essential for growth operably linked to a promoter.

3. The recombinant virulence attenuated Gram-negative bacterial strain of claim 2, wherein said virulence attenuated recombinant Gram-negative bacterial strain is deficient in producing at least one bacterial effector protein.

4. The recombinant virulence attenuated Gram-negative bacterial strain of claim 2, wherein the gene coding for an endogenous protein essential for growth is selected from a gene coding for an enzyme essential for amino acid production, a gene coding for an enzyme involved in peptidoglycan biosynthesis, a gene coding for an enzyme involved in LPS biosynthesis, a gene coding for an enzyme involved in nucleotide synthesis and a gene coding for a translation initiation factor.

5. The recombinant virulence attenuated Gram-negative bacterial strain of claim 2, wherein the gene coding for an endogenous enzyme essential for growth is a gene coding for an enzyme essential for amino acid production, wherein the enzyme essential for amino acid production is aspartate-beta-semialdehyde dehydrogenase (asd).

6. The recombinant virulence attenuated Gram-negative bacterial strain of claim 2, wherein the gene coding for the endogenous enzyme essential for growth located on the endogenous virulence plasmid comprises its endogenous promoter and its endogenous transcriptional terminator.

7. The recombinant virulence attenuated Gram-negative bacterial strain of claim 6, wherein the gene coding for the endogenous enzyme essential for growth, its endogenous promoter and its endogenous transcriptional terminator are located 122 bp upstream of the start of orf155 on the endogenous virulence plasmid.

8. The recombinant virulence attenuated Gram-negative bacterial strain of claim 1, wherein the recombinant virulence attenuated Gram-negative bacterial strain further comprises a modulation within a RNA thermosensor region upstream of a gene coding for an endogenous AraC-type DNA binding protein.

9. The recombinant virulence attenuated Gram-negative bacterial strain of claim 8, wherein the modulation within a RNA thermosensor region upstream of a gene coding for an endogenous AraC-type DNA binding protein comprises a deletion which removes a RNA hairpin structure or parts thereof formed by intramolecular base-pairing leading to a stem-loop structure upstream of the gene coding for an endogenous AraC-type DNA binding protein.

10. The recombinant virulence attenuated Gram-negative bacterial strain of claim 8, wherein the AraC-type DNA binding protein is VirF.

11. A method of treating cancer in a subject, the method comprising:

administering to the subject the recombinant virulence attenuated Gram-negative bacterial strain of claim 1, wherein the recombinant virulence attenuated Gram-negative bacterial strain is administered in an amount that is sufficient to treat the subject, and wherein the cancer is breast cancer or melanoma.

12. The method of claim 11, wherein the cancer is breast cancer.

13. The method of claim 11, the cancer is melanoma.

14. The method of claim 11, wherein the recombinant virulence attenuated Gram-negative bacterial strain further comprises:

a deletion of a chromosomal gene coding for an endogenous protein essential for growth; and an endogenous virulence plasmid which comprises a nucleotide sequence comprising a gene coding for said endogenous protein essential for growth operably linked to a promoter.

15. The method of claim 14, wherein the gene coding for an endogenous protein essential for growth is a gene coding for an enzyme essential for amino acid production, wherein the enzyme essential for amino acid production is aspartate-beta-semialdehyde dehydrogenase (asd).

16. The method of claim 14, wherein the gene coding for the endogenous enzyme essential for growth located on the endogenous virulence plasmid comprises its endogenous promoter and its endogenous transcriptional terminator.

17. The method of claim 16, wherein the gene coding for the endogenous enzyme essential for growth, its endogenous promoter and its endogenous transcriptional terminator are located 122 bp upstream of the start of orf155 on the endogenous virulence plasmid.

* * * * *